US008129154B2

(12) United States Patent  
Burk et al.

(10) Patent No.: US 8,129,154 B2  
(45) Date of Patent: Mar. 6, 2012

(54) MICROORGANISMS AND METHODS FOR THE BIOSYNTHESIS OF FUMARATE, MALATE, AND ACRYLATE

(75) Inventors: Mark J. Burk, San Diego, CA (US); Anthony P. Burgard, Bellefonte, PA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 56 days.

(21) Appl. No.: 12/486,724

(22) Filed: Jun. 17, 2009

(65) Prior Publication Data

US 2010/0009419 A1    Jan. 14, 2010

Related U.S. Application Data

(60) Provisional application No. 61/073,348, filed on Jun. 17, 2008, provisional application No. 61/077,127, filed on Jun. 30, 2008, provisional application No. 61/088,628, filed on Aug. 13, 2008.

(51) Int. Cl.  
*C12P 7/46* (2006.01)

(52) U.S. Cl. ....................................... 435/145

(58) Field of Classification Search ............. 435/145  
See application file for complete search history.

(56) References Cited

U.S. PATENT DOCUMENTS

| | | |
|---|---|---|
| 3,513,209 A | 5/1970 | Clement |
| 3,912,586 A | 10/1975 | Kaneyuki et al. |
| 3,965,182 A | 6/1976 | Worrel |
| 4,048,196 A | 9/1977 | Broecker et al. |
| 4,082,788 A | 4/1978 | Mims |
| 4,190,495 A | 2/1980 | Curtiss, III |
| 4,301,077 A | 11/1981 | Pesa et al. |
| 4,624,920 A | 11/1986 | Inoue et al. |
| 4,652,685 A | 3/1987 | Cawse et al. |
| 4,871,667 A | 10/1989 | Imada et al. |
| 5,079,143 A | 1/1992 | Klein et al. |
| 5,143,833 A | 9/1992 | Datta |
| 5,143,834 A | 9/1992 | Glassner et al. |
| 5,168,055 A | 12/1992 | Datta et al. |
| 5,173,429 A | 12/1992 | Gaddy et al. |
| 5,182,199 A | 1/1993 | Hartley |
| 5,192,673 A | 3/1993 | Jain et al. |
| 5,403,721 A | 4/1995 | Ward, Jr. et al. |
| 5,413,922 A | 5/1995 | Matsuyama et al. |
| 5,416,020 A | 5/1995 | Severson et al. |
| 5,457,040 A | 10/1995 | Jarry et al. |
| 5,478,952 A | 12/1995 | Schwartz |
| 5,487,987 A | 1/1996 | Frost et al. |
| 5,504,004 A | 4/1996 | Guettler et al. |
| 5,521,075 A | 5/1996 | Guettler et al. |
| 5,573,931 A | 11/1996 | Guettler et al. |
| 5,616,496 A | 4/1997 | Frost et al. |
| 5,686,276 A | 11/1997 | Lafend et al. |
| 5,700,934 A | 12/1997 | Wolters et al. |
| 5,770,435 A | 6/1998 | Donnelly et al. |
| 5,807,722 A | 9/1998 | Gaddy et al. |
| 5,869,301 A | 2/1999 | Nghiem et al. |
| 5,908,924 A | 6/1999 | Burdette et al. |
| 5,958,745 A | 9/1999 | Gruys et al. |
| 6,117,658 A | 9/2000 | Dennis et al. |
| 6,133,014 A | 10/2000 | Mukouyama et al. |
| 6,136,577 A | 10/2000 | Gaddy et al. |
| 6,159,738 A | 12/2000 | Donnelly et al. |
| 6,194,572 B1 | 2/2001 | Buijs et al. |
| 6,214,592 B1 | 4/2001 | Crouzet et al. |
| 6,274,790 B1 | 8/2001 | Kunst et al. |
| 6,280,986 B1 | 8/2001 | Hespell et al. |
| RE37,393 E | 9/2001 | Donnelly et al. |
| 6,340,581 B1 | 1/2002 | Gaddy et al. |
| 6,353,100 B1 | 3/2002 | Guit et al. |
| 6,432,686 B1 | 8/2002 | Bulthuis et al. |
| 6,448,061 B1 | 9/2002 | Pan et al. |
| 6,455,284 B1 | 9/2002 | Gokarn et al. |
| 6,485,947 B1 * | 11/2002 | Rajgarhia et al. ............. 435/139 |
| 6,660,857 B2 | 12/2003 | Agterberg et al. |
| 6,686,194 B1 | 2/2004 | Mutzel et al. |
| 6,686,310 B1 | 2/2004 | Kourtakis et al. |
| 6,743,610 B2 | 6/2004 | Donnelly et al. |
| 6,852,517 B1 | 2/2005 | Cameron et al. |
| 7,127,379 B2 | 10/2006 | Palsson et al. |
| 7,186,541 B2 | 3/2007 | Gorkarn et al. |

(Continued)

FOREIGN PATENT DOCUMENTS

CN          1 358 841          7/2002

(Continued)

OTHER PUBLICATIONS

Pfanner and Geissler, "Versatility of the mitochondrial protein import machinery" *Nat Rev Mol Cell Biol.* 2(5):339-49 (2001).

Truscott et al., "Mechanisms of protein import into mitochondria" *Curr Biol.* 13(8):R326-R337 (2003).

Chang et al., "Effects of deletions at the carboxyl terminus of Zymomonas mobills pyruvate decarboxylase on the kinetic properties and substrate specificity," *Biochemistry* 39(31):9430-9437 (2000).

Fukumura et al, "Hydrolysis of cyclic and linear oligomers of 6-aminocaproic acid by a bacterial cell extract," *J. Biochem.* 59(6):531-536 (1966).

(Continued)

*Primary Examiner* — Mary Monshipouri  
(74) *Attorney, Agent, or Firm* — Jones Day

(57) ABSTRACT

A non-naturally occurring eukaryotic or prokaryotic organism includes one or more gene disruptions occurring in genes encoding enzymes imparting increased fumarate, malate or acrylate production in the organism when the gene disruption reduces an activity of the enzyme. The one or more gene disruptions confers increased production of acrylate onto the organism. Organisms that produce acrylate have an acrylate pathway that at least one exogenous nucleic acid encoding an acrylate pathway enzyme expressed in a sufficient amount to produce acrylate, the acrylate pathway comprising a decarboxylase. Methods of producing fumarate, malate or acrylate include culturing these organisms.

5 Claims, 21 Drawing Sheets

U.S. PATENT DOCUMENTS

| | | | |
|---|---|---|---|
| 7,223,567 B2 | 5/2007 | Ka-Yiu et al. |
| 7,241,594 B2 | 7/2007 | Lee et al. |
| 7,244,610 B2 | 7/2007 | San et al. |
| 7,256,016 B2 | 8/2007 | San et al. |
| 7,262,046 B2 | 8/2007 | Ka-Yiu et al. |
| 7,285,402 B2 | 10/2007 | Gaddy et al. |
| 7,309,597 B2 | 12/2007 | Liao et al. |
| 7,371,558 B2 | 5/2008 | Cervin et al. |
| 7,393,676 B2 | 7/2008 | Gokarn et al. |
| 7,432,091 B2 | 10/2008 | Yukawa et al. |
| 7,491,520 B2 | 2/2009 | Raemakers-Franken et al. |
| 7,569,380 B2 | 8/2009 | San et al. |
| 2002/0012939 A1 | 1/2002 | Palsson |
| 2002/0040123 A1 | 4/2002 | Patil et al. |
| 2002/0168654 A1 | 11/2002 | Maranas et al. |
| 2003/0059792 A1 | 3/2003 | Palsson et al. |
| 2003/0087381 A1 | 5/2003 | Gokarn et al. |
| 2003/0113886 A1 | 6/2003 | Brzostowicz et al. |
| 2003/0182678 A1 | 9/2003 | Mitsky et al. |
| 2003/0224363 A1 | 12/2003 | Park et al. |
| 2003/0233218 A1 | 12/2003 | Schilling |
| 2004/0009466 A1 | 1/2004 | Maranas et al. |
| 2004/0029149 A1 | 2/2004 | Palsson et al. |
| 2004/0072723 A1 | 4/2004 | Palsson et al. |
| 2004/0096946 A1 | 5/2004 | Kealey et al. |
| 2004/0152159 A1 | 8/2004 | Causey et al. |
| 2005/0042736 A1 | 2/2005 | San et al. |
| 2005/0079482 A1 | 4/2005 | Maranas et al. |
| 2005/0287655 A1 | 12/2005 | Tabata et al. |
| 2006/0073577 A1 | 4/2006 | Ka-Yiu et al. |
| 2006/0099578 A1 | 5/2006 | Wallace et al. |
| 2006/0110810 A1 | 5/2006 | Rajgarhia et al. |
| 2006/0172399 A1 | 8/2006 | Nomoto et al. |
| 2006/0281156 A1 | 12/2006 | Aoyama et al. |
| 2007/0042476 A1 | 2/2007 | Lee et al. |
| 2007/0072279 A1 | 3/2007 | Meynial-Salles et al. |
| 2007/0087425 A1 | 4/2007 | Ohto |
| 2007/0092957 A1 | 4/2007 | Donaldson et al. |
| 2007/0111294 A1 | 5/2007 | Burgard et al. |
| 2007/0117191 A1 | 5/2007 | Kamachi et al. |
| 2007/0184539 A1 | 8/2007 | San et al. |
| 2007/0259410 A1 | 11/2007 | Donaldson et al. |
| 2008/0171371 A1 | 7/2008 | Yukawa et al. |
| 2008/0274522 A1 | 11/2008 | Bramucci et al. |
| 2008/0293125 A1 | 11/2008 | Subbian et al. |
| 2009/0047719 A1 | 2/2009 | Burgard et al. |
| 2009/0075351 A1 | 3/2009 | Burk et al. |
| 2009/0305364 A1 | 12/2009 | Burgard et al. |
| 2010/0099925 A1 | 4/2010 | Kharas |

FOREIGN PATENT DOCUMENTS

| | | |
|---|---|---|
| EP | 0 494 078 A1 | 7/1992 |
| EP | 1 473 368 A1 | 11/2004 |
| EP | 2017344 | 1/2009 |
| GB | 1230276 | 4/1971 |
| GB | 1314126 | 4/1973 |
| GB | 1344557 | 1/1974 |
| GB | 1512751 | 6/1978 |
| JP | 50 006776 | 1/1975 |
| WO | WO 82/03854 | 11/1982 |
| WO | WO 91/13997 | 9/1991 |
| WO | WO 99/06532 | 2/1999 |
| WO | WO 99/58686 | 11/1999 |
| WO | WO 01/16346 | 3/2001 |
| WO | WO 02/42418 | 5/2002 |
| WO | WO 02/055995 | 7/2002 |
| WO | WO 02/090312 | 11/2002 |
| WO | WO 03/010322 | 2/2003 |
| WO | WO 03/106691 | 12/2003 |
| WO | WO 03/106998 | 12/2003 |
| WO | WO 2005/026338 | 3/2005 |
| WO | WO 2005/047498 | 5/2005 |
| WO | WO 2005/068643 | 7/2005 |
| WO | WO 2006/031424 | 3/2006 |
| WO | WO 2006/034156 | 3/2006 |
| WO | WO 2007/001982 | 1/2007 |
| WO | WO 2007/030830 | 3/2007 |
| WO | WO 2007/141208 | 12/2007 |
| WO | WO 2008/018930 | 2/2008 |
| WO | WO 2008/024023 | 2/2008 |
| WO | WO 2008/027742 | 3/2008 |
| WO | WO 2008/115840 | 3/2008 |
| WO | WO 2008/080124 | 7/2008 |
| WO | WO 2008/131286 A1 | 10/2008 |
| WO | WO 2008/137403 | 11/2008 |
| WO | WO 2008/152016 | 12/2008 |
| WO | WO 2009/014437 | 1/2009 |
| WO | WO 2009/023493 | 2/2009 |
| WO | WO 2009/031766 | 3/2009 |
| WO | WO 2009/049274 A2 | 4/2009 |
| WO | WO 2009/103026 A1 | 8/2009 |
| WO | WO 2009/113853 | 9/2009 |
| WO | WO 2009/113855 | 9/2009 |
| WO | WO 2009/131040 | 10/2009 |

OTHER PUBLICATIONS

Gescher et al., "Genes coding for a new pathway of aerobic benzoate metabolism in Azoarcus evansii," J Bacteriol. 184(22):6301-6315 (2002).

Kinoshita et al., "Purification and characterization of 6-aminohexanoic-acid-oligomer hydrolase of *Flavobacterium* sp. K172," Eur. J. Biochem. 116(3):547-551 (1981).

Bühler and Simon, "On the kinetics and mechanism of enoate reductase," *Hoppe Seyler Z. Physiol. Chem.* 363(6):609-625 (1982).

Chaparro-Riggers et al., "Comparison of Three Enoate Reductases and their Potential Use for Biotransformations," *Adv. Synth. Catal.* 349:1521-1531 (2007).

Engel, "Butyryl-CoA Dehydrogenase from *Megasphaera elsdenii*," *Methods Enzymol.* 71:359-366 (1981).

Jäger and Färber, "Die Alanatreduktion von β-Carbonyl-oxalylsäure-estern," *Chem. Ber.* 92:2492-2499 (1959).

McPherson et al., "Multiple interactions of lysine-128 of *Escherichia coli* glutamate dehydrogenase revealed by site-directed mutagenesis studies," *Protein Eng.* 2(2):147-152 (1988).

Miura et al., "Molecular Cloning of the nemA Gene Encoding N-Ethylmaleimide Reductase from *Escherichia coli*," *Biol. Pharm. Bull.* 20(1):110-112 (1997).

Rohdich et al., "Enoate reductases of Clostridia. Cloning, sequencing, and expression,"*J. Biol. Chem.* 276(8):5779-5787 (2001).

Simon et al., "Chiral Compounds Synthesized by Biocatalytic Reductions," *Angew. Chem. Int. Ed. Engl.* 24:539-553 (1985).

Steinbacher et al., "Enoate reductase family," in Flavins and Flavoproteins, Proceedings of the Fourteenth International Symposium, St. John's College, University of Cambridge, UK, Jul. 14-18, 2002, Chapman et al., pp. 941-949, Rudolf Weber, Agency for Scientific Publications Berlin.

Tanous et al., "Glutamate dehydrogenase activity can be transmitted naturally to *Lactococcus lactis* strains to stimulate amino acid conversion to aroma compounds,"*Appl. Environ. Microbiol.* 72(2):1402-1409 (2006).

Thanos and Simon, "Electro-enzymic viologen-mediated stereospecific reduction of 2-enoates with free and immobilized enoate reductase on cellulose filters or modified carbon electrodes," *J. Biotechnol.* 6:13-29 (1987).

Tischer et al., "Purification and Some Properties of a Hitherto-Unknown Enzyme Reducing the Carbon-Carbon Double Bond of α,β-Unsaturated Carboxylate Anions," *Eur. J. Biochem.* 97(1):103-112 (1979).

Voellmy and Leisinger, "Role of 4-Aminobutyrate Aminotransferase in the Arginine Metabolism of *Pseudomonas aeruginosa*," *J. Bacteriol.* 128(3):722-729 (1976).

Whelan et al., "Nylon 6 (PA6)," *Kunststofen Rubber*, Wyt en Zonen Uitgevers. Rotterdam, NL. 39(3):38-39 (1986).

Bermejo et al., "Expression of *Clostridium acetobutylicum* ATCC 824 Genes in *Escherichia coli* for Acetone Production and Acetate Detoxification," *Appl. Environ. Microbiol.* 64(3):1079-1085 (1998).

Birrer et al., "Electro-transformation of *Clostridium beijerinckii* NRRL B-592 with shuttle plasmid pHR106 and recombinant derivatives," *Appl. Microbiol. Biotechnol.* 41(1):32-38 (1994).

Chen and Hiu, "Acetone-Butanol-Isopropanol Production by *Clostridium beijerinckii* (Synonym, Clostridium Butylicum)," *Biotechnology Letters* 8(5):371-376 (1986).

Clark, Progress Report for Department of Energy Grant DE-FG02-88ER13941, "Regulation of Alcohol Fermentation in *Escherichia coli*," pp. 1-7 for the period: Jul. 1991-Jun. 1994.

Durre and Bahl, "Microbial Production of Acetone/Butanol/Isopropanol," In *Biotechnology* vol. 6: "Products of Primary Metabolism", Second edition pp. 229-268, M. Roehr, ed. Published jointly by: VCH Verlagsgesellschaft mbH, Weinheim, Federal Republic of Germany and VCH Publishers Inc., New York, NY (1996).

Dürre, "New insights and novel developments in clostridial acetone/butanol/isopropanol fermentation," *Appl. Microbiol. Biotechnol.* 49:639-648 (1998).

Gerischer and Dürre, "mRNA Analysis of the *adc* Gene Region of *Clostridium acetobutylicum* during the Shift to Solventogenesis " *J. Bacteriol.*174(2):426-433 (1992).

Li, Guang-Shan, "Development of a reporter system for the study of gene expression for solvent production in Clostridium beijerinckii NRRL B592 and Clostridium acetobutylicum ATCC 824," Dissertation, Department of Biochemestry, Virginia Polytechnic Institute and State University (Sep. 1998).

Mermelstein et al., "Metabolic Engineering of *Clostridium acetobutylicum* ATCC 824 for Increased Solvent Production by Enhancement of Acetone Formation Enzyme Activities Using a Synthetic Acetone Operon," *Biotechnol. Bioeng.* 42(9):1053-1060 (1993).

Matta et al., "Interactions of the antizyme AtoC with regulatory elements of the *Escherichia coli* atoDAEB operon," *J. Bacteriol.* 189(17):6324-6332 (2007).

Steen et al., "Metabolic engineering of *Saccharomyces cerevisiae* for the production of n-butanol," *Microb. Cell Fact*. 7:36 (provided electronically by publisher as pp. 1-8) (2008).

Zou et al., "Metabolic engineering for microbial production and applications of copolyesters consisting of 3-hydroxybutyrate and medium-chain-length 3-hydroxyalkanoates," *Macromol. Biosci.* 7:174-182 (2007).

Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).

Abe et al., "Discovery of amide (peptide) bond synthetic activity in Acyl-CoA synthetase," *J. Biol. Chem.* 283(17):11312-11321 (2008).

Aberhart and Hsu, "Stereospecific hydrogen loss in the conversion of [$^2$H$_7$]isobutyrate to β-hydroxyisobutyrate in *Pseudomonas putida*. The stereochemistry of β-hydroxyisobutyrate dehydrogenase," *J. Chem. Soc. [Perkin1]*1404;1406 (1979).

Abiko et al., "Localization of NAD-isocitrate dehydrogenase and glutamate dehydrogenase in rice roots: candidates for providing carbon skeletons to NADH-glutamate synthase," *Plant Cell Physiol* 46:1724-1734 (2005).

Abo-Dalo et al., "A novel member of the GCN5-related N-acetyltransferase superfamily from *Caenorhabditis elegans* preferentially catalyses the N-acetylation of thialysine [S-(2-aminoethyl)-L-cysteine]," *Biochem. J.* 384:129-137 (2004).

Adams and Kletzin, "Oxidoreductase-type enzymes and redox proteins involved in fermentative metabolisms of hyperthermophilic Archaea," *Adv. Protein Chem.* 48:101-180 (1996).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri and Liu, "Enoyl-CoA Hydratase: Reaction, Mechanism, and Inhibition," *Bioorg. Med. Chem.* 11(1):9-20 (2003).

Ahmed and Lewis, "Fermentation of Biomass-Generated Synthesis Gas: Effects of Nitric Oxide," *Biotechol. Bioeng.* 97:1080-1086 (2007).

Ahmed et al., "Effects of biomass-generated producer gas constituents on cell growth, product distribution and hydrogenase activity of *Clostridium carboxidivorans* P7$^T$," *Biomass Bioenergy* 30(7):665-672 (2006).

Akashi et al., "Molecular and biochemical Characterization of 2-Hydroxyisoflavanone Dehydratase. Involvement of Carboxylesterase-Like Proteins in Leguminous Isoflavone Biosynthesis," *Plant. Physiol.* 137:882-891 (2005).

Akatsuka et al., "The *Serratia marcescens bioH* gene encodes an esterase," *Gene* 302(1-2):185-192 (2003).

Akhtar and Jones, "Construction of a synthetic YdbK-dependent pyruvate: H$_2$ pathway in *Escherichia coli* BL21(DE3)," *Metab. Eng.* 11(3):139-147 (2009).

Alam et al., "Anaerobic Fermentation Balance of *Escherichia coli* as Observed by In Vivo Nuclear Magnetic Resonance Spectroscopy," *J. Bacteriol.* 171(11):6213-6217 (1989).

Alber et al., "3-Hydroxypropionyl-Coenzyme A synthetase from *Metallosphaera sedula*, an enzyme involved in autotrophic CO$_2$ fixation," *J. Bacteriol.* 190:1383-1389 (2008).

Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).

Alber et al., "Propionyl-Coenzyme A synthase from *Chloroflexus aurantiacus*, a key enzyme of the 3-hydroxypropionate cycle for autotrophic CO$_2$ fixation," *J. Biol. Chem.* 277:12137-12143 (2002).

Alber et al., "Study of an alternate glyoxylate cycle for acetate assimilation by *Rhodobacter sphaeroides*," *Mol. Microbiol.* 61(2):297-309 (2006).

Alberty, Biochemical thermodynamics. Biochim. Biophys. Acta 1207:1-11 (1994).

Aldor and Keasling, "Metabolic engineering of poly(3-hydroxybutyrate-co-3-hydroxyvalerate) composition in recombinant *Salmonella enterica* serovar typhimurium," *Biotechnol. Bioeng.* 76(2):108-114 (2001).

Aldor et al., "Metabolic Engineering of a Novel Propionate-Independent Pathway for the Production of Poly(3-Hydroxybutyrate-co-3-Hydroxyvalerate) in Recombinant *Salmonella enterica* Serovar Typhimurium," *Appl. Environ. Microbiol.* 68(8):3848-3854 (2002).

Aldrich Catalog, Sigma-Aldrich Company, Milwaukee, WI, p. 481 (2002).

Aldrich et al., "Cloning and complete nucleotide sequence determination of the catB gene encoding cis,cis-muconate lactonizing enzyme," *Gene* 52:185-195 (1987).

Alexeeva et al., "Requirement of ArcA for redox regulation in *Escherichia coli* under microaerobic but not anaerobic or aerobic conditions," J. Bacteriol 185(1):204-209 (2003).

Alexson et al., "NADH-sensitive propionyl-CoA hydrolase in brown-adipose-tissue mitochondria of the rat," *Biochim. Biophys. Acta* 1005(1):13-19 (1989).

Alhapel et al., "Molecular and functional analysis of nicotinate catabolism in *Eubacterium barkeri*," *Proc. Natl. Acad. Sci. USA* 103(33):12341-12346 (2006).

Alper et al., "Construction of lycopene-overproducing *E. coli* strains by combining systematic and combinatorial gene knockout targets," *Nat. Biotechnol.* 23(5):612-616 (2005).

Alper et al., "Identifying gene targets for the metabolic engineering of lycopene biosynthesis in *Escherichia coli*," *Metab. Eng.* 7(3):155-164 (2005).

Alper et al., "Engineering yeast transcription machinery for improved ethanol tolerance and production," *Science* 314(5805):1565-1568 (2006).

Altamirano et al., "Decoupling cell growth and product formation in Chinese hamster ovary cells throguh metabolic control," *Biotechnol. Bioeng.* 76(4):351-360 (2001).

Altmiller and Wanger, "Purification and properties of dihydroxy acid dehydratase from soluble and mitochondrial fractions of *Neurospora crassa*," *Arch. Biochem. Biophys.* 138:160-170 (1970).

Amann et al., "Tightly regulated tac promoter vectors useful for the expression of unfused and fused proteins in *Escherichia coli*," *Gene* 69:301-315 (1988).

Andersen and Hansen, "Cloning of the lysA gene from *Mycobacterium tuberculosis*," *Gene* 124(1):105-109 (1993).

Andersen et al., "A gene duplication led to specialized γ-aminobutyrate and β-alanine aminotransferase in yeast," *FEBS J.* 274:1804-1817 (2007).

Anderson and Dawes, "Occurrence, metabolism, metabolic role, and industrial uses of bacterial polyhydroxyalkanoates," *Microbiol. Rev.* 54(4):450-472 (1990).

Anderson et al., "Evaluation of 5-enolpyruvoylshikimate-3-phosphate synthase substrate and inhibitor binding by stopped-flow and equilibrium fluorescence measurements," *Biochemistry* 27:1604-1610 (1988).

Andersson et al., "Effect of different carbon sources on the production of succinic acid using metabolically engineered *Escherichia coli*," *Biotechnol. Prog.* 23(2):381-388 (2007).

Andreesen and Ljungdahl, "Formate Dehydrogenase of *Clostridium thermoaceticum*: Incorporation of Selenium-75, and the Effects of Selenite, Molybate, and Tungstate on the Enzyme," *J. Bacteriol.* 116(2):867-873 (1973).

Aneja and Charles, "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).

Angrand et al., "Simplified generation of targeting constructs using ET recombination," *Nucleic Acids Res.* 27(17):e16 (1999).

Ansorge and Kula, "Production of Recombinant L-Leucine Dehydrogenase from *Bacillus cereus* in Pilot Scale Using the Runaway Replication System *E. coli*[pIET98]," *Biotechnol. Bioeng.* 68:557-562 (2000).

Aoshima and Igarashi, "A novel biotin protein required for reductive carboxylation of 2-oxoglutarate by isocitrate dehydrogenase in *Hydrogenobacter thermophilus* TK-6," *Mol. Microbiol.* 51(3):791-798 (2004).

Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel enzyme, citryl-CoA lyase, catalysing the second step of the citrate cleavage reaction in *Hydrogenobacter thermophilus* TK-6," *Mol. Microbiol.* 52(3):763-770 (2004).

Aoshima et al., "A novel enzyme, citryl-CoA synthetase, catalysing the first step of the citrate cleavage reaction in *Hydrogenobacter thermophilus* TK-6," *Mol. Microbiol.* 52(3):751-761 (2004).

Aoshima et al., "A novel oxalosuccinate-forming enzyme involved in the reductive carboxylation of 2-oxoglutarate in *Hydrogenobacter thermophilus* Tk-6," Mol. Microbiol. 62(3):748-759 (2006).

Aoshima, "Novel enzyme reactions related to the tricarboxylic acid cycle: phylogenetic/functional implications and biotechnological applications," *Appl. Microbiol. Biotechnol.* 75(2):249-255 (2007).

Aragon and Lowenstein, "A survey of Enzymes Which Generate or Use Acetoacetyl Thioesters in Rat Liver," *J. Biol. Chem.* 258(8):4725-4733 (1983).

Arendsen et al., "Nitrate-Dependent Regulation of Acetate Biosynthesis and Nitrate Respiration by *Clostridium thermoaceticum*," *J. Bacteriol.* 181:1489-1495 (1999).

Argyrou and Blanchard, "Kinetic and chemical mechanism of *Mycobacterium tuberculosis* 1-deoxy-D-xylulose-5-phosphate isomeroreductase," *Biochemistry* 43:4375-4384 (2004).

Arikawa et al., "Soluble fumarate reductase isoenzymes from *Saccharomyces cerevisiae* are required for anaerobic growth," *FEBS Microbiol. Lett.* 165:111-116 (1998).

Aristidou et al., "Metabolic Engineering of *Escherichia coli* to Enhance Recombinant Protein Production through Acetate Reduction," *Biotechnol. Prog.* 11(4):475-458 (1995).

Aristidou et al., "Metabolic flux analysis of *Escherichia coli* expressing the *Bacillus subtilis* Acetolactate Synthase in Batch and Continuous Cultures," *Biotechnol Bioeng.* 63(6):737-749 (1999).

Armstrong et al., "Steroselectivity and sterospecificity of the α,β-dihydroxyacid dehydratase from *Salmonella typhimurium*," *Biochim. Biophys Acta* 498:282-293 (1977).

Arps et al., "Genetics of serine pathway enzymes in Methylobacterium extorquens AM1: phosphoenolpyruvate carboxylase and malyl Coenzyme A lyase," *J. Bacteriol.* 175:3776-3783 (1993).

Asano and Kato, "Crystalline 3-methylaspartase from a facultative anaerobe, *Escherichia coli* strain YG1002," FEMS *Microbiol. Lett.* 118(3):255-258 (1994).

Asano et al., "Alteration of substrate specificity of aspartase by directed evolution," *Biomol. Eng.* 22(1-3):95-101 (2005).

Asanuma et al., "Characterization and transcription of the genes encoding enzymes involved in butyrate production in *Butyrivibrio fibrisolvens*," *Curr. Microbiol.* 47:203-207 (2003).

Asuncion et al., "Overexpression, purification, crystallization and data collection of 3-methylaspartase from *Clostridium tetanomorphum*," *Acta. Crystallogr. D. Biol. Crystallogr.* 57(Pt 5):731-733 (2001).

Asuncion, et al., "The structure of 3-methylaspartase from *Clostridium tetanomorphum* functions via the common enolase chemical step," *J. Biol. Chem.* 277(10):8306-8311 (2002).

Atsumi et al., "Metabolic engineering of *Escherichia coli* for 1-butanol production," *Metab. Eng.* 10(6):305-311 (2007).

Atsumi et al., "Non-fermentative pathways for synthesis of branched-chain higher alcohols as biofuels," *Nature* 451(7174):86-89 (2008).

Atteia et al., "Pyruvate formate-lyase and a novel route of eukaryotic ATP synthesis in *Chlamydomonas* mitochondria," *J. Biol. Chem.* 281:9909-9918 (2006).

Auerbach et al., "Lactate dehydrogenase from the hyperthermophilic bacterium *Thermotoga maritima*: the crystal structure at 2.1 Å resolution reveals strategies for intrinsic protein stabilization," *Structure* 6:769-781 (1998).

Baba et al., "Construction of *Escherichia coli* K-12 in-frame, single-gene knockout mutants: the Keio collection," *Mol. Syst. Biol.* 2:2006.0008 (2006).

Bachmann and Townsend, "β-Lactam synthetase: a new biosynthetic enzyme," *Proc. Natl. Acad. Sci. USA* 95(16):9082-9086 (1998).

Bai et al., "Lewis-acid assisted cross metathesis of acrylonitrile with functionalized olefins catalyzed by phosphine-free ruthenium carbene complex," *Org. Biomol. Chem.* 3:4139-4142 (2005).

Bailey et al., "Identification, cloning, purification, and enzymatic characterization of *Mycobacterium tuberculosis* 1-deoxy-$_D$-xylulose 5-phosphate synthase," *Glycobiology* 12:813-820 (2002).

Baird et al., "Enzymes involved in acetoacetate formation in various bovine tissues," *Biochem. J.* 117(4):703-709 (1970).

Baker and van der Drift, "Purification and properties of $_L$erythro-3,5-diaminohexanoate dehydrogenase from *Clostridium sticklandii*," *Biochemistry* 13(2):292-299 (1974).

Baker et al., "Purification and properties of $_L$erythro-3,5-diaminohexanoate dehydrogenase from a lysine-fermenting *Clostridium*," *J. Biol. Chem.* 247:7724-7734 (1972).

Bakker et al., "Stoichiometry and compartmentation of NADH metabolism in *Saccharomyces cerevisiae*," *FEMS Microbiol. Rev.* 25: 15-37 (2001).

Banerji et al., "The cloning and characterization of the arom gene of *Pneumocystis carinii*," *J. Gen. Microbiol.* 139:2901-2914 (1993).

Barber et al., "Structure and regulation of acetyl-CoA carboxylase genes of metazoa," *Biochimica. Biophysica. Acta* 1733:1-28 (2005).

Barker and Frost, "Microbial synthesis of p-hydroxybenzoic acid from glucose," *Biotechnol. Bioeng.* 76:376-390 (2001).

Barker et al., "Butyryl-CoA:Acetoacetate CoA-transferase from Lysine-fermenting *Clostridium*," *J. Biol. Chem.* 253(4):1219-1225 (1978).

Barker et al., "Pathway of Lysine Degradation in *Fusobacterium nucleatum*," *J. Bacteriol.* 152(1):201-207 (1982).

Barrick, et al., "Quantitative analysis of ribosome binding sites in *E.coli*," *Nucleic Acids Res*, 22(7):1287-1295 (1994).

Barrowman et al., "Immunological comparison of microbial TPP-dependent non-oxidative α-keto acid decarboxylase," FEMS Microbiol. Lett. 34:57-60 (1986).

Barthelmebs et al., "Exression of *Escherichia coli* of Native and chimeric Phenolic Acid Decarboxylases with Modified Enzymatic Activities and Method for Screening Recombinant *E. coli* Strains Expressing These Enzymes," *Appl. Environ. Microbiol.* 67:1063-1069 (2001).

Barthelmebs et al., "Inducible metabolism of phenolic acids in *Pediococcus pentosaecus* is encoded by an autoregulated operon which involves a new class of negative transcriptional regulator," *J. Bacteriol.* 182:6724-6731 (2000).

Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J Bacteriol*, 172(12):7035-7042 (1990).

Basset et al., "Folate synthesis in plants: the p-aminobenzoate branch is initiated by a bifunctional PabA-PabB protein that is targeted to plastids," *Proc. Natl. Acad. Sci U. S. A* 101:1496-1501 (2004).

Battaile et al., "Structures of isobutyryl-CoA dehydrogenase and enzyme-product complex: comparison with isovaleryl- and short-chain acyl-CoA dehydrogenases," *J. Biol. Chem.* 279:16526-16534 (2004).

Baudin et al., "A simple and efficient method for direct gene deletion in *Saccharomyces cerevisiae*," *Nucleic Acids Res*. 21(14):3329-3330 (1993).

Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302. (1990).

Beatrix et al., "The biotin-dependent sodium ion pump glutaconyl-CoA decarboxylase from *Fusobactevium nucleatum* (subsp. nucleatum). Comparison with the glutaconyl-CoA decarboxylases from gram-positive bacteria," *Arch. Microbiol.* 154(4):362-369 (1990).

Beckers et al., "Large-scale mutational analysis for the annotation of the mouse genome," *Curr. Opin. Chem. Biol.* 6:17-23 (2001).

Benner et al., "Stereospecificity and sterochemical infidelity of acetoacetate decarboxylase (AAD)," *J. Am. Chem. So*. 103:993-994 (1981).

Benning et al., "New reactions in the crotonase superfamily: structure of methylmalonyl CoA decarboxylase from *Escherichia coli*," *Biochemistry* 39:4630-4639 (2000).

Berg et al., "A 3-Hydroxypropionate/4-Hydroxybutyrate Autotrophic Carbon Dioxide Assimilation Pathway in Archaea," *Science* 318(5857) 1782-1786 (2007).

Bergquist and Gibbs, "Degenerate oligonucleotide gene shuffling," *Meth. Mol. Biol.* 352:191-204 (2007).

Bergquist et al., "Degenerate oligonucleotide gene shuffling (DOGS) and random drift mutagenesis (RNDM): two complementary techniques for enzyme evolution," *Biomol. Eng.* 22:63-72 (2005).

Berkovitch et al., "A locking mechanism preventing radical damage in the absence of substrate, as revealed by the x-ray structure of lysine 5,6-aminomutase," *Proc. Natl. Acad. Sci. USA* 101:15870-15875 (2004).

Berman and Magasanik, "The pathway of myo-inositol degradation in Aerobacter aerogenes," *J. Biol. Chem.* 241(4):800-806 (1966).

Berrios-Rivera, et al., "Metabolic Engineering of *Escherichia coli*: Increase of NADH Availability by Overexpressing an NAD(+)-Dependent Formate Dehydrogenase" *Metab Eng*. 4(3):217-229 (2002).

Berthold et al., "Structure of the branched-chain keto acid decarboxylase (KdcA) from *Lactococcus lactis* provides insights into structural basis for the chemoselective enantioselective carboligation reaction," *Acta Cryst*. D63:1217-1224 (2007).

Biellmann et al., "Aspartate-β-semialdehyde dehydrogenase from *Escherichia coli*. Purification and general properties," *Eur. J. Biochem.* 104(1):53-58 (1980).

Binieda et al., "Purification, characterization, DNA sequence and cloning of a pimeloyl-CoA synthetase from *Pseudomonas mendocina* 35," *Biochem. J.* 340:793-801 (1999).

Binstock and Schulz, "Fatty acid oxidation complex from *Escherichia coli*," *Methods Enzymol*. 71(Pt C):403-411 (1981).

Birch et al., "Cloning, sequencing, and expression of the gene encoding methylmalonyl-Coenzyme a mutase from *Streptomyces cinnamonensis*," *J. Bacteriol.* 175(11):3511-3519 (1993).

Bisswanger, "Substrate specificity of the Pyruvate Dehydrogenase Complex from *Escherichia coli*," *J. Biol. Chem.* 256(2):815-822 (1981).

Blanco et al., "Critical catalytic functional groups in the mechanism of aspartate-β-semialdehyde dehydrogenase," *Acta Cryst*. D60:1808-1815 (2004).

Blanco et al., "The role of substrate-binding groups in the mechanism of aspartate-β-semialdehyde dehydrogenase," *Acta Crysta*. D60:1388-1395 (2004).

Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem*. 123(3):563-569 (1982).

Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).

Blombach et al., "*Corynebacterium glutamicum* tailored for high-yeild L-valine production," *Appl. Microbiol. Biotechnol.* 79(3):471-479 (2008).

Blomqvist et al., "Characterization of the genes of the 2,3-butanediol operons from Klebsiella terrigena and Enterobacter aerogenes," *J. Bacteriol*. 175:1392-1404 (1993).

Bobik and Rasche, "HPLC assay for methylmalonyl-CoA epimerase," *Anal. Bioanal. Chem*. 375(3):344-349 (2003).

Bobik and Rasche, "Identification of the human methylmalonyl-CoA racemase gene based on the analysis of prokaryotic gene arrangements. Implications for decoding the human genome," *J. Biol. Chem*. 276(40):37194-37198 (2001).

Bobik et al., "Propanediol Utilization Genes (pdu) of *Salmonella typhimurium*: Three Genes for the Propanediol Dehydratase," *J. Bacteriol*. 179(21):6633-6639 (1997).

Bock et al., "Purification and characterization of two extremely thermostable enzymes, phosphate acetyltransferase and acetate kinase, from the hyperthermophilic eubacterium *Thermotoga maritima*," *J. Bacteriol*. 181:1861-1867 (1999).

Boiangiu et al., "Sodium Ion Pumps and Hydrogen Production in Glutamate Fermenting Anaerobic Bacteria," J. Mol. Microbiol. Biotechnol. 10:105-119 (2005).

Boles et al., "Characterization of a glucose-repressed pyruvate kinase (Pyk2p) in *Saccharomyces cerevisiae* that is catalytically insensitive to fructose-1,6-bisphosphate," *J. Bacteriol.* 179:2987-2993 (1997).

Bonnarme et al., "Itaconate biosynthesis in Aspergillus terreus," *J. Bacteriol*. 177(12):3573-3578 (1995).

Bonner and Bloch, "Purification and properties of fatty acyl thioesterase I from *Escherichia coli*," *J. Biol. Chem*. 247(10):3123-3133 (1972).

Boronin, et al., "Plasmids specifying ϵ-caprolactam degradation in *Pseudomonas* strains," *FEMS Microbiol Lett*, 22(3):167-170 (1984).

Bose et al., "Genetic analysis of the methanol- and methylamine-specific methyltransferase 2 genes of *Methanosarcina acetivorans* C2A," *J. Bacteriol.* 190(11):4017-4026 (2008).

Bott et al., "Methylmalonyl-CoA decarboxylase from Propionigenium modestum. Cloning and sequencing of the structural genes and purification of the enzyme complex," *Eur. J. Biochem*. 250:590-599 (1997).

Botting et al., "Substrate Specificity of the 3-Methylaspartate Ammonia-Lyase Reactin: Observation of Differential relative Reaction Rates for Substrate-Product Pairs," *Biochemistry* 27:2953-2955 (1988).

Bottomley et al., "Cloning, sequencing, expression, purification and preliminary characterization of type II dehydroquinase from *Helicobacter pylori*," *Biochem. J*. 319:559-565 (1996).

Bower et al., "Cloning, sequencing, and characterization of the *Bacillus subtilis* biotin biosynthetic operon," *J. Bacteriol.* 178(14):4122-4130 (1996).

Boylan and Dekker, "L-Threonine Dehydrogenase of *Escherichia coli* K-12," *Biochem. Biophys. Res. Commun*. 85(1):190-197 (1978).

Boynton et al., "Cloning, sequencing, and expression of clustered genes encoding β-hydroxybutyryl-Coenzyme A (CoA) dehydrogenase, crotonase, and butyryl-CoA dehydrogenase from *Clostridium acetobutylicum* ATCC 824," *J. Bacteriol*. 178(11):3015-3024 (1996).

Brachmann et al., "Designer deletion strains derived from *Saccharomyces cerevisiae* S288C: a useful set of strains and plasmids for PCR-mediated gene disruption and other applications," *Yeast* 14(2):115-132 (1998).

Bradford, "A rapid and sensitive method for the quantitation of microgram quantities of protein utilizing the principle of protein-dye binding," *Anal. Biochem*. 72:248-254 (1976).

Branlant, "Nucleotide sequence of *Escherichia coli* gap gene. Different evolutionary behavior of the NAD⁺-binding domain and of the catalytic domain of D-glyceraldehyde-3-phosphate dehydrogenase," *Eur. J. Biochem.* 150:61-66 (1985).

Bräsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," *Arch. Microbiol.* 182(4):277-287 (2004).

Braune et al., "The sodium ion translocating glutaconyl-CoA decarboxylase from Acidaminococcus fermentans: cloning and function on the genes forming a second operon," *Mol. Microbiol.* 31(2):473-487 (1999).

Bravo et al., "Reliable, sensitive, rapid and quantitative enzyme-based assay for gamma-hydroxybutyric acid (GHB)," *J. Forensic Sci.* 49:379-387 (2004).

Bredwell et al., "Reactor Design Issues for Synthesis-Gas Fermentations," *Biotechnol. Prog.* 15(5):834-844 (1999).

Breese et al., "Genes coding for the benzoyl-CoA pathway of anaerobic aromatic metabolism in the bacterium Thauera aromatica," *Eur. J. Biochem.* 256(1):148-154 (1998).

Breitkruez et al., "A novel γ-hydroxybutyrate dehydrogenase: Identification and expression of an Arabidopsis cDNA and potential role under oxygen deficiency," *J. Biol. Chem.* 278:41552-41556 (2003).

Bremer, "Pyruvate Dehydrogenase, Substrate Specificity and Product Inhibition," *Eur. J. Biochem.* 8:535-540 (1969).

Brey et al., "Cloning of multiple genes involved with cobalamin (Vitamin $B_{12}$) biosynthesis in *Bacillus megaterium*," *J. Bacteriol.* 167:623-630 (1986).

Bro et al., "In silico aided metabloic engineering of *Saccharomyces cerevisiae* for improved bioethanol production," *Metab. Eng.* 8(2):102-111 (2006).

Brooke et al., "GAMS: A User's Guide. GAMS Development Corporation" (1998).

Broun et al., "Catalytic plasticity of fatty acid modification enzymes underlying chemical diversity of plant lipids," *Science* 282:1315-1317 (1998).

Brown et al., "A role for *pabAB*, a p-aminobenzoate synthase gene of *Streptomyces venezuelae* ISP5230, in chloramphenicol biosynthesis," *Microbiol.* 142 (Pt 6):1345-1355 (1996).

Brown et al., "Comparative structural analysis and kinetic properties of lactate dehydrogenases from the four species of human malarial parasites," *Biochemistry* 43:6219-6229 (2004).

Browner et al., "Sequence analysis, biogenesis, and mitochondrial import of the α-subunit of rat liver propionyl-CoA carboxylase," *J. Biol. Chem.* 264:12680-12685 (1989).

Bu and Tobin, "The exon-intron organization of the genes (GAD1 and GAD2) encoding two human glutamate decarboxylases (GAD67 and GAD65) suggests that they derive from a common ancestral GAD," *Genomics* 21:222-228 (1994).

Bu et al., "Two human glutamate decarboxylases, 65-kDa GAD and 67-kDa GAD, are each encoded by a single gene," *Proc Natl.Acad Sci US.A.* 89:2115-2119 (1992).

Buchanan et al., "An extremely thermostable aldolase from *Sulfolobus* solfataricus with specificity for non-phosphorylated substrates," *Biochem. J.* 343:563-570 (1999).

Buck et al., "Primary structure of the succinyl-CoA synthetase of *Escherichia coli*," *Biochem.* 24(22):6245-6252 (1985).

Buckel and Barker, "Two pathways of glutamate fermentation by anaerobic bacteria," *J. Bacteriol.* 117(3):1248-1260 (1974).

Buckel and Golding, "Radical enzymes in anaerobes," *Annu. Rev. Microbiol.* 60:27-49 (2006).

Buckel and Golding, "Radical species in the catalytic pathways of enzymes from anaerobes," *FEMS Microbiol. Rev.* 22(5):523-541 (1999).

Buckel et al., "ATP-Driven electron transfer in enzymatic radical reactions," *Curr. Opin. Chem. Biol.* 8:462-467 (2004).

Buckel et al., "Glutaconate CoA-Transferase from Acidaminococcus fermentans," *Eur. J. Biochem.* 118:315-321 (1981).

Buckel et al., "Radical-mediated dehydration reactions in anaerobic bacteria," *Biol. Chem.* 386:951-959 (2005).

Buckel, "Sodium ion-translocating decarboxylases," Biochimica. Biophysica. Acta 1505:15-27 (2001).

Bueding and Yale, "Production of α-methylbutyric acid by bacteria-free Ascaris lumbricoides," *J. Biol. Chem.* 193:411-423 (1951).

Bunch, et al., "The *IdhA* gene encoding the fermentative lactate dehydrogenase of *Escherichia coli*," *Microbial.* 143:187-195 (1997).

Burgard and Maranas, "Probing the performance limits of the *Escherichia coli* metabolic network subject to gene additions or deletions," *Biotechnol. Bioeng.* 74:364-375 (2001).

Burgard et al., Minimal Reaction Sets for *Escherichia coli* Metabolism under Different Growth Requirements and Uptake Environments. *Biotechnol. Prog.* 17:791-797 (2001).

Burgard et al., "Optknock: a bilevel programming framework for identifying gene knockout strategies for microbial strain optimization," *Biotechnol. Bioeng.* 84(6):647-657 (2003).

Burke et al, "The Isolation, Characterization, and Sequence of the Pyruvate Kinase Gene of *Saccharomyces cerevisiae*," *J. Biol. Chem.* 258(4):2193-2201 (1983).

Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).

Buu et al., "Functional characterization and localization of acetyl-CoA hydrolase, Ach1p, in *Saccharomyces cerevisiae*," *J. Biol. Chem.* 278:17203-17209 (2003).

Buzenet et al., "Purification and properties of 4-Aminobutyrate 2-Ketoglutarate Aminotransferase From Pig Liver," *Biochimica Biophysica Acta* 522:400-411 (1978).

Byrnes et al., "Thermodynamics of reactions catalyzed by anthranilate synthase," *Biophys. Chem.* 84:45-64 (2000).

Cahyanto et al., "Regulation of aspartokinase, asparate semialdehyde dehydrogenase, dihydrodipicolinate synthease and dihydropdipicolinate reductase in *LactoBacillus plantarum*," *Microbiology.* 152 (Pt 1): 105-112.

Caldovic and Tuchman, "N-Acetylglutamate and its changing role through evolution," *Biochem. J.* 372:279-290 (2003).

Calhoun et al., "Threonine deaminase from *Eschericiha coli*. I. Purification and properties," J. Biol. Chem. 248(10):3511-3516 (1973).

Camara et al., "Characterization of a Gene Cluster Involved in 4-Chlorocatechol Degradation by *Pseudomonas reinekei* MT1," *J. Bacteriol.* 191(15):4905-4915 (2009).

Campbell and Cronan, Jr., "The enigmatic *Escherichia coli fadE* gene is *yafH*," *J. Bacteriol.* 184(13):3759-3764 (2002).

Campbell et al., "A complete shikimate pathway in Toxoplasma gondii: an ancient eukaryotic innovation," *Int. J. Parasitol.* 34:5-13 (2004).

Campbell et al., "A new *Escherichia coli* metabolic competency: growth on fatty acids by a novel anaerobic βoxidation pathway," *Mol. Microbiol.* 47(3):793-805 (2003).

Canovas et al., "Characterization of the genes for the biosynthesis of the compatible solute ectoine in the moderately haliphilic bacterium Halomonas elongata DSM 3043," *Syst. Appl. Microbiol.* 21:487-497 (1998).

Cao et al., "Simultaneous Production and recovery of Fumaric Acid from Immobilized *Rhizopus oryzae* with a Rotary biofilm Contactor and an Adsorption Column," *Appl. Environ. Microbiol.* 62(8):2926-2931 (1996).

Carlini et al., "Guerbet condensation of methanol with n-propanol to isobutyl alcohol over heterogeneous copper chromite/Mg-Al mixed oxides catalysts," *J. Molecular Catalysis A: Chemical* 220:215-220 (2004).

Carlini et al., "Selective synthesis of isobutanol by means of the Guebet reaction Part 1. Methanol/n-propanol condensation by using copper based catalytic systems," *J. Mol. Catal. A: Chem.* 184:273-280 (2002).

Carlini et al., "Selective synthesis of isobutanol by means of the Guerbet reaction Part 2. Reaction of methanol/ethanol and methanol/ethanol/n-propanol mixtures over copper based Me0Na catalytic systems," *J. Mol. Catal. A: Chemical* 200:137-146 (2003).

Carlini et al., "Selective synthesis of isobutanol by means of the Guerbet reaction Part 3: Methanol/n-propanol condensation by using bifunctional catalytic systems based on nickel, rhodium and ruthenium species with basic components," *J. Mol. Catal. A: Chem.* 206:409-418 (2003).

Carpenter et al., "Structure of dehydroquinate synthase reveals an active site capable of multistep catalysis," *Nature* 394:299-302 (1998).

Carretero-Paulet et al., "Expression and molecular analysis of the Arabidopsis DXR gene encoding 1-deoxy-D-xylulose 5-phosphate reductoisomerase, the firszt committed enzyme of the 2-C-methyl-D-erythritiol 4-phosphate pathway," *Plant Physiol.* 129:1581-1591 (2002).

Carta et al., "Production of fumaric acid by fermentation of enzymatic hydrolysates derived from Cassava bagasse," *Biores. Tech.* 68:23-28 (1999).

Cary et al., "Cloning and Expression of *Clostridium acetobutylicum* ATCC 824 Acetoacetyl-Coenzyme A:Acetate/Butyrate:Coenzyme A-Transferase in *Escherichia coli*," *App. Environ. Microbiol.* 56(6):1576-1583 (1990).

Cary et al., "Cloning and expression of *Clostridium acetobutylicum* phosphotransbutyrylase and butyrate kinase genes in *Escherichia coli*," *J. Bacteriol.* 170(10):4613-4618 (1988).

Casero and Pegg, "Spermidine/spermine N$^1$-acetyltransferase-the turning point in polyamine metabolism," *FASEB J.* 7:653-661 (1993).

Caspi et al., "MetaCyc: a multiorganism database of metabolic pathways and enzymes," *Nucleic Acids Res.* 34(Database issue):D511-D516 (2006).

Cavin et al., "Gene cloning, transcriptional analysis, purification, and characterization of phenolic acid decarboxylase from *Bacillus subtilis*," *Appl. Environ. Microbiol.* 64(4):1466-1471 (1998).

Cha and Bruce, "Stereo- and regiospecific cis,cis-muconate cycloisomerization by *Rhodococcus* rhodochrous N75," *FEMS Microbiol. Lett.* 224:29-34 (2003).

Cha and Parks, Jr., "Succinic Thiokinase. I. Purification of the Enzyme from Pig Heart," *J. Biol. Chem.* 239:1961-1967 (1964).

Chandra et al. "Pyruvate decarboxylase: a key enzyme for the oxidative metabolism of lactic acid by Acetobacter pasteurianus," *Arch. Microbiol.* 176:443-451 (2001).

Chang et al., "p-Aminobenzoic acid and chloramphenicol biosynthesis in *Streptomyces venezuelae*: gene sets for a key enzyme, 4-amino-4-deoxychorismate synthase," *Microbiology* 147:2113-2126 (2001).

Chao and Ramsdell, "The effects of wall populations on coexistence of bacteria in the liquid phase of chemostat cultures," *J. Gen. Microbiol.* 131(5):1229-1236 (1985).

Charles et al., "The isolation and nucleotide sequence of the complex AROM locus of Aspergillus nidulans," *Nucleic Acids Res.* 14:2201-2213 (1986).

Charrier et al., "A novel class of CoA-transferase involved in short-chain fatty acid metabolism in butyrate-producing human colonic bacteria," *Microbiology* 152:179-185 (2006).

Chatterjee et al., "A general model for selectively in olefin cross methathesis," *J. Am Chem. Soc.* 125(37):11360-11370 (2003).

Chatterjee et al., "Mutation of the pts*G* Gene Results in Increased Production of Succinate in Fermentation of Glucose by *Escherichia coli*," *Appl. Env. Microbiol.* 67:148-154 (2001).

Chaudhuri et al., "Identification of the active-site lysine residues of two biosynthetic 3-dehydroquinases," *Biochem. J.* 275:1-6 (1991).

Chen et al., "A novel lysine 2,3-aminomutase encoded by the yodO gene of *Bacillus subtilis*: characterization and the observation of organic radical intermediates," *Biochem. J.* 348:539-549 (2000).

Chen et al., "Cloning, Sequencing, Heterologous Expression, Purification, and Characterization of Adenosylcobalamin-dependent D-Ornithine Aminomutase from *Clostridium sticklandii*," *J. Biol. Chem.* 276:44744-44750 (2001).

Chen et al., "The control region of the *pdu/cob* regulon in *Salmonella typhimurium*," *J. Bacteriol.* 176:5474-5482 (1994).

Cheng et al., "Genetic Analysis of a Gene Cluser for Cyclohexanol Oxidation in *Acinetobacter* sp. Strain SE19 by In Vitro Transportation," *J. Bacteriol.* 182(17):4744-4751 (2000).

Cheng et al., "Mammalian Wax Biosynthesis. I. Identification of two fatty acyl-Coenzyme A reductases with different substrate specificities and tissue distributions," *J. Biol. Chem.* 279(36):37789-37797 (2004).

Cheng et al., "Mammalian Wax Biosynthesis. II. Expression cloning of wax synthase cDNAS encoding a member of the acyltransferase enzyme family," *J. Biol. Chem.* 279(36):37798-37807 (2004).

Cheng et al., "Structural basis for shikimate-binding specificity of *Helicobacter pylori* shikimate kinase," *J. Bacteriol.* 187:8156-8163 (2005).

Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).

Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).

Cho et al., "Critical residues for the Coenzyme specificity of NAD$^+$-dependent 15-hydroxyprostaglandin dehydrogenase," *Arch. Biochem. Biophys.* 419:139-146 (2003).

Choi et al, "Olefin Metathesis Involving Ruthenium Enoic Carbene Complexes," *J. Am. Chem. Soc.* 123(42):10417-10418 (2001).

Choi et al., "Enhanced production of cis,cis-muconate in a cell-recycle bioreactor," *J. Ferment. Bioeng.* 84:70-76 (1997).

Choi-Rhee and Cronan, "The biotin carboxylase-biotin carboxyl carrier protein complex of *Escherichia coli* acetyl-CoA carboxylase," *J. Biol. Chem.* 278:30806-30812 (2003).

Chopra et al., "Expression, purification, and biochemical characterization of *Mycobacterium tuberculosis* aspartate decarboxylase, PanD," *Protein Expr. Purif.* 25:533-540 (2002).

Chou et al., "Effect of Modulated Glucose Uptake on High-Level Recombinant Protein Production in a Dense *Escherichia coli* Culture," *Biotechnol. Prog.* 10:644-647 (1994).

Chowdhury et al., "3-Hydroxyisobutyrate dehydrogenase from *Pseudomonas putida* E23: purification and characterization," *Biosci Biotechnol Biochem*, 60(12):2043-2047 (1996).

Chowdhury et al., "Cloning and overexpression of the 3-hydroxyisobutyrate dehydrogenase gene from *Pseudomonas putida* E23," *Biosci. Biotechnol. Biochem.* 67(2):438-441 (2003).

Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).

Chuakrut et al., "Characterization of a bifunctional archael acyl Coenzyme A carboxylase," *J. Bacteriol.* 185:938-947 (2003).

Clark and Ljungdahl, "Purification and properties of 5,10-methylenetetrahydrofolate reductase from *Clostridium formicoaceticum*," *Methods Enzymol.* 122:392-399 (1986).

Clark and Ljungdahl, "Purification and Properties of 5,10-Methylenetetrahydrofolate Reductase, an Iron-sulfur Flavoprotein from *Clostridium formicoaceticum*," *J. Biol. Chem.* 259(17)10845-10849 (1984).

Clark, et al., "Mutants of *Escherichia coli* defective in acid fermentation," *Appl. Biochem. Biotechnol.* 17:163-173 (1988).

Clarke et al., "Rational construction of a 2-Hydroxyacid Dehydrogenase With New Substrate Specificity," *Biochem. Biophys. Res. Commun.* 148:15-23 (1987).

Clausen et al., "PAD1 encodes phenylarcrylic acid decarboxylase which confers resistance to cinnamic acid in *Saccharomyces cerevisiae*," *Gene* 142:107-112 (1994).

Coco et al., "DNA shuffling method for generating highly recombined genes and evolved enzymes," *Nat. Biotechnol.* 19:354-359 (2001).

Coggins et al., "The arom multifunctional enzyme from *Neurospora crassa*," *Methods Enzymol.* 142:325-341 (1987).

Colby and Chen, "Purification and properties of 3-hydroxybutyryl-Coenzyme A dehydrogenase from *Clostridium beijerinckii* ("Clostridium butylicum") NRRL B593," *Appl. Environ. Microbiol.* 58:3297-3302 (1992).

Coleman, "Expression of a glutamate decarboxylase homologue is required for normal oxidative stress tolerance in *Saccharomyces cerevisiae*," *J. Biol. Chem.* 276:244-250. (2001).

Conrad et al., "D- and L -Isoleucine Metabolism and Regulation of Their Pathways in *Pseudomonas putida*," *J. Bacteriol.* 118(1):103-111 (1974).

Cooper, "Glutamate-γ-aminobutyrate transaminase," *Methods Enzymol*, 113:80-82 (1985).

Corthesy-Theulaz et al., "Cloning and Characterization of *Helicobacter pylori* Succinyl CoA:Acetoacetate CoA-transferase, a Novel Prokaryotic Member of the CoA-transferase Family," *J. Biol. Chem.* 272(41):25659-25667 (1997).

Couturier et al., "A Cyclometalated Aryloxy(chloro)neopentylidenetungsten Complex: A Highly Active and Stereoselective Catalyst for the Metathesis of cis- and trans-2-Pentene, Norbornene, 1-Methyl-norbornene, and Ethyl Oleate," *Angew. Chem Int. Ed. Engl.* 31(5):628-631 (1992).

Cox, et al., "Development of a metabolic network design and optimization framework incorporating implementation constraints: A succinate production case study," *Metab. Eng*, 8(1):46-57 (2006).

Craney et al., "A synthetic luxCDABE gene cluster optimized for expression in high-GC bacteria," *Nucleic Acids Res.* 35(6):e46 (2007).

Cunningham et al., "Transcriptional regulation of the aconitase genes (acnA and acnB) of *Escherichia coli,*" *Microbiology* 143(Pt 12):3795-3805 (1997).

Dai et al., "Highly Selective Diels-Alder Reactions of directly Connected Enzyne Dienphiles," *J. Am. Chem. Soc.* 129:645-657 (2007).

Dakoji et al., "Studies on the inactivation of bovine liver enoyl-CoA hydratase by (methylenecyclopropyl)formyl-CoA: elucidation of the inactivation mechanism and identification of cysteine-114 as the entrapped nucleophile," *J. Am. Chem. Soc.* 123(4):9749-9759 (2001).

Dal et al., "Transcriptional Organization of Genes for Protocatechuate and quinate Degradation from *Acinetobacter* sp. Strain ADP1," *Appl. Environ. Microbiol.* 71(2):1025-1034 (2005).

Dangel et al., "Anaerobic metabolism of cyclohexanol by denitrifying bacteria," *Arch. Microbiol.* 150(4):358-362 (1988).

Dangel et al., "Enzyme reactions involved in anaerobic cyclohexanol metabolism by a dentitrifying Psedomonas species," *Arch. Microbiol.* 152:273-279 (1989).

D'Ari and Rabinowitz, "Purification Characterization, cloning, and Amino Acid Sequence of the Bifunctional Enzyme 5,10-Methylenetetrahydrofolate Dehydrogenase/5,10-Methenyltetrahydrofolate Cyclohydrolase from *Escherichia coli,*" *J. Biol. Chem.* 266(35):23953-23958 (1991).

Das et al., "Characterization of a corrinoid protein involved in the C1 metabolism of strict anaerobic bacterium *Moorella thermoacetica,*" *Proteins* 67(1):167-176 (2007).

Datar et al., "Fermentation of biomass-generated producer gas to ethanol," *Biotechnol. Bioeng,* 86(5):587-594 (2004).

Datsenko et al., "One-step inactivation of chromosomal genes in *Escherichia coli* K-12 using PCR products," *Proc. Natl. Acad. Sci. USA* 97:6640-6645 (2000).

Datta et al., "Covalent structure of biodegradative threonine dehydratase of *Escherichi coli*: homology with other dehydratases," *Proc. Natl. Acad. Sci. USA* (84(2):393-397 (1987).

Davey and Trudgill, "The metabolism of trans-cyclohexan-1,2-diol by an Acinetobacter species," *Eur. J. Biochem.* 74(1):115-127 (1977).

Davids et al, "Characterization of the N-acetyltransferases respectively responsible for arylalkylamine and diamine acetylation in *Ascaris suum,*" *Mol. Biochem. Parasitol.* 64(2):341-344 (1994).

Davie et al., "Expression and assembly of a functional E1 component (α2β2) of mammalian branched-chain α-ketoacid dehydrogenase complex in *Escherichia coli,*" *J. Biol. Chem.* 267:16601-16606 (1992).

De Biase et al., "Isolation, overexpression, and biochemical characterization of the two isoforms of glutamic acid decarboxylase from *Escherichia coli,*" *Protein Expr Purif* 8:430-438 (1996).

de Bok et al., "Two W-containing formate dehydrogenases ($CO_2$-reductases) involving syntrophic propionate oxidation by Syntrophobacter fumaroxidans," *Eur. J. Biochem.* 270:2476-2485 (2003).

de Crecy et al., "Development of a novel continuous culture device for experimental evolution of bacterial populations," *Appl. Microbiol. Biotechnol.* 77(2): 489-496 (2007).

de la Torre et al., "Identification and functional analysis of a prokaryotic-type aspartate aminotransferase: implications for plant amino acid metabolism," *Plant. J.* 46(3):414-425 (2006).

de Mata and Rabinowitz, "Formyl-methenyl-methylenetetrahydrofolate synthetase (combined) from yeast. Biochemical characterization of the protein from an ADE3 mutant lacking the formyltetrahydrofolate synthetase function," *J. Biol Chem.* 255:2569-2577 (1980).

de Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).

de Smidt et al., "The alcohol dehydrogenases of *Saccharomyces cerevisiae*: a comprehensive review," *FEMS Yeast Rev.* 7:967-978 (2008).

Deana, "Substrate specificity of a dicarboxyl-CoA: dicarboxylic acid Coenzyme A transferase from rat liver mitochondria," *Biochem. Int.* 26(4):767-773 (1992).

DeFeyter and Pittard, "Purification and properties of shikimate kinase II from *Escherichia coli* K-12," *J. Bacteriol.* 165:331-333 (1986).

Del Campillo-Campbell et al., "Biotin-requiring Mutants of *Escherichia coli* K-12," *J. Bacteriol.* 94(6):2065-2066 (1967).

Deno, "The Diels-Alder Reaction with α, β, γ, δ-Unsaturated Acids," *J. Am. Chem. Soc.* 72:4057-4059 (1950).

Department of Energy, "Top value added chemicals from biomass. vol. I—Results of Screening for Potential Candidates from Sugars and Synthesis Gas," Biomass, Aug. 2004.

Desvaux, "Clostridium cellulolyticum: model organism of mesophilic cellulolytic *Clostridia,*" *FEMS Microbiol. Rev.* 29(4):741-764 (2005).

Devos et al., "Practical limits of function prediction" *Proteins* 41:98-107 (2000).

Di Gennaro, "Styrene lower catabolic pathway in *Pseudomonas fluorescens* ST: identification and characterization of genes for phenylacetic acid degradation," *Arch. Microbiol.* 188(2):117-125 (2007).

Diao et al., "Crystal structure of butyrate kinase 2 from Thermotoga maritima, a member of the ASKHA superfamily of phosphotransferases," *J. Bacteriol.* 191:2521-2529 (2009).

Diao et al., "Crystallization of the butyrate kinase 2 from Thermotogo maritima mediated by vapor diffusion of acetic acid," *Acta Cryst.* D59:1100-1102 (2003).

Dias et al., "Well-Defined Ruthenium Olefin Metathesis Catalyst: Mechanism and Activity," J. Am. Chem. Soc. 119(17):3887-3897 (1997).

Diaz et al., "Gene cloning, heterologous overexpression and optimized refolding of the NAD-glutamate dehydrogenase from *Haloferax mediterranei,*" *Extremophiles* 10:105-115 (2006).

Diderichsen et al., "Cloning of aldB, Which Encodes α-Acetolactate Decarboxylase, an Exoenzyme from *Bacillus brevis,*" *J. Bacteriol.* 172(8):4315-4321 (1990) 172(8):4315-4321 (1990).

Dittrich, et al., "Redistribution of Metabolic Fluxes in the Central Aerobic Metabolic Pathway of *E. coli* Mutant Strains with Deletion of the *ackA-pta* and *poxB* Pathways for the Synthesis of Isoamyl Acetate," *Biotechnol Prog.* 21(21):627-631 (2005).

Do et al., "Engineering *Escherichia coli* for fermentative dihydrogen production: potential role of NADH-ferredoxin oxidoreductase from the hydrogenosome of anaerobic protozoa," *Appl. Biochem. Biotechnol.* 153(1-3):21-33 (2009).

Do et al., "Growth of *Rhodospirillum rubrum* on synthesis gas: conversion of CO to $H_2$ and Poly-β-hydroxyalkanoate," *Biotechnol. Bioeng.* 97(2):279-286 (2007).

Dobbek et al., "Crystal structure of a carbon monoxide dehydrogenase reveals a [Ni-4Fe-5S] cluster," *Science* 293(5533):1281-1285 (2001).

Dombek and Ingram, "Ethanol production during batch fermentation with *Saccharomyces cerevisiae*: Changes in glycolytic enzymes and internal pH," *Appl Environ Microbiol* 53:1286-1291 (1987).

Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).

Donnelly and Cooper, "Two succinic semialdehyde dehydrogenases are induced when *Escherichia coli* K-12 Is grown on γ-aminobutyrate," *J. Bacteriol.* 145:1425-1427 (1981).

Donnelly et al., "A novel fermentation pathway in an *Escherichia coli* mutant producing succinic acid, acetic acid, and ethanol," *App. Biochem. Biotech.* 70-72:187-198 (1998).

Doten et al., "Cloning and Genetic Organization of the pca Gene cluster from *Acinetobacter calcoaceticus,*" *J. Bacteriol.* 169(7):3168-3174 (1987).

Doyle et al., "Structural Basis for a Change in substrate Specificity: Crystal Structure of S113E Isocitrate Dehydrogenase in a Complex with Isopropylmalate, $Mg^{2+}$ and NAPD," *Biochemistry* 40:4234-4241 (2001).

Drake and Daniel, "Physiology of the thermophilic acetogen *Moorella thermoacetica*," *Res. Microbiol.* 155(10):869-883 (2004).

Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).

Drake, "Demonstration of hydrogenase in extracts of the homoacetate-fermenting bacterium Clostridium thermoaceticum," *J. Bacteriol.* 150(2):702-709 (1982).

Draths and Frost, "Environmentally compatible synthesis of adipic acid from D-glucose," *J. Am. Chem. Soc.* 116:399-400 (1994).

Drevland et al., "Enzymology and Evolution of the Pyruvate Pathway to 2-Oxobutyrate in Methanocaldococcus jannachii," *J. Bacteriol.* 189(12):4391-4400 (2007).

Drewke et al., "4-O-Phosphoryl-L-threonine, a substrate of the pdxC(serC) gene product involved in vitamin $B_6$ biosynthesis," *FEBS Lett.* 390:179-182 (1996).

Drewke et al., "Ethanol formation in $adh^0$ mutants reveals the existence of a novel acetaldehyde-reducing activity in *Saccharomyces cerevisiae*," *J. Bacteriol.* 172:3909-3917 (1990).

Driscoll and Taber, "Sequence Organization and Regulation of the *Bacillus subtilis* menBE Operon," *J. Bacteriol.* 174(15):5063-5071 (1992).

Drummond and Stern, "Enzymes of ketone body metabolism. II. Properties of an acetoacetate-synthesizing enzyme prepared from ox liver," *J. Biol. Chem.* 235:318-325 (1960).

Du et al., "Succinic acid production from wheat using a biorefining strategy," *Appl. Microbiol. Biotechnol.* 76:1263-1270 (2007).

Duarte et al., "Reconstruction and validation of *Saccharomyces cerevisiae* iND750, a fully compartmentalized genome-scale metabolic model," *Genome Res.* 14(7):1298-1309 (2004).

Duckworth et al., "The Binding of Reduced Nicotinamide Adenine Dinucleotide to Citrate Synthase of *Escherichia coli* K12," *Biochemistry* 15(1):108-114 (1976).

Duncan et al., "The pentafunctional arom enzyme of *Saccharomyces cerevisiae* is a mosaic of monofunctional domains," *Biochem. J.* 246:375-386 (1987).

Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).

Duncombe and Frerman, "Molecular and catalytic properties of the acetoacetyl-Coenzyme A thiolase of *Escherichia coli*," *Arch. Biochem. Biophys.* 176(1):159-170 (1976).

Duran et al., "Characterization of cDNA clones for the 2-methyl branched-chain enoyl-CoA reductase. An enzyme involved in branched-chain fatty acid synthesis in anaerobic mitochondria of the parasitic nematode *Ascaris suum*," *J. Biol. Chem.* 268(30):22391-22396 (1993).

Durner et al., "Accumulation of Poly[(R)-3-Hydroxyalkanoates] *Pseudomonas oleovorans* during Growth with Octanoate in continuous culture at Different Dilution Rates," *Appl. Environ. Microbiol.* 66(8):3408-3414 (2000).

Dürre et al., "Solventogenic enzymes of Clostridium acetobutylicum: catalytic properties, genetic organization, and transcriptional regulation," *FEMS Microbiol. Rev.* 17:251-262 (1995).

Dürre, "Biobutanol: an attractive biofuel," *Biotechnol. J.* 2(12):1525-1534 (2007).

Dusch et al., "Expression of the *Corynebacterium glutamicum* panD gene encoding L-aspartate-α-decarboxylase leads to pantothenate overproduction in *Escherichia coli*," *Appl. Environ. Microbiol.* 65(4) 1530-1539 (1999).

Dutscho et al., "Cloning and sequencing of the genes of 2-hydroxyglutaryl-CoA dehydratase from Acidaminococcus fermentans," *Eur. J. Biochem.* 181(3):741-746 (1989).

Dwiarti et al., "Purification and characterization of cis-aconitic acid decarboxylase from *Aspergillus terreus* TN484-M1," *J. Biosci. Bioeng.* 94(1):29-33 (2002).

Dwyer et al., "Proton Abstraction reaction, Steady-State kinetics, and Oxidation-Reduction Potential of Human Glutaryl-CoA Dehydrogenase," *Biochemistry* 39:11488-11499 (2000).

Dykhuizen, "Chemostats used for studying natural selection and adaptive evolution," *Methods. Enzymol.* 224:613-631 (1993).

Eberhard and Gerlt, "Evolution of Function in the Crotonase Superfamily: The Stereochemical course of the Reaction catalyzed by 2-Ketocyclohexanecarboxyl-CoA Hydrolase," *J. Am. Chem. Soc.* 126:7188-7189 (2004).

Edegger et al., "Biocatalytic deuterium- and hydrogen-transfer using over-expressed ADH-'A': enhanced steroselectivity and $^2$H-labeled chiral alcohols," *Chem. Commun.* 22:2402-2404 (2006).

Eden et al., "Involvement of branched-chain amino acid aminotransferases in the production of fusel alcohols during fermentation in yeast," *Appl. Microbiol. Biotechnol* 55:296-300 (2001).

Edwards and Palsson, "Metabolic flux balance analysis and the in silico analysis of *Escherichia coli* K-12 gene deletions," *BMC Bioinform.* 1:1 (2000).

Edwards and Palsson, "Systems properties of the *Haemophilus influenzae* Rd metabolic genotype," *J. Biol. Chem.* 274(25):17410-17416 (1999).

Edwards and Palsson, "The *Escherichia coli* MG1655 in silico Metabolic Genotype: Its Definition, Characteristics, and Capabilities," *Proc. Natl. Acad. Sci. USA* 97(10):5528-5533 (2000).

Edwards et al., "Metabolic modelling of microbes: the flux-balance approach," *Environ. Microbiol.* 4(3):133-140 (2002).

Edwards et al., "In Silico Predictions of *Escherichia coli* metabolic capabilities are Consistent with Experimental Data," *Nat. Biotechnol.* 19(2):125-130 (2001).

Efe et al., "Options for biochemical production of 4-hydroxybutyrate and its lactone as a substitute for petrochemical production," *Biotechnol Bioeng* 99:1392-1406 (2008).

Egland et al., "A cluster of bacterial genes for anaerobic benzene ring biodegradation," *Proc. Natl. Acad. Sci. USA* 94:6484-6489 (1997).

Eikmanns et al., "The phosphoenolpyruvate carboxylase gene of *Corynebacterium glutamicum*: molecular cloning, nucleotide sequence, and expression." *Mol. Gen. Genet.* 218:330-339 (1989).

Elshahed et al., "Metabolism of Benzoate, Cyclohex-1-ene Carboxylate, and Cyclohexane Carboxylate by "Syntrophus aciditrophicus" Strain SB in Syntrophic Association with $H_2$-Using Microorganisms," *Appl. Environ. Microbiol.* 67(4):1728-1738 (2001).

Enomoto et al., "Cloning and sequencing of the gene encoding the soluble fumarate reductase from *Saccharomyces cerevisiae*," *DNA Res.* 3:263-267 (1996).

Ensign and Ludden, "Characterization of the CO Oxidation/ $H_2$ Evolution System of *Rhodospirillum rubrum*. Role of a 22-kDa ironsulfur protein in mediating electron transfer between carbon monoxide dehydrogenase and hydrogenase," *J. Biol. Chem.* 266(27)18395-18403 (1991).

Estévez et al., "X-ray crystallographic and kinetic correlation of a clinically observed human fumarase mutation," *Protein Sci.* 11(6):1552-1557 (2002).

Eulberg et al., "Characterization of a protocatechuate catabolic gene cluster from *Rhodococcus* opacus 1CP: evidence for a merged enzyme with 4-carboxymuconolactone-cecarboxylating and 3-oxoadipate enol-lactone-hydrolyzing activity," *J. Bacteriol.* 180:1072-1081 (1998).

Evans et al., "[$^{13}$C]propionate oxidatin in wild-type and citrate synthase mutant *Escherichia coli*: evidence for multiple pathways of propionate utilization," *Biochem. J.* 291(Pt 3):927-932 (1993).

Ezeji et al., "Butanol fermentation research: upstream and downstream manipulations," *Chem. Rec.* 4(5):305-314 (2004).

Faehnle et al., "A New Branch in the Family: Structure of Aspartate-β-semialdehyde Dehydrogenase from Methanococcus jannaschii," *J. Mol. Biol.* 353:1055-1068 (2005).

Feldberg and Datta, "L-threonine deaminase of *Rhodospirillum rubrum*. Purification and characterization," *Eur. J. Biochem.* 21(3):438-446 (1971).

Fell and Small, "Fat Synthesis in Adipose Tissue. An Examination of Stoichiometric Constraints," *Biochem. J.* 238(3):781-786 (1986).

Fernandez-Canon and Penalva, "Characterization of a fungal maleylacetoacetate isomerase gene and indentification of its human homologue," *J. Biol. Chem.* 273:329-337 (1998).

Fernandez-Valverde et al., "Purification of *Pseudomonas putida* Acyl Coenzyme A Ligase Active with a Range of aliphatic and Aromatic substrates," *Appl. Environ. Microbiol.* 59(4):1149-1154 (1993).

Fischer and Sauer, "Metabolic flux profiling of *Escherichi coli* mutants in central carbon metabolism using GC-MS," *Eur. J. Biochem.* 270(5):880-891 (2003).

Fish and Blumenthal, "2-Keto-3-deoxy-D-glucarate aldolase," *Methods Enzymol.* 9:529-534 (1966).

Fishbein and Bessman, "Purification and properties of an enzyme in human blood and rat liver microsomes catalyzing the formation and hydrolysis of γ-lactones. I. Tissue localization, stoichiometry, specificity, distinction from esterase," *J. Biol. Chem.* 241:4835-4841 (1966).

Fishbein and Bessman, "Purification and properties of an enzyme in human blood and rat liver microsomes catalyzing the formation and hydrolysis of γ-lactones. II. Metal ion effects, kinetics, and equilibra," *J. Biol. Chem*241:4842-4847 (1966).

Fitzgerald and Flanagan, "Characterization and sequence analysis of the human ornithine decarboxylase gene," *DNA* 8:(9):623-634 (1989).

Flint et al., "The role and properties of the iron-sulfur cluster in *Escherichia coli* dihydroxy-acid dehydratase," *J. Biol. Chem.* 268:14732-14742 (1993).

Flint, "Initial kinetic and mechanistic characterization of *Escherichia coli* fumarase A," *Arch. Biochem. Biophys.* 311(2):509-516 (1994).

Fochi, "Selective catalytic dehydrogenation of 1,4-cyclohexadiene to benzene. 1. Radical anions derived from transition-metal arene complexes as *promoters*," *Organometallics* 7:2255-2256 (1988).

Fomine and Tlenkopatchev, "Cross-methathesis of dimethyl maleate and ethylene catalyzed by second generation ruthenium carbene complexes: B3LYP and MPW1K comparison study," J. Org. Chem. 691:5189-5196 (2006).

Fong and Palsson, "Metabolic gene-deletion strains of *Escherichia coli* evolve to computationally predicted growth phenotypes," *Nat. Genet.* 36(10):1056-1058 (2004).

Fong et al., "Description and Interpretation of Adaptive Evolution of *Escherichia coli* K-12 MG1655 by Using a Genome-Scale In Silico Metabolic Model," *J. Bacteriol.* 185:6400-6408 (2003).

Fong et al., "In Silico design and adaptive evolution of *Escherichia coli* for production of lactic acid," *Biotechnol. Bioeng* . 91(5):643-648 (2005).

Fonknechten et al., "A conserved gene cluster rules anaerobic oxidative degradation of L-ornithine," *J. Bacteriol.* 191(9):3162-3167 (2009).

Fontaine et al., "Molecular charcterization and transcriptional analysis of adhE2, the gene encoding the NADH-dependent aldehyde/alcohol dehydrogenase responsible for butanol production in alcohologenic cultures of *Clostridium acetobutylicum* ATCC 824," *J. Bacteriol.* 184:821-830 (2002).

Fontaine et al., "A New Type of Glucose Fermentation by *Clostridium thermoaceticum* N.Sp.," *J. Bacteriol.* 43(6):701-715 (1942).

Ford et al., "Molecular properties of the lys1+ gene and the regulation of α-aminoadipate reductase in *Schizosaccharomyces pombe*," *Curr. Genet.* 28:131-137 (1995).

Forouhar et al., "Structural and Functional Evidence for *Bacillus subtilis* PaiA as a Novel N$^{1-\text{ Spermidine/spermine Acetyltransferase}}$," *J. Biol. Chem.* 280(48):40328-40336 (2005).

Förster et al., "Genome-scale reconstruction of the *Saccharomyces cerevisiae* metabolic network," *Genome Res.* 13(2):244-253 (2003).

Fox et al., "Characterization of the region encoding the CO-induced hydrogenase of *Rhodospirillum rubrum*," *J. Bacdteriol.* 178(21):6200-6208 (1996).

Freiberg, et al., "Identification and characterization of the first class of potent bacterial acetyl-CoA carboxylase inhibitors with antibacterial activity," *J. Biol. Chem.* 279:26066-26073 (2004).

Freidrich et al., "The complete stereochemistry of the enzymatic dehydration of 4-hydroxybutyryl Coenzyme A to crontonyl Coenzyme A," *Angew. Chem. Int. Ed.* 47:3254-3257 (2008).

Frerman and Duncombe,"Studies on the subunits of *Escherichia coli* Coenzyme A transferase. Reconstitution of an active enzyme," *Biochim. Biophys. Acta.* 580(2):289-297 (1979).

Fries et al., "Reaction Mechanism of the heterotetrameric (α2β2) E1 Component of 2-Oxo Acid Dehydrogenase Multienzyme Complexes," *Biochemistry* 42:6996-7002 (2003).

Frost and Draths, "Synthesis of adipic acid from biomass-derived carbon sources," *Biotechnol Adv.* 15(1):294 (1997).

Frost et al., "Dehydroquinate synthase from *Escherichia coli*: purification, cloning, and construction of overproducers of the enzyme" *Biochemistry.* 23:4470-4475 (1984).

Frost, "Redefining chemical manufacture. Replacing petroleum with plant-derived feedstocks," *Ind. Biotechnol.* 1(1):23-24 (2005).

Fu et al., "Crystal structures of human glutaryl-CoA dehydrogenase with and without an alternate substrate: structural bases of dehydrogenation and decarboxylation reactions," *Biochemistry* 43(30):9674-9684 (2004).

Fuji et al., "Characterization of L-lysine 6-aminotransferase and its structural gene from *Flavobacterium lutescens* IFO3084," *J. Biochem.* 128:391-397 (2000).

Fujii et al., "Error-prone rolling circle amplification: the simplest random mutagenesis protocol," *Nat. Protoc.* 1:2493-2497 (2006).

Fujii et al., "One-step random mutagenesis by error-prone rolling circle amplification," *Nucleic Acids Res.* 32:e145 (2004).

Fujii, T. et al. "Molecular Cloning, Sequence Analysis, and Expression of the Yeast Alcohol Acetyltransferase Gene," *Appl. Environ. Microbiol.* 60:2786-2792 (1994).

Fujishiro et al., "Crystallization and Some Properties of Acetylpolyamine Amidohydrolase From *Mycoplana Bullata*," *Biochem. Biophys. Res. Commun.* 157(3):1169-1174 (1988).

Fujita et al., "Novel Substrate Specificity of Designer 3-Isopropylmalate Dehydrogenase Derived from *Thermus thermophilus* HB8," *Biosci. Biotechnol. Biochem.* 65(12):2695-2700 (2001).

Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).

Fukuda and Wakagi, "Substrate recognition by 2-oxoacid:ferredoxin oxidoreductase from *Sulfolobus* sp. Strain 7," *Biochim. Biophys. Acta* 1597:74-80 (2002).

Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 268:5639-5646 (2001).

Fukui et al., "Engineering of *Ralstonia eutropha* for production of poly(3-hydroxybutyrate-co-3-hydroxyhexanoate) from fructose and solid-state properties of the copolymer," *Biomacromolecules*, 3(3):618-624 (2002).

Fukumura et al, "Hydrolysis of cyclic and linear oligomers of 6-aminocaproic acid by a bacterial cell extract," J. Biochem. 59(6):531-536 (1966).

Fukumura et al., "Purification and properties of a novel enzyme, L-α-amino-ε-caprolactamase from *Cryptococcus laurentii*," *FEBS Lett.* 89(2):298-300 (1978).

Fuller and Leadlay, "Proton transfer in methylmalonyl-CoA epimerase from Propionibacterium shermanii. The reaction of (2R)-methylmalonyl-CoA in tritiated water," *Biochem. J.* 213(3):643-650 (1983).

Furdui and Ragsdale, "The role of pyruvate ferredoxin oxidoreductase in pyruvate synthesis during autotrophic growth by the Wood-Ljungdahl pathway," *J. Biol. Chem.* 275(37):28494-28499 (2000).

Furukawa et al., "Increased alcohol acetyltransferase activity by inositol limitation in *Saccharomyces cerevisiae* in sake mash," *J. Biosci. Bioeng.* 96(4):380-386 (2003).

Galagan et al., "The genome of *M. acetivorans* reveals extensive metabolic and physiological diversity," *Genome Res.* 12(4):532-542 (2002).

Gallagher et al., "The crystal structure of chorismate lyase shows a new fold and a tightly retained product," *Proteins* 44:304-311 (2001).

Gangloff et al., "Molecular cloning of the Yeast Mitochondrial Aconitase Gene (ACO1) and Evidence of a Synergistic Regulation of Expression by Glucose plus Glutamate," *Mol. Cell. Biol.* 10(7):3551-3561 (1990).

Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys Acta* 1255(2):154-160 (1995).

Garvie, "Bacterial lactate dehydrogenases," *Microbiol. Rev.* 44:106-139 (1980).

Gay et al., "Cloning Structural Gene sacB, Which Codes for Exoenzyme Levansucrase of *Bacillus subtilis*: Expression of the Gene in *Escherichia coli*," *J. Bacteriol.* 153(3):1424-1431 (1983).

Genda et al., "Purification and characterization of fumarase from *Corynebacterium glutamicum*," *Biosci. Biotechnol. Biochem.* 70:1102-1109 (2006).

Gene Bridges, "Quick & Easy BAC Modification Kit by Red®/ET® Recombination," Technical Protocol, Cat. No. K001, Version 2.6 (2007).

Gerhardt et al. "Fermentation of 4-aminobutyrate by *Clostridium aminobutyricum*: cloning of two genes involved in the formation dehydration of 4-hydroxybutyrl-CoA," *Arch. Microbiol.* 174:189-199 (2000).

Gescher et al., "Genes coding for a new pathway of aerobic benzoate metabolism in *Azoarcus evansii*," *J Bacteriol.* 184(22):6301-6315 (2002).

Giaever et al., "Functional profiling of the *Saccharomyces cerevisiae* genome," *Nature* 418(6896):387-391 (2002).

Gibbs et al., "Degenerate olignucleotide gene shuffling (DOGS): a method for enhancing the frequence of recombination with family shuffling," *Gene*. 271:13-20 (2001).

Gibson and McAlister-Henn, "Physical and genetic interactions of cytosolic malate dehydrogenase with other gluconeogenic enzymes," *J. Biol. Chem.* 278:25628-25636 (2003).

Gibson (née Thomas) et al., "Cross metathesis of the amino acid homoallylglycine," *Chem. Commun.* 1107-1108 (1997).

Giesel and Simon, "On the occurrence of enoate reductase and 2-oxo-carboxylate reductase in *Clostridia* and some observations on the amino acid fermentation by Peptostreptococcus anaerobius," *Arch. Microbiol.* 135(1):51-57 (1983).

Gillyon et al., "Putrescine Breakdown in the Yeast Candida boidinii: Subcellular Location of Some of the Enzymes Involved and Properties of Two Acetamidoaldehyde Dehydrogenases," *J. of Gen. Microbiol.* 133:2477-2485 (1987).

Glasemacher et al., "Purification and properties of acetyl-CoA synthetase (ADP-forming), an archael enzyme of acetate formation and ATP synthesis, from the hyperthermophile *Pyrococcus furiosus*," *Eur. J. Biochem.* 244:561-567 (1997).

Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).

Goda et al., "Cloning, sequencing, and expression in *Escherichia coli* of the *Clostridium tetanomorphum* gene encoding β-methylaspartase and characterization of the recombinant protein," *Biochem.* 31(44):10747-10756 (1992).

Gokarn et al., "Expression of pyruvate carboxylase enhances succinate production in *Escherichia coli* without affecting glucose uptake" *Biotechnol. Lett.* 20:795-798 (1998).

Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).

Gokarn, et al., "The physiological effects and metabolic alterations caused by the expression of Rhizobium etli pyruvate carboxylase in *Escherichia coli*," *Appl. Microbiol. Biotechnol.* 56(1-2):188-195 (2001).

Gokulan et al., "Crystal structure of *Mycobacterium tuberculosis* diaminipimelate decarboxylase, an essential enzyme in bacterial lysine biosynthesis," *J. Biol. Chem.* 278(20):18588-18596 (2003).

Goldberg et al., "Improved Conversion of Fumarate to Succinate by *Escherichia coli* Strains Amplified for Fumarate Reductase," *Appl. Environ. Microbiol.* 45:1838-1847 (1983).

Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).

González and Robb, "Genetic analysis of *Carboxydothermus hydrogenoformans* carbon monoxide dehydrogenase genes cooF and cooS," *FEMS Microbiol. Lett.* 191(2):243-247 (2000).

Gonzalez et al., "Characterization of a (2R,3R)-2,3-Butanediol Dehydrogenase as the *Saccharomyces cerevisiae* YAL060W Gene Product," *J. Biol. Chem.* 275(46):35876-35885 (2000).

Gonzalez-Pajuelo et al., "Metabolic engineering of *Clostridium acetobutylicum* for the industrial production of 1,3-propanediol from glycerol," *Met. Eng.* 7:329-336 (2005).

Gordon and Doelle, "Purification, properties and immunological relationship of L(+)-lactate dehydrogenase from *LactoBacillus casei*," *Eur. J. Biochem.* 67:543-555 (1976).

Goupil et al., "Imbalance of Leucine Flux in *Lactococcus lactis* and Its Use for the Isolation of Diacetyl-Overproducing Strains," *Appl. Environ. Microbiol.* 62(7):2636-2640 (1996).

Goupil-Feuillerat et al., "Transcriptional and Translational Regulation of α-Acetolactate Decarboxylase of *Lactococcus lactis* subsp. Lactis," *J. Bacteriol.* 182(19):5399-5408 (2000).

Gourley et al., "The two types of 3-dehydroquinase have distinct structures but catalyze the same overall reaction," *Nat. Struct. Biol.* 6:521-525 (1999).

Grant and Patel. "The non-oxidative decarboxylation of p-hydroxybenzoic acid, gentisic acid, protocatechuic acid and gallic acid by *Klebsiella aerogenes* (*Aerobacter aerogenes*)," *Antonie Van Leeuwenhoek* 35:325-343 (1969).

Green and Bennett, "Genetic manipulation of acid and solvent formation in *Clostridium acetobutylicum* ATCC 824," *Biotechnol. Bioeng.* 58(2-3):215-221 (1998).

Green and Nichols, "p-Aminobenzoate biosynthesis in *Escherichia coli*. Purification of aminodeoxychorismate lyase and cloning of pabC," *J. Biol. Chem.* 266:12971-12975 (1991).

Green et al., "Catabolism of α-ketoglutarate by a sucA mutant of Bradyrhizobium japonicum: evidence for an alternative tricarboxylic acid cycle," *J. Bacteriol.* 182:2838-2844 (2000).

Green et al., "Characterization and sequence of *Escherichia coli* pabC, the gene encoding aminodeoxychorismate lyase, a pyridoxal phosphate-containing enzyme," *J Bacteriol.* 174:5317-5323 (1992).

Grethlein and Jain, "Bioprocessing of coal-derived synthesis gases by anaerobic bacteria," *Trends Biotech.* 10:418-423 (1992).

Grolle et al., "Isolation of the dxr gene of Zymomonas mobilis and characterization of the 1-deoxy-D-xylulose 5-phosphate reductoisomerase," *FEMS Microbiol. Lett.* 191:131-137 (2000).

Grubbs "Olefin Meethathesis," *Tetrahedron* 60:7117-7140 (2004).

Gu et al., "Crystal structure of shikimate kinase from *Mycobacterium tuberculosis* reveals the dynamic role of the LID domain in catalysis," *J. Mol. Biol.* 319:779-789 (2002).

Gueldener et al., "A second set of loxP marker cassettes for Cre-mediated multiple gene knockouts in budding yeast," *Nucleic Acids Res.* 30(6):e23 (2002).

Guerra et al., "Role of transmembrane segment M8 in the biogenesis and function of yeast plasma-membrane $H^+$-ATPase," *Biochim. Biophys Acta*. 1768:2383-2392 (2007).

Guest et al., "The fumarase genes of *Escherichia coli*: location of the fumB gene and discovery of a new gene (fumC)," *J. Gen. Microbiol.* 131(11):2971-2984 (1985).

Guettler et al., "*ActinoBacillus succinogenes* sp. nov., a novel succinic-acid-producing strain from the bovine rumen," *Int. J. Syst. Bacteriol.* 49 :207-216 (1999).

Guirard and Snell, "Purification and properties of ornithine decarboxylase from *LactoBacillus* sp. 30a," *J. Biol. Chem.* 255:5960-5964 (1980).

Guo and Bhattacharjee, "Posttranslational activation, site-directed mutation and phylogenetic analyses of the lysine biosynthesis enzymes α-aminoadipate reductase Lys1p (AAR) and the phosphopantetheinyl transferase Lys7p (PPTase) from Schizosaccharomyces pombe," *Yeast* 21:1279-1288 (2004).

Guo and Bhattacharjee, "Site-directed mutational analysis of the novel catalytic domains of α-aminoadipate reductase (Lys2p) from candida albicans," *Mol. Gen. Gemonics* 269:271-279 (2003).

Guterman et al., "Generation of phenylpropanoid pathway-derived volatiles in transgenic plants: rose alcohol acetyltransferase produces phenylethyl acetate and benzyl acetate in petunia flowers," *Plant Mol. Biol.* 60(4):555-563 (2006).

Gutierrez et al., "A mutant D-amino acid aminotransferase with broad substrate specificity: construction by replacement of the interdoman loop Pro 119-Arg120-Pro121 by Gly-Gly-Gly," *Protein Eng.* 11:53-58 (1998).

Gutknecht, R., et al., "The dihydroxyacetone kinase of *Escherichia coli* utilizes a phosphoprotein instead of ATP as phosphoryl donor," *EMBO J.* 20(10):2480-2486 (2001).

Guyer, et al., "Identification of a sex-factor-affinity site in *E. coli* as γδ," *Cold Spring Harbor Symp. Quant. Biol.* 45:135-140 (1981).

Guzman et al., "Tight regulation, modulation, and high-level expression by vectors containing the arabinose $P_{BAD}$ promoter," *J Bacteriol.* 177:4121-4130 (1995).

Haarasilta and Oura, "On the activity and regulation of anaplerotic and gluconeogenetic enzymes during the growth process of baker's yeast. The biphasic growth," *Eur. J. Biochem.* 52:1-7 (1975).

Hadfield et al., "Active Site Analysis of the Potential Antimicrobial Target Aspartate Semialdehyde Dehydrogenase," *Biochemistry* 40:14475-14483 (2001).

Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).

Hagemeier et al., "Insight into the mechanism of biological methanol activation based on the crystal structure of the methanol-cobalamin methyltransferase complex," *Proc. Natl. Acad. Sci. USA*, 103(50):18917-18922 (2006).

Hahm et al., "Characterization and evaluation of a pta (phosphotransacetylase) negative mutant of *Escherichia coli* HB101 as a production host of foreign lipase," *Appl. Microbiol. Biotechnol.* 42:100-107 (1994).

Haller et al., "Discovering new enzymes and metabolic pathways: conversion of succinate to propionate by *Escherichia coli*," *Biochem.* 39(16):4622-4629 (2000).

Hambraeus and Nyberg, "Enzymatic Hydrogenation of trans-2-Nonenal in Barley," *J. Agric. Food Chem.* 53:8714-8721 (2005).

Hamilton-Kemp et al., "Production of the long-chain alcohols octanol, decanol, and dodecanol by *Escherichia coli*," *Curr. Microbiol.* 51:82-86 (2005).

Hammer and Bode, "Purification and characterization of an inducible L-lysine:2-oxoglutarate 6-aminotransferase from *Candida utilis*," *J. Basic Microbiol.* 32:21-27 (1992).

Han et al., "Biochemical characterization and inhibitor discovery of shikimate dehydrogenase from *Helicobacter pylori*," *FEBS J.* 273:4682-4692 (2006).

Hanai et al., "Engineered synthetic pathway for isopropanol production in *Escherichia coli*," *Appl. Environ. Microbiol.* 73(24):7814-7818 (2007).

Hansford, Control of mitochondrial substrate oxidation, *Curr. Top Bioenergy* 10:217-278 (1980).

Harder, "Anaerobic degradation of cyclohexane-1,2-diol by a new Azoarcus species," *Arch. Microbiol.* 168:199-204 (1997).

Hardison et al., "Globin Gene Server: A prototype E-Mail Database Server Featuring Extensive Multiple Alignments and Data Compilation for Electronic Genetic Analysis," *Genomics* 21:344-353 (1994).

Harker and Bramley, "Expression of prokaryotic 1-deoxy-D-xylulose-5-phosphatases in *Escherichia coli* increases carotenoid and ubiquinone biosynthesis," *FEBS Lett.* 448:115-119 (1999).

Harms and Thauer, "Methylcobalamin: Coenzyme M methyltransferase isoenzymes MtaA and MtbA from *Methanosarcina barkeri*. Cloning, sequencing and differential transcription of the encoding genes, and functional overexpression of the mtaA gene in *Escherichia coli*," *Eur. J. Biochem.* 235(3):653-659 (1996).

Harrison and Harwood, "The pimFABCDE operon from Rhodo*Pseudomonas palustris* mediates dicarboxylic acid degradation and participates in anaerobic benzoate degradation," *Microbiology* 151:727-736 (2005).

Härtel et al., "Purification of glutaryl-CoA dehydrogenase from *Pseudomonas* sp., an enzyme involved in the anaerobic degradation of benzoate," *Arch. Mirobiol.* 159:174-181 (1993).

Harwood and Parales, "The β-ketoadipate pathway and the biology of self-identity," *Annu. Rev. Microbiol.* 50:553-590 (1996).

Harwood et al., "Anaerobic metabolism of aromatic compounds via the benzoyl-CoA pathway," *FEMS Microbiol. Rev.* 22:439-458 (1999).

Harwood et al., "Identification of the pcaRKF Gene cluster from *Pseudomonas putida*: Involvement in Chemotaxis, Biodegradation, and Transport of 4-Hydroxybenzoate," *J. Bacteriol.* 176(21):6479-6488 (1994).

Hasan and Nester, "Dehydroquinate synthase in *Bacillus subtilis*. An enzyme associated with chorismate synthase and flavin reductase," *J. Biol. Chem.* 253:4999-5004 (1978).

Hasegawa et al., "Transcriptional regulation of ketone body-utilizing enzyme, acetoacetyl-CoA synthetase, by C/EBPα during adipocyte differentiatiion," *Biochimica. Biophysica. Acta* 1779:414-419 (2008).

Haselbeck and McAlister-Henn, "Isolation, nucleotide sequence, and disruption of the *Saccharomyces cerevisiae* gene encoding mitochondrial NADP(H)-specific isocitrate dehydrogenase," *J. Biol. Chem.* 266(4):2339-2345 (1991).

Hashidoko et al., "Cloning of a DNA fragment carrying the 4-hydroxycinnamate decarboxylase (PofK) gene from Klebsielss oxytoca and its constitutive expression in *Escherichia coli* JM109 cells," *Biosci. Biotech. Biochem.* 58:217-218 (1994).

Hashimoto et al., "Activation of L-Lysine ε-Dehydrogenase from Agrobacterium tumefaciens by Several Amino Acids and Monocarboxylates," *J. Biochem.* 106:76-80 (1989).

Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).

Hatakeyama et al., "Analysis of oxidation sensitivity of maleate cis-trans isomerase from *Serratia marcescens*," *Biosci. Biotechnol. Biochem.* 64:1477-1485 (2000).

Hatakeyama et al., "Gene Cloning and Characterization of Maleate cis-trans Isomerase from *Alcaligenes faecalis*," *Biochem. Biophys. Res. Comm.* 239:74-79 (1997).

Hawes et al., "Primary structure and tissue-specific expression of human β-hydroxyisobutyryl-Coenzyme A hydrolase," *J. Biol. Chem.* 271:26430-26434 (1996).

Hawes et al., "Mammalian 3-hydroxyisobutyrate dehydrogenase," *Methods Enzymol.* 324:218-228 (2000).

Hayashi et al., "Properties of 2-hydroxyglutarate dehydrogenase from Fusobacterium," *J. Nihon. Univ. Sch. Dent.* 28(1):12-21 (1986).

Hayden et al., "Glutamate dehydrogenase of Halobacterium salinarum: evidence that the gene sequence currently assigned to the NADP+-dependent enzyme is in fact that of the NAD+-dependent glutamate dehydrogenase," *FEMS Microbiol. Lett.* 211:37-41 (2002).

Hayes et al., "Combining computational and experimental screening for rapid optimization of protein properties," *Proc. Natl. Acad. Sci. USA* 99:15926-15931 (2002).

Hayes et al., "The Biofine Process: Production of Levulinic Acid, Furfural and Formic Acid from Lignocellulosic Feedstocks," P. 139-164. In Biorefineries: Industrial Proceses and Products. Wiley, Weinheim, Germany (2006).

Haywood and Large, "4-Acetamidobutyrate Deacetylase in the Yeast Candida boidinii Grown on Putrescine or Spermidine as Sole Nitrogen, Source and Its Probable Role in Polyamine Catabolism," *J. Gen. Microbiol.* 132:7-14 (1986).

Haywood et al., "Characterization of two 3-ketothiolases possessing differing substrate specificities in the polyhydroxyalkanoate synthesizing organism *Alcaligenes eutrophus*," *FEMS Microbiol. Lett.* 52:91-96 (1988).

He and Wiegel. "Purification and characterization of an oxygen-sensitive reversible 4-hydroxybenzoate decarboxylase from *Clostridium hydroxybenzoicum*," *Eur. J Biochem.* 229:77-82 (1995).

Heidlas and Tressl, "Purification and Properties of two oxidoreductases catalyzing the enantioselective reduction of diacetyl and other diketones from baker's yeast," *Eur. J. Biochem.* 188:165-174 (1990).

Heipieper et al., "Ethanol tolerance and membrane fatty acid adaptation in adh multiple and null mutants of *Kluyveromyces lactis*," *Res. Microbiol.* 151(9):777-784 (2000).

Helin et al., "The refined x-ray structure of muconate lactonizing enzyme from *Pseudomonas putida* PRS2000 at 1.85 Åresolution," *J. Mol. Biol.* 254:918-941 (1995).

Heller et al., "Cloning and expression of the gene for the vitamin B12 receptor protein in the outer membrane of *Escherichia coli*," *J. Bacteriol.* 161:896-903 (1985).

Hemschemeier et al., "Biochemical and physiological characterization of the pyruvate formate-lyase Pfl1 of Chlamydomonas reinhardtii, a typically bacterial enzyme in eukaryotic alga," *Eukaryot. Cell* 7:518-526 (2008).

Henne, et al., "Construction of environmental DNA libraries in *Escherichia coli* and screening for the presence of genes conferring utilization of 4-hydroxybutyrate," *Appl. Environ. Microbiol.* 65(9):3901-3907 (1999).

Hennessy, et al., "The reactivity of gamma-hydroxybutyric acid (GHB) and gamma-butyrolactone (GBL) in alcoholic solutions," *J. Forensic. Sci.* 49(6):1220-1229 (2004) (provided electronically by publisher as pp. 1-10).

Henning et al., "Identification of novel benzoylformate decarboxylases by growth selection," *Appl. Environ. Microbiol.* 72:7510-7517 (2006).

Henriksson et al., "The 1.9 Å resolution structure of *Mycobacterium tuberculosis* 1-deoxy-D-xylulose 5-phosphate reductoisomerase, a potential drug target," Acta *Crystallogr. D. Biol. Crystallogr.* 62:807-813 (2006).

Henstra et al., "Microbiology of synthesis gas fermentation for biofuel production," *Curr. Opin. Biotechnol.* 18:200-206 (2007).

Herrmann et al., "Energy Conservation via Electron-Transferring Flavoprotein in Anaerobic Bacteria," *J. Bacteriol.* 190(3):784-791 (2008).

Hermes et al., "Searching sequence space by definably random mutagenesis: Improving the catalytic potency of an enzyme," *Proc. Natl. Acad. Sci USA* 87:696-700 (1990).

Herrmann et al., "Two beta-alanyl-CoA:ammonia lyases in *Clostridium propionicum*," *FEBS J.* 272:813-821 (2005).

Hespell et al., "Stabilization of *pet* Operon Plasmids and Ethanol Production in *Escherichia coli* Strains Lacking Lactate Dehydrogenase and Pyruvate Formate-Lyase Activities," *Appl. Environ. Microbiol.* 62:4594-4597 (1996).

Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).

Hester et al., "Purification of active E1$\alpha_2\beta_2$ of *Pseudomonas putida* branched-chain-oxoacid dehydrogenase," *Eur. J. Biochem.* 233:828-836 (1995).

Hetzel et al., "Acryloyl-CoA reductase from clostridium propionicum. An enzyme complex of pripionyl-CoA dehydrogenase and electron-transferring flavoprotein," *Eur. J. Biochem.* 270:902-910 (2003).

Heydari et al., "Highly Stable L-Lysine 6-Dehydrogenase from the thermophile Geo*Bacillus stearothermophilus* Isolated from a Japanese Hot Spring: characterization, Gene Cloning and sequencing, and Expression," *Appl. Environ. Microbiol.* 70(2):937-942 (2004).

Hibbert et al., "Directed evolution of biocatalytic processes," *Biomol. Eng.* 22:11-19 (2005).

Highbarger et al., "Mechanism of the reaction catalyzed by acetoacetate decarboxylase. Importance of lysine 116 in determining the p$K_a$ of active-site lysine 115," *Biochemistry* 35(1):41-46 (1996).

Hijarrubia et al., "Domain Structure Characterization of the Multifunctional α-Aminoadipate Reductase from *Penicillium chrysogenum* by Limited Proteolysis," *J. Biol. Chem.* 278(10):8250-8256 (2003).

Hill et al., "PCR based gene engineering of the Vibrio harveyi lux operon and the *Escherichia coli* trp operon provides for biochemically functional native and fused gene products," *Mol. Gen. Genet.* 226:41-48 (1991).

Hillmer and Gottschalk, "Particulate Nature of Enzymes Involved in the Fermentation of Ethanol and Acetate by *Clostridium kluyveri*," *FEBS Lett.* 21(3):351-354 (1974).

Hillmer and Gottschalk, "Solubilization and partial characterization of particulate dehydrogenases from *Clostridium kluyveri*," *Biochim. Biophys. Acta* 334:12-23 (1974).

Hirano et al., "Purification and characerization of the Alcohol Dehydrogenase with a Broad Substrate Specificy Originated from 2-Phenylethanol-Assimilating *Brevibacterium* sp. KU 1309," *J. Biosci. Bioeng.* 100(3): 318-322 (2005).

Hirata et al., "Sterochemistry of reduction of the endocyclic double bond of (-)-carvone with the enzyme preparation from cultured cells of Nicotiana tabacum," *Phytochemistry* 28(12):3331-3333 (1989).

Hiser et al., "ERG10 from *Saccharomyces cerevisiae* encodes acetoacetyl-CoA thiolase," *J. Biol. Chem.* 269:31383-31389 (1994).

Ho et al., "Regulation of serine biosynthesis in Arabidopsis. Crucial role of plastidic 3-phosphoglycerate dehydrogenase in non-photosynthetic tissues," *J. Biol. Chem.* 274:397-402 (1999).

Hoang et al., "A broad-host-range Flp-FRT recombination system for site-specific excision of chromosomally-located DNA sequences: application for isolation of unmarked *Pseudomonas aeruginosa* mutants," *Gene* 212(1):77-86 (1998).

Hoffmann and Dimroth, "Sterochemistry of the methylmalonyl-CoA decarboxylation reaction," *FEBS Lett.* 220:121-125 (1987).

Hoffmeister et al., "Mitochondrial trans-2-enoyl-CoA reductase of wax ester fermentation from *Euglena Gracilis* defines a new family of enzymes involved in lipid synthesis," *J. Biol. Chem.* 280:4329-4338 (2005).

Hofmeister and Buckel, "(R)-lactyl-CoA dehydratase from Clostridium propionicum. Stereochemistry of the dehydration of (R)-2-hydroxybutyryl-CoA to crotonly-CoA," *Eur. J. Biochem.* 206(2):547-552 (1992).

Hofmeister et al., "Cloning and expression of the two genes coding for L -serine dehydratase from Peptostreptococcus asaccharolyticus: relationship of the iron-sulfur protein to both L -serine dehydratases from *Escherichia coli*," *J. Bacteriol.* 179(15):4937-4941 (1997).

Hogan et al., "Improved Specificity toward Substrates with Positively Charged Side chains by Site-Directed Mutagenesis of the L-lactate Dehydrogenase of *Bacillus stearothermophilus*," *Biochemistry* 34:4225-4230 (1995).

Holloway and Marsh, "Adenosylcobalamin-dependent glutamate mutase from Clostridium tetanomorphum. Overexpression in *Escherichia coli*, purification, and characterization of the recombinant enzyme," *J. Biol. Chem.* 269(32):20425-20430 (1994).

Holms, "The central metabolic pathways in *Escherichia coli*: relationship between flux and control at a branch point, efficiency of conversion to biomass, and excretion of acetate," *Curr. Top Cell. Regul.* 28:69-105 (1986).

Hong and Lee, "Metabolic flux analysis for succinic acid production by recombinant *Escherichia coli* with amplified malic enzyme activity," *Biotechnol. Bioeng.* 74(2):89-95 (2001).

Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:252-255 (2004).

Hong et al., "The genome sequence of the capnophilic rumen bacterium Mannheimia succiniciproducens." *Nat. Biotechnol.* 22(10):1275-1281 (2004).

Hong and Lee, "Importance of redox balance on the production of succinic acid by metabolically engineered *Escherichia coli*," *Appl. Microbiol. Biotechnol.* 58:286-290 (2002).

Horswill and Escalante-Semerena, "In vitro conversion of propionate to pyruvate by Salmonella enterica enzymes: 2-methylcitrate dehydratase (PrpD) and aconitas Enzymes catalyze the conversion of 2-methylcitrate to 2-methylisocitrate," *Biochemistry* 40(15):4703-4713 (2001).

Horton et al., "Heterologous expression of the *Saccharomyces cerevisiae* alcohol acetyltransferase genes in *Clostridium acetobutylicum* and *Escherichia coli* for the production of isoamyl acetate," *J. Ind. Microbiol. Biotechnol.* 30(7):427-432 (2003).

Howard et al., "Titanium Metallacarbene-Metallacylobutane Reactions: Stepwise Metathesis," *J. Am. Chem. Soc.* 102:6876-6878 (1980).

Hsu et al., "Expression of an aromatic-dependent decarboxylase which provides growth-essential $CO_2$ equivalents for the acetogenic (Wood) pathway of *Clostridium thermoaceticum*," *J Bacteriol.* 172:5901-5907 (1990).

Hu et al., "The catalytic intermediate stabilized by a "down" active site loop for diaminopimelate decarboxylase from *Helicobacter pylori*. Enzymatic characterization with crystal structure analysis," *J. Biol. Chem.* 283(30):21284-21293 (2008).

Huang et al., "Genetic characterization of the resorcinol catabolic pathway in *Corynebacterium glutamicum*," *Appl. Environ. Microbiol.* 72:7238-7245 (2006).

Huang et al., "Purification and characterization of a ferulic acid decarboxylase from *Pseudomonas fluorescens*," *J. Bacteriol.* 176:5912-5918 (1994).

Huang et al., "Identification and characterization of a second butyrate kinase from *Clostridium acetobutylicum* ATCC 824," *J. Mol. Microbiol. Biotechnol.* 2(1):33-38 (2000).

Hübner et al., "The mechanism of substrate activation of pyruvate decarboxylase: A first approach," *Eur. J. Biochem.* 92:175-181 (1978).

Huder and Dimroth, "Sequence of the sodium ion pump methylmalonyl-CoA decarboxylase from Veillonella parvula," *J. Biol. Chem.* 268:24564-24571 (1993).

Hughes et al., "Cloning and expression of pca genes from *Pseudomonas putida* in *Escherichia coli*," *J. Gen. Microbiol.* 134:2877-2887 (1988).

Hughes et al., "Evidence for isofunctional enzymes in the degradation of phenol, m- and p-toluate, and p-cresol via catechol meta-cleavage pathways in *Alcaligenes eutrophus*," *J. Bacteriol.* 158(1):79-83 (1984).

Hugler et al., "Malonyl-Coenzyme A Reductase from *Chloroflexus aurantiacus*, a Key Enzyme of the 3-Hydroxypropionate Cycle for Autotrophic $CO_2$ Fixation," *J. Bacteriol.* 184(9):2404-2410 (2002).

Huh et al., "Global analysis of protein localization in budding yeast," *Nature* 425:686-691 (2003).

Huisman and Lalonde, "Enzyme evolution for chemical process applications," In R.N. Patel (ed.), *Biocatalysis in the pharmaceutical and biotechnology industries*, CRC Press, p. 717-742 (2007).

Huo and Viola, "Substrate Specificity and Identification of Functional Groups of Homoserine Kinase from *Escherichia coli*," *Biochemistry* 35:16180-16185 (1996).

Husain and Steenkamp, "Partial purification and characterization of glutaryl-Coenzyme A dehydrogenase, electron transfer flavoprotein, and electron transfer flavoprotein-Q oxidoreductase from *Paracoccus denitrificans*," *J. Bacteriol.* 163:709-715 (1985).

Hustede et al., "Cloning of poly(3-hydroxybutyric acid) synthase genes of Rhodobacter sphaeroides and Rhodospirillum rubum and heterologous expression in Alcaligenes eutrophys," *FEMS Microbiol. Lett.* 93:285-290 (1992).

Ibarra et al., "*Escherichia coli* K-12 undergoes adaptive evolution to achieve in silico predicted optimal growth," *Nature* 420(6912):186-189 (2002).

Ichikawa et al. Catalytic reaction of 1,3-butanediol over solid acids, *J. Mol. Catalysis A Chem.* 256:106-112 (2006).

Ichikawa et al., "PIO study on 1,3-butanediol dehydration over $CeO_2$ (1 1 1) surface," *J. Mol. Catalysis A Chem.* 231:181-189 (2005).

Iffland et al., "Directed Molecular Evolution of Cytochrome c Peroxidase," *Biochemistry* 39:10790-10798 (2000).

Ikai and Yamamoto, "Identification and analysis of a gene encoding L-2,4-diaminobutyrate:2-ketoglutarate 4-aminotransferase involved in the 1,3-diaminopropane production pathway in Acinetobacter baumanni," *J. Bacteriol.* 179:5118-5125 (1997).

Imai and Ohno, "Measurement of yeast intracellular pH by image processing and the change it undergoes during growth phase," *J.Biotechnol.* 38:165-172 (1995).

Ingoldsby et al., "The discovery of four distinct glutamate dehydrogenase genes in a strain of Halobacterium salinarum," *Gene* 349:237-244 (2005).

Ingram and Vreeland, "Differential-Effects of Ethanol and Hexanol on the *Escherichia-coli* Cell-Envelope," *J. Bacteriol.* 144:481-488 (1980).

Inui et al., "Occurrence of Oxygen-Sensitive, Nadp+-Dependent Pyruvate-Dehydrogenase in Mitochondria of Euglena-Gracilis," *J. Biochem.* 96:931-934 (1984).

Inui et al., "Pyruvate-Nadp+ Oxidoreductase from Euglena-Gracilis—the Kinetic-Properties of the Enzyme," *Arch. Biochem Bipophys.* 274:434-442 (1989).

Inui et al., "Wax Ester Fermentation in euglena-Gracilis," *FEBBS Lett.* 150:89-93 (1982).

Inui et al., "Fatty acid synthesis in mitochondria of Euglena Gracilis," *Euro. J. Biochem.* 142(1):121-126 (1984).

Inui et al., "Production and Composition of Wax Esters by Fermentation of Euglena Gracilis,"*Agr. Biol. Chem.* 47(11):2669-2671 (1983).

Inui et al., "Purification and characterization of pyruvate:NADP+oxidoreductase in *Euglena gracilis*," *J. Biol. Chem.* 262(19):9130-9135 (1987).

Inui et al., "Pyruvate:NADP+ oxidoreductase from *Euglena gracilis*: mechanism of O2-inactivation of the enzyme and its stability in the aerobe," *Arch. Biochem. Biophys.* 280:292-298 (1990).

Inui et al., "The physiological role of oxygen-sensitive pyruvate dehydrogenase in mitochondrial fatty acid synthesis in *Euglena gracilis*," *Arch. Biochem. Biophys.* 237(2):423-429 (1985).

Ishida et al., Efficient production of L-Lactic acid by metabolically engineered *Saccharomyces cerevisiae* with a genome-integrated L-lactate dehydrogenase gene. *Appl. Envirom. Microbiol.* 71:1964-1970 (2005).

Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).

Ishige et al, "Long-chain aldehyde dehydrogenase that participates in n-alkane utilization and wax ester synthesis in *Acinetobacter* sp, strain M-1," *Appl. Environ. Microbiol.* 66:3481-3486 (2000).

Ismaiel et al., "Purification and Characterization of a Primary-Secondary Alcohol Dehydrogenase from Two Strains of *Clostridium beijerinckii*," *J. Bacteriol.* 175(16):5097-5105 (1993).

Ismail et al., "Functional genomics by NMR spectroscopy. Phenylacetate catabolism in *Escherichia coli*," *Eur. J. Biochem.* 270(14):3047-3054 (2005).

Ito and Yanofsky, "Anthranilate synthetase, an enzyme specified by the tryptophan operon of *Escherichia coli*: Comparative studies on the complex and the subunits," *J Bacteriol.* 97:734-742 (1969).

Ito et al., "Colistin nephrotoxicity: report of a case with light and electron microscopic studies," *Acta Pathol. Jpn.* 19:55-67 (1969).

Ito et al., "D-3-hydroxybutyrate dehydrogenase from Pseudomonas fragi: molecular cloning of the enzyme gene and crystal structure of the enzyme," *J. Mol. Biol.* 355(4):722-733 (2006).

Iverson et al., "Structure of the *Escherichia coli* fumarate reductase respiratory complex," *Science* 284(5422):1961-1966 (1999).

Iwakura et al., "Studies on regulatory functions of malic enzymes. VI. Purification and molecular properties of NADP-linked malic enzyme from *Escherichia coli* W," *J. Biochem.* 85:1355-1365 (1979).

Izard and Blackwell, "Crystal structures of the metal-dependent 2-dehydro-3-deoxy-galacarate aldolase suggest a novel reaction mechanism," *EMBO J.* 19:3849-3856 (2000).

Izumi et al., "Structure and Mechanism of HpcG, a Hydratase in the Homoprotocatechuate Degradation Pathway of *Escherichia coli*," *J. Mol. Biol.* 370:899-911 (2007).

Jacobi et al., "The hyp operon gene products are required for the maturation of catalytically active hydrogenase isoenzymes in *Escherichia coli*," *Arch. Microbiol.* 158(6):444-451 (1992).

Jacques et al., "Characterization of yeast homoserine dehydrogenase, an antifungal target: the invariant histidine 309 is important for enzyme integrity," *Biochem. Biophys. Acta* 1544:28-41 (2001).

James and Cronan, "Expression of two *Escherichia coli* acetyl-CoA carboxylase subunits is autoregulated," *J. Biol. Chem.* 279:2520-2527 (2004).

James and Viola, "Production and characterization of bifunctional enzymes. Domain swapping to produce new bifunctional enzymes in the aspartate pathway," *Biochemistry* 41(11) 3720-3725 (2002).

Jansen and Wanders, "L-2-hydroxyglutarate dehydrogenase: identification of a novel enzyme activity in rat and human liver. Implications for L-2-hydroxyglutaric academia," *Biochim. Biophys. Acta* 1225(1):53-56 (1993).

Janssen, "Propanol as an end product of theonine fermentation," *Arch. Microbiol.* 182:482-486 (2004).

Jantama et al., "Combining metabolic engineering and metabolic evolution to develop nonrecombinant strains of *Escherichia coli* C that produce succinate and malate," Biotechnol. Bioeng 99(5):1140-1153 (2008).

Jantama et al., "Eliminating Side Products and Increasing succinate Yields in Engineered Strains of *Escherichia coli* C," *Biotechnol. Bioeng.* 101(5) 881-893 (2008).

Javid-Majd and Blanchard, "Mechanistic Analysis of the argE-Encoded N-Acetylornithine Deacetylase," *Biochemistry* 39:1285-1293 (2000).

Jeng et al., "Ornithine degradation in Clostridium sticklandii; pyridoxial phosphate and coenzyme A dependent thiolytic cleavage of 2-amino-4-ketopentanoate to alanine and acetyl coenzyme A," *Biochemistry* 13(14):2898-2903 (1974).

Jenkins and Nunn, "Genetic and molecular characterization of the genes involved in short-chain fatty acid degradation in *Escherichia coli*: the ato system," *J. Bacteriol.* 169(1):42-52 (1987).

Jennert et al., "Gene transfer to *Clostridium cellulolyticum* ATCC 35319," *Microbiol.* 146:3071-3080 (2000).

Jenssen et al., "A literature network of human genes for high-throughput analysis of gene expression,"*Nat. Gene.* 28:21-28 (2001).

Jeon et al., "Heterologous expression of the alcohol dehydrogenase (adhI) gene from *Geobacillius thermoglucosidasius* strain M10EXG," *J. Biotechnol.* 135:127-133 (2008).

Jewell et al., "Bioconversion of propionic, valeric and 4-hydroxybutyric acids into the corresponding alcohols by *Clostridium acetobutylicum* NRRL 527," *Curr. Microbiol.* 13(4):215-219 (1986).

Jiang et al., "De Novo Computational Design of Retro-Aldol Enzymes," *Science* 319: 1387-1391 (2008).

Jin and Sonenshein, "Characterization of the major citrate synthase of *Bacillus subtilis," J. Bacteriol.* 178(12):3658-3660 (1996).

Johanson et al., "Strain engineering for steroselective bioreduction of dicarbonyl compounds by yeast reductases," *FEMS Yeast Res.* 5:513-525 (2005).

Johnson et al., "Alteration of a single amino acid changes the substrate specificity of dihydroflavonol 4-reductase," *Plant J.* 25(3):325-333 (2001).

Johnston et al., "Structure of naphthoate synthase (MenB) from *Mycobacterium tuberculosis* in both native and product-bound forms," *Acta Crystyallogr. D. Biol. Crystallogr.* 61:1199-1206 (2005).

Jojima et al., "Production of isopropanol by metabolically engineered *Escherichia coli," Appl. Microbiol. Biotechnol.* 77:1219-1224 (2008).

Jones and Woods,"Acetone-butanol fermentation revisited," *Microbiol. Rev.* 50(4):484-524 (1986).

Junker and Ramos, "Involvement of the cis/trans isomerase Cti in solvent resistance of *Pseudomonas putida* DOT-T1E," *J. Bacteriol.* 181:5693-5700 (1999).

Kaclikova et al., "Fumaric acid overproduction in yeast mutants deficient in fumarase," *FEMS Microbiol. Lett.* 91(2):101-106 (1992).

Kahng et al., "Characterization of strain HY99, a novel microorganism capable of aerobic and anaerobic degradation of aniline," *FEMS Microbiol Lett.* 190:215-221 (2000).

Kai et al., "Phosphoenolpyruvate carboxylase: three-dimensional structure and molecular mechanisms," *Arch. Biochem. Biophys.* 414:170-179 (2003).

Kakimoto et al., "B-aminoisobutyrate-α-ketoglutarate transaminase in relation to β-aminoisobutyric aciduria," *Biochim. Biophys. Acta* 156(2):374-380 (1968).

Kalapos, "On the mammalian acetone metabolism: from chemistry to clinical implications," *Biochim. Biophys. Acta* 1621(2):122-139 (2003).

Kalousek et al., "Isolation and characterization of propionyl-CoA carboxylase from normal human liver. Evidence for a protomeric tetramer of nonidentical subunits," *J. Biol. Chem.* 255:60-65 (1980).

Kalscheuer and Steinbuchel, "A novel bifunctional wax ester synthase/acyl-CoA:diacylglycerol acyltransferase mediates wax ester and triacylglycerol biosynthesis in *Acinetobacter calcoaceticus* ADP1," *J. Biol. Chem.* 278(10):8075-8082 (2003).

Kalscheuer et al., "Analysis of storage lipid accumulation in *Alcanivorax borkumensis*: Evidence for alternative triacylglycerol biosynthesis routs in bacteria," *J. Bacteriol.* 189(3):918-928 (2007).

Kanagawa, et al., "Characterization of the 6-aminohexanoate-dimer hydrolase from *Pseudomonas* sp. NK87," *J Gen Microbiol*, 139(4):787-795 (1993).

Kanamasa et al., "Cloning and functional characterization of the cis-aconitic acid decarboxylase (CAD) gene from *Aspergillus terreus," Appl. Microbiol. Biotechnol.* 80(2):223-229 (2008).

Kanao et al., "Characterization of isocitrate dehydrogenase from the green sulfur bacterium Chlorbium limicola. A carbon dioxide-fixing enzyme in the reductive tricarboxylic acid cycle," *Eur. J. Biochem.* 269(7):1926-1931 (2002).

Kanaujia et al., "Cloning, expression, purification, crystallization and preliminary X-ray crystallographic study of DHNA synthetase from *GeoBacillus* kaustophilus," *Acta Crystallogr. Sect. F Struct. Biol. Cryst. Commun.* 63(Pt. 2):103-105 (2007).

Kanehisa and Goto, "KEGG: Kyoto Encyclopedia of Genes and Genomes database," Nucleic Acids Res. 28(1):27-30 (2000).

Kapatral et al., "Genome Sequence and Analysis of the Oral Bacterium Fusobacterium nucleatum Strain ATCC 25586," *J. Bacteriol.* 184(7):2005-2018 (2002).

Karyakin et al., "Kinetic properties of L-lysine-2-monooxygenase from Pseufomonas putida and its application to biosensors for L-lysine," *Prikladnaya Biokhimiya I Mikrobiologiya* 27:825-832 (1991).

Kasberg et al., "Cloning, characterization, and sequence analysis of the clcE gene encoding the maleylacetate reductase of *Pseufomonas* sp. Strain B13," *J. Bacteriol.* 179:3801-3803 (1997).

Kaschabek and Reineke, "Degradation of chloroaromatics: purification and characterization of maleylacetate reductase from *Pseudomonas* sp. Strain B13," *J. Bacteriol.* 175:6075-6081 (1993).

Kaschabek and Reineke, "Maleylacetate reductase of *Pseufomonas* sp. Strain B13: specificity of substrate conversion and halide elimination," *J. Bacteriol.* 177:320-325 (1995).

Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase,"*JBacteriol*, 184(1):207-215 (2002).

Kashket and Cao, "Isolation of a Degeneration-Resistant Mutant of *Clostridium acetobutylicum* NCIMB 8052," *Appl. Environ. Microbiol.* 59:4198-4202 (1993).

Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).

Katti, et al., "Crystal structure of muconolactone isomerase at 3.3 Å resolution," *J. Mol. Biol.* 205:557-571 (1989).

Katz et al., "Screening of two complementary collections of *Saccharomyces cerevisiae* to identify enzymes involved in stereo-selective reductions of specific carbonyl compounds: an alternative to protein purification," *Enzyme Microb. Technol.* 33:163-172 (2003).

Kawabata and Kaneyama, "The Effect of Growth Temperature on Wax Ester Content and Composition of *Euglena gracilis" J. Gen. Microbiol.* 135: 1461-1467 (1989).

Kazahaya et al, "Aerobic Dissimilation of Glucose by Heterolactic Bacteria. III. Aldehyde Dehydrogenase and Alcohol Dehydrogenase of Leuconostoc mesenteroides," *J. Gen. Appl. Microbiol.* 18(1):43-55 (1972).

Kefala et al., "Cloning, expression, purification, crystallization and preliminary x-ray diffraction analysis of LysA (Rv1293) from *Mycobacterium tuberculosis," Acta. Crystallog. Sect. F. Struct. Biol. Cryst. Commun.* 61:782-784 (2005).

Kellum and Drake, "Effects of cultivation gas phase on hydrogenase of the acetogen *Clostridium thermoaceticum," J. Bacteriol.* 160(1):466-469 (1984).

Kenealy et al., "Biochemical Aspects of Fumaric Acid Accumulation by *Rhizopus arrhizus*," *Appl. Environ. Microbiol.* 52:128-133 (1986).

Keng and Viola, "Specificity of Aspartokinase III from *Escherichia coli* and Examination of Important Catalytic Residues," *Arch. Biochem. Biophys.* 335(1):73-81 (1996).

Kenklies et al., "Proline biosynthesis from L-ornithine in Clostridium sticklandii: purification of $\Delta^1$-pyrroline-5-carboxylate reductase, and sequence and expression of encoding gene, proC," *Microbiology* 145(Pt 4):819-826 (1999).

Kerby et al., "Carbon Monoxide-Dependent Growth of *Rhodospirillum rubrum*," *J. Bacteriol.* 177:2241-2244 (1995).

Kerby, et al., "Genetic and physiological characterization of the *Rhodospirillum rubrum* carbon monoxide dehydrogenase system," *J. Bacteriol,* 174(16):5284-5294 (1992).

Kern et al., "Isoamyl alcohol-induced morphological change in *Saccharomyces cerevisiae* involves increases in mitochondria and cell wall chitin content," *FEMS Yeast Res.* 5:43-49 (2004).

Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).

Khan et al., "Molecular Properties and Enhancement of Thermostability by Random Mutagenesis of Glutamate Dehydrogenase from *Bacillus subtilis*," *Biosci. Biotechnol. Biochem.* 69(10):1861-1870 (2005).

Killenberg-Jabs et al., "Active oligomeric states of pyruvate decarboxylase and their functional characterization," *Eur. J. Biochem.* 268:1698-1704 (2001).

Kim et al, "Effect of Overexpression of *ActinoBacillus succinogenes* Phosphoenolpyruvate Carboxykinase on Succinate Production in *Escherichia coli*," *Appl. Env. Microbiol.* 70(2) 1238-1241 (2004).

Kim et al., "2-Hydroxyisocaproyl-CoA dehydratase and its activator from Clostridium difficile," *FEBS J.* 272:550-561 (2005).

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).

Kim et al., "Dehydration of (R)-2-hydroxyacyl-CoA to enoyl-CoA in the fermentation of $\alpha$-amino acids by anaerobic bacteria," *FEMS Microbiol. Rev.* 28:455-468 (2004).

Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).

Kim et al., "Studies of the hyperthermophile *Thermotoga maritima* by random sequencing of cDNA and genomic libraries. Identification and sequencing of the *trpEG* (D) operon," *J Mol. Biol.* 231:960-981 (1993).

Kim, "Purification and Properties of a diamine $\alpha$-Ketoglutarate Transminase from *Escherichia coli*," *J. Biol. Chem.* 239(3):783-786 (1964).

Kino et al. Synthesis of DL-tryptophan by modified broad specificity amino acid racemase from Pseudomonas putida IFO 12996, *Appl. Microbiol. Biotechnol.* 73:1299-1305 (2007).

Kinoshita et al., "Purification and characterization of 6-aminohexanoic-acid-oligomer hydrolase of *Flavobacterium* sp. KI72," *Eur. J. Biochem.* 116(3):547-551 (1981).

Kinoshita, "Purification of two alcohol dehydrogenases from Zymomonas mobilis and their properties," *Appl. Microbiol. Biotechnol.* 22:249-254 (1985).

Kisselev L., "Polypeptide release factors in prokaryotes and eukaryotes: same function, different structure" *Structure* 10:8-9 (2002).

Klasson, et al., "Biological conversion of coal and coal-derived synthesis gas," *Fuel* 72(12):1673-1678 (1993).

Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).

Kleanthous et al., "A comparison of the enzymological and biophysical properties of two distinct classes of dehydroquinase enzymes," *Biochem. J.* 282(Pt3):687-695 (1992).

Klyosov, "Kinetics and specificity of human liver aldehyde dehydrogenase toward aliphatic, aromatic, and fused polycyclic aldehydes," *Biochemistry* 35(14):4457-4467 (1996).

Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).

Knappe and Sawers, "A radical-chemical route to acetyl-CoA: the anaerobically induced pyruvate formate-lyase system of *Escherichia coli*," *FEMS. Microbiol. Rev.* 75:383-398 (1990).

Knappe et al., "Post-translational activation introduces a free radical into pyruvate formate-lyase," *Proc. Natl. Acad. Sci. USA* 81:1332-1335 (1984).

Knothe, "'Designer' Biodiesel: Optimizing Fatty Ester Composition to Improve Fuel Properties," *Energy Fuels* 22:1358-1364 (2008).

Kobayashi et al., "Physicochemical, catalytic, and immunochemical properties of fumarases crystallized separately from mitochondrial and cytosolic fractions of rat liver," *J. Biochem.* 89(6):1923-1931 (1981).

Koch and Fuchs, "Enzymatic reduction of benzoyl-CoA to alicyclic compounds, a key reaction in anaerobic aromatic metabolism," *Eur. J. Biochem.* 205:195-202 (1992).

Koch et al., "Products of enzymatic reduction of benzoyl-CoA, a key reaction in anaerobic aromatic metabolism," *Eur. J. Biochem.* 211:649-661 (1993).

Koland and Gennis, "Proximity of Reactive Cysteine Residue and Flavin in *Escherichia coli* Pyruvate Oxidase As Estimated by Flourescence Energy Transfer," *Biochemistry* 21:4438-4442 (1982).

Kollmann-Koch and Eggerer,"Nicotinic acid metabolism. Dimethylmaleate hydratase," *Hoppe Seylers Z Physiol Chem.* 365:s. 847-857 (1984).

Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).

Korbert et al., "Crystallization of the $NADP^+$-dependent Glutamate Dehydrogenase from *Escherichia coli*," *J. Mol. Biol.* 234:1270-1273 (1993).

Kornberg, "The role and control of the glyoxylate cycle in *Escherichia coli*," *Biochem. J.* 99:1-11 (1966).

Korolev et al., "Autotracing of *Escherichia coli* acetate CoA-transferase $\alpha$-subunit structure using 3.4 Å MAD and 1.9 Å native data," *Acta Cryst.* D58:2116-2121 (2002).

Korotkova and Lidstrom, "Connection between poly-$\beta$-hydroxybutyrate biosynthesis and growth on $C_1$ and $C_2$ compounds in the methylotroph Methylobacterium extorquens AM1," *J. Bacteriol.* 183(3):1038-1046 (2001).

Korotkova and Lidstrom, "MeaB is a component of the methylmalonyl-CoA mutase complex required for protection of the enzyme from inactivation," *J. Biol. Chem.* 279(14):13652-13658 (2004).

Kort et al., "Glutamate dehydrogenase from the hyperthermophilic bacterium *Thermotoga maritima*: molecular characterization and phylogenetic implications," *Extremophiles* 1:52-60 (1997).

Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).

Kosjek et al., "Purification and characterization of a chemotolerant alcohol dehydrogenase applicable to coupled redox reactions," *Biotechnol. Bioeng.* 86(1):55-62 (2004).

Kouzarides, "Acetylation: a regulatory modification to rival phosphorylation?" *EMBO J.* 19(6):1176-1179 (2000).

Kovachy et al., "Recognition, Isolation, and Characterization of Rat Liver D-Methylmalonyl Coenzyme A Hydrolase," *J. Biol. Chem.* 258(18):11415-11421 (1983).

Kowalchuk et al., "Contrasting patterns of evolutionary divergence within the *Acinetobacter calcoaceticus* pca operon," *Gene* 146:23-30 (1994).

Kraus et al., "Biosynthesis and mitochondrial processing of the $\beta$ subunit of propionyl Coenzyme A carboxylase from rat liver," *J. Biol. Chem.* 258:7245-7248 (1983).

Kreimeyer et al., "Identification of the Last Unknown Genes in the Fermentation Pathway of Lysine," *J. Biol. Chem.* 282(10):7191-7197 (2007).

Kress et al., "First direct observation of the simultaneous presence and of the interconversion of chain-propagating metal-carbene and metallacyclobutane complexes in a catalytic olefin metathesis reaction: the ring-opening polymerization of norbornene," *J. Am. Chem. Soc.* 109(3):899-901 (1987).

Kress et al., "Tungsten(VI) and molybdenum(VI) oxo-alkyl species. Their role in the metathesis of olefins," *J. Chem. Soc., Chem. Commun.* 431-432 (1980).

Kretz et al., "Gene site saturation mutagenesis: a comprehensive mutagenesis approach," *Methods Enzymol.* 388:3-11 (2004).

Krieger et al., "Pyruvate decarboxylase from Kluyveromyces lactis an enzyme with an extraordinary substrate activation behaviour," *Eur. J. Biochem.* 269:3256-3263 (2002).

Krishna, et al., "Enzymatic synthesis of isoamyl acetate using immobilized lipase from *Rhizomucor miehei*," *J. Biotechnol.* 87:193-201 (2001).

Kuchta and Abeles, "Lactate Reduction in Clostridium propionicum Purification and properties of lactyl-CoA dehydratase" *J. Biol Chem.* 260(24):13181-13189 (1985).

Kühnl et al., "Functional analysis of the methylmalonyl-CoA epimerase from *Caenorhabditis elegans*," *FEBS J.* 272(6):1465-1477 (2005).

Kulkarni and Kanekar, "Bioremediation of ε-carprolactum from nylon-6 waster water by use of *Pseudomonas aeruginosa* MCM B-407," *Curr. Microbiol.* 37(3):191-194 (1998).

Kumamaru et al., "Enhanced degradation of polychlorinated biphenyls by directed evolution of biphenyl dioxygenase," *Nat. Biotechnol.* 16:663-666 (1998).

Kumari et al., "Cloning, Characterization, and Functional Expression of acs, the Gene Which Encodes Acetyl Coenzyme A Synthetase in *Escherichia coli*," *J. Bacteriol.* 177(10): 2878-2886 (1995).

Kuntze et al., "6-Oxocyclohex-1-ene-1-carbonyl-Coenzyme A hydrolases from obligately anaerobic bacteria: characterization and indentification of its gene as a functional marker for aromatic compounds degrading anaerobes," *Environ. Microbiol.* 10(6):1547-1556 (2008).

Kurihara et al., "A Novel Putrescine Utilization Pathway Involves γ-Glutamylated Intermediates of *Escherichia coli* K-12," *J. Biol. Chem.* 280(6):4602-4608 (2005).

Kurihara et al., "Γ-Glutamyputrescine synthetase in the putrescine utilization pathway of *Escherichia coli* K-12," *J. Biol. Chem.* 283(29)19981-19990 (2008).

Kuznetsova et al., "Enzyme genomics: Application of general enzymatic screens to discover new enzymes," *FEMS Microbiol. Rev.* 29(2):263-279 (2005).

Kwok and Hanson, "GFP-labelled Rubisco and aspartate aminotransferase are present in plastid stromules and traffic between plastids," *J. Exp. Bot.* 55(397):595-604 (2004).

Kwon et al., "Influence of gluconegoenic phosphoenolpyruvate carbosykinase (PCK) expression on succinic acid fermentation in *Escherichi coli* under high bicarbonate condition," *J. Microbiol. Biotechnol.* 16(9):1448-1452 (2006).

Laempe et al., "6-Hydroxycyclohex-1-ene-1-carbonyl-CoA dehydrogenase and 6-oxocyclohex-1-ene-1-carbonyl-CoA hydrolase, enzymes of the benzoyl-CoA pathway of anaerobic aromatic metabolism in the denitrifying bacterium Thauera aromatica," *Eur. J. Biochem.* 263(2):420-429 (1999).

Laivenieks et al., "Cloning sequencing, and overexpression of the Anaerobiospirillum succinicproducens phosphoenolpyruvate carboxykinase (*pckA*) gene," *Appl. Environ. Microbiol.* 63:2273-2280 (1997).

Lam and Winkler, "Metabolic Relationships between Pyridoxine (Vitamin $B_6$) and Serine Biosynthesis in *Escherichia coli* K-12," *J. Bacteriol.* 172(11):6518-6528 (1990).

Lamas-Maceiras et al., "Amplification and disruption of the phenylacetyl-CoA ligase gene of *Penicillium chrysogenum* encoding an aryl-capping enzyme that supplies phenylacetic acid to the isopenicillin N-acyltransferase," *Biochem J*, 395(1):147-155 (2006).

Lamed and Zeikus, "Novel NADP-linked alcohol-aldehyde/ketone oxidoreductase in thermophilic ethanologenic bacteria," *Biochem. J.* 195:183-190 (1981).

Lardizabal, et al., "Purification of a jojoba embryo wax synthase, cloning of its cDNA, and production of high levels of wax in seeds of transgenic arabidopsis," *Plant Physiol.* 122(3):645-655 (2000).

Lawrence and Roth, "Evolution of Coenzyme $B_{12}$ synthesis among enteric bacteria: evidence for loss and reacquisition of a multigene complex," *Genetics*142(1):11-24 (1996).

Lawrence and Roth, "The cobalamin (Coenzyme $B_{12}$) biosynthetic genes of *Escherichia coli*," *J. Bacteriol.* 177(22):6371-6380 (1995).

Lebbink et al., "Engineering activity and stability of *Thermotoga maritima* glutamate dehydrogenase I. Introduction of a six-residue ion-pair network in the hinge region," *J. Mol. Biol.* 280:287-296 (1998).

Lebbink et al., "Engineering Activity and Stability of *Thermotoga maritima* glutamate Dehydrogenase. II: construction of a 16-Residue Ion-pair Network at the Subunit Interface," *J. Mol. Biol.* 289:357-369 (1999).

Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).

Lee and Cho, "Identification of essential active-site residues in ornithing decarboyxlase of Nicotiana glutinosa decarboxylating both L-ornithine and L-lysine," *Biochem. J.* 360:657-665 (2001).

Lee et al., "A new approach to directed gene evolution by recombined extension on truncated templates (RETT)," *J. Molec. Catalysis* 26:119-129 (2003).

Lee et al., "Batch and continuous cultivation of *Anaerobiospirillum succiniciproducens* for the production of succinic acid from whey," *Appl. Microbiol. Biotechnol.* 54(1):23-27 (2000).

Lee et al., Biological conversion of wood hydrolysate to succinic acid by *Anaerobiospirillum succiniciproducens. Biotechnol. Lett.* 25(2):111-114 (2003).

Lee et al., "Biosynthesis of enantiiopure (S)-3-hydroxybutyric acid in metabolically engineered *Escherichia coli*," *App. Microbiol. Biotechnol.* 79:633-641 (2008).

Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).

Lee et al., "Cloning and Characterization of *Mannheimia succiniciproducens* MBEL55E Phosphoenolpyruvate Carboxykinase (*pckA*) Gene," *Biotechnol. Bioprocess Eng.* 7:95-99 (2002).

Lee et al., "Fermentative production of chemicals that can be used for polymer synthesis," *Macromol. Biosci.* 4:157-164 (2004).

Lee et al., "Genome-based metabolic engineering of *Mannheimia succiniciproducens* for succinic acid productiion," *Appl. Environ. Microbiol.* 72(3):1939-1948 (2006).

Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).

Lee et al., "Phylogenetic diversity and the structural basis of substrate specificity in the β/α-barrel fold basic amino acid decarboxylases," *J. Biol. Chem.* 282:27115-27125 (2007).

Lee et al., "Metabolic engineering of *Escherichia coli* for enhanced production of succinic acid, based on genome comparison and in silico gene knockout simulation," *Appl Environ Microbiol.* 71(12):7880-7887 (2005).

Lehtiö and Goldman, "The pyruvate format lyase family: sequences, structures and activation," *Protein Eng. Des.Sel.* 17:545-552 (2004).

Lehtiö et al., "Crystal structure of glycyl radical enzyme from *Archaeoglobus fulgidus*," *J. Mol. Biol.* 357(1):221-235 (2006).

Lei et al., "A shared binding site for NAD+ and Coenzyme A in an acetaldehyde dehydrogenase involved in bacterial degradation of aromatic compounds," *Biochemistry* 47:6870-6882 (2008).

Lemoine et al., "Microcorrespondence: Monofunctional biosynthetic peptidoglycan transglycosylases," *Mol. Microbiol.* 19(3):639-647 (1996).

Lemonnier and Lane, "Expression of the second lysine decarboxylase gene of *Escherichia coli*," *Microbiology* 144(Pt 3):751-760 (1998).

Lenski and Travisano, "Dynamics of adaptation and diversification: a 10,000-generation experiment with bacterial populations," *Proc. Natl. Acad. Sci. USA.* 91(15):6808-6814 (1994).

Leonardo et al., "Anaerobic Regulation of the *adhE* gene, Encoding the Fermentative Alcohol Dehydrogenase of *Escherichia coli*," *J. Bacteriology*. 175(3):870-878 (1993).

Lepore et al., "The x-ray crystal structure of lysine-2,3-aminomutase from Clostridium subterminale," *Proc. Natl. Acad. Sci USA* 102:13819-13824 (2005).

Leppänen et al., "Pyruvate formate lyase is structurally homologous to type I ribonucleotide reductase," *Structure* 7:733-744 (1999).

Lessner et al., "An unconventional pathway for reduction of $CO_2$ to methane in CO-grown *Methanosarcina acetivorans* revealed by proteomics," *Proc. Natl. Acad. Sci. USA* 103(47):17921-17926 (2006).

Leutwein and Heider, "Succinyl-CoA(R)-benzylsuccinate CoA-Transferase: an enzyme of the anaerobic toluene catabolic pathway in denitrifying bacteria," *J. Bacteriol.* 183(14):4288-4295 (2001).

Levanon S. S., et al., "Effect of Oxygen on the *Escherichia coli* ArcA and FNR Regulation Systems and Metabolic Responses," *Biotechnol Bioeng.* 89(5):556-564 (2005).

Li and Jordan, "Effects of substitution of tryptophan 412 in the substrate activation pathway of yeast pyruvate decarboxylase," *Biochemistry* 38:10004-10012 (1999).

Li et al., "Properties of Nicotinamide Adenine Dinucleotide Phosphate-Dependent Formate Dehydrogenase from *Clostridium thermoaceticum*," *J Bacteriol*. 92(2):405-412 (1966).

Li et al., "Purification, crystallization and preliminary crystallographic studies on 2-dehydro-3-deoxygalactarate aldolase from *Leptospira interrogans*," *Acta. Cryst*. F62:1269-1270 (2006).

Lian and Whitman, "Stereochemical and Isotopic Labeling Studies of 4-Oxalocrotonate Decarboxylase and Vinylpyruvate hydratase: Analysis and Mechanistic Implications," *J. Am. Chem Soc.* 116:10403-10411 (1994).

Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng*. 7(5-6):337-352 (2005).

Lin et al., "Functional Expression of Horseradish Peroxidase in *E. coli* by Directed Evolution," *Biotechnol. Prog*. 15:467-471 (1999).

Lin et al., "Effect of carbon sources differing in oxidation state and transport route on succinate production in metabolically engineered *Escherichia coli*," *J. Ind. Microbiol. Biotechnol*. 32:87-93 (2005).

Lin et al., "Fed-batch culture of a metabolically engineered *Escherichia coli* strain designed for high-level succinate production and yield under aerobic conditions," *Biotechnol. Bioeng*. 90:775-779 (2005).

Lin et al., "Genetic Reconstruction of the Aerobic Central Metabolism in *Escherichia coli* for the Absolute Aerobic Production of Succinate," *Biotechnol. Bioeng*. 89(2):148-156 (2005).

Lin et al., "Increasing the Acetyl-CoA pool in the Presence of Overexpressed Phosphoenolpyruvate Carboxylase or Pyruvate Carboxylase Enhances Succinate Production in *Escherichia coli*," *Biotechnol Prog*. 20(5):1599-1604 (2004).

Lin et al., "Metabolic engineering of aerobic succinate production systems in *Escherichia coli* to improve process productivity and achieve the maximum theoretical succinate yield," *Metab Eng*. 7(2):116-127 (2005).

Lin, "Metabolic Network Design and Engineering in *Escherichia coli*" Ph.D. Thesis, Rice University, Dept. of Bioengineering (2005).

Lin, H et al., "Effect of *Sorghum vulgare* phosphoenolpyruvate carboxylase and *Lactococcus lactis* pyruvate carboxylase coexpression on succinate production in mutant strains of *Escherichia coli*," *Appl Microbiol Biotechnol*. 67(4): 515-523 (2005).

Lingen et al., "Alteration of the substrate specificity of benzoylformate decarboxylase from *Pseudomonas putida* by directed evolution," *Chembiochem*. 4:721-726 (2003).

Lingen et al., "Improving the carboligase activity of benzoylformate decarboxylase from *Pseudomonas putida* by a combination of directed evolution and site-directed mutagenesis," *Protein Eng*. 15:585-593 (2002).

Link et al., "Methods for generating precise deletions and insertions in the genome of wild-type *Eshcerichia coli*: application to open reading frame characterization," *J. Bacteriol*. 179:6228-6237 (1997).

Liou et al., "*Clostridium carboxidivorans* sp. nov., a solvent-producing clostridium isolated from an agricultural settling lagoon, and reclassification of the acetogen *Clostridium scatologenes* strain SL1 as *Clostridium drakei* sp. nov.," *Int. J. Syst. Evol. Microbiol*. 55(Pt 5):2085-2091 (2005).

Liu et al., "Kinetic and crystallographic analysis of active site mutants of *Escherichia coli* γ-aminobutyrate aminotransferase," *Biochemistry*, 44:(8):2982-2992 (2005).

Liu et al., "Microbial production of R-e-hydroxybutyric acid by recombinant *E. coli* harboring genes of phbA, phbB , and tesB," *Appl. Microbiol. Biotechnol* 76:811-818 (2007).

Liu et al., "Purification and characterization of ornithine acetyltransferase from *Saccharomyces cerevisiae*," *Eur. J. Biochem*. 228:291-296 (1995).

Liu et al., "Crystal structures of unbound and aminooxyacetate-bound *Escherichia coli* γ-aminobutyrate aminotransferase," *Biochem*. 43(34):10896-10905 (2004).

Liu et al., "Economical succinic acid production from cane molasses by *ActinoBacillus succinogenes*. " *Bioresour Technol* 99(6):1736-1742 (2008).

Ljungdahl and Andreesen, "Formate dehydrogenase, a selenium-tungsten enzyme from Clostridium thermoaceticum," *Methods Enzymol*. 53:360-372 (1978).

Ljungdahl and Andreesen, "Tungsten, a component of active formate dehydrogenase from *Clostridium thermoacetium*," *FEBS Lett*. 54:279-282 (1975).

Ljungdahl, "The Autotrophic Pathway of Acetate Synthesis in Acetogenic Bacteria," *Ann. Rev. Microbiol*. 40:415-450 (1986).

Lloyd-Jones et al., "Rate Enhancement by Ethylene in the Ru-Catalyzed Ring-Closing Metathesis of Enynes: Evidence for an "Ene-then-Yne" Pathway that Diverts through a Second Catalytic Cycle," Angew Chem Int Ed. 44(45):7442-7447 (2005).

Locher et al., "Crystal structure of the Acidaminococcus fermentans 2-hydroxyglutaryl-CoA dehydratase component A" J. Mol. Biol. 307(1):297-308 (2001).

Lokanath et al., "Crystal structure of novel NADP-dependent 3-hydroxyisobutyrate dehydrogenase from Thermus thermophilus HB8," *J. Mol. Biol*. 352(4):905-917 (2005).

Loke et al., "Active acetyl-CoA synthase from *Clostridium thermoaceticum* obtained by cloning and heterologous expression of acsAB in *Escherichia coli*," *Proc Natl Acad Sci U S A*. 97:12530-12535 (2000).

Longtine et al., "Additional modules for versatile and economical PCR-based gene deletion and modification in *Saccharomyces cerevisiae*," *Yeast* 14(10):953-961 (1998).

Lopez-Barragan et al., "The *bzd* gene cluster, coding for anaerobic benzoate catabolism, in *Azoarcus* sp. Strain CIB," *J. Bacteriol*. 186(17):5762-5774 (2004).

Louie and Chan, "Cloning and characterization of the γ-glutamyl phosphate reductase gene of *Campylobacter jejuni*," *Mol. Gen. Genet*. 240:29-35 (1993).

Louis et al., "Restricted distribution of the butyrate kinase pathway among butyrate-producing bacteria from the human colon," *J. Bacteriol*. 186:2099-2106 (2004).

Lovell et al., "Cloning and expression in *Escherichia coli* of the *Clostridium thermoaceticum* gene encoding thermostable formyltetrahydrofolate synthetase," *Arch. Microbiol*. 149(4):280-285 (1988).

Lovell, et al., "Primary structure of the thermostable formyltetrahydrofolate synthetase from *Clostridium thermoaceticum*," *Biochemistry* 29:5687-5694 (1990).

Low et al., "Mimicking somatic hypermutation: affinity maturation of antibodies displayed on baceriophage using a bacterial mutator strain," *J. Mol. Biol*. 260(3):359-368 (1996).

Lu et al., "Controlled Poetntial Enzymology of Methyl Transfer Reactions Involved in Acetyl-CoA Synthesis by CO Dehydrogenase and the Corrinoid/Iron-Sulfur Protein from *Clostridium thermoaceticum*," *J. Biol. Chem*. 265(6):3124-3133 (1990).

Lu et al., "Functional Analysis and Regulation of the Divergent spuABCDEFGH-spuI Operons for Polyamine Uptake and Utilization in *Pseudomonas aeruginosa* PAO1," *J. Bacteriol*. 184(14):3765-3773 (2002).

Lu et al., "Sequence and expression of the gene encoding the corrinoid/iron-sulfur protein from *Clostridium thermoaceticum* and reconstitution of the recombinant protein to full activity," *J. Biol. Chem.* 268(8):5605-5614 (1993).

Lüersen, "Leishmania major thialsine N$^\epsilon$-acetyltransferase: Identification of amino acid residues crucial for substrate binding," *FEBS Lett.* 579:5347-5352 (2005).

Luli and Strohl "Comparison of Growth, Acetate Production, and Acetate Inhibition of *Escherichia coli* Strains in Batch and Fed-Batch Fermentations," *Appl Environ Microbiol.* 56:1004-1011 (1990).

Lupa et al., "Distribution of genes encoding the microbial non-oxidative reversible hydroxyarylic acid decarboxylases/phenol carboxylases," *Genomics* 86(342-351 (2005).

Lupa et al., "Properties of the reversible nonoxidative vanillate/4-hydroxybenzoate decarboxylase from *Bacillus subtilis*," *Can. J Microbiol* 54:75-81 (2008).

Lütke-Eversloh and Steinbüchel, "Biochemical and molecular characterization of a succinate semialdehyde dehydrogenase involved in the catabolism of 4-hydroxybutyric acid in *Ralstonia eutropha*," *FEMS Microbiol. Lett.* 181(1):63-71 (1999).

Lutz and Bujard, "Independent and tight regulation of transcriptional units in *Escherichia coli* via the LacR/O, the TetR/O and AraC/I$_1$-I$_2$ regulatory elements," *Nucleic Acids Res.* 25(6):1203-1210 (1997).

Lutz et al., "Creating multiple-crossover DNA libraries independent of sequence identity," *Proc. Natl. Acad. Sci USA* 98:11248-11253 (2001).

Lutz et al., "Dissecting the functional program of *Escherichia coli* promoters: the combined mode of action of Lac repressor and AraC activator," *Nucleic Acids Res.* 29(18):3873-3881 (2001).

Lutz et al., "Rapid generation of incremental truncation libraries for protein enginering using α-phosphothioate nucleotides," *Nucleic Acids Res.* 29:E16 (2001).

Lynch et al., "SCALEs: multiscale analysis of library enrichment," *Nat. Methods* 4(1):87-93 (2007).

Lynd et al., "Microbial Cellulose Utilization: Fundamentals and Biotechnology," *Microbiol. Mol. Biol. Rev.* 66:506-577 (2002).

Lynn et al., "Living Ring-Opening Metathesis Polymerization in Aqueous Media Catalyzed by Well-Defined Ruthenium Carbene Complexes," J. Am. Chem. Soc. 118(4):784-790 (1996).

Lynn et al., "Living Ring-Opening Metathesis Polymerization in Water," J. Am. Chem. Soc. 120(7):1627-1628 (1998).

Ma et al., "Induced rebuilding of aspartase conformation," *Ann. NY Acad. Sci.* 672:60-65 (1992).

Macis et al., "Properties and sequence of the Coenzyme B$_{12}$-dependent glycerol dehydratase of *Clostridium pasteruianum*," *FEMS Microbiol. Lett.* 164:21-28 (1998).

Mack and Buckel, "Conversion of glutaconate CoA-transferase from *Acidaminococcus fermentans* into an acyl-CoA hydrolase by site-directed mutagenesis," *FEBS Lett.* 405(2):209-212 (1997).

Mack et al., "Location of the two genes encoding glutaconate Coenzyme A-transferase at the beginning of the hydroxyglutarate operon in Acidaminococcus fermentans," *Eur. J. Biochem.* 226:41-51 (1994).

Maeda et al., "Enhanced hydrogen production from glucose by metabolically engineered *Escherichia coli*," *Appl. Microbiol. Biotechnol.* 77:879-890 (2007).

Maeder et al., "The *Methanosarcina barkeri* genome: comparative analysis with *Methanosarcina acetivorans* and Methanosarcina mazei reveals extensive rearrangement within methanosarcinal genomes," *J. Bacteriol.* 188(22):7922-7931 (2006).

Maes et al., "Crystallization of ornithine acetyltransferase from yeast by counter-diffusion and preliminary x-ray study," *Acta Cryst* F62:1294-1297 (2006).

Mahadevan and Schilling, "The effects of alternate optimal solutions in constraint-based genome-scale metabolic models," *Metab. Eng.* 5(4):264-276 (2003).

Mahan and Csonka, "Genetic analysis of the proBA genes of *Salmonella typhimurium*: physical and genetic analyses of the cloned proB$^+$ A$^+$ genes of *Escherichia coli* and of a mutant allele that confers proline overproduction and enhanced osmotolerance," *J. Bacteriol.* 156:1249-1262 (1983).

Mai and Adams, "Purification and characterization of two reversible and ADP-dependent acetyl Coenzyme A synthetases from the hyperthermophilic archaeon *Pyrococcus furiosus*," *J. Bacteriol.* 178:5897-5903 (1996.).

Maicas, S. et al., "Nad(P)H regeneration is the key for heterolactic fermentation of hexoses in *Oenococcus oeni*," *Microbiology* 148:325-332 (2002).

Maitra and Sprinson, "5-Dehydro-3-deoxy-D-arabino-heptulosonic acid 7-phosphate. An intermediate in the 3-dehydroquinate synthase reaction," *J Biol. Chem.* 253:5426-5430 (1978).

Majewski and Domach, "Simple Constrained-Optimization View of Acete Overflow in *E. coli*," *Biotechnol. Bioeng.* 35(7):732-738 (1990).

Maklashina et al., "Anaerobic expression of *Escherichia coli* succinate dehydrogenase: functional replacement of fumarate reductase in the respiratory chain during anaerobic growth," *J. Bacteriol.* 180(22):5989-5996 (1998).

Manjasetty et al., "Crystallization and preliminary X-ray analysis of dmpFG-encoded 4-hydroxy-2-ketovalerate aldolase-aldehyde dehydrogenase (acylating) from *Pseudomonas* sp. strain CF600," *Acta Crystallogr. D. Biol. Crystallogr.* 57:582-585 (2001).

Manning and Pollitt, "Tracer studies of the interconversion of R- and S-methylmalonic semialdehydes in man," *Biochem. J.* 231(2):481-484 (1985).

Marco-Marín et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).

Marek and Henson, "Cloning and expression of the *Escherichia coli* K-12 sad gene," *J. Bacteriol.* 170:991-994 (1988).

Marks et al., "Molecular cloning and characterization of (R)-3-hydroxybutyrate dehydrogenase from human heart," *J. Biol. Chem.* 267(22):15459-15463 (1992).

Martin et al., "Engineering a mevalonate pathway in *Escherichia coli* for production of terpenoids," *Nat. Biotechnol.* 21:796-802 (2003).

Martin et al., "Nematode.net update 2008: improvements enabling more efficient data mining and comparative nematode genomics," *Nucleic Acids Res.* 37:D571-D578 (2009).

Martínez-Blanco, et al, "Purification and biochemical characterization of phenylacetyl-CoA ligase from *Pseudomonas putida*. A specific enzyme for the catabolism of phenylacetic acid," *J. Biol. Chem.* 265(12):7084-7090 (1990).

Martinez-Carrion and Jenkins, "D-Alanine-D-glutamate transminase. I. Purification and characterization," *J. Biol. Chem.* 240(9):3538-3546 (1965).

Martins et al., "Crystal structure of 4-hydroxybutyryl-CoA dehydratase: radical catalysis involving a [4Fe-4S] cluster and flavin," *Proc. Natl. Acad. Sci. USA* 101(44):15645-15649 (2004).

Mason and Dufour, "Alcohol acetyltransferases and the significance of ester synthesis in yeast," *Yeast* 16(14):1287-1298 (2000).

Matiasek et al., "Volatile ketone formation in bacteria: release of 3-oxopentanoate by soil pseudomonads during growth on heptanoate," *Curr. Microbiol.* 42:276-281 (2001).

Mat-Jan et al., "Mutants of *Escherichia coli* Deficient in the Fermentative Lactate Dehydrogenase," *J. Bacteriol.* 171(1):342-348 (1989).

Matsumura et al., "Constitutive expression of catABC genes in the aniline-assimilating bacterium *Rhodococcus* species AN-22: production, purification, characterization and gene analysis of CatA, CatB and CatC," *Biochem. J.* 393:219-226 (2006).

Matsushima et al., "An enone reductase from Nicotiana tabacum: cDNA cloning, expression in *Escherichia coli*, and reduction of enones with the recombinant proteins," *Bioorg. Chem.* 36:23-28 (2008).

Mattevi et al., "Atomic structure of the cubic core of the pyruvate dehydrogenase multienzyme complex," *Science* 255(5051):1544-1550 (1992).

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

Maurus, et al., "Insights into the Evolution of Allosteric Properties. The NADH Binding Site of Hexameric Type II Citrate Synthases," *Biochemistry* 42:5555-5565 (2003).

Mavrovouniotis, Estimation of standard Gibbs energy changes of biotransformations, *J. Biol. Chem.* 266:14440-14445 (1991).

Maynard et al., "Autocatalytic activation of acetyl-CoA synthase," *J. Biol. Inorg. Chem.* 9:316-322 (2004).

Mazur et al., "Cis,cis-muconate lactonizing enzyme from Trichosporon cutaneum: evidence for a novel class of cycloisomerases in eucaryotes," *Biochemistry* 33:1961-1970 (1994).

McAlister-Henn and Thompson, "Isolation and expression of the gene encoding yeast mitochondrial malate dehydrogenase," *J. Bacteriol.* 169:5157-5166 (1987).

McCarthy et al., "Crystal structure of methylmalonyl-Coenzyme A epimerase from *P. shermanii*: a novel enzymatic function on an ancient metal binding scaffold," *Structure* 9(7):637-646 (2001).

McCullough et al., "Enzymatic decarboxylation of the aminobenzoates," *J. Am. Chem. Soc.* 79:628-630 (1957).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McInerney et al., "The genome of Syntrophus aciditrophicus: Life at the thermodynamic limit of microbial growth," *Proc. Natl. Acad. Sci USA* 104:7600-7605 (2007).

McPherson and Wootton, "Complete nucleotide sequence of the *Escherichia coli* gdhA gene," Nucleic Acids Res. 11:5257-5266 (1983).

Meagher, "Purification and partial amino acid sequence of the cyanogen bromide fragments of muconolactone isomerase from *Pseudomonas putida*," *Biochim. Biophys. Acta* 494:33-47 (1977).

Mechichi et al., "Alicycliphilus denitrificans gen. nov., sp. nov., a cyclohexanol-degrading, nitrate-reducing β-proteobacterium," *Int. J. Syst. Evol. Microbiol.* 53:147-152 (2003).

Megraw et al., "Formation of lactyl-Coenzyme A and pyruvyl-Coenzyme A from lactic acid by *Escherichia coli*," *J. Bacteriol.* 90(4):984-988 (1965).

Meinnel et al., "Structural and Biochemical Characterization of the *Escherichia coli* argE Gene Product," *J. Bacteriol.* 174(7):2323-2331 (1992).

Melchiorsen et al., "The level of pyruvate-formate lyase controls the shift from homolactic to mixed-acid product formation in *Lactococcus lactis*," *Appl. Microbiol. Biotechnol.* 58:338-344 (2002).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

Meng and Li, "Cloning, expression and characterization of a thiolase gene from Clostridium pasteurianum," *Biotechnol. Lett.* 28(16):1227-1232 (2006).

Menon and Ragsdale, "Mechanism of the Clostridium thermoaceticum pyruvate:ferredoxin oxidoreductase: evidence for the common catalytic intermediacy of the hydroxyethylthiamine pyropyrosphate radical," *Biochemistry* 36(28):8484-8494 (1997).

Menzel et al., "Enzymatic evidence for an involvement of pyruvate dehydrogenase in the anaerobic glycerol metabolism of *Klebsiella pneumoniae*," *J. Biotech.* 56:135-142 (1997).

Menzel et al., "Kinetic, dynamic, and pathway studies of glycerol metabolism by *Klebsiella pneumoniae* in anaerobic continuous culsutre: IV. Enzynmes and fluxes of pyruvate metabolism," *Botechnol. Bioeng.* 60(5):617-626 (1998).

Merkel and Nichols, "Characterization and sequence of the *Escherichia coli* panBCD gene cluster," *FEMS Microbiol. Lett.* 143(2-3):247-252 (1996).

Metz et al., "Purification of a jojoba embryo fatty acyl-Coenzyme A reductase and expression if its cDNA in high erucic acid rapeseed," *Plant Phys.* 122:635-644 (2000).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli*," *Appl. Environ. Microbiol.* 62(5):1808-1810 (1996).

Miller and Jenesel, "Enzymology of butyrate Formation by Butyrivibrio-Fibrisolvens," *J. Bacteriol.* 138:99-104 (1979).

Miller et al., "Structure of β-lactam synthetase reveals how to synthesize antibiotics instead of asparagine," *Nat. Struct. Biol.* 8(8):684-689 (2001).

Miller et al., "The catalytic cycle of β-lactam synthetase observed by x-ray crystallographic snapshots," *Proc. Natl. Acad. Sci. USA* 99(23):14752-14757 (2002).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono et al., "Properties of L-lysine ε-dehydrogenase from *Agrobacterium tumefaciens*," *J. Biochem.* 105(6):1002-1008 (1989).

Miyazaki et al., "α-Aminoadipate aminotransferase from an extremely thermophilic bacterium, *Thermus thermophilus*," *Microbiology* 150:2327-2334 (2004).

Mizobata et al., "Purification and characterization of a thermostable class II fumarase from Thermus thermophilus," *Arch. Biochem. Biophys.* 355(1):49-55 (1998).

Mizugaki et al. "Studies on the metabolism of unsaturated fatty acids. IX. Stereochemical studies of the reaction catalyzed by trans-2-enoyl-Coenzyme a reductase of *Escherichia coli*," *J. Biochem.* 92(5):1649-1654 (1982).

Mizugaki et al., "Studies on the Metabolism of Unsaturated Fatty Acids. V. Isomerization of Thiol Esters of cis-2-Alkenoic Acids during Their Preparation and Alkaline Hydrolysis," *Chem. Pharm. Bull.* 30(1):206-213 (1982).

Momany et al., "Crystallization of diaminopimelate decarboxylase from *Escherichia coli*, a stereo specific D-amino-acid decarboxylase," *Acta Cryst.* D58:549-552 (2002).

Momany et al., "Crystallographic Structure of PLP-Dependent Ornithine Decarboxylase from *LactoBacillus* 30a to 3.0 Å Resolution," *J. Mol. Biol.* 252:643-655 (1995).

Monnet et al., "Regulation of branched-chain amino acid biosynthesis by α-acetolactate decarboxylase in *Streptococcus thermophilus*," *Lett. Appl. Microbiol.* 36(6):399-405 (2003).

Moon et al., "Metabolic engineering of *Escherichia coli* for the production of malic acid, "*Biochem. Eng. J.* 40(2):312-320 (2008).

Moore et al., "Expression and Purification of Aspartate β-Semialdehyde Dehydrogenase from Infectious Microorganisms," *Protein Expr. Purif.* 25:189-194 (2002).

Moresi et al., "Fumaric acid production from hydrolysates of starch-based substrates," *J. Chem. Technol. Biotechnol.* 54(3):283-290 (1992).

Mori et al., "Characterization, Sequencing, and Expression of the Genes Encoding a Reactivating Factor for Glycerol-inactivated Adenosylcobalamin-dependent Diol Dehydratase," *J. Biol. Chem.* 272(51):32034-32041 (1997).

Morris and Jinks-Robertson, "Nucleotide sequence of the LYS2 gene of *Saccharomyces cerevisiae*: homology to *Bacillus* brevis tyrocidine synthetase 1," *Gene* 98:141-145 (1991).

Morsomme et al., "Single point mutations in various domains of a plant plasma membrane $H^+$-ATPase expressed in *Saccharomyces cerevisiae* increase $H^+$-pumping and permit yeast growth at low pH,"*EMBO. J.* 15(20):5513-5526 (1996).

Morton et al., "Cloning, sequencing, and expression of genes encoding enzymes of the autotrophic acetyl-CoA pathway in the acetogen *Clostridium thermoaceticum*," In M. Sebald (ed.), *Genetics and molecular biology of anaerobic bacteria*, Springer Verlag, New York, 389-406 (1992).

Morton et al., "The primary structure of the subunits of carbon monoxide dehydrogenase/acetyl-CoA synthase from *Clostridium thermoaceticum*," *J. Biol. Chem.* 266(35):23824-23828 (1991).

Moskowitz et al., "Metabolism of poly-β-hydroxybutyrate. II. Enzymatic synthesis of D-(-)-β—hydroxybutyryl coenzyme A by an enoyl hydrase from rhodospirillum rubrum," *Biochemistry* 8:2748-2755 (1969).

Moszer, "The complete genome of *Bacillus subtilis*: from sequence annotation to data management and analysis," *FEBS Lett.* 430:28-36 (1998).

Mouttaki et al., "Cyclohexane Carboxylate and Benzoate Formation from Crotonate in Syntrophus aciditrophicus," *Appl. Environl. Microbiol.* 73(3):930-938 (2007).

Müh et al., "4-Hydroxybutyryl-CoA dehydratase from *Clostridium aminobutyricum*: characterization of FAD and iron-sulfur clusters involved in an overall non-redox reaction," *Biochemistry* 35:11710-11718 (1996).

Müh et al., "Mossbauer study of 4-hydroxybutyryl-CoA dehydratase probing the role of an iron-sulfur cluster in an overall non-redox reaction," *Eur. J. Biochem.* 248:380-384 (1997).

Mukhopadhyay and Purwantini, "Pyruvate carboxylase from Mycobacterium smegmatis: stabilization, rapid purification, moleculare and biochemical characterization and regulation of the cellular level," *Biochim. Biophys. Acta.* 1475(3):191-206 (2000).

Muller and Buckel, "Activation of (R)-2-hydroxyglutaryl-CoA dehydratase from Acidaminococcus fermentans" Eur. J. Biochem. 230(2):698-704 (1995).

Muller et al., "Nucleotide exchange and excision technology (NExT) DNA shuffling; a robust method for DNA fragmentation and directed evolution," *Nucleic Acids Res.* 33:e117 (2005).

Müller, "Energy Conservation in Acetogenic Bacteria," *Appl. Environ. Microbiol.* 69:6345-6353 (2003).

Murakami et al., "Purification and characterization of two muconate cycloisomerase isozymes from aniline-assimilating Frateuria species ANA-18," *Biosci. Biotechnol. Biochem.* 62:1129-1133 (1998).

Muratsubaki and Enomoto, "One of the fumarate reductase isoenzymes from *Saccharomyces cerevisiae* is encoded by the OSM1 gene," *Arch. Biochem. Biophys.* 352:175-181 (1998).

Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen *Methanococcus jannaschii*," *J. Bacteriol.* 184(3):636-644 (2002).

Muyrers et al., "Rapid modification of bacterial artificial chromosomes by ET-recombination," *Nucleic Acids Res.* 27:1555-1557 (1999).

Nagasawa et al., "Cloning and Nucleotide Sequence of the Alcohol Acetyltransferase II gene (ATF2) from *Saccharomyces cerevisiae* Kyokai No. 7," Biosci. Biotechnol. Biochem. 62:1852-1857 (1998).

Nagata et al., "Gene cloning, purification, and characterization of thermostable and halophilic leucine dehydrogenase from a halophilic thermophile, Bacillus licheniformis TSN9," *Appl. Microbiol. Biotechnol.* 44:432-438 (1995).

Naggert et al., "Cloning, sequencing, and characterization of *Escherichia coli* thioesterase II," *J. Biol. Chem.* 266(17):11044-11050 (1991).

Nahvi et al., "Genetic Control by a Metabolite Binding mRNA," *Chem. Biol.* 9:1043-1049 (2002).

Naidu and Ragsdale, "Characterization of a three-component vanillate O-demethylase from *Moorella thermoacetica*," *J. Bacteriol.* 183(11):3276-3281 (2001).

Najafpour and Younesi, "Ethanol and acetate synthesis from waste gas using batch culture of Clostridium ljungdahlii," *Enzyme Microb. Technol.* 38:223-228 (2006).

Najmudin et al., "Purification, crystallization and preliminary X-ray crystallographic studies on acetolactate decarboxylase," *Acta Crystallog. D. Biol. Crystallogr.* (Pt6):1073-1075 (2003).

Nakahigashi and Inokuchi, "Nucleotide sequence of the fadA and fadB genes from *Escherichia coli*," *Nucleic Acids Res.* 18(16):4937 (1990).

Nakano et al., "Characterization of Anaerobic Fermentative Growth of *Bacillus subtilis*: Identification of Fermentation End Products and Genes Required for Growth," *J. Bacteriol.* 179(21):6749-6755 (1997).

Nakazawa et al., "Studies on monooxygenases. V. Manifestation of amino acid oxidase activity by L-lysine monooxygenase," *J. Biol. Chem.* 247:3439-3444 (1972).

Namba et al., "Coenzyme A- and Nicotinamide Adenine Dinucleotide-dependent Branched Chain α-Keto Acid Dehydrogenase. I. Purification and properties of the enzyme from Bacillus subtilis," *J. Biol. Chem.* 244(16):4437-4447 (1969).

Neidhart et al., "Mandelate racemase and muconate lactonizing enzyme are mechanistically distinct and structurally homologous," *Nature* 347:692-694 (1990).

Ness et al., "Synthetic shuffling expands functional protein diversity by allowing amino acids to recombine independently," *Nat. Biotechnol.* 20:1251-1255 (2002).

Nicolaou et al., "The Diels-Alder Reaction in Total Synthesis," *Angew Chemie Int Ed.* 41:1668-1698 (2002).

Niegemann et al., "Molecular organization of the *Escherichia coli* gab cluster: nucleotide sequence of the structural genes gabD and gabP and expression of the GABA permease gene," *Arch.Microbiol* 160:454-460 (1993).

Nimmo, "Kinetic mechanism of *Escherichia coli* isocitrate dehydrogenase and its inhibition by glyoxylate and oxaloacetate," *Biochem. J.* 234(2):317-323 (1986).

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).

Nishizawa et al., "Gene expression and characterization of two 2-oxoacid:ferredoxin oxidoreductases from Aeropyrum pernix K1," *FEBS Lett.* 579:2319-2322 (2005).

Nissen et al., Expression of a cytoplasmic transhydrogenase in *Saccharomyces cerevisiae* results in formation of 2-oxoglutarate due to depletion of the NADPH pool. *Yeast* 18:19-32 (2001).

Niu et al., "Benzene-free synthesis of adipic acid," *Biotechnol. Prog.* 18:201-211 (2002).

Nogales et al., "Characterization of the last step of the aerobic phenylacetic acid degradation pathway," *Microbiology* 153(Pt 2):357-365 (2007).

Noichinda et al., "Subcellular Localization of Alcohol Acetyltransferase in Strawberry Fruit," *Food Sci. Technol. Res.* 5(3):239-242 (1999).

Nölling et al., "Genome sequence and comparative analysis of the solvent-producing bacterium *Clostridium acetobutylicum*," *J. Bacteriol.* 183(16):4823-4838 (2001).

Norton, "The Diels-Alder Diene Synthesis," *Chem. Rev.* 31:319-523 (1942).

Nowicki et al., "Recombinant tyrosine aminotransferase from Trypanosoma cruzi: structural characterization and site directed mutagenesis of a broad substrate specificity enzyme," *Biochima Biophysica Acta* 1546:268-281 (2001).

O'Brien and Gennis, "Studies of the Thiamin Pyrophosphate Binding Site of *Escherichia coli* Pyruvate Oxidase. Evidence for an essential tryptophan residue," *J. Biol. Chem.* 255(8):3302-3307 (1980).

O'Brien et al, "Regulation by Lipids of Cofactor Binding to a Peripheral Membrane Enzyme: Binding of Thiamin Pyrophosphate to Pyruvate Oxidase," *Biochemistry* 16(14):3105-3109 (1977).

O'Brien et al., "Chemical, physical and enzymatic comparisons of formyltetrahydrofolate synthetases from thermo- and mesophilic Clostridia," *Experientia. Suppl.* 26:249-262 (1976).

O'Brien et al., "Insight into the Mechanism of the $B_{12}$-Independent Glycerol Dehydratase from Clostridium butyricum: Preliminary Biochemical and Structural Characterization," *Biochemistry* 43:4635-4645 (2004).

Ofman et al., "2-Methyl-3-hydroxybutyryl-CoA dehydrogenase deficiency is caused by mutations in the HADH2 gene," *Am. J. Hum. Genet.* 72:1300-1307 (2003).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by *Pseudomonas*. Purification and Properties of a Deacetylase-Thiolestrerase Utilizing 4-Acetamidobutyryl CoA and Related Compounds," *J. Biol. Chem.* 256(14):7642-7651 (1981).

Overkamp et al., "In vivo analysis of the mechanism for oxidation of cytosolic NADH by *Saccharomyces cerevisiae* mitochondria," *J. Bacteriol.* 182:2823-2830 (2000).

Okino et al., "An efficient succinic acid production process in a metabolically engineered *Corynebacterium glutamicum* strain," *Appl. Microbiol. Biotechnol.* 81(3):459-464 (2008).

Oku and Kaneda, "Biosynthesis of branched-chain fatty acids in *Bacillus subtilis*. A decarboxylase is essental for branched-chain fatty acid synthetase," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism." *Enzyme Protein* 47:136-148 (1993).

Olivera et al., "Molecular characterization of the phenylacetic acid catabolic pathway in *Pseudomonas putida* U: the phenylacetyl-CoA catabolon," *Proc. Natl. Acad. Sci. USA* 95(11):6419-6424 (1998).

Onuffer and Kirsch, "Redesign of the substrate specificity of *Escherichia coli* aspartate aminotransferase to that of *Escherichia coli* tyrosine aminotransferase by homology modeling and site-directed mutagenesis," *Protein Sci.* 4:1750-1757 (1995).

O'Reilly and Devine, "Sequence and analysis of the citrulline biosynthetic operon argC-F from *Bacillus subtilis*," *Microbiology* 140:1023-1025 (1994).

Orencio-Trejo et al., "Metabolic regluation analysis of an ethanologenic *Escherichia coli* strain based on RT-PCR and enzymatic activities," *Biotechnol. Biofuels* 1:8 (2008). (provided electronically by publisher as pp. 1-13).

Ostermeier et al., "A Combinatorial approach to hybrid enzymes independent of DNA homology," *Nat. Biotechnol.* 17:1205-1209 (1999).

Ostermeier et al., "Combinatorial protein engineering by incremental truncation," *Proc. Natl. Acad. Sci. USA* 96:3562-3567 (1999).

O'Sullivan et al., "Purification and characterisation of acetolactate decarboxylase from *Leuconostoc lactis* NCW1," *FEMS Microbiol. Lett.* 194(2):245-249 (2001).

Otten and Quax, "Directed evolution:selecting today's biocatalysts," *Biomol. Eng.* 22:1-9 (2005).

Overkamp et al., "Functional analysis of structural genes for Nad$^+$-dependent formate dehydrogenase in *Saccharomyces cerevisiae*," *Yeast* 19:509-520 (2002).

Padovani and Banerjee, "Assembly and protection of the radical enzyme, methylmalonyl-CoA mutase, by its chaperone," *Biochem.* 45(30):9300-9306 (2006).

Paik and Kim, "Enzymic syntehsis of ε-N-Acetyl-L-Lysine," *Arch. Biochem. Biophys.* 108:221-229 (1964).

Palosaari and Rogers, "Purification and Properties of the Inducible Coenzyme A-Linked Butyraldehyde Dehydrogenase from *Clostridium acetobutylicum*," *J. Bacteriol.* 170(7):2971-2976 (1988).

Parales and Harwood, "Characterization of the Genes Encoding β-Ketoadipate: Succinyl-Coenzyme ATransferase in *Pseudomonas putida*," *J. Bacteriol.* 174(14):4657-4666 (1992).

Park and Lee, "Biosynthesis of poly(3-hydroxybutyrate- co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng.* 86(6):681-686 (2004).

Park et al., "Metabolic engineering of *Escherichia coli* for the production of L-valine based on transcriptome analysis and in silico gene knockout simulation," *Proc. Natl. Acad. Sci. USA* 104(19):7797-7802 (2007).

Park et al., "Regulation of succinate dehydrogenase (sdhCDAB) operon expression in *Escherichia coli* in response to carbon supply and anaerobiosis: role of ArcA and Fnr," *Mol. Microbiol.* 15(3):473-482 (1995).

Park et al., "Utilization of Electrically Reduced Neutral Red by *ActinoBacillus succinogenes*: Physiological Function of Neutral Red in Membrane-Driven Fumarate Reduction and Energy Conservation," *J. Bacteriol* 181(8):2403-2410 (1999).

Parkin et al., "Rapid and efficient electrocatalytic $CO_2/CO$ interconversions by *Carboxydothermus hydrogenoformans* CO dehydrogenase I on an electrode," *J. Am. Chem. Soc.* 129(34):10328-10329 (2007).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).

Patel and Clark, "Acetoacetate metabolism in rat brain. Development of acetoacetyl-Coenzyme A deacylase and 3-hydroxy-3-methylglutaryl-Coenzyme A synthase," *Biochem J.* 176(3):951-958 (1978).

Patel et al., "B-ketoadipate enol-lactone hydrolases I and II from *Acinetobacter calcoaceticus*," *J. Biol. Chem.* 250:6567-6577 (1975).

Patil et al., "Use of genome-scale microbial models for metabolic engineering," *Curr. Opin. Biotechnol.* 15(1)64-69 (2004).

Patnaik et al., "Genome shuffling of *LactoBacillus* for improved acid tolerance" *Nat Biotechnol.* 20:707-712 (2002).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peisach et al., "Crystallographic study of steps along the reaction pathway of D-amino acid aminotransferase," *Biochemistry* 37(14)4958-4967 (1998).

Pelletier and Harwood, "2-Ketocyclohexanecarboxyl Coenzyme A Hydrolase, the Ring cleavage Enzyme Required for Anaerobic Benzoate Degradation of Rhodo *Pseudomonas palustris*," *J. Bacteriol.* 180(9):2330-2336 (1998).

Peoples and Sinskey, "Fine structural analysis of the *Zoogloea ramigera* phhA-phhB locus encoding β-ketothiolase and acetoacetyl-CoA reductase: nucleotide sequence of phbB," *Mol. Microbiol.* 3:349-357 (1989).

Pereira et al., "Active site mutants of *Escherichia coli* citrate synthase. Effects of mutations on catalytic and allosteric properties," *J. Biol. Chem.* 269:412-417 (1994).

Peretz and Burstein, "Amino acid sequence of alcohol dehydrogenase from the thermophilic bacterium *Thermoanaerobium brockii*," *Biochemistry* 28(16):6549-6555 (1989).

Peretz et al., "Molecular cloning, nucleotide sequencing, and expression of genes encoding alcohol dehydrogenases from the thermophile *Thermoanaerobacter brockii* and the mesophile *Clostridium beijerinckii*," *Anaerobe.* 3:259-270 (1997).

Pérez et al., "*Escherichia coli* YqhD exhibits aldehyde reductase activity and protects from the harmful effect of lipid peroxidation-derived aldehydes," *J. Biol. Chem.* 283(12):7346-7353 (2008).

Perez-Prior, et al., "Reactivity of lactones and GHB formation," *J. Org. Chem.* 70:420-426 (2005).

Petersen and Bennett, "Purification of acetoacetate decarboxylase from *Clostridium acetobutylicum* ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in *Clostridia* of the butyric group," *Biochim. Biophys. Acta* 421(2):334-347 (1976).

Pfluger et al., "Lysine-2,3-Aminomutase and β-Lysine Acetyltransferase Genes of Methanogenic Archaea Are Salt Induced and Are Essential for the Biosynthesis of N$^ε$-Acetyl-β-Lysine and Growth at High Salinity," *Appl. Environ. Microbiol.* 69(10):6047-6055 (2003).

Phalip et al., "Purification and properties of the α-acetolactate decarboxylase from lactococcus lactis subsp. Lactis NCDO 2118," *FEBS Lett.* 351(1):95-99 (1994).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Phillips et al., "High Copy Number Plasmids Compatible with Commonly Used Cloning Vectors," *Biotechniques* 28:400-2, 404, 406 (2000).

Pierce et al., "The Complete Genome Sequence of *Moorella thermoacetia* (f. *Clostridum thermoaceticum*)," *Environ. Microbiol.* 10(10):2550-2573 (2008).

Pieulle et al., "Isolation and analysis of the gene encoding the pyruvate-ferredoxin oxidoreductase of Desulfovibrio africanus, production of the recombinant enzyme in *Escherichia coli*, and effect of carboxy-terminal deletions on its stability," *J. Bacteriol.* 179(18):5684-5692 (1997).

Pine et al., "Titanium-Mediated Methylene-Transfer Reactions. Direct Conversion of Esters into Vinyl Ethers," *J. Am. Chem. Soc.* 102:3270-3272 (1980).

Ploux et al., "Investigation of the first step of biotin biosynthesis in *Bacillus* sphericus," *Biochem. J.* 287:685-690 (1992).

Ploux et al., "The NADPH-linked acetoacetyl-CoA reductase from *Zoogloea ramigera*, Characterization and mechanistic studies of the cloned enzyme over-produced in *Escherichia coli*," *Eur. J. Biochem.* 174:177-182 (1988).

Pohl et al., "Remarkably broad Sutstrate Tolerance of Malonyl-CoA Synthetase, an Enzyme Capable of Intracellular Synthesis of Polyketide Precursors," *J. Am. Chem. Soc.* 123:5822-5823 (2001).

Pohlmann et al., "Genome sequence of the bioplastic-producing "Knallgas" bacterium *Ralstonia eutropha* H16," *Nat. Biotechnol.* 24(10):1257-1262 (2006).

Pollard and Bugg, "Purification, characterisation and reaction mechanisms of monofunctional 2-hydroxypentadienoic acid hydratase from *Escherichia coli*," *Eur. J. Biochem. FEBS* 251:98-106 (1998).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Ponce, E., et al., "Cloning of the two pyruvate kinase isoenzyme structural genes from *Escherichia coli*: the relative roles of these enzymes in pyruvate biosynthesis," *J Bacteriol* 177(19):5719-5722 (1995).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pritchett and Metcalf, "Genetic, physiological and biochemical characterization of multiple methanol methyltransferase isozymes in *Methanosarcina acetivorans* C2A," *Mol. Microbiol.* 56(5):1183-1194 (2005).

Pronk et al., "Pyruvate metabolism in *Saccharomyces cerevisiae*," *Yeast* 12:1607-1633 (1996).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Purnell et al., "Modulation of higher-plant Nad(H)-dependent glutamate dehydrogenase activity in transgenic tobacco via alteration of β subunit levels," *Planta* 222:167-180 (2005).

Qi et al., "Functional expression of prokaryotic and eukaryotic genes in *Escherichia coli* for conversion of glucose to p-hydroxystyrene," *Metab. Eng.* 9:268-276 (2007).

Qian et al., "Metabolic engineering of *Escherichia coli* for the production of putrescine: a four carbon diamine," *Biotechnol. Bioeng.* 104(4)651-662 (2009).

Qiu et al, "Metabolic engineering of *Aeromonas hydrophila* for the enhanced production of poly(3-hydroxybutyrate-co-3-hydroxyhexanoate)," *Appl. Microbiol. Biotechnol.* 69(5):537-542 (2006).

Qu et al., "Inhibition of human ornthine decarboxylase activity by enantiomers of difluoromethylornithine," *Biochem. J.* 375:465-470 (2003).

Quail and Guest, "Purification, characterization and mode of action of pdhR, the transcriptional repressor of the PdhR-aceEF-Ipd operon of *Escherichia coli*," *Mol. Microbiol.* 15(3):519-529 (1995).

Rado and Hoch, "Phosphotransacetylase from *Bacillus subtilis*: purification and physiological studies," *Biochim. Biophys. Acta* 321:114-125 (1973).

Rae et al., "Structure and Mechanism of HpcH: A Metal Ion Dependent Class II Aldolase from the Homoprotocatechuate Degradation Pathway of *Escherichia coli*," *J. Mol. Biol.* 373:866-876 (2007).

Ragsdale and Pierce, "Acetogenesis and the Wood-Ljungdahl pathway of $CO_2$ fixation," *Biochimica. Biophysica. Acta* 1784(12):1873-1898 (2008).

Ragsdale, "Enzymology of the wood-Ljungdahl pathway of acetogenesis," *Ann. NY Acad Sci*1125:129-136 (2008).

Ragsdale, "Life with carbon monoxide," *Crit. Rev. Biochem. Mol. Biol.* 39(3):165-195 (2004).

Ragsdale, "Pyruvate ferredoxin oxidoreductase and its radical intermediate," *Chem. Rev.* 103(6):2333-2346 (2003).

Rajpal et al., "A general method for greatly improving the affinity of antibodies by using combinatorial libraries," *Proc. Natl. Acad. Sci. USA* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramón-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J Biochem.* 149:401-404 (1985).

Rangarajan et al., "Structure of [NiFe] hydrogenase maturation protein HypE from *Escherichia coli* and its interaction with HypF," *J. Bacteriol.* 190(4):1447-1458 (2008).

Rasmussen, L.J., et al. "Carbon Metabolism Regulates Expression of the *pfl* (Pyruvate-Formate-Lyase) Gene in *Escherichia coli*," *J. Bacteriol.* 173(20):6390-6397 (1991).

Rathinasabapathi, "Propionate, a source of β-alanine, is an inhibitor of β-alanine methylation in Limonium latifoilium Plunbaginaces," *J. Plant Physiol.* 159:671-674 (2002).

Ratnatilleke et al., "Cloning and sequencing of the Coenzyme B(12)-binding domain of isobutyryl-CoA mutase from *Streptomyces cinnamonensis*, reconstitution of mutase activity, and characterization of the recombinant enzyme produced in *Escherichia coli*," *J. Biol. Chem.* 274(44):31679-31685 (1999).

Raux et al., "The role of *Saccharomyces cerevisiae* Met1p and Met8p in sirohaem and cobalamin biosynthesis," *Biochem. J.* 338 (pt. 3):701-708 (1999).

Raux et al., "*Salmonella typhimurium* cobalamin (vitamin $B_{12}$) biosynthetic genes: functional studies in *S. typhimurium* and *Escherichia coli*," *J. Bacteriol.* 178(3):753-767 (1996).

Ravagnani et al., "SpoOA directly controls the switch from acid to solvent production in solvent-forming *Clostridia*," *Mol. Microbiol.* 37(5):1172-1185 (2000).

Raybuck et al., "Kinetic characterization of the carbon monoxide-acetyl-CoA (carbonyl group) exchange activity of the acetyl-CoA synthesizing CO dehydrogenase from Clostridium thermoaceticum," *Biochemistry* 27(20):7698-7702 (1988).

Raynaud et al., "Molecular characterization of the 1,3-propanediol (1,3-PD) operon of clostridium butyricum," *Proc. Natl. Acad. Sci USA* 100:5010-5015 (2003).
Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reda et al., "Reversible interconversion of carbon dioxide and formate by an electroactive enzyme," *Proc. Natl. Acad. Sci. USA* 105:10654-10658 (2008).
Reed et al., An expanded genome-scale model of *Escherichia coli* K-12 (iJR904 GSM/GPR), *Genome. Biol.* 4(9):R54 (2003).
Reetz and Carballeira, "Iterative saturation mutagenesis (ISM) for rapid directed evolution of functional enzymes," *Nat. Protoc.* 2:891-903 (2007).
Reetz et al., "Creation of Enantioselective Biocatalysts for Organic Chemistry by In Vitro Evolution," *Angew. Chem. Int. Ed. Engl.* 36:2830-2832 (1997).
Reetz et al., "Directed Evolution of an Enantioselective Enzyme through Combinatorial Multiple-Cassette Mutagenesis," *Angew. Chem. Int. Ed.* 40:3589-3591 (2001).
Reetz et al., "Expanding the Range of Substrate Acceptance Enzymes: Cominatorial Active-Site Saturation Test," *Angew. Chem.* 117:4264-4268 (2005).
Reetz et al., "Iterative saturation mutagenesis on the basis of B factors as a strategy for incresing protein thermostability," *Angew. Chem. Int. Ed.* 45:7745-7751 (2006).
Regev-Rudzki et al., "Yeast Aconitase in Two Locations and Two Metabolic Pathways: Seeing Small Amounts Is Believing," *Mol. Biol. Cell* 16:4163-4171 (2005).
Reidhaar-Olson and Sauer, "Combinatorial cassette mutagenesis as a probe of the informational content of protein sequences," *Science* 241:53-57 (1988).
Reidhaar-Olson et al., "random mutagenesis of protein sequences using oligonucleotide cassettes," *Methods Enzymmol.* 208:564-586 (1991).
Reiser and Somerville, "Isolation of mutants of *Acinetobacter calcoaceticus* deficient in wax ester synthesis and complementation of one mutation with a gene encoding a fatty acyl Coenzyme A reductase," *J. Bacteriol.* 179(9):2969-2975 (1997).
Reitzer et al., "Crystallization and preliminary X-ray analysis of recombinant glutamate mutase and of the isolated component S from *Clostridium cochlearium*," *Acta Crystallogr. D. Biol. Crystallogr.* 54(Pt 5):1039-1042 (1998).
Repetto and Tzagoloff, "Structure and Regulation of KGD1, the Structural Gene for Yeast α-Ketoglutarate Dehydrogenase," *Mol. Cell. Biol.* 9(6):2695-2705 (1989).
Reshetnikov, et al., "Characterization of the ectoine biosynthesis genes of haloalkalotolerant obligate methanotroph *Methylomicrobium alcaliphilum* 20Z'," *Arch. Microbiol.* 184:286-297 (2006).
Resnekov et al., "Organization and regulation of the *Bacillus subtilis* odhAB operon, which encodes two of the subenzymes of the 2-oxoglutarate dehydrogenase complex, " *Mol. Gen. Genet.* 234:285-296 (1992).
Rhodes et al., "Production of fumaric acid by *Rhizopus arrhuzus*," *Appl. Microbiol.* 7:74-80 (1959).
Rhodes et al., "Production of Fumaric Acid in 20-Liter Fermentors," *Appl. Microbiol.* 10(1)9-15 (1962).
Rigden et al., "A cofactor-dependent phosphoglycerate mutase homolog from *Bacillus stearothermophilus* is actually a broad specificity phosphatase," *Protein Sci.* 10:1835-1846 (2001).
Ringer et al., "Monoterpene double-bond reductases of the (−)-menthol biosynthetic pathway: isolation and characterization of cDNAs encoding (−)-isopiperitenone reductase and (+)-pulegone reductase of peppermint," *Arch. Biochem. Biophys.* 418(1):80-92 (2003).
Ringquist et al., "Translation initiation in *Escherichia coli*: sequences within the ribosome-binding site," *Mol. Microbiol.* 6(9):1219-1229 (1992).
Riondet et al., "Measurement of the intracellular pH in *Escherichia coli* with the internally conjugated fluorescent probe 5- (and 6-)carboxyfluorescein succinimidyl ester." *Biotechnol. Tech.* 11:735-738 (1997).

Rioux et al., "Two outer membrane transport systems for vitamin $B_{12}$ in *Salmonella typhimurium*," *J. Bacteriol.* 171:2986-2993 (1989).
Rioux et al., "Vitamin $B_{12}$ transport in *Escherichia coli* K12 does not require the *btuE* gene of the *btuCED* operon," *Mol. Gen. Genet.* 217:301-308 (1989).
Rivière et al., "Acetyl:succinate CoA-transferase in procyclic Trypanosoma brucei. Gene identification and role in carbohydrate metabolism." *J. Biol. Chem.* 279:45337-45346 (2004).
Roa Engel et al., "Fumaric acid production by fermentation," *Appl. Microbiol. Biotechnol.* 78(3):379-389 (2008).
Roberts et al, "The Role of Enoyl-CoA Hydratase in the Metabolism of Isoleucine by *Pseudomonas putida*," *Arch. Microbiol.* 117:99-108 (1978).
Roberts et al., "Acetyl-Coenzyme A synthesis from methyltetrahydrofolate, CO, and Coenzyme A by enzymes purified from Clostridium thermoaceticum: attainment of in vivo rates and identification of rate-limiting steps," J. Bacteriol. 174(14):4667-4676 (1992).
Roberts et al., "Cloning and expression of the gene cluster encoding key proteins involved in acetyl-CoA synthesis in Clostridium thermoaceticum: CO dehydrogenase, the corrinoid/Fe-S protein, and Methyltransferase," *Proc. Natl. Acad. Sci. USA* 86(1):32-36 (1989).
Robinson et al., "Studies on Rat Brain Acyl-Coenzyme A Hydrolase (Short Chain)," *Biochem. Biophys. Res. Commun.* 71(4):959-965 (1976).
Roca et al., "Metabolic engineering of ammonium assimilation in xylose-fermenting *Saccharomyces cerevisiae* improves ethanol production," *Appl Environ Microbiol* 69:4732-4736 (2003).
Rodríguez et al., "Characterization of the p-Coumaric Acid Decarboxylase from *LactoBacillus* plantarium CECT 748," *J. Agric. Food Chem.* 56:3068-3072 (2008).
Roffia et al., "Byproduct Identification in the Terepthalic Acid Production Process and Possible Mechanisms of their Formation," *Ind. Eng. Chem. Prod. Res. Dev.* 23:629-634 (1984).
Rohdich et al., "Enoate reductases of *Clostridia*. Cloning, sequencing, and expression," *J. Biol. Chem.* 276(8):5779-5787 (2001).
Rohwerder et al., "The alkyl tert-butyl ether intermediate 2-hydroxyisobutyrate is degraded via a novel cobalamin-dependent mutase pathway," *Appl. Environ. Microbiol.* 72(6):4128-4135 (2006).
Romero et al., "Partial purification and characterization and nitrogen regulation of the lysine ε-aminotransferase of *Streptomyces clavuligers*," *J. Ind. Microbiol. Biotechnol.* 18:241-246 (1997).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rose and Weaver, "The role of the allosteric B site in the fumarase reaction," *Proc. Natl. Acad. Sci. USA* 101(10):3393-3397 (2004).
Rose et al., "Enzymatic phosphorylation of acetate," *J. Biol. Chem.* 211(2):737-756 (1954).
Rosenberg, "A Comparison of Lipid Patterns in Photosynthesizing and Nonphotosynthesizing Cells of *Euglena gracilis*," *Biochem.* 2:1148-1154 (1963).
Roszak et al., "The Structure and Mechanism of the Type II Dehydroquinase from Streptomyces coelicolor," *Structure* 10:493-503 (2002).
Roth et al., "Characterization of the cobalamin (vitamin $B_{12}$) biosynthetic genes of *Salmonella typhimurium*," *J. Bacteriol.* 175:3303-3316 (1993).
Rother and Metcalf, "Anaerobic growth of *Methanosarcina acetivorans* C2A on carbon monoxide: an unusual way of life for a methanogenic archaeon," *Proc. Natl. Acad. Sci. USA* 101(48):16929-16934 (2004).
Rother et al., "Genetic and proteomic analyses of CO utilization by *Methanosarcina acetivorans*," *Arch. Microbiol.* 188(5):463-472 (2007).
Rous, "On the occurrence of enzymes of ketone-body metabolism in human adipose tissue," *Biochem. Biophys. Res. Commun.* 69(1):74-78 (1976).
Roux and Walsh, "p-aminobenzoate synthesis in *Escherichia coli*: kinetic and mechanistic characterization of the amidotransferase PabA," *Biochemistry.* 31:6904-6910 (1992).

Roux and Walsh, "p-Aminobenzoate synthesis in *Escherichia coli*: mutational analysis of three conserved amino acid residues of the amidotransferase PabA," *Biochemistry* 32:3763-3768 (1993).

Roy and Dawes, "Cloning and Characterization of the gene Encoding Lipoamide Dehydrogenase in *Saccharomyces cerevisiae*," *J. Gen. Microbiol.* 133:925-933 (1987).

Roymoulik et al., "Rearrangement of L-2-hydroxyglutarate to L-threo-3-methylmalate catalyzed by adenosylcobalamin-dependent glutamate mutase," *Biochem.* 39(33):10340-10346 (2000).

Rozzell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).

Rudman and Meister, "Transamination in *Escherichia coli*," *J. Biol. Chem.* 200(2):591-604 (1953).

Ruldeekulthamrong et al., "Molecular characterization of lysine 6-dehydrogenase from Achromobacter denitrificans," *BMB Reports* 790-795 (2008).

Sabo et al., "Purification and physical properties of inducible *Escherichia coli* lysine decarboxylase," *Biochemistry* 13:622-670 (1974).

Sadowski, "The Flp recombinase of the 2- μm plasmid of *Saccharomyces cerevisiae*," *Prog. Nucleic Acid Res. Mol. Biol.* 51:53-91 (1995).

Saegesser et al., "Stability of broad host range cloning vectors in the phototrophic bacterium *Rhodospirillum rubrum*," *FEMS Microbiol. Lett.* 95:7-11 (1992).

Saito and Doi. "Microbial synthesis and properties of poly(3-hydroxybutyrate-co-4-hydroxybutyrate) in *Comamonas acidovorans*," *Int. J Biol Macromol.* 16:99-104 (1994).

Sakai et al, "Acetate and Ethanol Production from $H_2$ and $CO_2$ by *Morrella* sp. Using a Repeated Batch Culture," *J. Biosci. Bioeng.* 99:252-258 (2005).

Sakanyan et al., "A re-examination of the pathway for ornithine biosynthesis in a thermophilic and two mesophilic *Bacillus* species," J. Gen. Microbiol. 138:125-130 (1992).

Sakurada et al., "Acetylpolyamine Amidohydrolase from Mycoplana ramosa: Gene Cloning and Characterization of the Metal-Substituted Enzyme," *J. Bacteriol.* 178(19):5781-5786 (1996).

Salmon et al., "Global gene expression profiling in *Escherichia coli* K12: effects of oxygen availability and ArcA," *J. Biol. Chem.* 280(15):15084-15096 (2005).

Saltzgaber-Muller et al., "Nuclear genes coding the yeast mitochondrial adenosine triphosphatase complex. Isolation of ATP2 coding the F1-*ATPase β subunit*," *J. Bio. Chem* 258(19):11465-11470 (1983).

Samanta and Harwood, "Use of Rhodo *Pseudomonas palustris* genome sequence to identify a single amino acid that contributes to the activity of Coenzyme A ligase with chlorinated substrates," *Mol. Microbiol.* 55(4):1151-1159 (2005).

Samsonova et al., "Molecular cloning and characterization of *Escherichia coli* K12 ygjG gene, " *BMC Microbiol.* 3:2 (2003).

Samuelov et al., "Whey fermentation by *Anaerobiospirillum succiniciproducens* for production of a succinate-based animal feed additive," *Appl. Environ. Microbiol.* 65(5):2260-2263 (1999).

San et al., "Metabolic Engineering through Cofactor Manipulation and its Effects on Metabolic Flux Redistribution in *Escherichia coli*," *Metab Eng.* 4(2):182-192 (2002).

Sánchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).

Sánchez et al., "Novel pathway engineering design of the anaerobic central metabolic pathway in *Escherichia coli* to increase succinate yield and productivity," *Metab. Eng.* 7(3): 229-239 (2005).

Sánchez, et al., "Batch culture characterization and metabolic flux analysis of succinate-producing *Escherichia coli* strains," *Metab Eng.* 8(3):209-226 (2006).

Sánchez, et al., "Effect of different levels of NADH availability on metabolic fluxes of *Escherichia coli* chemostat cultures in defined medium," *J. Biotechnol.* 117(4):395-405 (2005).

Sankaranarayanan et al., "Preliminary x-ray crystallographic analysis of ornithine acetyltransferase (Rv1653) from *Mycobacterium tuberculosis*," *Acta Cryst*. F65:173-176 (2009).

Sanyal et al., "Biosyntehsis of pimeloyl-CoA, a biotin precursor in *Escherichia coli*, follows a modified fatty acid synthesis pathway: $^{13}$C-labeling studies," *J. Am. Chem. Soc.* 116:2637-2638 (1994).

Sariaslani, "Development of a Combined biological and Chemical Process for Production of Industrial aromatics from Renewable Resources," *Annu. Rev. Microbiol*. 61:51-69 (2007).

Sass et al., "Folding of fumarase during mitochondrial import determines its dual targeting in yeast," *J. Biol. Chem.* 278(46):45109-45116 (2003).

Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).

Sauer amd Thauer, "Methanol:coenzyme M methyltransferase from *Methanosarcina barkeri*. Identification of the active-site histidine in the corrinoid-harboring subunit MtaC by site-directed mutagenesis," *Eur. J. Biochem.* 253(3):698-705 (1998).

Sauer et al., "Methanol:Coenzyme M methyltransferase from *Methanosarcina barkeri*. Purification, properties and encoding genes of the corrinoid protein MT1," *Eur. J. Biochem.* 243(3):670-677 (1997).

Sauer, "Diels-Alder Reactions II: The Reaction Mechanism," *Angewandte Chemie* 6:16-33 (1967).

Sauvageot et al., "Characterisation of the diol dehydratase *pdu* operon of *LactoBacillus* collinoides," *FEMS Microbiol. Lett*. 209:69-74 (2002).

Sawers and Boxer, "Purification and properties of membrane-bound hydrogenase isoenzyme 1 from anaerobically grown *Escherichia coli* K12," *Eur. J. Biochem.* 156(2):265-275 (1986).

Sawers et al., "Characterization and physiological roles of membrane-bound hydrogenase isoenzymes from *Salmonella typhimurium*," *J. Bacteriol*. 168(1):398-404 (1986).

Sawers et al., "Differential expression of hydrogenase isoenzymes in *Escherichia coli* K-12: evidence for a third isoenzyme," *J. Bacteriol*. 164(3):1324-1331 (1985).

Sawers, "The hydrogenases and formate dehydrogenases of *Escherichia coli*," *Antonie Van Leeuwenhoek* 66(1-3):57-88 (1994).

Saz and Weil, "The mechanism of the formation of α-methylbutyrate from carbohydrate by Ascaris lumbricoides muscle," *J. Biol. Chem.* 235:914-918 (1960).

Schadt et al., "2-Amino-2-deoxyisochorismate is a key intermediate in *Bacillus subtilis* p-aminobenzoic acid biosynthesis" *J Am. Chem. Soc.* 131:3481-3483 (2009).

Schwarzer et al., "Nonribosomal peptides: from genes to products," *Nat. Prod. Rep* 20:275-287 (2003).

Scher and Jakoby, "Maleate isomerase," *J. Biol. Chem.* 244:1878-1882 (1969).

Scherf and Buckel, "Purification and properties of 4-hydroxybutyrate Coenzyme A transferase from *Clostridium aminobutyricum*," *Appl. Environ. Microbiol.*, 57(9):2699-2702 (1991).

Scherf and Buckel, "Purification and properties of an iron-sulfur and FAD-containing 4-hydroxybutyryl-CoA dehadratase/vinylacetyl-CoA $\Delta^3$-$\Delta^2$-isomerase from *Clostridium aminobutyricum*," *Eur. J. Biochem*. 215:421-429 (1993).

Scherf et al, "Succinate-ethanol fermentation in *Clostridium kluyveri*: purification and characterisation of 4-hydroxybutyryl-CoA dehydratase/vinylacetyl-CoA $\Delta^3$-$\Delta^2$-isomerase," *Arch. Microbiol.* 161(3):239-245 (1994).

Schilling et al., "Genome-Scale Metabolic Model of *Helicobacter pylori* 26695," *J. Bacteriol.* 184:4582-4593 (2002).

Schilling et al., "Combining Pathway Analysis with Flux Balance Analysis for the Comprehensive Study of Metabolic Systems," *Biotechnol. Bioeng*. 71(4):286-306 (2000/2001).

Schilling et al., "Theory for the Systematic Definition of Metabolic Pathways and Their Use in Interpreting Metabolic Function from a Pathway-Oriented Perspective," *J. Theor. Biol.* 203(3):229-248 (2000).

Schilling et al., "Toward Metabolic Phenomics: Analysis of Genomic Data Using Flux Balances," *Biotechnol. Prog.* 15(3):288-295 (1999).

Schmid et al., "Plasmid-mediated uptake and metabolism of sucrose by *Escherichia coli* K-12," *J. Bacteriol.* 151(1):68-76 (1982).

Schmitzberger et al., "Structural constraints on protein self-processing in L-aspartate-α-decarboxylase," *EMBO J.* 22:6193-6204 (2003).

Schneider and Betz, Waxmonoester Fermentation in Euglena-Gracilis T Factors Favoring the Synthesis of Odd-Numbered Fatty-Acids and Alcohols, *Planta.* 166:67-73 (1985).

Schneider et al., "The *Escherichia coli* gabDTPC operon: specific γ-aminobutyrate catabolism and nonspecific induction," *J. Bacteriol.* 184:6976-6986 (2002).

Schnell et al., "Anaerobic degradation of aniline and dihydroxybenzenes by newly isolated sulfate-reducing bacteria and description of *Desulfobacterium anilini*," *Arch. Microbiol.* 152:556-563 (1989).

Schousboe et al., "Purification and Characterization of the 4-Aminobutyrate-2-Ketoglurate Transminase from Mouse Brain," *Biochem.* 12(15):2868-2873 (1973).

Schrock et al., "Preparation and Reactivity of Several Alkylidene Complexes of the Type W(CHR')(N—2, 6-$C_6H_3$-i-$Pr_2$ )$(OR)_2$ and Related Tungstacyclobutane complexes. Controlling Metathesis Activity through the Choice of Alkoxide Ligand," *J. Am. Chem. Soc.* 110:1423-1435 (1988).

Schulz et al., "Stereospecific production of the herbicide phosphinothricin (glufosinate) by transamination: isolation and characterization of a phosphinothricin-specific transaminase from *Escherichia coli*," *Appl. Environ. Microbiol.* 56(1):1-6 (1990).

Schürmann and Sprenger, Fructose-6-phosphate aldolase is a novel class I aldolase from *Escherichia coli* and is related to a novel group of bacterial transaldolases. *J. Biol. Chem.* 276(14): p. 11055-11061 (2001).

Schweiger and Buckel, "On the dehydration of (R)-lactate in the fermentation of alanine to propionat by Clostridium propionicum" *FEBS Lett.* 171:79-84 (1984).

Schweiger et al., "Purification of 2-hydroxyglutaryl-CoA dehydratase from Acidaminococcus fermentans. An iron-sulfur protein," *Eur. J. Biochem.* 169(2):441-448 (1987).

Scott and Jakoby, "Soluble γ-aminobutyric-glutamic transaminase from *Pseudomonas* fluorescens," *J. Biol. Chem.* 234(4):932-936 (1959).

Scott, A.I., "Discovering nature's diverse pathways to vitamin $B_{12}$: a 35-year odyssey," *J. Org. Chem.* 68:2529-2539 (2003).

Seedorf et al., "The genome of *Clostridium kluyveri*, a strict anaerobe with unique metabolic features," *Proc. Natl. Acad. Sci. USA* 105(6):2128-2133 (2008).

Seffernick et al., "Melamine deaminase and Atrazine chlorohydrolase: 98 percent identical but functionally different," *J.Bacteriol.* 183 (8):2405-2410 (2001).

Segrè et al., "Analysis of optimality in natural and perturbed metabolic networks," *Proc. Natl. Acad. Sci. USA* 99:15112-15117 (2002).

Seibert et al., "Characterization of a gene cluster encoding the maleylacetate reductase from *Ralstonia eutropha* $335^T$, and enzyme recruited for growth with 4-fluorobenzoate," *Microbiology* 150:463-472 (2004).

Seibert et al., "Characterization of the maleylacteate reductase MacA of *Rhodococcus* opacus 1CP and evidence for the presence of an isofunctional enzyme," *J. Bacteriol.* 180:3503-3508 (1998).

Seibert et al., "Purification and characterization of maleylacetate reductase from Alcaligenes eutrophys JMP134(pJP4)," *J. Bacteriol.* 175:6745-6754 (1993).

Selifonova et al., "Rapid evolution of novel traits in microorganisms," *Appl. Environ Microbiol.* 67:3645-3649 (2001).

Selmer et al., "Propionate CoA-transferase from Clostridium propionicum. Cloning of gene identification of glutamate 324 at the active site," *Eur. J. Biochem.* 269:372-380 (2002).

Seltzer, "Purification and properties of maleylacetone cis-trans isomerase from vibrio 01," *J. Biol. Chem.* 248:215-222 (1973).

Sen et al., "Developments in directed evolution for improving enzyme functions," *Appl. Biochem. Biotechnol.* 143:212-223 (2007).

Sennett et al., "Transmembrane transport of cobalamin in prokaryotic and eukaryotic cells," *Ann. Rev. Biochem.* 50:1053-1086 (1981).

Seravalli et al., "Evidence that NiNi acetyl-CoA synthase is active and that the CuNi enzyme is not," *Biochemistry* 43(13):3944-3955 (2004).

Seravalli et al., "Mechanism of transfer of the methyl group from (6S)-methyltetrahydrofolate to the corrinoid/iron-sulfur protein catalyzed by the methyltransferase from clostridium thermoaceticum: a key step in the Wood-Ljungdahl pathway of acetyl-CoA synthesis," *Biochemistry* 38(18):5728-5735 (1999).

Seyfried et al., "Cloning, Sequencing, and Overexpression of the Genes Encoding Coenzyme $B_{12}$-Dependent Glycerol Dehydratase of Citrobacter freundii," *J. Bacteriol.* 178(19):5793-5796 (1996).

Shafiani et al., "Cloning and characterization of aspartate-β-semialdehyde dehydrogenase from *Mycobacterium tuberculosis* H37 Rv," *J. Appl. Microbiol.* 98:832-838 (2005).

Shalel-Levanon et al., "Effect of ArcA and FNR on the expression of genes related to the oxygen rregulation and the glycolysis pathway in *Escherichia coli* under microaerobic growth conditions," *Biotechnol. Bioeng.* 92(2):147-159 (2005).

Shames et al., "Interaction of Aspartate and Aspartate-derived Antimetabolites with the Enzymes of the Threonine Biosynthetic Pathway of *Escherichia coli*," *J. Biol. Chem.* 259(24):15331-15339 (1984).

Shanley et al., "Cloning and expression of *Acinetobacter calcoaceticus* catBCDE genes in *Pseudomonas putida* and *Escherichia coli*," *J. Bacteriol.* 165:557-563 (1986).

Shao et al., "Random-priming in vitro recombination: an effective tool for directed evolution," *Nucleic Acids Res.* 26:681-683 (1998).

Sharma et al., "Menaquinone (Vitamin $K_2$) Biosynthesis: Nucleotide Sequence and Expression of the menB Gene from *Escherichia coli*," *J. Bacteriol.* 174(15): 5057-5062 (1992).

Sheppard et al., "Purification and Properties of NADH-Dependent 5,10-Methylenetetrahydrofolate Reductase (MetF) from *Escherichia coli*," *J. Bacteriol.* 181(3):718-725 (1999).

Shi et al., "The Structure of I-Aspartate Ammonia-Lyase from *Escherichia coli*," *Biochemistry* 36:9136-9144 (1997).

Shiba et al., "Engineering of the pyruate dehydrogenase bypass in *Saccharomyces cerevisiae* for high-level production of isoprenoids," *Metab. Eng.* 9:160-168 (2007).

Shibata et al., "Purification, characterization, and immunological properties of fumarase from *Euglena gracilis* var. *bacillaris*," *J. Bacteriol.* 164(2):762-768 (1985).

Shigeoka and Nakano, "Characterization and molecular properties of 2-oxoglutarate decarboxylase from *Euglena gracilis*," *Arch. Biochem. Biophys.* 288:22-28 (1991).

Shigeoka and Nakano, "The effect of thiamin on the activation of thiamin pyrophosphate-dependent 2-oxoglutarate decarboxylase in *Euglena gracilis*," *Biochem. J.* 292 (Pt 2):463-467 (1993).

Shigeoka et al., "Effect of L-glutamate on 2-oxoglutarate decarboxylase in Euglena gracilis," *Biochem. J.* 282( Pt 2):319-323 (1992).

Shimaoka et al, "Effects of edd and pgi Disruptions on Inosine Accumulation in *Escherichia coli*," *Biosci. Boitechnol. Biochem.* 69(7):1248-1255 (2005).

Shimoda et al., "Asymmetric Transformation of Enones with *Synechococcus* sp. PCC 7942," *Bulletin of the Chemical Society of Japan* 77(12):2269-2272 (2004).

Shimomura et al., "3-hydroxyisobutyryl-CoA hydrolase," *Methods Enzymol.* 324:229-240 (2000).

Shimomura et al., "Purification and partial characterization of 3-hydroxyisobutyryl-Coenzyme A hydrolase of rat liver," *J. Biol. Chem.* 269(19):14248-14253 (1994).

Shimoyama et al., "MmcBC in Pelotomaculum thermopropionicum represents a novel group of prokaryotic fumarases," *FEMS Microbiol Lett.* 270(2):207-213 (2007).

Shingler et al., "Nucleotide sequence and functional analysis of the complete phenol/3,4-dimethylphenol catabolic pathway of *Pseudomonas* sp. strain CF600," *J. Bacteriol.* 174(3):711-724 (1992).

Shlomi et al., "Regulatory on/off minimization of metabolic flux changes after genetic perturbations," *Proc. Natl. Acad. Sci. USA* 102:7695-7700 (2005).

Shukla et al., "Production of D(−)-lactate from sucrose and molasses," *Biotechnol. Lett.* 26(9):689-693 (2004).

Shuler and Kargi, "Operating Considerations for Bioreactors for Suspension and Immobilized Cultures," In *Bioprocess Engineering: Basic Concepts*, Prentice Hall, Inc., Upper Saddle River, NJ, p. 245-247 (2002).

Sibilli et al., "Two regions of the bifunctional protein aspartokinase I-homoserine dehydrogenase I are connected by a short hinge," *J. Biol. Chem.* 256 (20):10228-10230 (1981).

Sieber et al., "Libraries of hybrid proteins from distantly related sequences," *Nat. Biotechnol.* 19:456-460 (2001).

Siegert et al., "Exchanging the substrate specificities of pyruvate decarboxylase from Zymomonas mobilis and benzoylformate decarboxylase from *Pseudomonas putida*," *Protein. Eng. Des. Sel.* 18:345-357 (2005).

Siew et al., "Localization and characteristics of rat liver mitochondrial aldehyde dehydrogenases," *Arch. Biochem. Biophys.* 176(2):638-649 (1976).

Sikorski and Hefter, "A system of shuttle vectors and yeast host strains designed for efficient manipulation of DNA in *Saccharomyces cerevisiae*," *Genetics* 122(1):19-27 (1989).

Simanshu et al., "Structure and function of enzymes involved in the anaerobic degradation of L-threonine to propionate," *J. Biosci.* 32(6):1195-1206 (2007).

Simonov et al.,"Application of Gas Chromatography and Gas Chromatography-Mass Spectrometry to the Detection of γ-Hydroxybutyric Acid and Its Precursors in Various Materials," *J. Anal. Chem.* 59:965-971 (2004).

Sinclair et al., Purification and characterization of the branched chain α-ketoacid dehydrogenase complex from *Saccharomyces cerevisiae*, Biochem. *Mol. Biol. Int.* 31(5):911-922 (1993).

Sipma et al., "Microbial CO conversions with applications in synthesis gas purification and bio-desulfurization," *Crit. Rev. Biotechnol.* 26:41-65 (2006).

Sivaraman et al., "Codon choice in genes depends on flanking sequence information-implications for theoretical reverse translation," *Nucleic Acids Res.* 36(3):e16 (2008).

Sjöström et al., "Purification and characterisation of a plasminogen-binding protein from *Haemophilus influenzae*. Sequence determination reveals identity with aspartase," *Biochim. Biophys. Acta.* 1324(2):182-190 (1997).

Skarstedt and Silverstein, "*Escherichia coli* acetate kinase mechanism studied by net initial rate, equilibrium, and independent isotopic exchange kinetics," *J. Biol. Chem.* 251:6775-6783 (1976).

Slater et al., "Multiple β-ketothiolases mediate poly(β-hydroxyalkanoate) copolymer synthesis in *Ralstonia eutropha*," *J. Bacteriol.* 180(8):1979-1987 (1998).

Sloane et al., "Studies on the metabolism of p-aminobenzoic acid by *Mycobacterium smegmatis*," *J Biol. Chem.* 193:453-458 (1951).

Slock et al., "An apparent *Bacillus subtilis* folic acid biosynthetic operon containing pab, an amphibolic *trpG* gene, a third gene required for synthesis of para-aminobenzoic acid, and the dihydropteroate synthase gene," *J Bacteriol.* 172:7211-7226 (1990).

Smit et al., "Identification, cloning and characterization of *Lactococcus lactis* branched-chain α-keto acid decarboxylase involved in flavor formation," *Appl. Environ. Microbiol.* 71:303-311 (2005).

Smith and Gray, Catalysis of the oxidation of 1,4-cyclohexadiene to benzene by electroactive binuclear rhodium complexes, *Catalysis Lett.* 6:195-199 (1990).

Smith and Kaplan, "Purification, properties and kinetic mechanism of Coenzyme A-linked aldehyde dehydrogenase from *Clostridium kluyveri*," *Arch. Biochem. Biophys.* 203:663-675 (1980).

Smith et al., "Purification and characteristics of a γ-glutamyl kinase involved in *Escherichia coli* proline biosynthesis," *J. Bacteriol.* 157:545-551 (1984).

Smith et al., "Fumarate metabolism and the microaerophily of Campylobacter species," *Int. J. Biochem. Cell Biol.* 31(9):961-975 (1999).

Smith et al., "Structural and functional organization of the animal fatty acid synthase," *Prog. Lipid. Res.* 42(4):289-317 (2003).

Sobue et al., "Action polymerization induced by calspectin, a calmodulin-binding spectrin-like protein," *FEBS Lett* 148(2):221-225 (1982).

Soda and Misono,"L-Lysine:α-ketoglutarate aminotransferase. II. Purification, crystallization, and properties," *J. Bacteriol.* 7:4110-4119 (1968).

Sohling and Gottschalk, "Molecular analysis of the anaerobic succinate degradation pathway in *Clostridium kluyveri*," *J. Bacteriol.* 178:871-880 (1996).

Sohling and Gottschalk, "Purification and characterization of a Coenzyme-A-dependent succinate-semialdehyde dehydrogenase from *Clostridium kluyveri*," *Eur. J. Biochem.* 212:121-127 (1993).

Söhling and Gottschalk, "Purification and characterization of a Coenzyme-A-dependent succinate-semialdehyde dehydrogenase from *Clostridium kluyveri*," *Eur. J. Biochem.* 212(1):121-127 (1993).

Soini et al., "High cell density media for *Escherichia coli* are generally designed for aerobic cultivations—consequences for large-scarle bioprocesses and shake flask cultures," *Microb. Cell. Fact.* 7:26 (2008).

Sokatch et al., "Purification of a Branched-Chain Keto Acid Dehydrogenase from *Pseudomonas putida*," *J. Bacteriol.* 148(2):647-652 (1981).

Somerville, "The Billion-Ton Biofuels Vision," *Science* 312(5778):1277 (2006).

Sone et al., "Nucleotide sequence and expression of the Enterobacter aerogenes α-acetolactate decarboxylase gene in brewer's yeast, " *Appl. Environ. Microbiol.* 54:38-42 (1988).

Song et al, "Effects of dissolved $CO_2$ levels on the growth of *Mannheimia succinicproducens* and succinic acid production," *Biotechnol. Bioeng.* 98(6):1296-1304 (2007).

Song et al., "Construction of recombinant *Escherichia coli* strains producing poly (4-hydroxybutyric acid) homopolyester from glucose," *Wei Sheng Wu Xue.Bao.* 45:382-386 (2005).

Song et al., "Ultrasound-mediated DNA transfer for bacteria," *Nucl. Acids Res.* 35:e129 (2007).

Song et al., "Recovery of succinic acid produced by fermentation of a metabolically engineered Mannheimia succiniciproducens strain," *J. Biotechnol.* 132:445-452 (2007).

Song et al., "Structure, function, and mechanism of the phenylacetate pathway hot dog-fold thioesterase PaaI," *J. Biol. Chem.* 281(16):11028-11038 (2006).

Soucaille et al., "Butanol tolerance and autobacteriocin production by Clostridium acetobutylicum," *Curr. Microbiol.* 14:295-299 (1987).

Sovik, "Mitochondrial 2-methylacetoacetyl-CoA thiolase deficiency: an inborn error of isoleucine and ketone body metabolism," *J. Inherit. Metab. Dis.* 16:46-54 (1993).

Sramek and Frerman, "Purification and properties of *Escherichia coli* Coenzyme A-transferase," *Arch. Biochem. Biophys.* 171(1):14-26 (1975).

St. Maurice et al., "Flavodoxin:quinone reductase (FqrB): a redox partner of pyruvate:ferredoxin oxidoreductase that reversibly couples pyruvate oxidation to NADPH production in *Helicobacter pylori* and Campylobacter jejuni," *J. Bacteriol.* 189:4764-4773 (2007).

Stadtman, The enzyme synthesis of βalanyl Coenzyme A, *J. Plant Chem. Soc.* 77:5765-5766 (1955).

Stanley et al., "Expression and stereochemical and isotope effect studies of active 4-oxalocrotonate decarboxylase," *Biochemistry* 39:718-726 (2000).

Starai et al., "Acetate excretion during growth of salmonella enerica on ethanolamine requires phosphotransacetylase (EutD) activity, and acetate recapture requires acetyl-CoA synthetase (Acs) and phosphotransacetylase (Pta) activities," *Micribioogy* 151:3793-3801 (2005).

Starai et al., "Residue Leu-641 of Acetyl-CoA synthetase is critical for the acetylation of residue Lys-609 by the Protein acetyltransferase enzyme of Salmonella enterica," *J. Biol. Chem.* 280(28):26200-26205 (2005).

Starnes et al., "Threonine-sensitive aspartokinase-homoserine dehydrogenase complex, amino acid composition, molecular weight, and subunit composition of the complex," *Biochemistry* 11:677-687 (1973).

Steffan and McAlister-Henn, "Isolation and characterization of the yeast gene encoding the MDH3 isozyme of malate dehydrogenase," *J. Biol. Chem.* 267:24708-24715 (1992).

Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).

Steinbuchel and Schlegel, "A multifunctional fermentative alcohol dehydrogenase from the strict aerobe *Alcaligenes eutrophus*: purification and properties," *Eur. J. Biochem.* 141:555-564 (1984).

Steiner and Sauer, "Long-term continuous evolution of acetate resistant *Acetobacter aceti*," *Biotechnol Bioeng*, 84:40-44 (2003).

Stemmer, "DNA shuffling by random fragmentation and reassembly: in vitro recombination for molecular evolution," *Proc. Natl. Acad. Sci. USA* 91:10747-10751 (1994).

Stemmer, "Rapid evolution of a protein in vitro by DNA shuffling," *Nature* 370:389-391 (1994).

Stim-Herndon et al., "Characterization of an acetyl-CoA C-acetyltransferase (thiolase) gene from *Clostridium acetobutylicum* ATCC 824," *Gene.* 154(1):81-85 (1995).

Stirling and Perry, "Purification and Properties of a Nicotinamide Adenine Dinucleotide-Linked Cyclohexanol Dehydrogenase from a nocardia Species," *Curr. Microbiol.* 4:37-40 (1980).

Stokell et al., "Probing the roles of key residues in the unique regulatory NADH binding site of type II citrate synthase of *Escherichia coli*," *J. Biol. Chem.* 278:35435-35443 (2003).

Stols and Donnelly, "Production of succinic acid through overexpression of $NAD^+$-dependent malic enzyme in an *Escherichia coli* mutant," *Appl. Environ. Microbiol.* 63(7):2695-2701 (1997).

Stols et al., "Expression of *Ascaris suum* malic enzyme in a mutant *Escherichia coli* allows production of succinic acid from glucose," *Appl. Biochem. Biotechnol.* 63-65: 153-158 (1997).

Stols et al., "New vectors for co-expression of proteins: Structure of *Bacillus subtilis* ScoAB obtained by High-throughput protocols," *Protein Expr. Purif.* 53:396-403 (2007).

Stoyan et al., "Cloning, sequencing and overexpression of the leucine dehydrogenase gene from *Bacillus cereus*," *J. Biotechnol.* 54:77-80 (1997).

Straathof et al., "Feasibility of acrylic acid production by fermentation," *Appl. Microbiol. Biotechnol.* 67:727-734 (2005).

Strauss and Fuchs, "Enzymes of a novel autotrophic $CO_2$ fixation pathway in the phototrophic bacterium *Chloroflexus aurantiacus*, the 3-hydroxypropionate cycle," *Eur. J. Biochem.* 215:633-643 (1993).

Streit and Entcheva, "Biotin in microbes, the genes involved in its biosynthesis, its biochemical role and perspectives for biotechnological production," *Appl. Microbiol. Biotechnol.* 61:21-31 (2003).

Stringfellow et al., "Sequence of the *Escherichia coli* C homoprotocatechuic acid degradative operon completed with that of the 2,4-dihydroxyhept-2-ene-1,7-dioic acide aldolase-encoding gene (hpcH)," *Gene* 166:73-76 (1995).

Stryer. *Biochemistry.* 3rd Ed. New York: W.H. Freeman and Company 374-376. (1988).

Suarez de Mata et al., "Propionyl-CoA condensing enzyme from Ascaris muscle mitochondria. I. Isolation and characterization of multiple forms," *Arch. Biochem. Biophys.* 285(1):158-165 (1991).

Suarez de Mata et al., "Propionyl-CoA condensing enzyme from Ascaris muscle mitochondria. II. Coenzyme A modulation," *Arch. Biochem. Biophys.* 285:166-171 (1991).

Suda et al., "Purification and properties of α-ketoadipate reductase, a newly discovered enzyme from human placenta," *Arch. Biochem. Biophys.* 176(2):610-620 (1976).

Suda et al., "Subcellular localization and tissue distribution of α-ketoadipate reduction and oxidation in the rat," *Biochem. Biophys. Res. Commun.* 77(2):586-591 (1977).

Suematsu et al., "Molecular cloning and functional expression of rat liver cytosolic acetyl-CoA hydrolase," *Eur. J. Biochem.* 268(9):2700-2709 (2001).

Sulzenbacher et al., "Crystal structure of *E.coli* alcohol dehydrogenase YqhD: evidence of a covalently modified NADP Coenzyme," *J. Mol. Biol.* 342(2):489-502 (2004).

Suthers et al., "Metabolic flux elucidation for large-scale models using 13C labeled isotopes," *Metab. Eng.* 9:387-405 (2007).

Suzuki et al., "Acetylputrescine deacetylase from *Micrococcus luteus* K-11," *Biochim. Biophys. Acta* 882:140-142 (1986).

Suzuki et al., "GriC and GriD Constitute a carboxylic acid reductase involved in grixazone biosynthesis in streptomyces griseus," *J. Antibiot.* 60(6):380-387 (2007).

Suzuki et al., "Properties and metabolic role of mesaconate hydratase of an aerobic bacterium," *J. Biochem.* 81:1917-1925 (1977).

Suzuki, "Phospotransacetylase of *Escherichia coli* B., activation by pyruvate and inhibition by NADH and certain nucleotides," *Biochem. Biophys. Acta.* 191:559-569 (1969).

Svensson et al., "Characterization and isolation of enzymes that hydrolyze short-chain acyl-CoA in rat-liver mitochondria," *Eur. J. Biochem.* 239(2):526-531 (1996).

Svetlitchnyi et al., "A functional Ni-Ni-[4Fe-4S] cluster in the monomeric acetyl-CoA synthase from *Carboxydothermus hydrogenoformans*," *Proc. Natl. Acad. Sci. USA* 101(2):446-451 (2004).

Svetlitchnyi et al., "Two membrane-associated NiFeS-carbon monoxide dehydrogenases from the anaerobic carbon-monoxide-utilizing eubacterium *Carboxydothermus hydrogenoformans*," *J. Bacteriol.* 183(17):5134-5144 (2001).

Switzer, "Glutamate mutase," In: Dolphin D. ed., *Vitamin $B_{12}$* (vol. 2: *Biochemistry and Medicine*), Wiley-Interscience: New York, p. 298-305 (1982).

Tae-Kang et al., "Purification and characterization of a cyclohexanol dehydrogenase from *Rhodococcus* sp. TK6," *J. Microbiol. Biotechnol.* 12:39-45 (2002).

Tahlan et al., "Two sets of paralogous genes encode the enzymes involved in the early stages of clavulanic acid and clavam metabolite biosynthesis in *Streptomyces clavuligerus*," *Antimicrob. Agents Chemother.* 48(3):930-939 (2004).

Takács et al., "Formate hydrogenlyase in the hyperthermophilic archaeon, Thermococcus litoralis," *BMC Microbiol.* 8:88 (2008).

Takagi et al, "Purification, crystallization, and molecular properties of aspartase from *Pseudomonas fluorescens*," *J. Biochem.* 96(2):545-552 (1984).

Takagi and Kisumi, "Isolation of a versatile *Serratia marcescens* mutant as a host and molecular cloning of the aspartase gene," *J. Bacteriol.* 161:1-6 (1985).

Takagi et al., "Cloning and nucleotide sequence of the aspartase gene of *Pseudomonas fluorescens*," *J. Biochem.* 100(3):697-705 (1986).

Takahashi et al., "Metabolic pathways for cytoxic and end product formation from glutamate- and aspartate-containing peptides by *Porphyromonas gingivalis*," *J. Bacteriol.* 182:4704-4710 (2000).

Takahashi-Abbe et al., "Biochemical and functional properties of a pyruvate formate-lyase (PFL)-activating system in Streptococcus mutans," *Oral. Microbiol. Immunol.* 18:293-297 (2003).

Takanashi et al., "Characterization of a novel 3-hydroxybutyrate dehydrogenase from *Ralstonia pickettii* T1," *Antonie van Leeuwnhoek* 95(3):249-262 (2009).

Takatsuka et al., "Gene cloning and molecular characterization of lysine decarboxylase from *Selenomonas ruminantium* delineate its evolutionary relationship to ornithine decarboxylases from eukaryotes," *J. Bacteriol.* 182:6732-6741 (2000).

Takatsuka et al., "Identification of the amino acid residues conferring substrate specificity upon *Selenomonas ruminantium* lysine decarboxylase," *Bioxci. Biotechnol. Biochem.* 63:1843-1846 (1999).

Takeo, "Existence and Properties of Two Malic Enzymes in *Escherichia coli* Especially of NAD-linked Enzyme," *J. Biochem.* 66:379-387 (1969).

Takigawa et al., "Probabilistic path ranking based on adjacent pairwise coexpression for metabolic transcripts analysis," *Bioinform.* 24(2):250-257 (2008).

Tallant and Krzycki, "Coenzyme M methylase activity of the 480-kilodalton corrinoid protein from Methanosarcina barkeri," *J. Bacteriol.* 175(5):1295-1301 (1996).

Tallant and Krzycki, "Methylthiol:Coenzyme M Methyltransferase from *Methanosarcina barkeri*, an enzyme of methanogenesis from dimethylsulfide and methylmercaptopropionate," *J. Bacteriol.* 179(22):6902-6911 (1997).

Tallant et al., "The MtsA subunit of the methylthiol:Coenzyme M methyltransferase of *Methanosarcina barkeri* catalyses both half-reactions of corrinoid-dependent dimethylsulfide: Coenzyme M methyl transfer," *J. Biol. Chem.* 276(6):4485-4493 (2001).

Tamaki et al., "Purification, properties, and sequencing of aminoisobutyrate aminotransferases from rat liver," *Methods Enzymol.* 324:376-389 (2000).

Tanaka et al., "Cloning and characterization of a human orthologue of testis-specific succinyl CoA: 3-oxo acid CoA transferase (Scot-t) cDNA," *Mol. Hum.* Reprod. 8:16-23 (2001).

Tanaka et al., "Lysine decarboxylase of Vibrio parahaemolyticus: kinetics of transcription and role in acid resistance," *J. Appl. Microbiol.* 104:1283-1293 (2008).

Tang et al., "Identification of a novel pyridoxal 5'-phosphaste binding site in adenosylcobalamin-dependent lysine 5,6-aminomutase from *Porphyromonas gingivalis*," *Biochemistry* 41(27):8767-8776 (2002).

Tani et al., "Thermostable NADP(+)-dependent medium-chain alcohol dehydrogenase from *Acinetobacter* sp. strain M-1: purification and characterization and gene expression in *Escherichia coli*," *Appl. Environ. Microbiol.* 66(12):5231-5235 (2000).

Tanizawa et al., "The primary structure of thermostable D-amino acid aminotransferase from a thermophilic Bacillus species and its correlation with L-amino acid aminotransferases," *J. Biol. Chem.* 264(5):2450-2454 (1989).

Tardif et al., "Electrotransformation studies in Clostridium cellulolyticum," *J. Ind. Microbiol. Biotechnol.* 27(5):271-274 (2001).

Taylor and Fotheringham, "Nucleotide sequence of the *Bacillus licheniformis* ATCC 10716 dat gene and comparison of the predicted amino acid sequence with thos of other bacterial species," *Biochim. Biophys. Acta* 1350(1):38-40 (1997).

Tebbe et al., "Titanium-Catalyzed Olefin Metathesis," *J. Am. Chem. Soc.* 101(17):5074-5075 (1979).

Teipel et al., "The substrate specificity of fumarase," *J. Biol. Chem.* 243:5684-5694 (1968).

Ter Schure et al., "Pyruvate decarboxylase catalyzes decarboxylation of branched-chain 2-oxo acids but is not essential for fusel alcohol production by *Saccharomyces cerevisiae*," *Appl. Environ. Microbiol.* 64:1303-1307 (1998).

Teufel et al., "3-hydroxypropionyl-Coenzyme A dehydratase and acryloyl-Coenzyme A reductase, enzymes of the autotrophic 3-hydroxypropionate/4-hydroxybutyrate cycle in the Sulfolbales," *J. Bacteriol.* 191:4572-4581 (2009).

Thauer, "Microbiology. A Fifth Pathway of Carbon Fixation," *Science* 318:1732-1733 (2007).

Thomas et al., "Bimetallic nanocatalysts for the conversion of muconic acid to adipic acid," *Chem. Commun.* 21:1126-1127 (2003).

Thornton et al., "Primary structure of the monomer of the 12S subunit of transcarboxylase as deduced from DNA and characterizatio nof the product expressed in *Escherichia coli*," *J. Bacteriol.* 175:5301-5308 (1993).

Thykaer, et al., "Metabolic network analysis of an adipoyl-7-ADCA-producing strain of *Penicillium chrysogenum*: elucidation of adipate degradation," *Metab. Eng*, 4(2):151-158 (2002).

Tian et al., "Variant tricarboxylic acid cycle in *Mycobacterium tuberculosis*: identification of α-ketoglutarate decarboxylase," *Proc. Natl. Acad. Sci. USA.* 102:10670-10675 (2005).

Tobimatsu et al., "Molecular cloning, Sequencing and Characterization of the Genes for Adenosylcobalamin-deptendent Diol Dehydratase of *Klebsiella pneumoniae*," *Biosci. Biotechnol. Biochem.* 62(9):1774-1777 (1998).

Tobimatsu et al., "Molecular cloning, Sequencing and Expression of the Genes Encoding Adenosylcobalamin-dependent Diol Dehydrase of *Klebsiella oxytoca*," *J. Biol. Chem.* 270(13):7142-7148 (1995).

Tobin et al., "Localization of the Lysine ε-Aminotransferase (lat) and δ-(L-α-Aminoadipyl)-L-Cysteinyl-D-Valine Synthetase (pcbAB) Genes from Streptomyces clavuligerus and Production of Lysine Δ-Aminotransferase Activity in *Escherichia coli*," *J. Bacteriol.* 173(19):6223-6229 (1991).

Tolentino et al., "A pH-regulated promoter for the expression of recombinant proteins in *Escherichia coli*," *Biotechnol. Lett.* 14:157-162. (1992).

Tomas et al., "Overexpression of groESL in *Clostridium acetobutylicum* Results in Increased Solvent Production and Tolerance, Prolonged Metabolism, and Changes in the Cell's Transcriptional Program," *Appl. Environ. Microbiol.* 69:4951-4965 (2003).

Toraya et al., "Substrate Specificity of Coenzyme $B^{12}$-Dependent Diol Dehydrase: Glycerol as Both a Good Substrate and a Potent Inactivator," *Biochem. Biophys. Res. Commun.* 69:475-480 (1976).

Toth et al., "The ald Gene, Encoding a Coenzyme A-Acylating Aldehyde Dehydrogenase, Distinguishes *Clostridium beijerinckii* and Two Other Solvent-Producing *Clostridia* from *Clostridium acetobutylicum*," *App. Environ. Microbiol.* 65(11):4973-4980 (1999).

Tretter and Adam-Vizi, "A-ketoglutarate dehydrogenase: a target and generator of oxidative stress," *Philos. Trans. R. Soc. Lond. B. Biol. Sci.* 360:2335-2345 (2006).

Trower et al., "Isolation and Characterization of a Cyclohexane-Metabolizing *Xanthobacter* sp.," *Appl. Environ. Microbiol.* 49(5):1282-1289 (1985).

Tsao et al., "Production of multifunctional organic acids from renewable resources," *Adv. Biochem. Eng. Biotechnol.* 65:243-280 (1999).

Tseng et al., "Metabolic Engineering of *Escherichia coli* for Enhanced Production of (R)- and (S)-3-Hydroxybutyrate," *App. Environ. Microbiol.* 75(10):3137-3145 (2009).

Tseng et al., "Oxygen- and growth rate-dependent regulation of *Escherichia coli* fumarase (FumA, FumB, and BumC) activity," *J. Bacteriol.* 183(2):461-467 (2001).

Tsujimoto et al., "L-Lysine biosynthetic pathway of Methylophilus methylotrophus and construction of an L-Lysine producer," *J. Biotechnol.* 124:327-337 (2006).

Tucci and Martin, "A novel prokaryotic trans-2-enoyl-CoA reductase from the spirochete *Treponema denticola*," *FEBS Lett.* 581(8):1561-1566 (2007).

Tutino et al., "Expression of *Sulfolobus solfataricus* trpE and trpG genes in *E. coli*," *Biochem. Biophys. Res. Commun.* 230:306-310 (1997).

Twarog and Wolfe, "Role of butyryl phosphate in the energy metabolism of *Clostridium tetanomorphum*," *J. Bacteriol.* 86:112-117 (1963).

Tyurin, et al., "Electrotransformation of *Clostridum acetobutylicum* ATCC 824 using high-voltage radio frequency modulated square pulses," *J. Appl. Microbiol.* 88(2):220-227 (2000).

Tyurin, et al., "Electrotransformation of *Clostridium thermocellum*," *Appl. Environ Microbiol*, 70(2):883-890 (2004).

Tzagoloff and Dieckmann, "PET genes of *Saccharomyces cerevisiae*," *Microbiol. Rev.* 54(9):211-225 (1990).

Uchiyama et al., "Identification of the 4-Hydroxycinnamate Decarboxylase (PAD) Gene of *Klebsiella oxytoca*," *Biosci. Biotechnol. Biochem.* 72: 116-123 (2008).

Ulaganathan et al., "Structure of Staphylococcus aureus 1,4-dihydroxy-2-naphthoyl-CoA synthase (MenB) in complex with acetoacetyl-CoA," *Acta. Crystallogr. Sect. F Struct. Biol. Cryst. Commun.* 63(Pt 11):908-913 (2007).

Umbarger and Brown, "Threonine deamination in *Escherichia coli*. II. Evidence fro two L-threonine deaminases," *J. Bacteriol.* 73(1):105-112 (1957).

Underwood et al., "Genetic Changes to Optimize Carbon Partitioning between Ethanol and Biosynthesis in Ethanologenic *Escherichia coli*," *App. Environ. Microbiol.* 68(12):6263-6272 (2002).

Urbance et al., "Evaluation of succinic acid continuous and repeat-batch biofilm fermentation by *ActinoBacillus succinogenes* using plastic composite support bioreactors," *Appl. Microbiol. Biotechnol.* 65(6):664-670 (2004).

Uttaro and Opperdoes, "Purification and characterisation of a novel isopropanol dehydrogenase from *Phytomonas* sp.," *Mol. Biochem. Parasitol.* 85:213-219 (1997).

Vadali, et al., "Enhanced Isoamyl Acetate Production upon Manipulation of the Acetyl-CoA node in *Escherichia coli*," *Biotech. Prog.* 20:692-697 (2004).

Vadali, et al., "Production of isoamyl acetate in ackA-pta and/or ldh mutants of *E. coli* with overexpression of yeast ATF2," *Appl. Microbiol. Biotechnol.* 63:698-704 (2004).

Vadali, et al., "Cofactor engineering of intercellular CoA/acetyl-CoA and its effect on metabolic flux redistribution in *Escherichia coli*," *Metab Eng*. 6(2): 133-139 (2004).

Valdés-Hevia and Gancedo, "Isolation and characterization of the gene encoding phosphoenolpyruvate carboxykinase from *Saccharomyces cerevisiae*," *FEBS Lett.* 258:313-316 (1989).

Valentin et al., "Metabolic pathway for biosynthesis of poly(3-hydroxybutyrate-co-4-hydroxybutyrate) from 4-hydroxybutyrate by *Alcaligenes eutrophus*," *Eur. J. Biochem.* 227(1-2):43-60 (1995).

Valentine and Wolfe, "Purification and role of phosphotransbutyrylase," *J. Biol. Chem.* 235:1948-1952 (1960).

Vamecq et al., "The microsomal dicarboxylyl-CoA synthetase," *Biochem. J.* 230(3):683-693 (1985).

Van Beilen et al., "Cloning of Baeyer-Villiger monoxygenases from comamonas, *Xantherobacter* and *Rhodococcus* using polymerase chain reaction with highly degenerate primers," *Environ. Microbiol.* 5(3):174-182 (2003).

van der Voorhorst et al., "Genetic and biochemcial characterization of a short-chain alcohol dehydrogenase from the hyperthermophilic archaeon *Pyrococcus furiosus*," *Eur. J. Biochem.* 268:3062-3068 (2001).

Van Der Westhuizen, et al., "Autolytic Activity and Butanol tolerance of *Clostridium acetobutylicum*," *Appl. Environ. Microbiol.* 44:1277-1281 (1982).

van Grinsven et al., "Acetate:succinate CoA-transferase in the hydrogenosomes of *Trichomonas vaginalis*: identification and characterization," *J. Biol. Chem.* 283:1411-1418 (2008).

van Loon and Yang, "Intracellular sorting of alcohol dehydregenase isoenzymes in yeast: a cytosolic location oreflects absence of an amino-terminal targeting sequence for the mitochondrion," *EMBO J.* 5:161-165 (1986).

van Maris et al., "Directed evolution of pyruvate decarboxylase-negative *Saccharomyces cerevisiae*, yielding a C2-independent, glucose-tolerant, and pyruvate-hyperproducing yeast," *Appl. Environ. Microbiol.* 70:159-166 (2004).

Van Mullem et al., "Construction of a set of *Saccharomyces cerevisiae* vectors designed for recombinational cloning," *Yeast* 20(8):739-746 (2003).

Vanderwinkel et al., "Growth of *Escherichia coli* on fatty acids: requirement for Coenzyme A transferase activity," *Biochem. Biophys. Res. Commun.* 33(6):902-908 (1968).

Vanrolleghem et al., "Validation of a Metabolic Network for *Saccharomyces cerevisiae* Using Mixed Substrate Studies," *Biotechnol. Prog.* 12(4):434-448 (1996).

Varadarajan and Miller, "Catalytic Upgrading of Fermentation-Derived Organic Acids," *Biotechnol. Prog.* 15:845-854 (1999).

Vardar-Schara et al., "Metabolically engineered bacteria for producing hydrogen via fermentation," *Microbio. Biotechnol.* 1:107-125 (2008).

Varma and Palsson, "Stoichiometric Flux Balance Models Quantitatively Predice Growth and Metabolic By-Product Secretion in Wild-Type *Escherichia coli* W3110," *Appl Env. Microbiol.* 60(10):3724-3731 (1994).

Varma and Palsson, "Metabolic Flux Balancing: Basic Concepts, Scientific and Practical Use," *Biotechnology* 12:994-998 (1994).

Varma et al., "Biochemical Production Capabilities of *Escherichia coli*," *Biotechnol. Bioeng.* 42:59-73 (1993).

Varma et al., "Stoichiometric Interpretation of *Escherichia coli* Glucose Catabolism under Various Oxygenation Rates," *Appl. Environ. Microbiol.* 59:2465-2473 (1993).

Vazquez et al., "Phosphtransbutyrylase expression in *Bacillus megaterium*," *Curr. Microbiol.* 42:345-349 (2001).

Vega et al., "The Biological Production of Ethanol from Synthesis Gas," *Appl. Biochem. Biotechnol.* 20/21:781-797 (1989).

Vellanki et al., "Expression of hepatitis B surface antigen in *Saccharomyces cerevisiae* utilizing glyceraldehyde-3-phosphate dehydrogenase promoter of Pichia pastoris," *Biotechnol. Lett.* 29(2):313-318 (2007).

Vemuri et al., "Effects of growth mode and pyruvate carboxylase on succinic acid production by metabolically engineered strains of *Escherichia coli*," *Appl. Environ. Microbiol.* 68(4): p. 1715-1727 (2002).

Vemuri et al., "Succinate production in dual-phase *Escherichia coli* fermentations depends on the time of transition from aerobic to anaerobic conditions," *J. Ind. Microbiol. Biotechnol.* 28(6): p. 325-332 (2002).

Venkitasubramanian et al. *Biocatalysis in the Pharmaceutical and Biotechnology Industries*, ed. R.N. Patel, Chapter 15, pp. 425-440, CRC Press LLC, Boca Raton, FL. 2007.

Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).

Verhaert et al., "Enzyme kinetics in reversed micelles. 2. Behaviour of enoate reductase," *Eur. J. Biochem.* 187:73-79 (1990).

Vermuri, et al. "Succinate production in dual-phase *Escherichia coli* fermentations depends on the time of transition from aerobic to anaerobic conditions," *J. Ind. Microbiol. Biotechnol.* 28:325-332 (2002).

Vernal et al., "Cloning and heterologous expression of a broad specificity aminotransferase of *Leishmania mexicana* promastigotes," *FEMS Microbiol. Lett.* 229:217-222 (2003).

Vernal et al., "Isolation partial characterization of a broad specificity aminotransferase from *Leishmania mexicana* promastigotes," *Mol. Biochem. Parasitol.* 96:83-92 (1998).

Vey et al., "Structural basis for glycyl radical formation by pyruvate formate-lyase activating enzyme," *Proc. Natl. Acad. Sci USA* 105:16137-16141 (2008).

Vijay et al., "Diels-Alder reactions between cyclic five-membered dienes and acetylene," *J. Mol. Struc.* 589-590:291-299 (2002).

Viola, "L-Aspartase: New Tricks From an Old Enzyme," *Adv. Enzymol. Relat. Areas. Mol. Biol.* 74:295-341 (2000).

Voets et al., "Reduced intracellular ionic strength as the initial trigger for activation of endothelial volume-regulated anion channels," *Proc Natl Acad Sci. U.S.A* 96:5298-5303 (1999).

Volkert, et al., "The Δ(*argF-lacZ*)205(U169) Deletion Greatly Enhances Resistance to Hydrogen Peroxide in Stationary-Phase *Escherichia coli*," *J. Bact.* 176(3):1297-1302 (1994).

Volkov et al., "Random chimeragenesis by heteroduplex recombination," *Methods Enzymol.* 328:456-463 (2000).

Volkov et al., "Recombination and chimeragenesis by in vitro heteroduplex formation and in vivo repair," *Nucleic Acids Res.* 27:e18 (1999).

Vrijbloed et al., "Insertional inactivation of methylmalonyl Coenzyme A (CoA) mutase and isobutyryl-CoA mutase genes in *Streptomyces cinnamonensis*: influence on polyketide antibiotic biosynthesis," *J. Bacteriol.* 181(18):5600-5605 (1999).

Wakil et al., "Studies on the fatty acid oxidizing system of animal tissues. VI. β-Hydroxyacyl Coenzyme A dehydrogenase," *J. Biol. Chem.* 207(2):631-638 (1954).

Walker et al., "Yeast pyruvate carboxylase: identification of two genes encoding isoenzymes," *Biochem. Biophys. Res. Commun.* 176:1210-1217 (2007).

Walter et al., "Molecular characterization of two *Clostridium acetobutylicum* ATCC 824 butanol dehydrogenase isozyme genes," *J. Bacteriol.* 174(22):7149-7158 (1992).

Walter et al., "Sequence and arrangement of two genes of the butyrate-synthesis pathway of *Clostridium acetobutylicum* ATCC 824," *Gene* 134(1):107-111 (1993).

Wang and Barker, "Purification and Properties of L-citramalate hydrolase," *J. Biol. Chem.* 244(10):2516-2526 (1969).

Wang and Seah, "Determination of the metal ion dependence and substrate specificty of a hydratase involve din the degradation pathway of biphenyl/chlorobiphenyl," *FEBS J.* 272: 966-974 (2005).

Wang et al, "Molecular cloning and functional identification of a novel phenylacetyl-CoA ligase gene from *Penicillium chrysogenum*," *Biochem. Biopyhs. Res. Commun.* 360(2):453-458 (2007).

Wang et al., "The primary structure of branched-chain α-oxo acid dehydrogenase from *Bacillus subtilis* and its similarity to other α-oxo acid dehydrogenases," *Eur. J. Biochem.* 213:1091-1099 (1993).

Wang et al., "Bioconversion of fumaric acid to succinic acid by recombinant *E. coli*," *App. Biochem. Biotechnol.* 70-72: 919-928 (1998).

Wang et al., "Cloning, Sequencing, and Expression of the Pyruvate Carboxylase Gene in *Lactococcus lactis* subsp. *lactis* C2," *App. Environ. Microbiol.* 66(3):1223-1227 (2000).

Wang et al., "Expression of galactose permease and pyruvate carboxylase in *Escherichia coli* ptsG mutant increases the growth rate and succinate yield under anaerobic conditions," *Biotechnol. Lett.* 28(2):89-93 (2006).

Wang et al., "Genome-scale in silica aided metabolic analysis and flux comparisons of *Escherichia coli* to improve succinate production," *Appl. Microbiol. Biotechnol.* 73(4):887-894 (2006).

Wang et al., "Site-directed mutagenesis of the phosphorylatable serine (Ser[8]) in C4 phosphoenolpyruvate carboxylase from sorghum. The effect of negative charge at position 8," *J. Biol. Chem.* 267:16759-16762. (1992).

Wanner and Tressl, "Purification and characterization of two enone reductases from *Saccharomyces cerevisiae*," *Eur. J. Biochem.* 255(1):271-278 (1998).

Ward et al., "Molecular analysis of the role of two aromatic aminotransferases and a broad-specificity aminotransferase in the aromatic amino acid metabolism of *Pyococcus furiosus*," *Archaea* 1:133-141 (2002).

Weaver, "Structure of free fumarase C from *Escherichia coli*," *Acta Crystallogr. D. Biol. Crystallogr.* 61(Pt 10):1395-1401 (2005).

Weber and Falbe, "Oxo Synthesis Technology," *Ind Eng Chem Res* 62:33-37 (1970).

Weidner and Sawers, "Molecular characterization of the Genes Encoding Pyruvate Formate-Lyase and Its Activating enzyme of *Clostridium pasteruianum*," *J. Bacteriol.* 178(8):2440-2444 (1996).

Welch et al., "Purification and Characterization of the NADH-Dependent Butanol Dehydrogenase from *Clostridium acetobutylicum* (ATCC 824)," *Arch. Biochem. Biophys.* 273(2):309-318 (1989).

Wengrovius et al., "Tungsten-Oxo Alkylidene Complexes as Olefin Metathesis Catalysts and the Crystal Structure of W(O)(CHCMe$_3$)(PTt$_3$)Cl$_2$$^1$," *J. Am. Chem. Soc.* 102:4515-4516 (1980).

Westin et al., "The identification of a succinyl-CoA thioesterase suggests a novel pathway for succinate production in peroxisomes," *J. Biol. Chem.* 280(46):38125-38132 (2005).

Wexler et al., "A wide host-range metagenomic library from a waste water treatment plant yields a novel alcohol/aldehyde dehdrogenase," *Environ. Microbiol.* 7:1917-1926 (2005).

Whalen and Berg, "Analysis of an *avtA*::Mu d1(Ap *lac*) Mutant: Metabolic Role of Transaminase C," *J. Bacteriol.* 150(2):739-746 (1982).

Whalen and Berg, "Gratuitous repression of avtA in *Escherichia coli* and *Salmonella typhimurium*," *J. Bacteriol.* 158(2):571-574 (1984).

Whisstock et al., "Prediction of protein function from protein sequence and structure," *Q. Rev. Biophysics.* 36(3):307-340 (2003).

White et al., "Long-chain alcohol production by yeasts," *7th Int. Symp. Yeasts* S465-S470 (1989).

White et al., "The structural biology of type II fatty acid biosynthesis," *Ann. Rev. Biochem.* 74:791-831 (2005).

Whitehead and Rabinowitz, "Cloning and expression in *Escherichia coli* of the gene for 10-formyltetrahydrofolate synthetase from *Clostridium acidiurici* ("*Clostridium acidi-urici*")," *J. Bacteriol.* 167:205-209 (1986).

Whitehead and Rabinowitz, "Nucleotide Sequence of the *Clostridium acidiurici* ("*Clostridium acidi-urici*") Gene for 10-Formyltetrahydrofolate Synthetase Shows Extensive Amino Acid Homology with the Trifunctional Enzyme C$_1$-Tetrahydrofolate Synthase from *Saccharomyces cerevisiae*," *J. Bacteriol.* 170(7):3255-3261 (1988).

Wiesenborn et al., "Coenzyme A Transferase from *Clostridium acetobutylicum* ATCC 824 and Its Role in the Uptake of Acids," *Appl. Environ. Microbiol.* 55(2):323-329 (1989).

Wiesenborn et al., "Phosphotransbutyrylase from *Clostridium acetobutylicum* ATCC 824 and its role in acidogenesis," *Appl. Environ. Microbiol.* 55:317-322 (1989).

Wilkie and Warren, "Recombinant expression, purification, and characterization of three isoenzymes of aspartate aminotransferase from *Arabidopsis thaliana*," *Protein Expr. Purif.* 12:381-389 (1998).

Wilks et al., "A specific, Highly Active Malate Dehydrogenase by Redesign of a Lactate Dehydrogenase Framework," *Science* 242:1541-1544 (1988).

Wilks et al., "Design of a Specific Phenyllactate Dehydrogenase by Peptide Loop Exchange on the *Bacillus stearothermophilus* Lactate Dehydrogenase Framework," *Biochemistry* 31:7802-7806 (1992).

Wilks et al., "Designs for a Broad Substrate Specificity Keto Acid Dehydrogenase," *Biochemistry* 29:8587-8591 (1990).

Willke and Vorlop, "Biotechnological production of itaconic acid," *Appl. Microbiol. Biotechnol.* 56(3-4):289-295 (2001).

Willke and Vorlop, "Industrial bioconversion of renewable resources as an alternative to conventional chemistry," *Appl. Microbiol. Biotechnol.* 66(2):131-142 (2004).

Winkler et al., "A new type of a multifunctional β-oxidation enzyme in euglena," *Plant. Physiol.* 131(2):753-762 (2003).

Winzeler et al., "Functional Characterization of *S. cerevisiae* Genome by Gene Deletion and Parallel Analysis," *Science* 285:901-906 (1999).

Winzer et al., "Differential regulation of two thiolase genes from *Clostridium acetobutylicum* DSM 792," *J. Mol. Microbiol. Biotechnol.* 2(4):531-541 (2000).

Witkowski et al., "Conversion of b-ketoacyl synthase to a Malonyl Decarboxylase by replacement of the active cysteine with glutamine," *Biochemistry* 38:11643-11650 (1999).

Wittich and Walter, "Putrescine N-acetyltransferase in *Onchocerca volvulus* and *Ascaris suum*, an enzyme which is involved in polyamine degradation and release of N-acetylputrescine," *Mol. Biochem. Parasitol.* 38:13-17 (1990).

Wolff and Kenealy, "Purification and characterization of the oxygen-sensitive 4-hydroxybutanoate dehydrogenase from *Clostridium kluyveri*," *Protein Expr. Purif.* 6:206-212 (1995).

Wong et al., "Molecular Properties of Pyruvate Formate-Lyase Activating Enzyme," *Biochemistry* 32:14102-14110 (1993).

Wong et al., "Sequence saturation mutagenesis (SeSaM): a novel method for directed evolution," *Nucleic Acids Res* 32:e26 (2004).

Wong et al., "Sequence saturation mutagenesis with tunable mutation frequencies," *Anal. Biochem.* 341:187-189 (2005).

Wong et al., "Transversion-enriched sequence saturation mutagenesis (SeSaM-Tv$^+$): a random mutagenesis method with consecutive nucleotide exchanges that complements the bias of error-prone PCR," *Biotechnol. J.* 3:74-82 (2008).

Wood, "Life with CO or $CO_2$ and $H_2$ as a source of carbon and energy," *Fed. Amer. Societies Experi. Biol. J.* 5:156-163 (1991).

Woods, "Two biochemically distinct classes of fumarase in *Escherichia coli*," *Biochim. Biophys. Acta* 954(1):14-26 (1988).

Wu and Woodard "New insights into the evolutionary links relating to the 3-deoxy-D-arabino-heptulosonate 7-phosphate synthase subfamilies," *J Biol. Chem.* 281:4042-4048 (2006).

Wu et al., "Microbial synthesis of cis-cis-muconic acid by *Sphingobacterium* sp. GCG generated from effluent of a styrene monomer (SM) production plant," *Enzyme Microbial Tech.* 35:598-604 (2004).

Wu et al., "Thermotoga maritima 3-deoxy-D-arabino-heptulosonate 7-phosphate (DAHP) synthase: the ancestral eubacterial DAHP synthase?" *J. Biol. Chem.* 278:27525-27531 (2003).

Wu et al., "Life in hot carbon monoxide: the complete genome sequence of *Carboxydothermus hydrogenoformans* Z-2901," *PLoS Genet*, 1(5):e65 (2005).

Wylie et al., "Nematode.net: a tool for navigating sequences from parasitic and free-living nematodes," *Nucleic Acids Res.* 32:D423-D426 (2004).

Wynn et al., "Chaperonins groEL and groES promote assembly of heterotetramers ($α_2β_2$) of mammalian mitochondrial branched-chain α-keto acid decarboxylase in *Escherichia coli*," *J. Biol. Chem.* 267:12400-12403 (1992).

Wynn et al., "Cloning and expression in *Escherichia coli* of mature E1β subunit of bovine mitochondrial branched-chain α-keto acide dehydrogenase complex. Mapping of the E1β-binding region on E2," *J. Biol. Chem.* 267:1881-1887 (1992).

Yabutani et al., "Analysis of β-ketothiolase and acetoacetyl-CoA reductase genes of a methylotrophic bacterium, *Paracoccus denitrificans*, and their expression in *Escherichia coli*," *FEMS Microbiol. Lett.* 133:85-90 (1995).

Yagi et al., "Aspartate: 2-oxoglutarate aminotransferase from bakers' yeast: crystallization and characterization," *J. Biochem.* 92(1):35-43 (1982).

Yagi et al., "Crystallization and properties of aspartate aminotransferase from *Escherichia coli* B," *FEBS Lett.* 100(1):81-84 (1979).

Yagi et al., "Glutamate-aspartate transaminase from microorganisms," *Methods Enzymol* 113:83-89 (1985).

Yamamoto et al., "Carboxylation reaction catalyzed by 2-oxoglutarate:ferredoxin oxidoreductases from *Hydrogenobacter thermophilus*," *Extremophiles* 14:79-85 (2010).

Yamamoto et al., "Purification and Properties of NADP-dependent Formate Dehydrogenase from Clostridium thermoaceticum, a tungsten-Selenium-Iron Protein," *J. Biol. Chem.* 258(3):1826-1832 (1983).

Yamano et al., "Construction of a brewer's yeast having α-acetolactate decarboxylase gene from *Acetobacter aceti* sp. xylinum integrted in the genome," *J. Biotechnol.* 32:173-178 (1994).

Yan and Chen, "Coenzyme A-acylating aldehyde dehydrogenase from *Clostridium beijerinckii* NRRL B692," *Appl. Environ. Microbiol.* 56:2591-2599 (1990).

Yang et al., "Nucleotide sequence of the promoter and *fadB* gene of the *fadBA* operon and primary structure of the multifunctional fatty acid oxidation protein from *Escherichia coli*," *Biochem.* 30(27):6788-6795 (1991).

Yang et al., "Aspartate Dehydrogenase, a Novel Enzyme Identified from Structural and Functional Studies of TM1643," *J. Biol. Chem.* 278(10):8804-8808 (2003).

Yang et al., "Metabolic Flux Analysis of *Escherichia coli* Deficient in the Acetate Production Pathway and Expressing the *Bacillus subtilis* Acetolactate Synthase," *Metab. Eng.* 1(1):26-34 (1999).

Yang et al., "Nucleotide sequence of the *fadA* gene. Primary structure of 3-ketoacyl-Coenzyme A thiolase from *Escherichia coli* and the structural organization of the *fadAB* operon," *J. Biol Chem.* 265(18):10424-10429 (1990).

Yang et al., "Nucleotide sequence of the *fadA* gene. Primary structure of 3-ketoacyl-Coenzyme A thiolase from *Escherichia coli* and the structural organization of the *fadAB* operon," *J. Biol. Chem.* 266(24):16255 (1990).

Yang et al., "The effects of feed and intracellular pyruvate levels on the redistribution of metabolic fluxes in *Escherichia coli*," *Metab Eng.* 3(2):115-123 (2001).

Yang, "Location of the *fadBA* operon on the physical map of *Escherichia coli*," *J. Bacteriol.* 173(23):7405-7406 (1991).

Yang, et al., "Effect of inactivation of *nuo* and *ackA-pta* on redistribution of metabolic fluxes in *Escherichia coli*," *Biotechnol Bioeng.* 65(3):291-297 (1999).

Yang, et al., "Effect of Variation of *Klebsiella pneumoniae* Acetolactate Synthase Expression on Metabolic Flux Redistribution in *Escherichia coli*." *Biotechnol. Bioeng.* 69(2)150-159 (2000).

Yang, et al., "Redistribution of Metabolic Fluxes in *Escherichia coli* with Fermentative Lactate Dehydrogenase Overexpression and Deletion," *Metab. Eng.* 1:141-152 (1999).

Yanisch-Perron et al., "Improved M13 phage cloning vectors and host strains: nucleotide sequences of the M13mp18 and pUC19 vectors," *Gene* 33:103-19 (1985).

Yano et al., "Directed evolution of an aspartate aminotransferase with new substrate specificities," *Proc. Natl. Acad. Sci USA* 95:5511-5515 (1998).

Yarlett et al., "*Trichomonas vaginalis*: characterization of ornithine decarboxylase," *Biochem. J.* 293(Pt2):487-493 (1993).

Yeh and Ornston, Evolutionarily Homologous α₂β₂ Oligomeric Structures in β-Ketoadipate Sccinyl-CoA Transferases from *Acinetobacter calcoaceticus* and *Pseudomonas putida, J. Biol. Chem.* 256(4):1565-1569 (1981).

Ylianttila et al., "Crystal Structure of Yeasat Peroxisomal Multifunctional Enzyme: Structural Basis for Substrate Specificity of (3R)-hydroxyacyl-CoA Dehydrogenase Units," *J. Mol. Biol.* 258:1286-1295 (2006).

Ylianttila et al., "Site-directed mutagenesis to enable and improve crystallizability of candida tropicalis (3R)-hydroxyacyl-CoA dehydrogenase," *Biochem. Biophys. Res. Commun.* 324:25-30 (2004).

Yoshida et al., "The Structures of L-Rhamnose Isomerase from Pseudomonas stutzeri in Complexes with L-Rhamnose and D-Allose Provide Insights into Broad Substrate Specificity," *J. Mol. Biol.* 365:1505-1516 (2007).

Yoshimoto, et al., "Isolation and Characterization of the *ATF2* Gene Encoding Alcohol Acetyltransferase II in the Bottom Fermenting Yeast *Saccharomyces pastorianus*," *Yeast* 15:409-417 (1999).

Yoshioka and Hashimoto, "Ester formation by Alcohol Acetyltransferase from Brewers' Yeast," *Agric. Biol. Chem.* 45:2183-2190 (1981).

Youngleson et al., "Homology between hydroxybutyryl and hydroxyacyl Coenzyme A dehydrogenase enzymes from *Clostridium acetobutylicum* fermentation and vertebrate fatty acid β-oxidation pathways," *J. Bacteriol.* 171(12):6800-6807 (1989).

Yun et al., "The genes for anabolic 2-oxoglutarate: ferredoxin oxidoreductse from *Hydrogenobacter thermophilus* TK-6," *Biochem. Biophys. Res. Commun.* 282(2):589-594 (2001).

Yun et al., "Enhancement of lactate and succinate formation in *adhE* or *pta-ackA* mutants of NADH dehydrogenase-deficient *Escherichia coli*," *J. Appl. Microbiol.* 99(6):1404-1412 (2005).

Yun et al., "ω-Amino acid:pyruvate transaminase from Alcaligenes denitrificans Y2k-2: a new catalyst for kinetic resolution of β-amino acids and amines," *Appl. Environ. Microbiol.* 70(4):2529-2534 (2004).

Zeiher and Randall, "Identification and characterization of Mitochondrial Acetyl-Coenzyme A Hydrolase from Pisum sativum L. Seedlings," *Plant. Physiol.* 94:20-27 (1990).

Zeikus et al., "Biotechnology of succinic acid production and markets for derived industrial products," *Appl. Microbiol. Biotechnol.* 51: 545-552 (1999).

Zelle et al., "Malic acid production by *Saccharomyces cerevisiae*: engineering of pyruvate carboxylation, oxaloacetate reduction, and malate export," *Appl. Environ. Microbiol.* 74(9):2766-2777 (2008).

Zerbe-Burkhardt et al., "Cloning, sequencing, expression, and insertional inactivation of the gene for the large subunit of the coenzyme B¹²-dependent isobutyryl-CoA mutase from *Streptomyces cinnamonensis*," *J. Biol. Chem.* 273(11):6508-6517 (1998).

Zhang et al., "2-Oxoacid:Ferredoxin Oxidoreductase from the thermoacidophilic Archaeon, Sulfolobus sp. Strain 7," *J. Biochem.* 120:587-599 (1996).

Zhang et al., "A new logic for DNA engineering using recombination in *Escherichia coli*," *Nat. Genet.* 20:123-128 (1998).

Zhang et al., "Directed evolution of a fucosidase from a galactosidase by DNA shuffling and screening," Proc. Natl. Acad. Sci. USA 94(9):4504-4509 (1997).

Zhang et al., "Functional characterization of the first two actinomycete 4-amino-4-deoxychorismate lyase genes," *Microbiology* 155:2450-2459 (2009).

Zhang et al., "Genes encoding acyl-CoA dehydrogenase (AcdH) homologues from *Streptomyces coelicolor* and *Streptomyces avermitilis* provide insights into the metabolism of small branched-chain fatty acids and marcrolide antibiotic production," *Microbiol.* 145 (Pt 9):2323-2334 (1999).

Zhang et al., "Isolation and properties of a levo-lactonase from *Fusarium proliferatum* ECU2002: a robust biocatalyst for production of chiral lactones," *Appl Microbiol Biotechnol* 75:1087-1094 (2007).

Zhang et al., "Molecular basis for the inhibition of the carboxyltransferase domain of acetyl-Coenzyme-A carboxylase by haloxfop and dicofop," *Proc. Natl. Acad. Sci. USA* 101:5910-5915 (2004).

Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).

Zhao et al., "Molecular evolution by staggered extension process (StEP) in vitro recombination," *Nat. Biotechnol.* 16:258-261 (1998).

Zhou et al., "Comparison of fumaric acid production by *Rhizopus oryzae* using different neutralizing agents," *Bioproc. Biosyst. Eng.* 25(3):179-181 (2002).

Zhou et al., "Engineering a native homoethanol pathway in *Escherichia coli* B for ethanol production," *Biotechnol. Lett.* 30:335-342 (2008).

Zhou et al., "Mycelial pellet formation by *Rhizopus oryzae* ATCC 20344," *Appl. Biochem. Biotechnol.* 84-86:779-789 (2000).

Zhou et al., "The remarkable structural and functional organization of the eukaryotic pyruvate dehydrogenase complexes," *Proc. Natl. Acad. Sci. USA* 98:14802-14807 (2001).

Zhou et al., "Isolation, crystallization and preliminary X-ray analysis of a methanol-induced corrinoid protein from *Moorella thermoacetica*," *Acta. Crystallogr. Sect F Struct. Biol. Cryst. Commun.* 61(Pt 5):537-540 (2005).
Zhu and Sadowski, "Cleavage-dependent ligation by the FLP recombinase. Characterization of a mutant FLP protein with an alteration in a catalytic amino acid," *J. Biol. Chem.* 270(39):23044-23054 (1995).
Zhuang, et al., "The YbgC protein encoded by the ybgC gene of the tol-pal gene cluster of *Haemophilus infuenzae* catalyzes acyl-Coenzyme A thioester hydrolysis," *FEBS Lett*, 516(1-3):161-162 (2002).
URL 1.eere.energy.gov/biomass/information_resources.html (printed Apr. 19, 2010).
URL expressys.de/. (Printed Dec. 21, 2009).
URL web.archive.org/web/20080302001450/http://www.verenium. com/Pages/Technology/EnzymeTech/TechEnzyTGR.html (printed Apr. 12, 2010).
URL toxnet. nlm.nih.gov/cgi-bin/sis/search/f?./temp/~FwAsma:1:BASIC (printed Feb. 17, 2010).
(YIL168W) Genbank Accession No. AAS56670.1; GI:45270578 (Apr. 24, 2007).
(YIL168W) Genbank Accession No. AY558344.1; GI:45270577 (Apr. 24, 2007).
(YIL168W) Genbank Accession No. CAA87024.1; GI:600809 (Apr. 18, 2005).
(YIL168W) Genbank Accession No. P17324.1; GI;134388 (Jan. 15, 2008).
(YIL168W) Genbank Accession No. Z46921.1; GI:600798 (Apr. 18, 2005).
Genbank Accession No. AB330293.1; GI:149941607 (Mar. 18, 2008).
Genbank Accession No. AB368798.1; GI:188496948 (May 16, 2008).
Genbank Accession No. ABX39017.1; GI:60415396 (Nov. 21, 2007).
Genbank Accession No. AF017117.1; GI:2394281 (Apr. 14, 1998).
Genbank Accession No. AJ276891.1; GI:11322456 (Nov. 21, 2000).
Genbank Accession No. AJ278683.1; GI:11691809 (Mar. 11, 2001).
Genbank Accession No. BAA23002.1; GI:2575787 (Aug. 18, 2007).
Genbank Accession No. BAA77296.1; GI:4760466 (Aug. 10, 2007).
Genbank Accession No. BAE66063.1; GI:83775944 (Dec. 23, 2005).
Genbank Accession No. CAA43225.1; GI:45682 (Apr. 18, 2005).
Genbank Accession No. CAA43228.1; GI:45685 (Apr. 18, 2005).
Genbank Accession No. NP_001018030.1; GI:63535562 (Jun. 16, 2008); with corresponding KEGG Database printout of YCL064C (Mar. 31, 2010).
Genbank Accession No. NP_009312.1; GI:6226526 (Jun. 16, 2008); with corresponding KEGG Database printout of Q0080 (Mar. 30, 2010).
Genbank Accession No. NP_009313.1; GI:6226527 (Jun. 16, 2008); with corresponding KEGG Database printout of Q0085 (Mar. 31, 2010).
Genbank Accession No. NP_009319.1; GI:6226533 (Jun. 16, 2008); with corresponding KEGG Database printout of Q0130 (Mar. 31, 2010).
Genbank Accession No. NP_009362.1; GI:6319279 (Jun. 16, 2008); with corresponding KEGG Database printout of YAL038W (Mar. 31, 2010).
Genbank Accession No. NP_009453.1; GI:6319370 (Jun. 16, 2008); with corresponding KEGG Database printout of YBL099W (Mar. 30, 2010).
Genbank Accession No. NP_009523.1; GI:6319441 (Jun. 16, 2008); with corresponding KEGG Database printout of YBL030C (Mar. 31, 2010).
Genbank Accession No. NP_009595.1; GI:6319513 (Jun. 16, 2008); with corresponding KEGG Database printout of YBR039W (Mar. 30, 2010).
Genbank Accession No. NP_009642.1; GI:6319560 (Jun. 16, 2008); with corresponding KEGG Database printout of YBR085W (Mar. 30, 2010).
Genbank Accession No. NP_009675.1; GI:6319593 (Jun. 16, 2008); with corresponding KEGG Database printout of YBR117C (Mar. 31, 2010).
Genbank Accession No. NP_009703.1; GI:6319621 (Jun. 16, 2008); with corresponding KEGG Database printout of YBR145W (Mar. 30, 2010).
Genbank Accession No. NP_009780.1; GI:6319698 (Jun. 16, 2008); with corresponding KEGG Database printout of YBR221C (Mar. 31, 2010).
Genbank Accession No. NP_009982.1; GI:6319901 (Jun. 16, 2008); with corresponding KEGG Database printout of YCR053W (Mar. 31, 2010).
Genbank Accession No. NP_010100.1; GI:6320020 (Jun. 16, 2008); with corresponding KEGG Database printout of YDL181W (Mar. 30, 2010).
Genbank Accession No. NP_010113.1; GI:6320033 (Jun. 16, 2008); with corresponding KEGG Database printout of YDL168W (Apr. 7, 2010).
Genbank Accession No. NP_010198.1; GI:6320118 (Jun. 16, 2008); with corresponding KEGG Database printout of YDL085W (Mar. 31, 2010).
Genbank Accession No. NP_010262.1; GI:6320181 (Jun. 16, 2008); with corresponding KEGG Database printout of YDL022W (Mar. 31, 2010).
Genbank Accession No. NP_010280.1; GI:6320200 (Jun. 16, 2008); with corresponding KEGG Database printout of YDL004W (Mar. 30, 2010).
Genbank Accession No. NP_010396.1; GI:6320317 (Jun. 16, 2008); with corresponding KEGG Database printout of YDR111C (Mar. 30, 2010).
Genbank Accession No. NP_010432.1; GI:6320352 (Jun. 16, 2008); with corresponding KEGG Database printout of YDR148C (Mar. 31, 2010).
Genbank Accession No. NP_010463.1; GI:6320383 (Jun. 16, 2008); with corresponding KEGG Database printout of YDR178W (Mar. 31, 2010).
Genbank Accession No. NP_010584.1; GI:6320504 (Jun. 16, 2008); with corresponding KEGG Database printout of YDR298C (Mar. 31, 2010).
Genbank Accession No. NP_010609.1; GI:6320529 (Jun. 16, 2008); with corresponding KEGG Database printout of YDR322C-A (Mar. 30, 2010).
Genbank Accession No. NP_010665.1; GI:6320585 (Jun. 16, 2008); with corresponding KEGG Database printout of YDR377W (Mar. 30, 2010).
Genbank Accession No. NP_010867.1; GI:6320788 (Jun. 16, 2008); with corresponding KEGG Database printout of YEL047C (Mar. 31, 2010).
Genbank Accession No. NP_010868.1; GI:6320789 (Jun. 16, 2008); with corresponding KEGG Database printout of YEL046C (Mar. 31, 2010).
Genbank Accession No. NP_010984.1; GI:6320905 (Jun. 16, 2008); with corresponding KEGG Database printout of YER062C (Mar. 31, 2010).
Genbank Accession No. NP_010987.1; GI:6320908 (Jun. 16, 2008); with corresponding KEGG Database printout of YER065C (Mar. 31, 2010).
Genbank Accession No. NP_011004.1; GI:6320925 (Jun. 16, 2008); with corresponding KEGG Database printout of YER081W (Mar. 31, 2010).
Genbank Accession No. NP_011005.2; GI:37362644 (Jun. 16, 2008); with corresponding KEGG Database printout of YER178W (Mar. 31, 2010).
Genbank Accession No. NP_011258.1; GI:6321181 (Jun. 16, 2008); with corresponding KEGG Database printout of YGL256W (Mar. 30, 2010).
Genbank Accession No. NP_011601.1; GI:6321524 (Jun. 16, 2008); with corresponding KEGG Database printout of YGR087C (Mar. 31, 2010).
Genbank Accession No. NP_011720.1; GI:6321643 (Jun. 16, 2008); with corresponding KEGG Database printout of YGR204W (Mar. 31, 2010).

Genbank Accession No. NP_011724.1; GI:6321647 (Jun. 16, 2008); with corresponding KEGG Database printout of YGR208W (Mar. 31, 2010).
Genbank Accession No. NP_011760.1; GI:6321683 (Jun. 16, 2008); with corresponding KEGG Database printout of YGR244C (Mar. 31, 2010).
Genbank Accession No. NP_011764.1; GI:6321687 (Jun. 16, 2008); with corresponding KEGG Database printout of YGR248W (Mar. 31, 2010).
Genbank Accession No. NP_011772.1; GI:6321695 (Jun. 16, 2008); with corresponding KEGG Database printout of YGR256W (Mar. 31, 2010).
Genbank Accession No. NP_011890.1; GI:6321814 (Jun. 16, 2008); with corresponding KEGG Database printout of YHR025W (Mar. 31, 2010).
Genbank Accession No. NP_012033.2; GI:82795254 (Jun. 16, 2008); with corresponding KEGG Database printout of YHR163W (Mar. 31, 2010).
Genbank Accession No. NP_012053.1; GI:6321977 (Jun. 16, 2008); with corresponding KEGG Database printout of YHR183W (Mar. 31, 2010).
Genbank Accession No. NP_012111.1; GI:6322036 (Jun. 16, 2008); with corresponding KEGG Database printout of YIL155C (Mar. 31, 2010).
Genbank Accession No. NP_012141.1; GI:6322066 (Jun. 16, 2008); with corresponding KEGG Database printout of YIL125W (Mar. 31, 2010).
Genbank Accession No. NP_012191.1; GI:6322116 (Jun. 16, 2008); with corresponding KEGG Database printout of YIL074W (Mar. 31, 2010).
Genbank Accession No. NP_012211.2; GI:86558907 (Jun. 16, 2008); with corresponding KEGG Database printout of YIL053W (Mar. 31, 2010).
Genbank Accession No. NP_012335.1; GI:6322261 (Jun. 16, 2008); with corresponding KEGG Database printout of YJL200C (Mar. 30, 2010).
Genbank Accession No. NP_012414.1; GI:6322341 (Jun. 16, 2008); with corresponding KEGG Database printout of YJL121C (Mar. 31, 2010).
Genbank Accession No. NP_012490.1; GI:6322416 (Jun. 16, 2008); with corresponding KEGG Database printout of YJL045W (Mar. 31, 2010).
Genbank Accession No. NP_012585.1; GI:6322511 (Jun. 16, 2008); with corresponding KEGG Database printout of YJR051W (Mar. 31, 2010).
Genbank Accession No. NP_012655.1; GI:6322581 (Jun. 16, 2008); with corresponding KEGG Database printout of YJR121W (Mar. 30, 2010).
Genbank Accession No. NP_012673.1; GI:6322599 (Jun. 16, 2008); with corresponding KEGG Database printout of YJR139C (Mar. 31, 2010).
Genbank Accession No. NP_012774.1; GI:6322701 (Jun. 16, 2008); with corresponding KEGG Database printout of YKL148C (Mar. 31, 2010).
Genbank Accession No. NP_012781.1; GI:6322708 (Jun. 16, 2008); with corresponding KEGG Database printout of YKL141W (Mar. 31, 2010).
Genbank Accession No. NP_012816.1; GI:6322743 (Jun. 16, 2008); with corresponding KEGG Database printout of YKL106W (Mar. 30, 2010).
Genbank Accession No. NP_012838.1; GI:6322765 (Jun. 16, 2008); with corresponding KEGG Database printout of YKL085W (Mar. 31, 2010).
Genbank Accession No. NP_012896.1; GI:6322823 (Jun. 16, 2008); with corresponding KEGG Database printout of YKL029C (Mar. 31, 2010).
Genbank Accession No. NP_012909.1; GI:6322836 (Jun. 16, 2008); with corresponding KEGG Database printout of YKL016C (Mar. 31, 2010).
Genbank Accession No. NP_013059.1; GI:6322987 (Jun. 16, 2008); with corresponding KEGG Database printout of YLL041C (Mar. 31, 2010).
Genbank Accession No. NP_013127.2; GI:37362677 (Jun. 16, 2008); with corresponding KEGG Database printout of YLR027C (Mar. 30, 2010).
Genbank Accession No. NP_013145.1; GI:6323073 (Jun. 16, 2008); with corresponding KEGG Database printout of YLR044C (Mar. 31, 2010).
Genbank Accession No. NP_013159.1; GI:6323087 (Jun. 16, 2008); with corresponding KEGG Database printout of YLR058C (Mar. 31, 2010).
Genbank Accession No. NP_013235.1; GI:6323163 (Jun. 16, 2008); with corresponding KEGG Database printout of YLR134W (Mar. 31, 2010).
Genbank Accession No. NP_013243.1; GI:6323171 (Jun. 16, 2008); with corresponding KEGG Database printout of YLR142W (Mar. 31, 2010).
Genbank Accession No. NP_013265.1; GI:6323193 (Jun. 16, 2008); with corresponding KEGG Database printout of YLR164W (Mar. 31, 2010).
Genbank Accession No. NP_013275.1; GI:6323203 (Jun. 16, 2008); with corresponding KEGG Database printout of YLR174W (Mar. 31, 2010).
Genbank Accession No. NP_013398.1; GI:6323326 (Jun. 16, 2008); with corresponding KEGG Database printout of YLR295C (Mar. 31, 2010).
Genbank Accession No. NP_013407.1; GI:6323335 (Jun. 16, 2008); with corresponding KEGG Database printout of YLR304C (Mar. 30, 2010).
Genbank Accession No. NP_013542.1; GI:6323470 (Jun. 16, 2008); with corresponding KEGG Database printout of YLR438W (Mar. 31, 2010).
Genbank Accession No. NP_013629.1; GI:6323558 (Jun. 16, 2008); with corresponding KEGG Database printout of YML081C-A (Mar. 31, 2010).
Genbank Accession No. NP_013772.1; GI:6323701 (Jun. 16, 2008); with corresponding KEGG Database printout of YMR056C (Mar. 31, 2010).
Genbank Accession No. NP_013780.1; GI:6323709 (Jun. 16, 2008); with corresponding KEGG Database printout of YMR064W (Apr. 8, 2010).
Genbank Accession No. NP_013836.1; GI:6323765 (Jun. 16, 2008); with corresponding KEGG Database printout of YMR118C (Mar. 31, 2010).
Genbank Accession No. NP_013865.1; GI:6323794 (Jun. 16, 2008); with corresponding KEGG Database printout of YMR145C (Mar. 31, 2010).
Genbank Accession No. NP_014032.1; GI:6323961 (Jun. 16, 2008); with corresponding KEGG Database printout of YMR303C (Mar. 30, 2010).
Genbank Accession No. NP_014158.1; GI:6324088 (Jun. 16, 2008); with corresponding KEGG Database printout of YNL241C (Mar. 31, 2010).
Genbank Accession No. NP_014328.1; GI:6324258 (Jun. 16, 2008); with corresponding KEGG Database printout of YNL071W (Mar. 31, 2010).
Genbank Accession No. NP_014361.1; GI:6324291 (Jun. 16, 2008); with corresponding KEGG Database printout of YNL037C (Apr. 8, 2010).
Genbank Accession No. NP_014432.1; GI:6324362 (Jun. 16, 2008); with corresponding KEGG Database printout of YNR034W (Mar. 31, 2010).
Genbank Accession No. NP_014515.2; GI:116006499 (Jun. 16, 2008); with corresponding KEGG Database printout of YOL126C (Mar. 31, 2010).
Genbank Accession No. NP_014555.1; GI:6324486 (Jun. 16, 2008); with corresponding KEGG Database printout of YOL086C (Mar. 30, 2010).
Genbank Accession No. NP_014564.1; GI:6324495 (Jun. 16, 2008); with corresponding KEGG Database printout of YOL077W-A (Mar. 30, 2010).
Genbank Accession No. NP_014582.1; GI:6324513 (Jun. 16, 2008); with corresponding KEGG Database printout of YOL059W (Mar. 31, 2010).

Genbank Accession No. NP_014779.1; GI:6324709 (Jun. 16, 2008); with corresponding KEGG Database printout of YOR136W (Mar. 31, 2010).
Genbank Accession No. NP_014785.1; GI:6324716 (Jun. 16, 2008); with corresponding KEGG Database printout of YOR142W (Mar. 31, 2010).
Genbank Accession No. NP_014827.1; GI:6324758 (Jun. 16, 2008); with corresponding KEGG Database printout of YOR184W (Mar. 31, 2010).
Genbank Accession No. NP_014992.1; GI:6324923 (Jun. 16, 2008); with corresponding KEGG Database printout of YOR347C (Mar. 31, 2010).
Genbank Accession No. NP_015052.1; GI:6324984 (Jun. 16, 2008); with corresponding KEGG Database printout of YPL271W (Mar. 31, 2010).
Genbank Accession No. NP_015061.1; GI:6324993 (Jun. 16, 2008); with corresponding KEGG Database printout of YPL262W (Mar. 31, 2010).
Genbank Accession No. NP_015247.1; GI:6325179 (Jun. 16, 2008); with corresponding KEGG Database printout of YPL078C (Mar. 30, 2010).
Genbank Accession No. NP_015345.1; GI:6325277 (Jun. 16, 2008); with corresponding KEGG Database printout of YPR020W (Mar. 30, 2010).
Genbank Accession No. NP_015399.1; GI:6325331 (Jun. 16, 2008); with corresponding KEGG Database printout of YPR074C (Mar. 31, 2010).
Genbank Accession No. NP_116623.1; GI:14318489 (Jun. 16, 2008); with corresponding KEGG Database printout of YFL030W (Mar. 30, 2010).
Genbank Accession No. NP_116635.1; GI:14318501 (Jun. 16, 2008); with corresponding KEGG Database printout of YFL018C (Mar. 31, 2010).
Genbank Accession No. NP_414549.1; GI:16128002 (May 17, 2008); with corresponding KEGG Database printout of b0008 (Mar. 30, 2010).
Genbank Accession No. NP_414656.1; GI:16128107 (May 17, 2008); with corresponding KEGG Database printout of b0114 (Mar. 25, 2010).
Genbank Accession No. NP_414657.1; GI:16128108 (May 17, 2008); with corresponding KEGG Database printout of b0115 (Mar. 25, 2010).
Genbank Accession No. NP_414658.1; GI:16128109 (May 17, 2008); with corresponding KEGG Database printout of b0116 (Mar. 17, 2010).
Genbank Accession No. NP_414777.1; GI:16128228 (May 17, 2008); with corresponding KEGG Database printout of b0242 (Mar. 25, 2010).
Genbank Accession No. NP_414778.1; GI:16128229 (May 17, 2008); with corresponding KEGG Database printout of b0243 (Mar. 25, 2010).
Genbank Accession No. NP_414857.1; GI:16128308 (May 17, 2008); with corresponding KEGG Database printout of b0323 (Mar. 25, 2010).
Genbank Accession No. NP_414890.1; GI:16128341 (May 17, 2008); with corresponding KEGG Database printout of b0356 (Mar. 17, 2010).
Genbank Accession No. NP_415054.1; GI:16128505 (May 17, 2008); with corresponding KEGG Database printout of b0521 (Mar. 25, 2010).
Genbank Accession No. NP_415249.1; GI:16128696 (May 17, 2008); with corresponding KEGG Database printout of b0721 (Mar. 25, 2010).
Genbank Accession No. NP_415250.1; GI:16128697 (May 17, 2008); with corresponding KEGG Database printout of b0722 (Mar. 25, 2010).
Genbank Accession No. NP_415251.1; GI:16128698 (May 17, 2008); with corresponding KEGG Database printout of b0723 (Mar. 30, 2010).
Genbank Accession No. NP_415252.1; GI:16128699 (May 17, 2008); with corresponding KEGG Database printout of b0724 (Mar. 30, 2010).
Genbank Accession No. NP_415254.1; GI:16128701 (May 17, 2008); with corresponding KEGG Database printout of b0726 (Mar. 17, 2010).
Genbank Accession No. NP_415255.1; GI:16128702 (May 17, 2008); with corresponding KEGG Database printout of b0727 (Mar. 17, 2010).
Genbank Accession No. NP_415256.1; GI:16128703 (May 17, 2008); with corresponding KEGG Database printout of b0728 (Mar. 30, 2010).
Genbank Accession No. NP_415257.1; GI:16128704 (May 17, 2008); with corresponding KEGG Database printout of b0729 (Mar. 30, 2010).
Genbank Accession No. NP_415288.1; GI:16128735 (May 17, 2008); with corresponding KEGG Database printout of b0767 (Mar. 25, 2010).
Genbank Accession No. NP_415422.1; GI:16128869 (May 17, 2008); with corresponding KEGG Database printout of b0902 (Mar. 25, 2010).
Genbank Accession No. NP_415423.1; GI:16128870 (May 17, 2008); with corresponding KEGG Database printout of b0903 (Mar. 25, 2010).
Genbank Accession No. NP_415534.1; GI:16128980 (May 17, 2008); with corresponding KEGG Database printout of b1014 (Mar. 25, 2010).
Genbank Accession No. NP_415619.1; GI:16129064 (May 17, 2008); with corresponding KEGG Database printout of b1101 (Mar. 25, 2010).
Genbank Accession No. NP_415627.1; GI:16129072 (May 17, 2008); with corresponding KEGG Database printout of b1109 (Mar. 25, 2010).
Genbank Accession No. NP_415707.1; GI:16129152 (May 17, 2008); with corresponding KEGG Database printout of b1189 (Mar. 25, 2010).
Genbank Accession No. NP_415757.1; GI:16129202 (May 17, 2008); with corresponding KEGG Database printout of b1241 (Mar. 17, 2010).
Genbank Accession No. NP_415898.1; GI:16129341 (May 17, 2008); with corresponding KEGG Database printout of b1380 (Mar. 25, 2010).
Genbank Accession No. NP_415938.1; GI:16129380 (May 17, 2008); with corresponding KEGG Database printout of b1421 (Apr. 8, 2010).
Genbank Accession No. NP_415995.4; GI:90111280 (May 17, 2008); with corresponding KEGG Database printout of b1478 (Mar. 17, 2010).
Genbank Accession No. NP_415996.2; GI:90111281 (May 17, 2008); with corresponding KEGG Database printout of b1479 (Mar. 25, 2010).
Genbank Accession No. NP_416119.1; GI:16129560 (May 17, 2008); with corresponding KEGG Database printout of b1602 (Mar. 30, 2010).
Genbank Accession No. NP_416120.1; GI:16129561 (May 17, 2008); with corresponding KEGG Database printout of b1603 (Mar. 30, 2010).
Genbank Accession No. NP_416128.1; GI:16129569 (May 17, 2008); with corresponding KEGG Database printout of b1611 (Mar. 25, 2010).
Genbank Accession No. NP_416129.1; GI:16129570 (May 17, 2008); with corresponding KEGG Database printout of b1612 (Mar. 25, 2010).
Genbank Accession No. NP_416138.1; GI:16129579 (May 17, 2008); with corresponding KEGG Database printout of b1621 (Mar. 25, 2010).
Genbank Accession No. NP_416191.1; GI:16129632 (May 17, 2008); with corresponding KEGG Database printout of b1676 (Mar. 25, 2010).
Genbank Accession No. NP_416237.3; GI:49176138 (May 17, 2008); with corresponding KEGG Database printout of b1723 (Mar. 25, 2010).
Genbank Accession No. NP_416275.1; GI:16129715 (May 17, 2008); with corresponding KEGG Database printout of b1761 (Mar. 25, 2010).

Genbank Accession No. NP_416287.1; GI:16129727 (May 17, 2008); with corresponding KEGG Database printout of b1773 (Mar. 25, 2010).
Genbank Accession No. NP_416331.1; GI:16129771 (May 17, 2008); with corresponding KEGG Database printout of b1817 (Mar. 25, 2010).
Genbank Accession No. NP_416332.1; GI:16129772 (May 17, 2008); with corresponding KEGG Database printout of b1818 (Mar. 25, 2010).
Genbank Accession No. NP_416333.3; GI:49176154 (May 17, 2008); with corresponding KEGG Database printout of b1819 (Mar. 25, 2010).
Genbank Accession No. NP_416363.1; GI:16129802 (May 17, 2008); with corresponding KEGG Database printout of b1849 (Mar. 17, 2010).
Genbank Accession No. NP_416364.1; GI:16129803 (May 17, 2008); with corresponding KEGG Database printout of b1850 (Mar. 25, 2010).
Genbank Accession No. NP_416365.1; GI:16129804 (May 17, 2008); with corresponding KEGG Database printout of b1851 (Mar. 25, 2010).
Genbank Accession No. NP_416366.1; GI:16129805 (May 17, 2008); with corresponding KEGG Database printout of b1852 (Apr. 7, 2010).
Genbank Accession No. NP_416368.1; GI:16129807 (May 17, 2008); with corresponding KEGG Database printout of b1854 (Mar. 25, 2010).
Genbank Accession No. NP_416533.1; GI:16129970 (May 17, 2008); with corresponding KEGG Database printout of b2029 (Mar. 25, 2010).
Genbank Accession No. NP_416600.4; GI:90111385 (May 17, 2008); with corresponding KEGG Database printout of b2097 (Mar. 25, 2010).
Genbank Accession No. NP_416637.1; GI:16130071 (May 17, 2008); with corresponding KEGG Database printout of b2133 (Mar. 25, 2010).
Genbank Accession No. NP_416779.2; GI:45698289 (May 17, 2008); with corresponding KEGG Database printout of b2276 (Mar. 25, 2010).
Genbank Accession No. NP_416780.1; GI:16130212 (May 17, 2008); with corresponding KEGG Database printout of b2277 (Mar. 25, 2010).
Genbank Accession No. NP_416781.1; GI:16130213 (May 17, 2008); with corresponding KEGG Database printout of b2278 (Mar. 25, 2010).
Genbank Accession No. NP_416782.1; GI:16130214 (May 17, 2008); with corresponding KEGG Database printout of b2279 (Mar. 25, 2010).
Genbank Accession No. NP_416783.1; GI:16130215 (May 17, 2008); with corresponding KEGG Database printout of b2280 (Mar. 25, 2010).
Genbank Accession No. NP_416784.1; GI:16130216 (May 17, 2008); with corresponding KEGG Database printout of b2281 (Mar. 25, 2010).
Genbank Accession No. NP_416785.1; GI:16130217 (May 17, 2008); with corresponding KEGG Database printout of b2282 (Mar. 25, 2010).
Genbank Accession No. NP_416786.4; GI:145698290 (May 17, 2008); with corresponding KEGG Database printout of b2283 (Mar. 25, 2010).
Genbank Accession No. NP_416787.1; GI:16130219 (May 17, 2008); with corresponding KEGG Database printout of b2284 (Mar. 25, 2010).
Genbank Accession No. NP_416788.1; GI:16130220 (May 17, 2008); with corresponding KEGG Database printout of b2285 (Mar. 25, 2010).
Genbank Accession No. NP_416789.2; GI:145698291 (May 17, 2008); with corresponding KEGG Database printout of b2286 (Mar. 25, 2010).
Genbank Accession No. NP_416790.1; GI:16130222 (May 17, 2008); with corresponding KEGG Database printout of b2287 (Mar. 25, 2010).
Genbank Accession No. NP_416791.3; GI:49176207 (May 17, 2008); with corresponding KEGG Database printout of b2288 (Mar. 25, 2010).
Genbank Accession No. NP_416799.1; GI:16130231 (May 17, 2008); with corresponding KEGG Database printout of b2296 (Mar. 17, 2010).
Genbank Accession No. NP_416800.1; GI:16130232 (May 17, 2008); with corresponding KEGG Database printout of b2297 (Mar. 25, 2010).
Genbank Accession No. NP_416889.1; GI:16130320 (May 17, 2008); with corresponding KEGG Database printout of b2388 (Mar. 25, 2010).
Genbank Accession No. NP_416910.1; GI:16130341 (May 17, 2008); with corresponding KEGG Database printout of b2415 (Mar. 25, 2010).
Genbank Accession No. NP_416911.1; GI:16130342 (May 17, 2008); with corresponding KEGG Database printout of b2416 (Mar. 25, 2010).
Genbank Accession No. NP_416912.1; GI:16130343 (May 17, 2008); with corresponding KEGG Database printout of b2417 (Mar. 25, 2010).
Genbank Accession No. NP_416958.1; GI:16130388 (May 17, 2008); with corresponding KEGG Database printout of b2463 (Mar. 25, 2010).
Genbank Accession No. NP_416959.1; GI:16130389 (May 17, 2008); with corresponding KEGG Database printout of b2464 (Mar. 30, 2010).
Genbank Accession No. NP_416960.1; GI:16130390 (May 17, 2008); with corresponding KEGG Database printout of b2465 (Mar. 30, 2010).
Genbank Accession No. NP_417074.1; GI:16130504 (May 17, 2008); with corresponding KEGG Database printout of b2579 (Mar. 25, 2010).
Genbank Accession No. NP_417259.1; GI:16130686 (May 17, 2008); with corresponding KEGG Database printout of b2779 (Mar. 25, 2010).
Genbank Accession No. NP_417350.1; GI:16130776 (May 17, 2008); with corresponding KEGG Database printout of b2874 (Mar. 25, 2010).
Genbank Accession No. NP_417379.1; GI:16130805 (May 17, 2008); with corresponding KEGG Database printout of b2903 (Mar. 25, 2010).
Genbank Accession No. NP_417380.1; GI:16130806 (May 17, 2008); with corresponding KEGG Database printout of b2904 (Mar. 25, 2010).
Genbank Accession No. NP_417381.1; GI:16130807 (May 17, 2008); with corresponding KEGG Database printout of b2905 (Mar. 25, 2010).
Genbank Accession No. NP_417400.1; GI:16130826 (May 17, 2008); with corresponding KEGG Database printout of b2925 (Mar. 25, 2010).
Genbank Accession No. NP_417585.2; GI:145698313 (May 17, 2008); with corresponding KEGG Database printout of b3115 (Mar. 17, 2010).
Genbank Accession No. NP_417703.1; GI:16131126 (May 17, 2008); with corresponding KEGG Database printout of b3236 (Mar. 25, 2010).
Genbank Accession No. NP_417845.1; GI:16131264 (May 17, 2008); with corresponding KEGG Database printout of b3386 (Mar. 25, 2010).
Genbank Accession No. NP_417862.1; GI:16131280 (May 17, 2008); with corresponding KEGG Database printout of b3403 (Mar. 25, 2010).
Genbank Accession No. NP_418069.1; GI:16131483 (May 17, 2008); with corresponding KEGG Database printout of b3612 (Mar. 25, 2010).
Genbank Accession No. NP_418187.1; GI:16131599 (May 17, 2008); with corresponding KEGG Database printout of b3731 (Mar. 17, 2010).
Genbank Accession No. NP_418188.1; GI:16131600 (May 17, 2008); with corresponding KEGG Database printout of b3732 (Mar. 17, 2010).

Genbank Accession No. NP_418189.1; GI:16131601 (May 17, 2008); with corresponding KEGG Database printout of b3733 (Mar. 17, 2010).
Genbank Accession No. NP_418190.1; GI:16131602 (May 17, 2008); with corresponding KEGG Database printout of b3734 (Mar. 17, 2010).
Genbank Accession No. NP_418191.1; GI:16131603 (May 17, 2008); with corresponding KEGG Database printout of b3735 (Mar. 17, 2010).
Genbank Accession No. NP_418192.1; GI:16131604 (May 17, 2008); with corresponding KEGG Database printout of b3736 (Mar. 17, 2010).
Genbank Accession No. NP_418193.1; GI:16131605 (May 17, 2008); with corresponding KEGG Database printout of b3737 (Mar. 17, 2010).
Genbank Accession No. NP_418194.1; GI:16131606 (May 17, 2008); with corresponding KEGG Database printout of b3738 (Mar. 17, 2010).
Genbank Accession No. NP_418195.2; GI:90111645 (May 17, 2008); with corresponding KEGG Database printout of b3739 (Mar. 25, 2010).
Genbank Accession No. NP_418200.1; GI:16131612 (May 17, 2008); with corresponding KEGG Database printout of b3744 (Mar. 17, 2010).
Genbank Accession No. NP_418351.1; GI:16131754 (May 17, 2008); with corresponding KEGG Database printout of b3916 (Mar. 25, 2010).
Genbank Accession No. NP_418354.1; GI:16131757 (May 17, 2008); with corresponding KEGG Database printout of b3919 (Mar. 30, 2010).
Genbank Accession No. NP_418386.1; GI:16131789 (May 17, 2008); with corresponding KEGG Database printout of b3951 (Mar. 25, 2010).
Genbank Accession No. NP_418387.3; GI:49176447 (May 17, 2008); with corresponding KEGG Database printout of b3952 (Mar. 25, 2010).
Genbank Accession No. NP_418391.1; GI:16131794 (May 17, 2008); with corresponding KEGG Database printout of b3956 (Mar. 25, 2010).
Genbank Accession No. NP_418397.2; GI:90111670 (May 17, 2008); with corresponding KEGG Database printout of b3962 (Mar. 30, 2010).
Genbank Accession No. NP_418449.1; GI:16131851 (May 17, 2008); with corresponding KEGG Database printout of b4025 (Mar. 25, 2010).
Genbank Accession No. NP_418477.1; GI:16131879 (May 17, 2008); with corresponding KEGG Database printout of b4053 (Mar. 17, 2010).
Genbank Accession No. NP_418546.1; GI:16131948 (May 17, 2008); with corresponding KEGG Database printout of b4122 (Mar. 25, 2010).
Genbank Accession No. NP_418562.4; GI:90111690 (May 17, 2008); with corresponding KEGG Database printout of b4139 (Mar. 17, 2010).
Genbank Accession No. NP_418575.1; GI:16131976 (May 17, 2008); with corresponding KEGG Database printout of b4151 (Mar. 25, 2010).
Genbank Accession No. NP_418576.1; GI:16131977 (May 17, 2008); with corresponding KEGG Database printout of b4152 (Mar. 25, 2010).
Genbank Accession No. NP_418577.1; GI:16131978 (May 17, 2008); with corresponding KEGG Database printout of b4153 (Mar. 25, 2010).
Genbank Accession No. NP_418578.1; GI:16131979 (May 17, 2008); with corresponding KEGG Database printout of b4154 (Mar. 25, 2010).
Genbank Accession No. NP_418721.1; GI:16132122 (May 17, 2008); with corresponding KEGG Database printout of b4301 (Mar. 25, 2010).
Genbank Accession No. NP_961187.1; GI:41408351 (Dec. 3, 2007).
Genbank Accession No. NP O09460.1; GI:3122621 (Jun. 10, 2008).
Genbank Accession No. P27443.1; GI:126732 (Jun. 10, 2008).
Genbank Accession No. U63827.1; GI:1762615 (May 14, 1997).
Genbank Accession No. X78576.1; GI:469102 (Nov. 14, 2006).
Genbank Accession No. XP_001209273.1; GI:115385453 (Mar. 31, 2008).
Genbank Accession No. XP_001209946.1; GI:115386810 (Mar. 31, 2008).
Genbank Accession No. XP_001217495.1; GI:115402837 (Mar. 31, 2008).
Genbank Accession No. XP_001383451.1; GI:126133853 (Apr. 11, 2008).
Genbank Accession No. XP_001389415.1; GI:145230213 (Feb. 28, 2008).
Genbank Accession No. XP_001393934.1; GI:145242722 (Feb. 28, 2008).
Genbank Accession No. XP_391316.1; GI:46139251 (Apr. 9, 2008).
Genbank Accession No. YP_001160461.1; GI:145596164 (Dec. 8, 2007).
Genbank Accession No. YP_001161088.1; GI:145596791 (Dec. 8, 2007).
Genbank Accession No. YP_001161180.1; GI:145596883 (Dec. 8, 2007).
Genbank Accession No. YP_026188.1; GI:49176286 (May 17, 2008); with corresponding KEGG Database printout of b2935 (Mar. 30, 2010).
Genbank Accession No. YP_026205.1; GI:49176316 (May 17, 2008); with corresponding KEGG Database printout of b3114 (Mar. 25, 2010).
Genbank Accession No. YP_026247.1; GI:49176403 (May 17, 2008); with corresponding KEGG Database printout of b3770 (Mar. 30, 2010).
Genbank Accession No. YP_089485.1; GI:52426348 (Dec. 3, 2007).
Genbank Accession No. YP_299880.1; GI:73539513 (Apr. 8, 2008).
Genbank Accession No. YP_299881.1; GI:73539514 (Apr. 8, 2008).
Genbank Accession No. YP_709328.1; GI:111116444 (Jun. 9, 2008).
Genbank Accession No. YP_709353.1; GI:111116469 (Jun. 9, 2008).
Genbank Accession No. YP_880968.1; GI:118466464 (Apr. 8, 2008).
Genbank Accession No. YP_891060.1; GI:118473159 (Dec. 3, 2007).
Genbank Accession No. ZP_01648681.1; GI:119882410 (Dec. 22, 2006).
Genbank Accession No. ZP_02009633.1; GI:153888491 (Jul. 25, 2007).

* cited by examiner

MICROORGANISMS AND METHODS FOR THE BIOSYNTHESIS OF FUMARATE, MALATE, AND ACRYLATE

This application claims the benefit of priority of U.S. Provisional Ser. No. 61/073,348, filed Jun. 17, 2008; U.S. Provisional Ser. No. 61/077,127, filed Jun. 30, 2008; and U.S. Provisional Ser. No. 61/088,628, filed Aug. 13, 2008, each of which is incorporated by reference in their entirety.

BACKGROUND

The present disclosure relates generally to the design of engineered organisms and, more specifically to organisms having selected genotypes for the production of fumarate, malate, and acrylate.

Fumaric acid is used in industrial processes as a raw material in a wide range of chemical syntheses. The presence of a double bond and two carboxyl groups in this compound facilitates its use in making polyesters and other polymers. Some of its industrial applications include manufacturing of synthetic resins and biodegradable polymers. It also finds widespread use as a food acidulant, a dietary supplement and as a beverage ingredient. Fumaric acid is currently derived from maleic anhydride, which is produced by the catalytic oxidation of benzene or butene feedstocks. Even though fumaric acid is approximately 10% more expensive than maleic anhydride, the non-toxic nature of the former and the special properties, such as greater hardness, that it imparts to the polymer structure makes it a good option for polymer industry as compared to maleic anhydride. Recently, two new applications for fumaric acid have been developed: (i) it can be used medicinally for treating a skin condition called psoriasis, and (ii) it can be used as a supplement for cattle feed.

Malic acid is used as an acidulant and taste enhancer in the beverage and food industry. Racemic malic acid is synthesized petrochemically from maleic anhydride whereas enantiometrically pure L-malic acid (used in pharmaceutical production) is produced from fumarate by hydration with fumarase.

Acrylic acid is a large volume petrochemical product. For example, acrylic acid is a commodity monomer intermediate used for the production of polymeric materials such polyacrylic acid, which is a major component of superabsorbant diapers. Acrylic acid also is used for the production of acrylate esters, which are utilized in water-soluble latex coatings, adhesives and inks. Acrylic acid and acrylate esters are manufactured by petrochemical processes such as oxidation of propylene, followed by esterification with alcohols such as methanol, butanol, and 2-ethylhexanol.

Chemicals manufactured from petroleum feedstocks suffer the burden of high and volatile prices, insecure foreign supply chains, and declining reserves (Frost, J. W., Redefining chemical manufacture. *Ind. Biotechnol.* 1:23-24 (2005)). Therefore, a method of producing large volume chemicals or their intermediates by alternative means that reduce petroleum-based processes and also use less energy- and capital-intensive processes would be beneficial.

Thus, there is a need to gain access to microorganisms having the commercially valuable characteristics of efficiently bio synthesizing fumarate, malate, and acrylate in high yields. The present invention satisfies this need and provides related advantages as well.

SUMMARY OF THE INVENTION

In some embodiments, the present invention provides a non-naturally occurring microbial organism that includes one or more gene disruptions occurring in genes encoding enzymes selected from the group of fumarate reductase (FRD), alcohol dehydrogenase (ADHEr) and lactate dehydrogenase (LDH_D) such that the one or more gene disruptions confers increased production of fumarate onto said non-naturally occurring microbial organism.

In some embodiments, the present invention provides a method for producing fumaric acid that includes culturing a non-naturally occurring microbial organism having one or more gene disruptions occurring in genes encoding enzymes selected from the group of fumarate reductase (FRD), alcohol dehydrogenase (ADHEr) and lactate dehydrogenase (LDH_D) such that the one or more gene disruptions confers increased production of fumarate onto said non-naturally occurring microbial organism.

In some embodiments, the present invention provides a non-naturally occurring microbial organism that includes one or more gene disruptions occurring in genes encoding enzymes selected from a group of fumarate reducatse (FRD), alcohol dehydrogenase (ADHEr), fumarase (FUM) and lactate dehydrogenase (LDH_D), when the gene disruption reduces an activity of the enzyme it confers increased production of malate onto said non-naturally occurring microbial organism.

In some embodiments, the present invention provides a method for producing malic acid that includes culturing a non-naturally occurring microbial organism having one or more gene disruptions occurring in genes encoding enzymes selected from a group of fumarate reducatse (FRD), alcohol dehydrogenase (ADHEr), fumarase (FUM) and lactate dehydrogenase (LDH_D), when the gene disruption reduces an activity of the enzyme it confers increased production of malate onto said non-naturally occurring microbial organism.

In some embodiments, the present invention provides a non-naturally occurring eukaryotic organism, comprising one or more gene disruptions occurring in genes encoding enzymes imparting increased fumarate production in the organism when the gene disruption reduces an activity of the enzyme, whereby the one or more gene disruptions confers increased production of fumarate onto the organism.

In some embodiments, the present invention provides a method for producing fumaric acid that includes culturing a non-naturally occurring eukaryotic organism having one or more gene disruptions occurring in genes encoding an enzyme providing increased fumarate production in the organism when the gene disruption reduces an activity of the enzyme, whereby the one or more gene disruptions confers increased production of fumarate onto the organism.

In some embodiments, the present invention provides a non-naturally occurring eukaryotic organism that includes one or more gene disruptions occurring in genes encoding enzymes imparting increased malate production in the organism when the gene disruption reduces an activity of the enzyme, whereby the one or more gene disruptions confers enhanced production of malate onto the organism.

In some embodiments, the present invention provides a method for producing malic acid that includes culturing a non-naturally occurring eukaryotic organism having one or more gene disruptions occurring in genes encoding enzymes imparting increased malate production to the organism when the gene disruption reduces an activity of the enzyme, whereby the one or more gene disruptions confers increased production of malate onto the organism.

In some embodiments, the present invention provides a non-naturally occurring eukaryotic organism that includes one or more gene disruptions occurring in genes encoding enzymes imparting increased acrylate production in the organism when the gene disruption reduces an activity of the enzyme, whereby the one or more gene disruptions confers increased production of acrylate onto the organism.

In some embodiments, the present invention provides a method for producing acrylic acid that includes culturing a non-naturally occurring eukaryotic organism having one or more gene disruptions occurring in genes encoding enzymes imparting enhanced acrylate production in the organism when the gene disruption reduces an activity of the enzyme, whereby the one or more gene disruptions confers increased production of acrylate onto the organism.

In some embodiments, the present invention provides a non-naturally occurring microbial organism that includes a microbial organism having an olefin pathway having at least one exogenous nucleic acid encoding an olefin pathway enzyme expressed in a sufficient amount to produce an olefin, the olefin pathway including a decarboxylase.

In some embodiments, the present invention provides a method for producing an olefin that includes culturing a non-naturally occurring microbial organism having an olefin pathway that includes at least one exogenous nucleic acid encoding an olefin pathway enzyme expressed in a sufficient amount to produce an olefin under conditions and for a sufficient period of time to produce an olefin, the olefin pathway including a decarboxylase.

In some embodiments, the present invention provides a non-naturally occurring microbial organism that includes a microbial organism having an acrylate pathway having at least one exogenous nucleic acid encoding an acrylate pathway enzyme expressed in a sufficient amount to produce acrylate, the acrylate pathway including a decarboxylase.

In some embodiments, the present invention provides a method for producing acrylate that includes culturing a non-naturally occurring microbial organism having an acrylate pathway, the pathway includes at least one exogenous nucleic acid encoding an acrylate pathway enzyme expressed in a sufficient amount to produce acrylate under conditions and for a sufficient period of time to produce acrylate, the acrylate pathway including a decarboxylase.

In some embodiments, the present invention provides a method for producing acrylate that includes a) culturing a first non-naturally occurring microbial organism that includes one or more gene disruptions occurring in one or more genes encoding one or more enzymes that enhance fumarate production in the organism when the one or more genes disruptions reduces an activity of the one or more enzymes, whereby the one or more gene disruptions confers increased production of fumarate onto the non-naturally occurring organism, and b) adding a decarboxylase to the cultured first non-naturally occurring microbial organism, the decarboxylase catalyzing the decarboxylation of fumarate.

BRIEF DESCRIPTION OF THE DRAWINGS

FIG. 10, light gray; FIG. 11 dark gray, dashed; and FIG. 12 light gray, dashed, compared with each other and with the production characteristics of the wild-type *S. cerevisiae* network (black). Note the reduction in feasible solution space as additional deletions are imposed on the network.

DETAILED DESCRIPTION OF THE INVENTION

Figure 1:
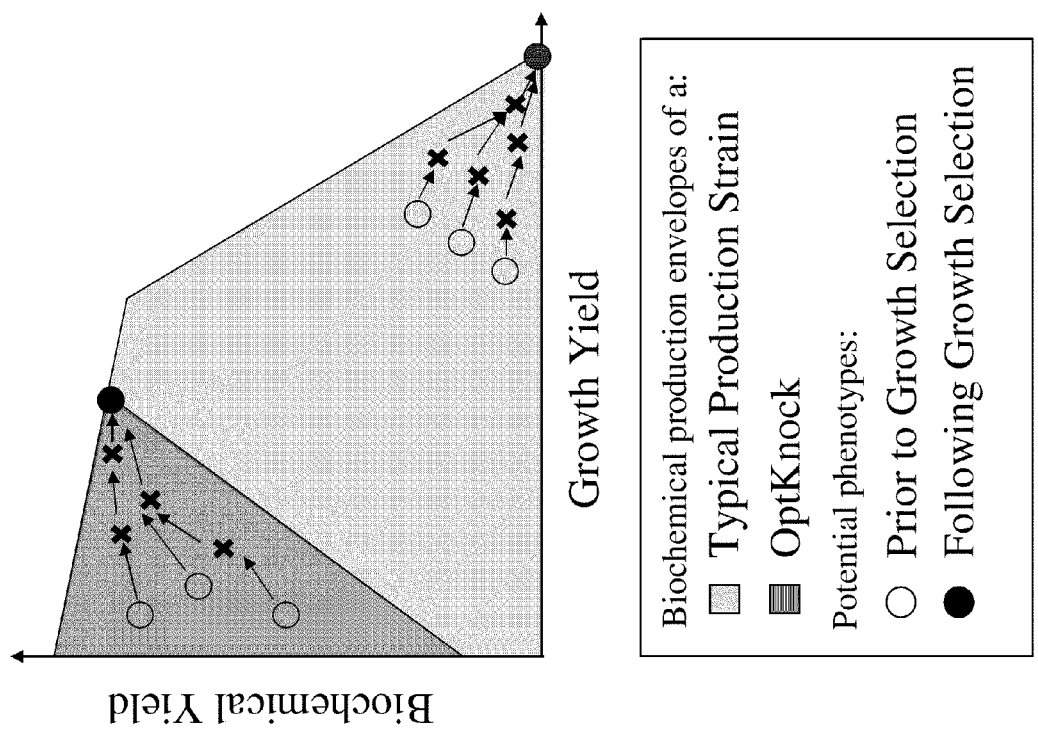
FIG. 1 shows the hypothetical production envelopes of an OptKnock-designed strain contrasted against a typical non-growth-coupled production strain. Note that the potential evolutionary trajectories of the OptKnock strain are fundamentally different in that they will lead to a high producing phenotype.

This invention is directed, in part, to engineered organisms having biosynthetic pathways to fumarate, malate, and acrylate. In some embodiments, the invention utilizes optimization-based approaches based on in silico stoichiometric models of *Escherichia coli* and *Saccharomyces cerevisiae* metabolism that identify metabolic designs for increased production of fumarate, malate, and acrylate in these organisms. A bilevel programming framework, OptKnock, is applied within an iterative algorithm to predict multiple sets of gene disruptions, that collectively result in increased production of fumarate, malate, or acrylate. As disclosed herein, various combinations of gene deletions or functional disruptions of genes significantly improve the fumarate, malate, or acrylate production capabilities of *E. coli* and *S. cerevisiae*.

Production of acrylate, in particular, involves not only primary metabolic production of fumarate, but also subsequent mono-decarboxylation. Thus, the invention is also directed, in part, to a developing a route to acrylate from fumarate by reaction with a decarboxylase enzyme. The decarboxylase enzyme can be introduced as an exogenous nucleic acid into the same organism that has been engineered for increased fumarate production via gene disruptions, or alternatively through a secondary transformation involving extracellular addition of a decarboxylase to a culture containing overproduced fumarate. Another alternative is to provide a second organism having decarboxylase activity. In such a case, the fumarate-producing organism can be co-cultured or serially cultured with the second organism possessing the requisite decarboxylase.

The engineering designs are equally applicable if an organism other than *E. coli* or *S. cerevisiae* is chosen as the production host, even if the organism naturally lacks the activity or exhibits low activity of a subset of the gene products marked for disruption. In those cases, disruptions must only be introduced to eliminate or lessen the enzymatic activities of the gene products that are naturally present in the chosen production host. Production of fumarate, malate, or acrylate for the in silico designs are confirmed by construction of strains having the designed metabolic genotype. These metabolically engineered cells or organisms can also be subjected to adaptive evolution to further augment product production.

In a further embodiment, the invention is directed to an integrated computational and engineering platform for developing metabolically altered microorganism strains having enhanced fumarate, malate, or acrylate producing characteristics. Strains identified via the computational component of the platform are put into actual production by genetically engineering the predicted metabolic alterations which lead to the enhanced production of fumarate, malate, or acrylate. Production of the desired product is optionally coupled to optimal growth of the microorganism. Strains exhibiting increased production of these products can be further subjected to adaptive evolution to further augment product biosynthesis. The levels of product production following adaptive evolution also can be predicted by the computational component of the system where, in this specific embodiment, the elevated product levels are realized following evolution.

Currently, the only organisms known to produce fumarate at a reasonable level are *Rhizopus* (Tsao et al., *Adv. Biochem. Eng. Biotechnol.*, 65:243-280 (1999); Lee et al., *Macromolecular Bioscience*, 4:157-164 (1999); Rhodes et al., *Appl. Microbiol.* 1962, 10(1):9-15; and Rhodes et al., *Appl. Microbiol.* 7(2):74-80 (1959)). Fumarate production in these organisms utilizes pyruvate carboxylase to fix carbon dioxide, converting pyruvate into oxaloacetate (Kenealy et al., *Appl. Environ. Microbiol.* 52(1):128-133 (1986)). This is subsequently converted into malate and finally into fumarate. Some reports on fumarate production in *Rhizopus* have outlined fermentation and culture conditions for obtaining fumarate (Moresi et al., *J. Chem. Technol. Biotechnol.* 54(3):283-2890 (1992)). Optimum concentrations of metal ions and phosphate have been determined to maximize the fumarate production during the fermentation process (Zhou et al., *Appl. Biochem. Biotechnol.* 84-86:779-89 (2000)). Another study examined various cassava bagasse hydrolysates as a cheap carbon source, reporting a yield of 22 g/L of fumarate (Carta et al., *Bioresource Technology* 68(1):23-28 (1999)). A study of neutralizing agents for fumarate production was also undertaken. It was determined that utilizing $CaCO_3$ provides the highest fumaric acid weight yield (53.4%) and volumetric productivity (1.03 g/L.hr) (Zhou et al., *Bioprocess Biosyst. Eng.* 25(3):179-181 (2002)).

However, growing mycelia often form interlocking hyphae mingled with calcium carbonate, resulting in oxygen transfer limitations, thus slowing down the rate of fermentation. Another difficulty involved in fumarate production is the tendency of *Rhizopus* sporangiospores to grow into mycelial mats or mycelial lumps (Zhou et al., *Appl. Biochem. Biotechnol.* 84-86:779-89 (2000)), interfering with the function of bafflers and propellers inside a reactor. A rotary biofilm contactor has been utilized in a simultaneous fermentation-adsorption process to obtain yields of 85 g/L of fumarate from 100 g/L of glucose. Finally, *R. arrhizus* NRR11526 immobilized on a polyurethane sponge was used to facilitate continuous fermentation for fumarate production. Yields of approximately 12.3 g/L of fumaric acid were obtained in this work (Lee et al., *Macromolecular Bioscience* 4:157-164 (2004)). However, despite the above efforts, the approaches employed have several drawbacks which hinder applicability in commercial settings. Chemical processes remain predominantly used in fumarate production because of (a) the cost benefits of chemical production and (b) the complications associated with maintaining the right size of mycelial particles for fumarate production.

Malic acid production has been reported in a wide range of organisms, including both yeast and bacteria (Jantama, K., et al., *Biotechnol Bioeng*, 99(5):1140-53 (2008); Moon, S. Y., et al., *Biochemical Engineering Journal* (2008).). Most recently, malic acid titers of up to 59 g/L with yields of 0.42 mol/mol glucose were reported in *Saccharomyces cerevisiae*. (Zelle, R. M., et al., *Appl Environ Microbiol*, 74(9):2766-77 (2008)). This level of malic acid production was achieved by introducing three genetic modifications: (i) overexpression of the native pyruvate carboxylase, (ii) increasing the expression of malate dehydrogenase and retargeting it to cytosol, and (iii) functional expression of a heterologous malate transporter gene. Other yeasts in which malic acid has been produced successfully include *Aspergillus flavus, Rhizopus arrhizus*, and *Zygosaccharomyces rouxii*. (Zelle, R. M., et al., *Appl Environ Microbiol*, 74(9):2766-77 (2008)). The highest malic acid titer has been reported in *A. flavus* (113 g/L) with malic acid yield at 63% of the maximum theoretical yield on glucose. However, potential aflatoxin production has rendered this organism unusable for the production of food-grade malic acid. Malic acid yields with other yeasts are not high enough to pursue commercial production. (Zelle, R. M., et al., *Appl Environ Microbiol*, 74(9):2766-77 (2008)). Relatively higher malate yields have been reported in a mutant strain of *Escherichia coli* C (1.4 mol/mol glucose) which was engineered to inhibit secretion of byproducts such as acetate, lactate, formate, and ethanol. (Jantama, K., et al., *Biotechnol Bioeng*, 99(5):1140-53 (2008)).

This invention is also directed, in part, to methods for producing olefins by decarboxylation an alpha, beta-unsaturated carboxylic acids as exemplified in FIG. 19a. The unsaturated carboxylic acid substrate can be of any structural olefin geometry. For example the unsaturated carboxylic acid may be substituted at either the alpha or beta position. Additionally, beta-substituted unsaturated carboxylic acid substrates can have either E or Z olefin geometry. The product will typically be a terminal olefin. Furthermore, the carboxylic acid substrate can be further conjugated as shown in FIG. 19b, wherein pentadienoic acid is decarboxylated to the commercially valuable commodity chemical 1,3-butadiene. 1,3-butadiene is an important chemical in the manufacture of synthetic rubbers, for example.

Figure 20:
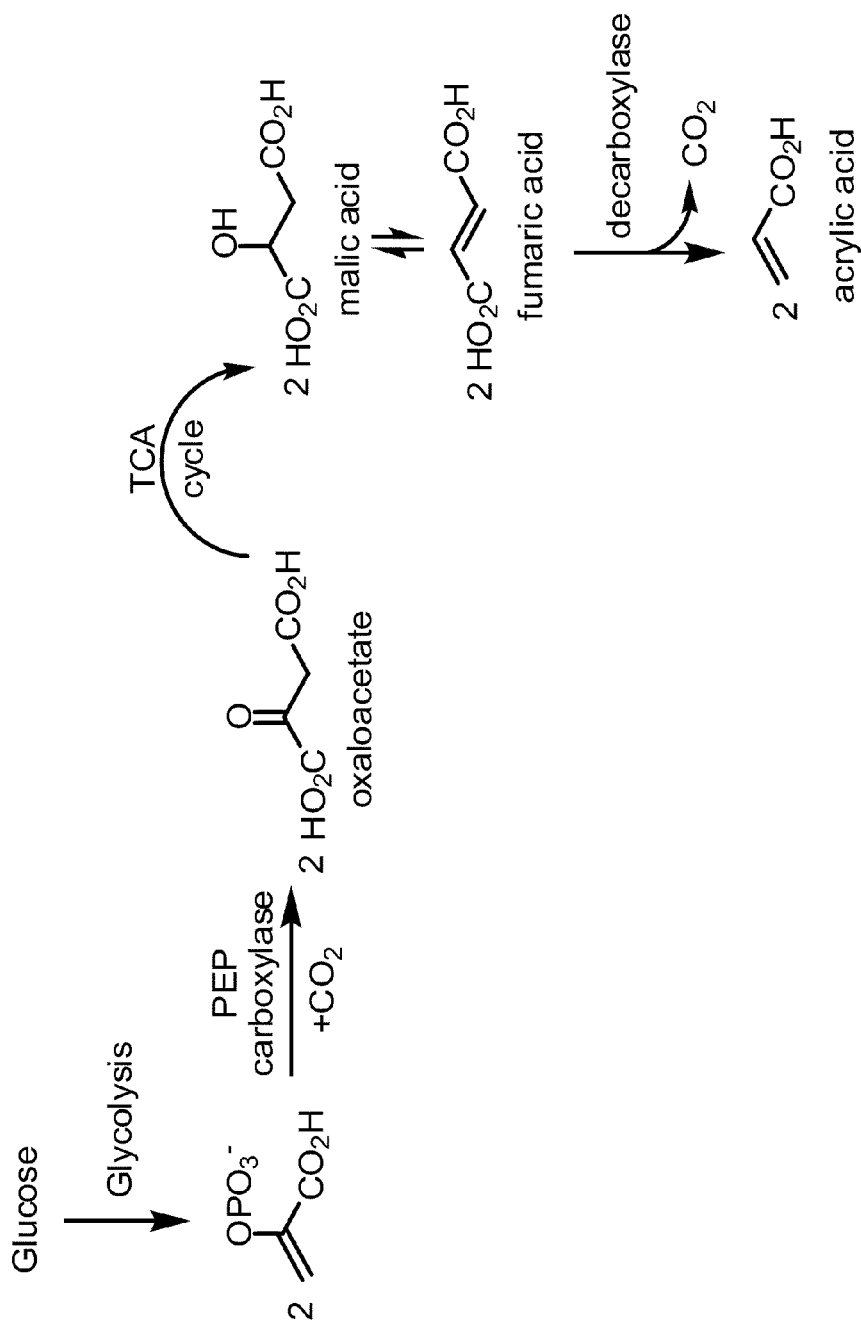
FIG. 20 shows a biosynthetic pathway for the direct production of acrylate through decarboxylation of fumarate.

In some embodiments this invention is directed to methods of producing acrylic acid involving primary metabolic production of fumaric acid, followed by decarboxylation. FIG. 20 shows a biosynthetic scheme for producing acrylic acid which involves treatment of fumaric acid with a decarboxylase enzyme in a pathway leading directly to acrylate, or alternatively through a secondary transformation involving extracellular addition of a decarboxylase to a culture containing over-produced fumarate.

As shown in FIG. 20, two moles of acrylic acid are produced from each mole of glucose consumed and carbon is utilized in a very efficient manner. Carbon from 1 mole of glucose provides two moles of phosphoenol pyruvate (PEP) through glycolysis, which then reacts with carbon dioxide (via PEP carboxylase or PEP caboxykinase) to afford a maximum theoretical yield of 2.0 moles of fumaric acid, which upon decarboxylation leads to two moles of acrylic acid. This efficient use of carbon is important for achieving high yields (0.8 g acrylic acid/g glucose) and favorable process economics in the production of acrylic acid from renewable feedstocks. In addition, although the final decarboxylation step leads to release of carbon dioxide, the conversion of phosphoenolpyruvate to oxaloacetate actually consumes one mole of carbon dioxide, leading to an overall process that is $CO_2$ neutral. The decarboxylation of fumarate to acrylate also will drive the equilibrium between malate and fumarate, thus leading to all carbon being funneled to the desired acrylic acid product.

Production of acrylic acid by fermentation involving renewable feedstocks has been investigated previously, and several designs have been proposed (Straathof, A. J. et al., *Appl. Microbiol. Biotechnol.*, 67:727-34 (2005)). In particular, processes involving conversion of lactate or lactoyl-CoA to acrylate or acryloyl-CoA have been explored, but suffer from unfavorable thermodynamics and undesirably high levels of lactate secretion. Another bioprocess for acrylic acid production proceeds through the intermediate 3-hydroxypropionic acid (3-HP), which is produced first by fermentation and then isolated and dehydrated in a second step under anhydrous conditions (Cameron, D. C. and P. F. Suthers WO0242418).

Such two-step routes to acrylic acid via 3-HP have presented challenges and are still under development. Direct conversion of biomass-derived sugars to acrylic acid is highly desirable due to substantial economic benefits associated with reduction in capital and energy costs relative to multi-step processes.

The maximum theoretical yield of each of the acid products described herein is 2 moles per mole of glucose consumed (see equations 1-3 below), indicating a significant potential for improving the existing biochemical processes further.

$$C_6H_{12}O_6 + 2CO_2 \rightarrow 2C_4H_4O_4 + 2H_2O \text{ (fumaric acid)} \quad \text{equation 1}$$

$$C_6H_{12}O_6 + 2CO_2 \rightarrow 2C_4H_6O_5 \text{ (malic acid)} \quad \text{equation 2}$$

$$C_6H_{12}O_6 \rightarrow 2C_3H_4O_2 + 2H_2O \text{ (acrylic acid)} \quad \text{equation 3}$$

Many different substrates derived from renewable feedstocks, such as glucose, xylose, arabinose, sorbitol, sucrose, glycerol, or even synthesis gas (a mixture carbon monoxide, hydrogen and carbon dioxide), can serve as carbon and energy sources for a fermentation process. Each of these substrates can be used for biological production of fumarate, malate, or acrylate.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a cyclohexanone biosynthetic pathway.

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene with results in a truncated gene product or by any of various mutation methods that inactivate the encoded gene product. One particularly useful method of gene disruption is complete gene deletion because it reduces or eliminates the occurrence of genetic reversions in the non-naturally occurring eukaryotic organisms of the invention. The term "gene disruption" is also intended to mean a genetic alteration that lowers the activity of a given gene product relative to its activity in a wild-type organism. This attenuation of activity can be due to, for example, a deletion in a portion of the gene which results in a truncated gene product or any of various mutation methods that render the encoded gene product less active than its natural form, replacement or mutation of the promoter sequence leading to lower or less efficient expression of the gene, culturing the organism under a condition where the gene is less highly expressed than under normal culture conditions, or introducing antisense RNA molecules that interact with complementary mRNA molecules of the gene and alter its expression.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein the term "parent decarboxylase" refers to both wild-type and previously engineered decarboxylases that serve as a starting point for further optimization of the decarboxylation activity. Optimizations can include not only changes made to the nucleic acid sequence encoding the decarboxylase, but also post-translational modifications to the enzyme product.

As used herein the terms "acrylate" and "acrylic acid" are used interchangeably. One skilled in the art will appreciate that the ionization state of a typical carboxylic acid will depend on the pH of its environment. For example, with a $pK_a$ of approximately 4, acrylic acid can be significantly in its ionized acrylate form when the pH is 6 or more. While the final isolated product of any given process can be acrylic acid, the direct product of fermentation will frequently be the corresponding acrylate salt, although this can vary depending on the pH conditions employed. In a similar manner, "fumarate" and "fumaric acid," "malate" and "malic acid," and "carboxylate" and "carboxylic acid" are used interchangeably.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having cyclohexanone biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionally related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% can represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16-1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the invention provides a non-naturally occurring microbial organism, that includes one or more gene disruptions. The disruptions occur in genes encoding an enzyme that is obligatory to coupling fumarate production to growth of the microorganism when the gene disruption reduces the activity of the enzyme, such that the gene disruptions confer stable growth-coupled production of fumarate onto the non-naturally occurring microorganism. In other embodiments, engineered organisms that include one or more gene disruptions can enhance non-growth coupled production fumarate by linking the production of fumarate to energy generation and/or redox balance.

In other embodiments, the disruptions occur in genes encoding an enzyme obligatory to coupling malate production to growth of the microorganism when the gene disruption reduces the activity of the enzyme, such that the gene disruptions confer stable growth-coupled production of malate onto the non-naturally occurring microorganism. Engineered organisms that include one or more gene disruptions can also enhance non-growth coupled production malate by linking the production of malate to energy generation and/or redox balance.

In other embodiments, the invention provides a non-naturally occurring microbial organism that includes one or more gene disruptions. The disruptions occur in genes encoding an enzyme obligatory to coupling acrylate production to growth of the microorganism when the gene disruption reduces the activity of the enzyme, such that the gene disruptions confer stable growth-coupled production of acrylate onto the non-naturally occurring microorganism. In other embodiments, engineered organisms that include one or more gene disruptions can also enhance non-growth coupled production acrylate by linking the production of acrylate to energy generation and/or redox balance.

In some embodiments, the invention provides a non-naturally occurring prokaryotic organism, that includes one or more gene disruptions. The disruptions occur in genes encoding an enzyme obligatory to coupling fumarate production to growth of the microorganism when the gene disruption reduces the activity of the enzyme, such that the gene disruptions confer stable growth-coupled production of fumarate onto the non-naturally occurring microorganism. In other embodiments, an engineered prokaryotic organism that includes one or more gene disruptions can also enhance non-growth coupled production fumarate by linking the production of fumarate to energy generation and/or redox balance.

In other embodiments, the invention provides a non-naturally occurring prokaryotic organism that includes one or more gene disruptions. The disruptions occur in genes encoding an enzyme obligatory to coupling malate production to growth of the microorganism when the gene disruption reduces the activity of the enzyme, such that the gene disruptions confer stable growth-coupled production of malate onto the non-naturally occurring microorganism. In other embodiments, an engineered prokaryotic organism that includes one or more gene disruptions can also enhance non-growth coupled production malate by linking the production of malate to energy generation and/or redox balance.

In still further embodiments, the invention provides a non-naturally occurring prokaryotic organism that includes one or more gene disruptions. The disruptions occur in genes encoding an enzyme obligatory to coupling acrylate production to growth of the organism when the gene disruption reduces the activity of the enzyme, such that the gene disruptions confer stable growth-coupled production of acrylate onto the non-naturally occurring organism. In other embodiments, an engineered prokaryotic organism that includes one or more gene disruptions can also enhance non-growth coupled production acrylate by linking the production of acrylate to energy generation and/or redox balance.

In some embodiments, the invention provides a non-naturally occurring eurakoytic organism, that includes one or more gene disruptions. The disruptions occur in genes encoding an enzyme obligatory to coupling fumarate production to growth of the organism when the gene disruption reduces the activity of the enzyme, such that the gene disruptions confer stable growth-coupled production of fumarate onto the non-naturally occurring organism. In other embodiments, an engineered eukaryotic organism that includes one or more gene disruptions can also enhance non-growth coupled production fumarate by linking the production of fumarate to energy generation and/or redox balance.

In other embodiments, the invention provides a non-naturally occurring eukaryotic organism that includes one or more gene disruptions. The disruptions occur in genes encoding an enzyme obligatory to coupling malate production to growth of the organism when the gene disruption reduces the activity of the enzyme, such that the gene disruptions confer stable growth-coupled production of malate onto the non-naturally occurring organism. In other embodiments, an engineered eukaryotic organism that includes one or more gene disruptions can also enhance non-growth coupled production malate by linking the production of malate to energy generation and/or redox balance.

In still further embodiments, the invention provides a non-naturally occurring eukaryotic organism that includes one or more gene disruptions. The disruptions occur in genes encoding an enzyme obligatory to coupling acrylate production to growth of the organism when the gene disruption reduces the activity of the enzyme, such that the gene disruptions confer stable growth-coupled production of acrylate onto the non-naturally occurring organism. In other embodiments, an engineered eukaryotic organism that includes one or more gene disruptions can also enhance non-growth coupled production acrylate by linking the production of acrylate to energy generation and/or redox balance.

Further, the present invention provides methods of producing such non-naturally prokaryotic or eukaryotic organisms having stable growth-coupled production of fumarate, malate, or acrylate. For fumarate production, for example, the method includes: (a) identifying in silico a set of metabolic modifications requiring fumarate production during cell growth, and (b) genetically modifying a microorganism to contain the set of metabolic modifications requiring fumarate production.

The engineered organisms described herein are useful not only for enhancing growth-coupled production, but they are also well-suited for enhancing non-growth coupled production because they link the production of fumarate, malate and/or acrylate to energy generation and/or redox balance. Exemplary non-growth coupled production methods include implementing an aerobic growth phase followed by an anaerobic production phase. For example, Vemuri et al. *J. Ind. Microbiol. Biotechnol.*, 6:325-332, (2002) describe a dual-phase process for the production of succinate in *E. Coli*. A similar non-growth couple production process in a strain of *Corynebacterium glutamicum* has been described (Okino et al., *Appl. Microbiol. Biotechnol.* 81:459-464 (2008)).

Another such method involves withholding an essential nutrient from a propagated cell culture, thereby limiting growth, but not precluding production as described in Durner et al., *Appl. Environ. Microbiol.* 8:3408-3414 (2000). Yet another strategy aimed at decoupling growth from production involves replacing the growth substrate with another compound that is more slowly metabolizable as described in Altamirano et al., *Biotechnol. Bioeng.* 76:351-360 (2001). Growth decoupled-product formation can also be brought about by specific genetic modifications as described in Blombach et al. *Appl. Microbiol. Biotechnol.* 79:471-479 (2008).

One computational method for identifying and designing metabolic alterations favoring growth-coupled production of a product is the OptKnock computational framework, Burgard et al., *Biotechnol Bioeng*, 84:647-657 (2003). OptKnock is a metabolic modeling and simulation program that suggests gene disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production.

The concept of growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources. Thus, enhanced rates of biochemical production will necessarily result in sub-maximal growth rates. The knockouts suggested by OptKnock are designed to restrict the allowable solution boundaries forcing a change in metabolic behavior from the wild-type strain as depicted in FIG. 1. Although the actual solution boundaries for a given strain will expand or contract as the substrate uptake rate(s) increase or decrease, each experimental point should lie within its calculated solution boundary. Plots such as these enable one to visualize how close strains are to their performance limits or, in other words, how much room is available for improvement. The OptKnock framework has already been able to identify promising gene deletion strategies for biochemical overproduction, (Burgard et al., *Biotechnol Bioeng,* 84:647-657 (2003); Pharkya et al., *Biotechnol Bioeng,* 84:887-899 (2003)) and establishes a systematic framework that will naturally encompass future improvements in metabolic and regulatory modeling frameworks. Lastly, when complete gene deletions are constructed there is a negligible possibility of the designed strains reverting to their wild-type states because the genes selected by OptKnock are completely removed from the genome.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. patent application Ser. No. 10/043,440, filed Jan. 10, 2002, and in International Patent No. PCT/US02/00660, filed Jan. 10, 2002.

Another computational method for identifying and designing metabolic alterations favoring growth-coupled production of a product is metabolic modeling and simulation system termed SimPheny®. This computational method and system is described in, for example, U.S. patent application Ser. No. 10/173,547, filed Jun. 14, 2002, and in International Patent Application No. PCT/US03/18838, filed Jun. 13, 2003.

SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *S. cerevisiae* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement growth-coupled production of a biochemical product. Such metabolic modeling and simulation methods include, for example, the computational systems exemplified above as SimPheny® and OptKnock. For simplicity in illustrating the invention, the methods and strains will be described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to obligatory couple growth to the production of a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. As shown in FIG. 1, the production of a desired biochemical generally is in direct competition with biomass formation for intracellular resources. Under these circumstances, enhanced rates of biochemical production will necessarily result in sub-maximal growth rates. The knockouts suggested by the above metabolic modeling and simulation programs such as OptKnock are designed to restrict the allowable solution boundaries forcing a change in metabolic behavior from the wild-type strain as depicted in FIG. 1. Although the actual solution boundaries for a given strain will expand or contract as the substrate uptake rate(s) increase or decrease, each experimental point will lie within its calculated solution boundary. Plots such as these enable accurate predictions of how close the designed strains are to their performance limits which also indicates how much room is available for improvement.

The OptKnock mathematical framework is exemplified herein for pinpointing gene deletions leading to growth-coupled biochemical production as illustrated in FIG. 1. The procedure builds upon constraint-based metabolic modeling which narrows the range of possible phenotypes that a cellular system can display through the successive imposition of governing physico-chemical constraints, Price et al., *Nat Rev Microbiol*, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1\ldots,N\}$ of metabolites and a set $M=\{1,\ldots,M\}$ of metabolic reactions is expressed mathematically as follows:

$$\text{maximize } v_{cellular\ objective}$$

subject to $$\sum_{j=1}^{M} S_{ij}v_j = 0, \quad \forall\, i \in N$$

$$v_{substrate} = v_{substrate\_uptake} \text{mmol/gDW·hr} \quad \forall\, i \in \{\text{limiting substrate}(s)\}$$

$$v_{atp} \geq v_{atp\_main} \text{mmol/gDW·hr}$$

$$v_j \geq 0, \quad \forall\, i \in \{irrev.\ \text{reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol Bioeng*, 74: 364-375 (2001), Burgard et al., *Biotechnol Prog*, 17: 791-797 (2001). These binary variables, $$y_j = \begin{cases} 1, & \text{if reaction } flux\ v_j \text{ is active} \\ 0, & \text{if reaction } flux\ v_j \text{ is not active} \end{cases}, \forall\, j \in M$$

assume a value of 1 if reaction j is active and a value of 0 if it is inactive. The following constraint, $$v_j^{min} \cdot y_j \leq b_j \leq v_j^{max} \cdot y_j, \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab Eng*, 5: 264-76 (2003).

Figure 2:
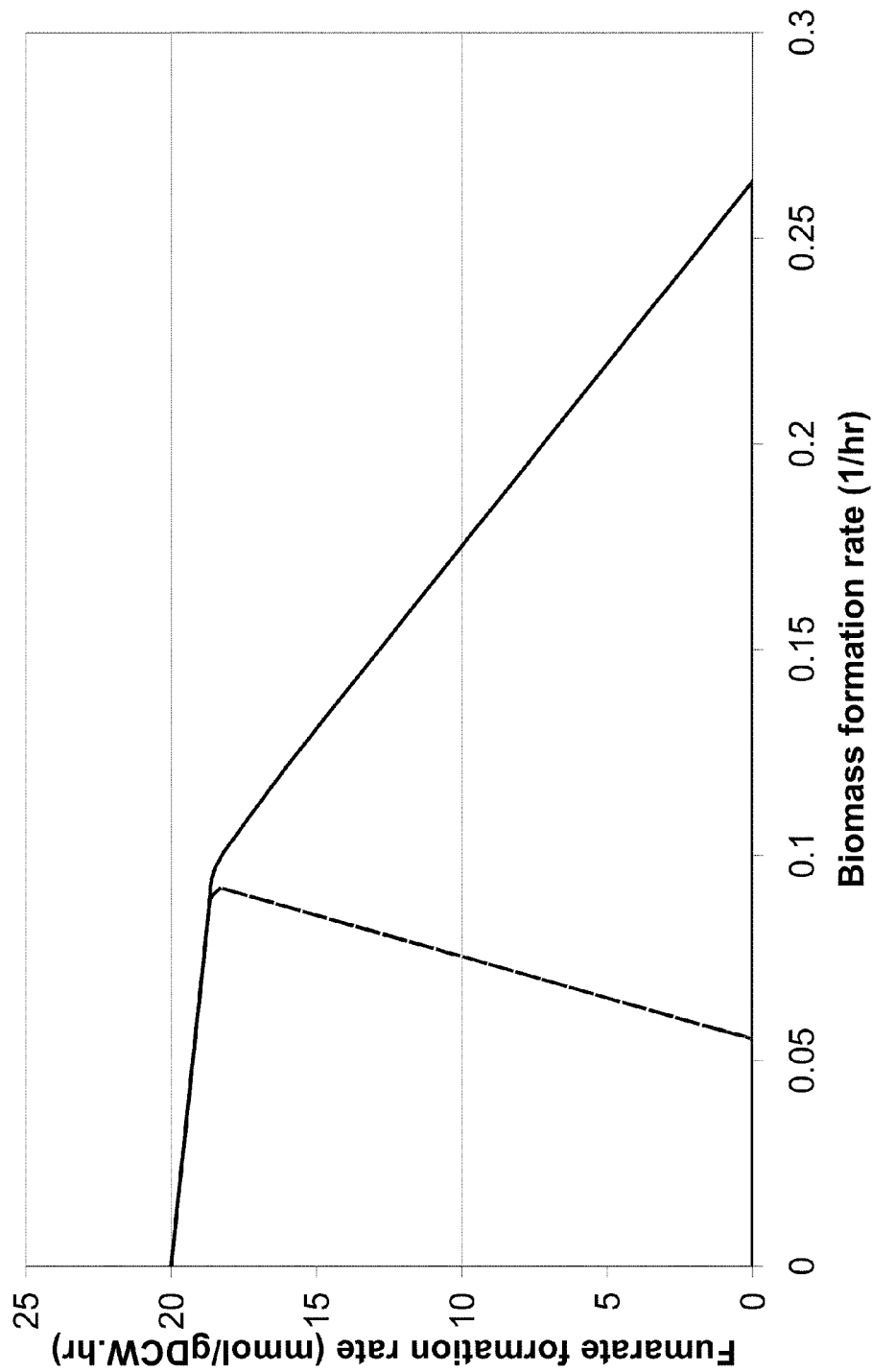
FIG. 2 shows increased fumarate production characteristics of one strain (black, dashed) compared with those of the wild-type *E. coli* network (black). At the maximum rate of growth, the wild-type network is not expected to form any fumarate.

Optimal gene/reaction knockouts are identified by solving a bilevel optimization problem that chooses the set of active reactions ($y_j=1$) such that an optimal growth solution for the resulting network overproduces the chemical of interest. Schematically, this bilevel optimization problem is illustrated in FIG. 2. Mathematically, this bilevel optimization problem is expressed as the following bilevel mixed-integer optimization problem:

$$\underset{y_j}{\text{maximize}}\ v_{chemical} \quad (OptKnock)$$

$$\begin{pmatrix} \text{subject to} & \text{maximize} & v_{biomass} \\ v_j & & \\ \text{subject to} & & \\ \sum_{j=1}^{M} S_{ij}v_j = 0, & \forall\, i \in N & \\ v_{substrate} = v_{substrate\_uptake} & \forall\, i \in \{\text{limiting substrate}(s)\} & \\ v_{atp} \geq v_{atp\_main} & & \\ v_{biomass} \geq v_{biomass}^{target} & & \end{pmatrix}$$

$$v_j^{min} \cdot y_j \leq v_j \leq v_j^{max} \cdot y_j, \quad \forall\, j \in M$$

$$\sum_{j \in M^{forward}} (1 - y_j) = K$$

$$y_j \in \{0, 1\}, \quad \forall\, j \in M$$

where $v_{chemical}$ is the production of the desired target product, for example fumarate or other biochemical product, and K is the number of allowable knockouts. Note that setting K equal to zero returns the maximum biomass solution of the complete network, while setting K equal to one identifies the single gene/reaction knockout ($y_j=0$) such that the resulting network involves the maximum overproduction given its maximum biomass yield. The final constraint ensures that the resulting network meets a minimum biomass yield. Burgard et al., *Biotechnol Bioeng*, 84: 647-57 (2003), provide a more detailed description of the model formulation and solution procedure. Problems containing hundreds of binary variables can be solved in the order of minutes to hours using CPLEX 8.0, GAMS: *The Solver Manuals*. 2003: GAMS Development Corporation, accessed via the GAMS, Brooke et al., *GAMS Development Corporation* (1998), modeling environment on an IBM RS6000-270 workstation. The OptKnock framework has already been able to identify promising gene deletion strategies for biochemical overproduction, Burgard et al., *Biotechnol Bioeng*, 84: 647-57 (2003), Pharkya et al., *Biotechnol Bioeng*, 84: 887-899 (2003), and establishes a systematic framework that will naturally encompass future improvements in metabolic and regulatory modeling frameworks.

Any solution of the above described bilevel OptKnock problem will provide one set of metabolic reactions to disrupt. Elimination of each reaction within the set or metabolic modification can result in fumarate as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve increased fumarate, malate, or acrylate production are implemented in the target cell or organism by functional disruption of at least one gene encoding each metabolic reaction within the set. As described previously, one particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the product coupling are desired or when genetic reversion is less likely to occur.

To identify additional productive solutions to the above described bilevel OptKnock problem which lead to further sets of reactions to disrupt or metabolic modifications that can result in the growth-coupled production of fumarate, malate, acrylate, or other biochemical products, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatory couples product biosynthesis to growth. For example, if a previously identified growth-coupled metabolic modification specifies reactions 1, 2, and 3 for disruption, then the following constraint prevents the same reactions from being simultaneously considered in subsequent solutions: $y_1+y_2+y_3 \geq 1$. The integer cut method is well known in the art and can be found described in, for example, reference, Burgard et al., *Biotechnol Prog*, 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny.

Constraints of the above form preclude identification of larger reaction sets that include previously identified sets. For example, employing the integer cut optimization method above in a further iteration would preclude identifying a quadruple reaction set that specified reactions 1, 2, and 3 for disruption since these reactions had been previously identified. To ensure identification of all possible reaction sets leading to growth-coupled production of a product, a modification of the integer cut method was employed.

Briefly, the modified integer cut procedure begins with iteration 'zero' which calculates the maximum production of the desired biochemical at optimal growth for a wild-type network. This calculation corresponds to an OptKnock solution with K equaling 0. Next, single knockouts are considered and the two parameter sets, $\text{objstore}_{iter}$ and $\text{ystore}_{iter,j}$, are introduced to store the objective function ($v_{chemical}$) and reaction on-off information ($y_j$), respectively, at each iteration, ($y_j$). The following constraints are then successively added to the OptKnock formulation at each iteration.

$$v_{chemical} \geq \text{objstore}_{iter} + \epsilon - M \cdot \Sigma_{j \epsilon ystore_{iter,j}=0} y_j$$

In the above equation, $\epsilon$ and M are a small and a large numbers, respectively. In general, $\epsilon$ can be set at about 0.01 and M can be set at about 1000. However, numbers smaller and/or larger then these numbers also can be used. M ensures that the constraint can be binding only for previously identified knockout strategies, while $\epsilon$ ensures that adding knockouts to a previously identified strategy must lead to an increase of at least $\epsilon$ in biochemical production at optimal growth. The approach moves onto double deletions whenever a single deletion strategy fails to improve upon the wild-type strain. Triple deletions are then considered when no double deletion strategy improves upon the wild-type strain, and so on. The end result is a ranked list, represented as desired biochemical production at optimal growth, of distinct deletion strategies that differ from each other by at least one knockout. This optimization procedure as well as the identification of a wide variety of reaction sets that, when disrupted, lead to increased production of a biochemical product are exemplified in detail further below. Given the teachings and guidance provided herein, those skilled in the art will understand that the methods and metabolic engineering designs exemplified herein are applicable to linking cell or microorganism growth to any biochemical product.

Employing the methods exemplified above, one can construct cells and organisms that obligatorily couple the production of a target biochemical product to growth of the cell or organism engineered to harbor the identified genetic alterations. In this regard, metabolic alterations have been identified that obligatorily couple the production of fumarate, malate, or acrylate to organism growth. Prokaryotic or eukaryotic organism strains constructed with the identified metabolic alterations produce elevated levels of fumarate, malate, or acrylate during the exponential growth phase. These strains can be beneficially used for the commercial production of fumarate, malate, or acrylate in continuous fermentation process without being subjected to the negative selective pressures described previously.

As described above, the metabolic alterations also enable non-growth coupled production of fumarate, malate, or acrylate. The invention is described herein with general reference to the metabolic reaction, reactant or product thereof, or with specific reference to one or more genes associated with the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constitutes also references the gene or genes encoding the enzymes that catalyze the referenced reaction, reactant or product. Likewise, given the well known fields of metabolic biochemistry, enzymology and genomics, reference herein to a gene also constitutes a reference to the corresponding encoded enzyme and the reaction it catalyzes as well as the reactants and products of the reaction.

The methods of the invention provide a set of metabolic modifications that are identified by an in silico method selected from OptKnock. The set of metabolic modifications can include functional disruption of one or more metabolic reactions including, for example, disruption by gene deletion. Exemplary reactions, reaction nomenclature, reactants, products, cofactors and genes encoding enzymes catalyzing a reaction involved in the growth-coupled production of fumarate and malate in E. Coli are set forth in Tables 1, 2, 3, and 4.

The invention provides non naturally occurring microorganisms having increased production of fumarate or malate. Fumarate or malate production can be obligatorily linked to the exponential growth phase of the microorganism by genetically altering the metabolic pathways of the cell. The genetic alterations make fumarate an obligatory product during the growth phase. In some embodiments, fumarate or malate production is not obligatorily linked to growth. In such a case, the production of fumarate or malate takes place during a non-growth phase, for example. Sets of metabolic alterations or transformations that result in elevated levels of fumarate or malate biosynthesis are exemplified in Tables 1 and 2, respectively. Each alteration within a set corresponds to the requisite metabolic reaction that can be functionally disrupted. Functional disruption of all reactions within each set results increased production of fumarate or malate by the engineered strain. The corresponding reactions to the referenced alterations in Tables 1 and 2, and the gene or genes that potentially encode them in E. coli, are set forth in Table 3.

For example, for each strain exemplified in Table 1, the metabolic alterations that can be generated for increased fumarate production are shown in each row. These alterations include the functional disruption of from one to six or more reactions. In particular, 348 strains are exemplified in Table 1 that have non-naturally occurring metabolic genotypes. Each of these non-naturally occurring alterations result in an enhanced level of fumarate production during the exponential growth phase of the microorganism compared to a wild-type strain, under appropriate culture conditions. Appropriate conditions include, for example, those exemplified further below in the Example I such as particular carbon sources or reactant availabilities and/or adaptive evolution.

One such strain design for fumarate production involves deletions in fumarate reductase (FRD), alcohol dehydrogenase (ADHEr), lactate dehydrogenase (LDH_D), and glutamate dehydrogenase (GLUDy). This strain is predicted to have a growth-coupled yield of 1.83 moles of fumarate per mole of glucose consumed and the maximum growth rate is anticipated to be 0.09/hr as shown in FIG. 2. The deletion of FRD, ADHEr, and LDH_D prevents the formation and secretion of byproducts, namely succinate, ethanol and lactate. The elimination of glutamate dehydrogenase that transaminates alpha-ketoglutarate into glutamate with the utilization of a molecule of NADPH, disrupts a loop of reactions that form and use NADPH for synthesis of amino acids such as alanine and valine. All the disruptions can be implemented sequentially based on the necessity to do so. FIG. 2 shows the growth-coupled fumarate production characteristics of the strain (black, dashed) incorporating these disruptions compared with those of the wild-type E. coli network (black, at the maximum rate of growth, the wild-type network is not expected to form any fumarate.)

Figure 3:
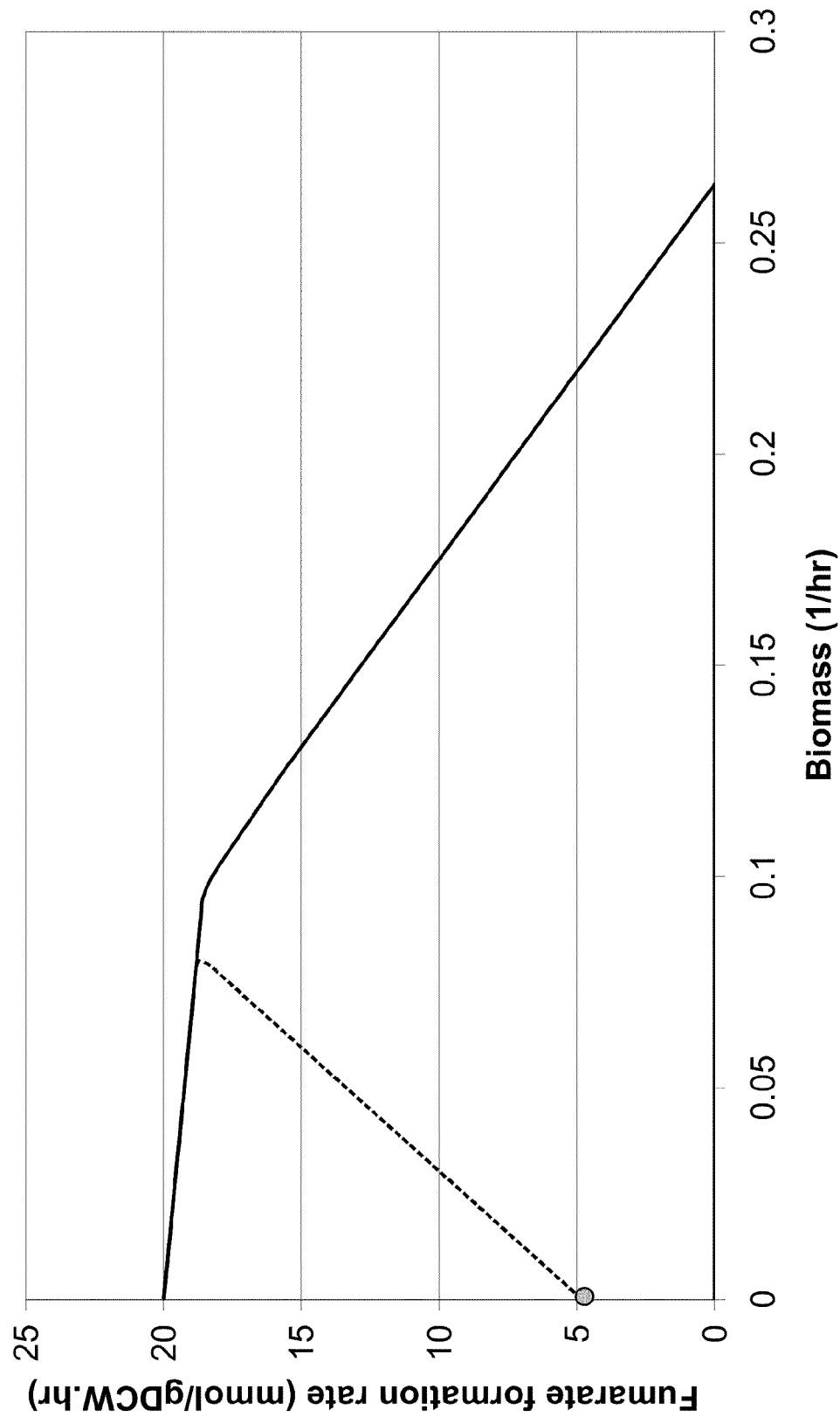
FIG. 3 shows increased fumarate production characteristics of another strain (black, dotted) compared with those of the wild-type *E. coli* network (black). The grey point shows the minimum amount of product formation expected from this strain.

Another strain, shown in FIG. 3, has three common deletions with the strain shown in FIG. 2 and involves elimination of malic enzyme (ME2) and transhydrogenase (THD2) activity additionally. Malic enzyme catalyzes the decarboxylation of malate to form pyruvate with the concomitant reduction of a molecule of NADP to form NADPH. Transhydrogenase catalyzes the oxidation of NADH causing the reduction of NADP into NADPH. The deletion of the NADPH-forming malic enzyme and the membrane-bound proton-translocating transhydrogenase catalyzed by PntAB prevents or reduces the formation of NADPH, thus preventing or reducing carbon from being funneled into amino acids instead of being converted into fumarate. The efficacy of the two latter knockouts for fumarate production can be assessed and implemented sequentially based on the necessity to do so.

The strain of FIG. 3 is expected to have a maximum growth-coupled yield of 1.87 moles of fumarate per mole of glucose consumed at an expected maximum growth rate of 0.08/hr. Note also that the strain is has a minimum theoretical product yield of 0.48 moles per mole of glucose (the grey point on the black, dotted curve). FIG. 3 shows the growth-coupled fumarate production characteristics of the strain (black, dotted) compared with those of the wild-type E. coli network (black). The grey point shows the minimum amount of product formation expected from this strain.

An additional disruption in PFL (pyruvate formate lyase) can improve the theoretical yield of fumarate marginally to 1.89 moles per mole of glucose consumed and the expected growth rate of this strain is 0.07 per hour.

Figure 4:
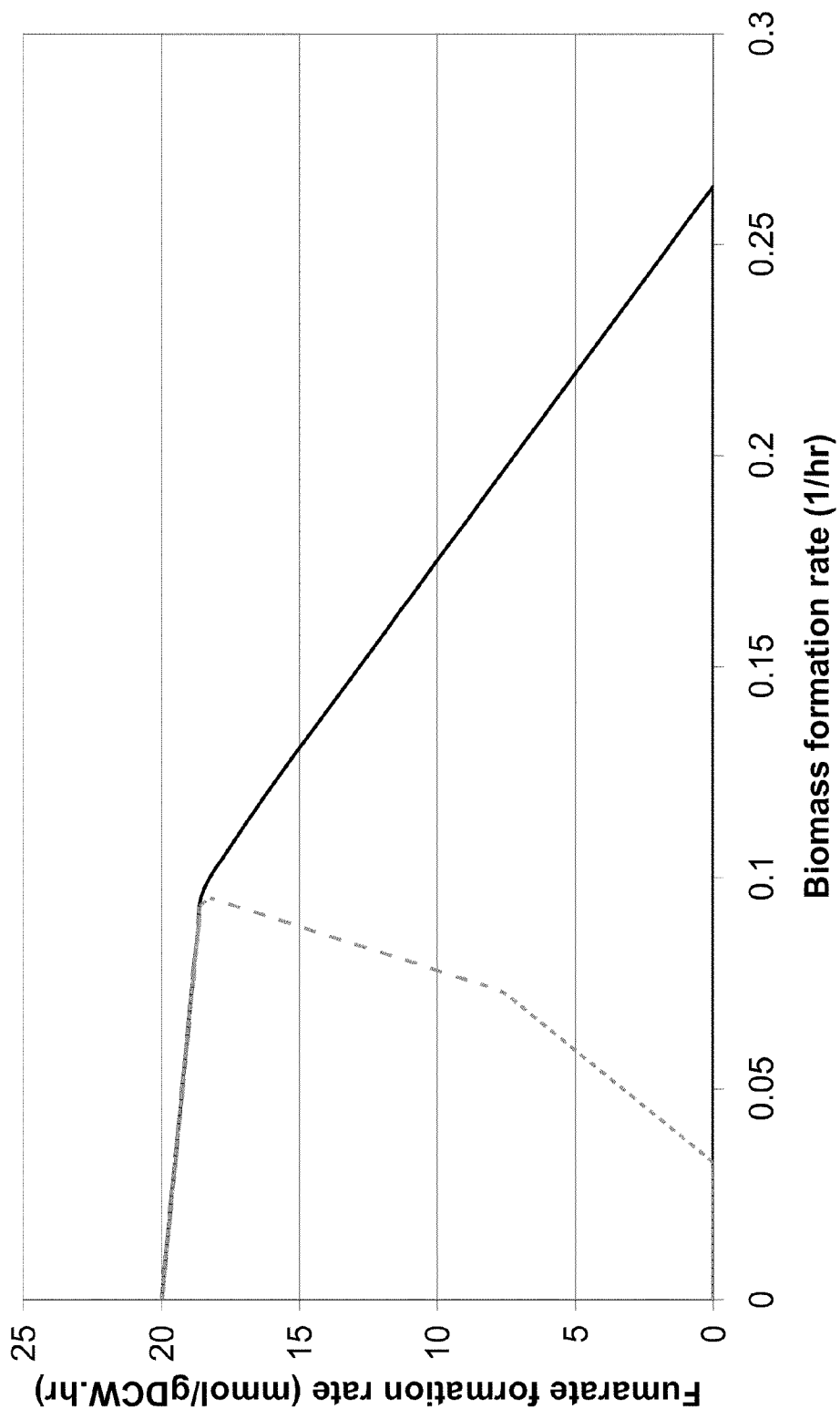
FIG. 4 shows the production curve for still another strain (grey, dashed) compared with the production curve for the wild-type *E. coli* network (black). Note that this strain design is equivalent to design B if an additional deletion in THD2 is introduced.

Another strain, shown in FIG. 4, disrupts the GLCpts mechanism of glucose transport and instead relies on hexokinase activity. This disruption along with disruption of FRD, ADHEr, LDH_D, and ME2 leads to an expected maximum growth rate for the strain at approximately 0.1 per hour. The product yield is expected to be 1.82 moles per mole of glucose consumed. The strain is expected to start producing fumarate once it reaches approximately 36% of its maximum theoretical biomass formation rate. FIG. 4 shows the production curve for this strain (grey, dashed) compared with the production curve for the wild-type E. coli network (black). Note that this strain is equivalent to the strain of FIG. 2 if an additional deletion in THD2 is introduced.

Figure 5:
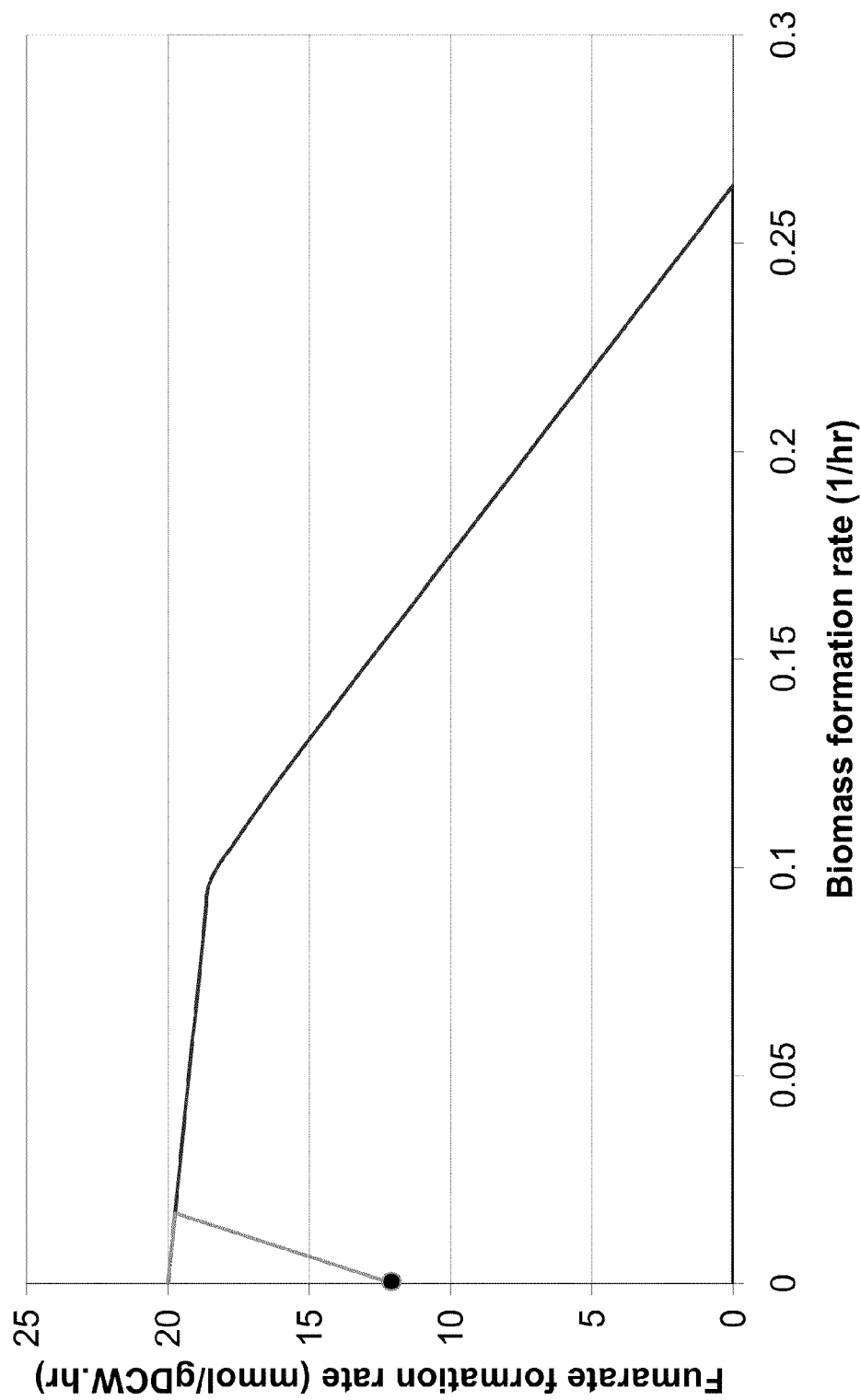
FIG. 5 shows the production curve for yet another strain (grey, dashed) compared with the production curve of the wild type *E. coli* network (black). The black point indicates the minimum amount of product formation expected from this strain.

Another strain, shown in FIG. 5, has deletions in FRD, ADHEr, LDH_D, ME2, THD2 and HEX1. The deletion in HEX1 forces glucose flux through the PTS system, converting an equivalent molar amount of phosphoenolpyruvate (PEP) into pyruvate. To attain a balance of cofactors, the network is forced to convert most of the pyruvate back into PEP through PEP synthase. This is an energy-intensive step and limits the biomass formation in the network. However, the carbon distribution provides PEP to be used by PPCK and subsequent channeling into the reductive TCA cycle. This leads to the very high fumarate yields in the network of up to 1.97 moles per mole of glucose consumed as shown in FIG. 5. These disruptions reduce the feasible solution space of the mutant network significantly and the strain is expected to have a minimum product yield of at least 1.25 moles per mole of glucose consumed as shown by the black point in FIG. 5. Although strain is predicted to grow slowly at a rate of approximately 0.02 per hour, the prospect of achieving near maximum theoretical product yields makes this design particularly useful. The strain is expected to secrete very small quantities of acetate and formate. FIG. 5 shows the production curve for the strain (grey, dashed) compared with the production curve of the wild type *E. coli* network (black). The black point indicates the minimum amount of product formation expected from this strain.

Figure 6:
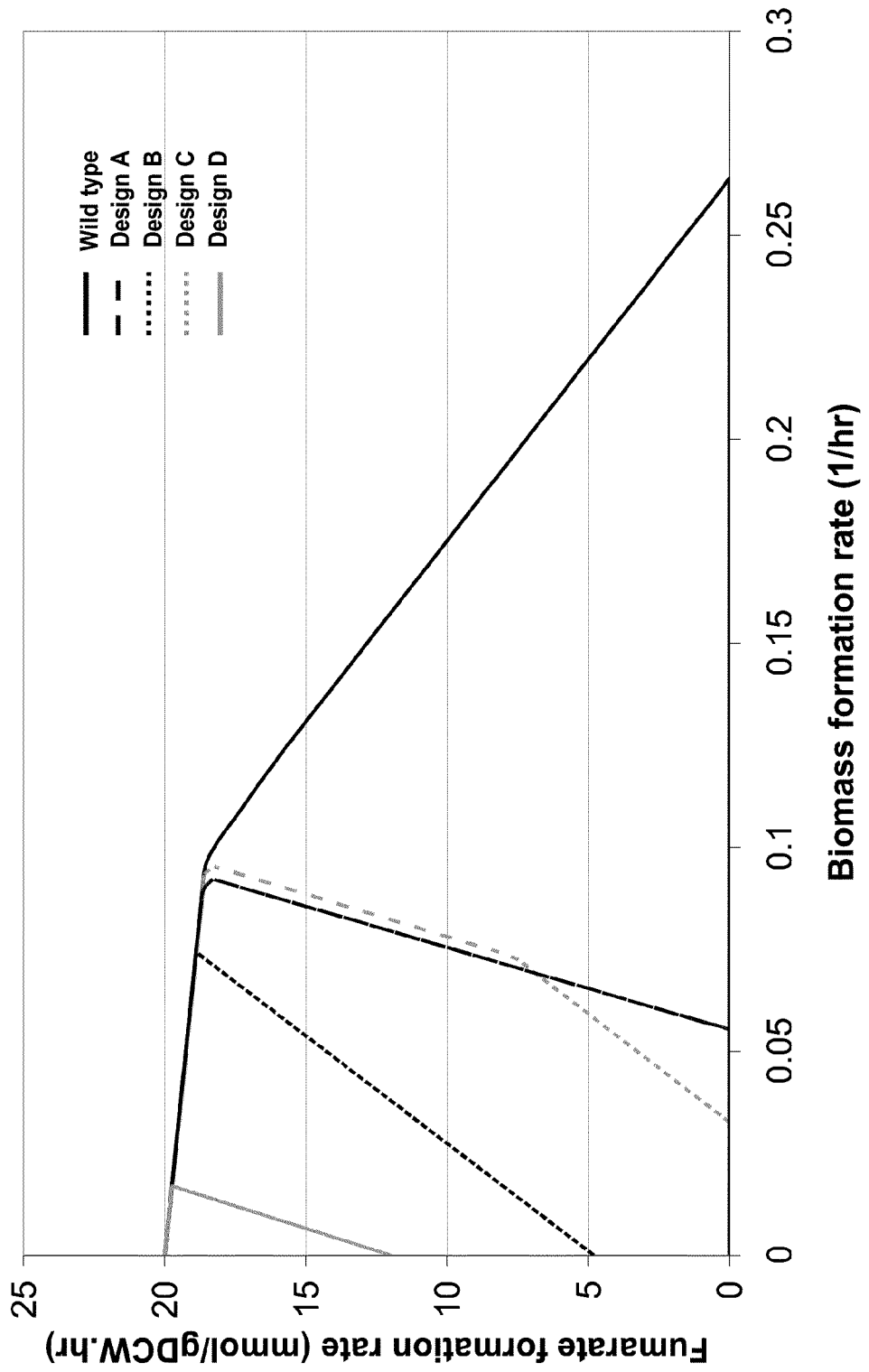
FIG. 6 shows the production curves for the strains in FIG. 2 (black, dashed), FIG. 3 (black, dotted), FIG. 4 (grey, dashed) and FIG. 5 (grey) compared with each other and with the production characteristics of the wild-type *E. coli* network (black). Note the reduction in feasible solution space as additional deletions are imposed on the network.

To provide a comparison of the fumarate production characteristics of the four strains discussed above, the production curves are presented on the same plot and compared with those of the wild-type *E. coli* network as shown in FIG. 6. Other strains for fumarate production in *E. Coli* are listed in Table 1. FIG. 6 shows the production curves for the strains in 1) black, dashed, 2) black, dotted, 3) grey, dashed and 4) grey compared with each other and with the production characteristics of the wild-type *E. coli* network in black. Note the reduction in feasible solution space as additional deletions are imposed on the network.

The anaerobic designs for the formation of malate are described below and utilize disruptions that have already been described for fumarate production. The strain designs for malate production have additional knockouts that preclude fumarate formation in the network.

Figure 7:
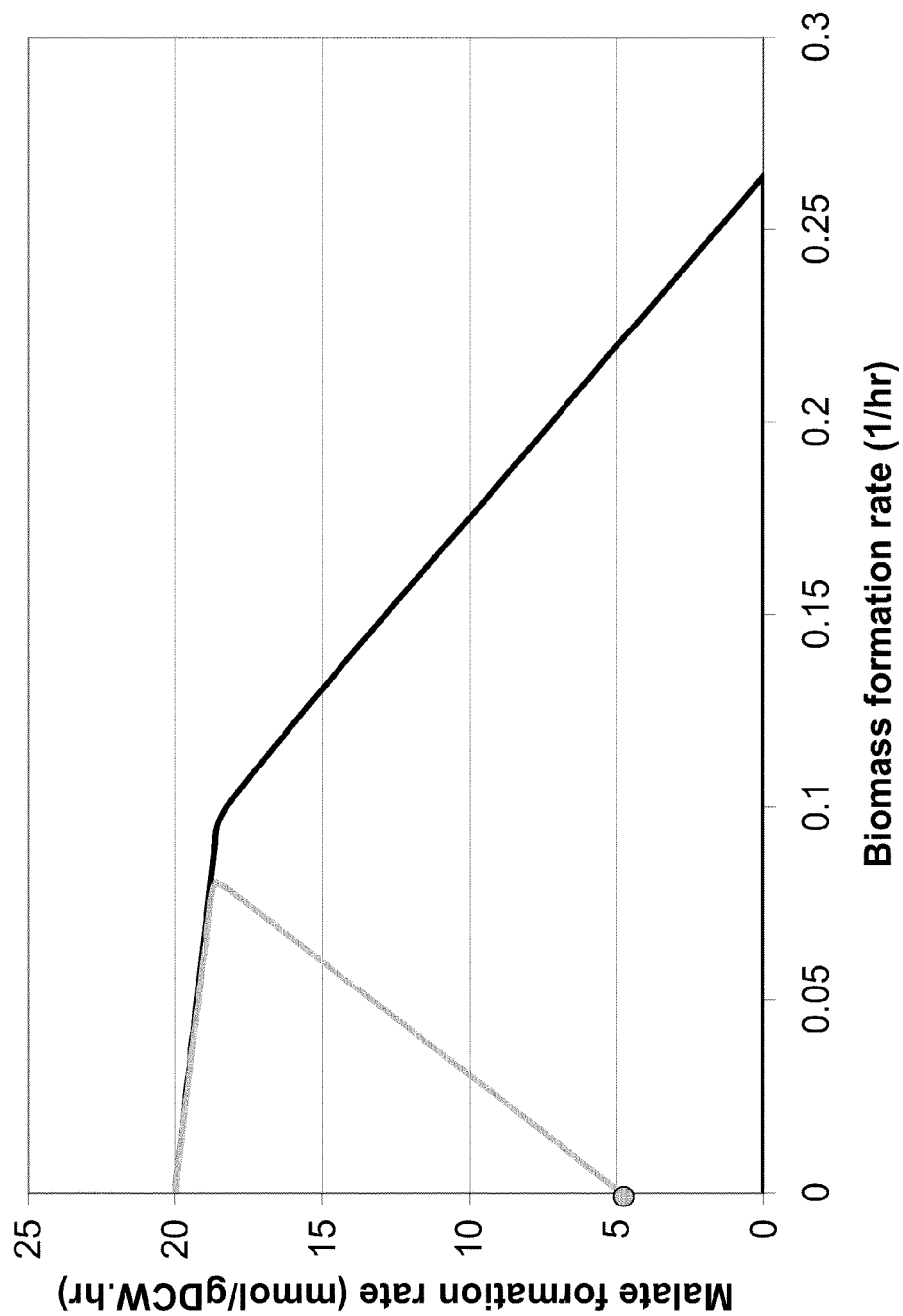
FIG. 7 shows the malate production curve for one strain (light grey) compared with the production curve for the wild type *E. coli* network (black).
Figure 8:
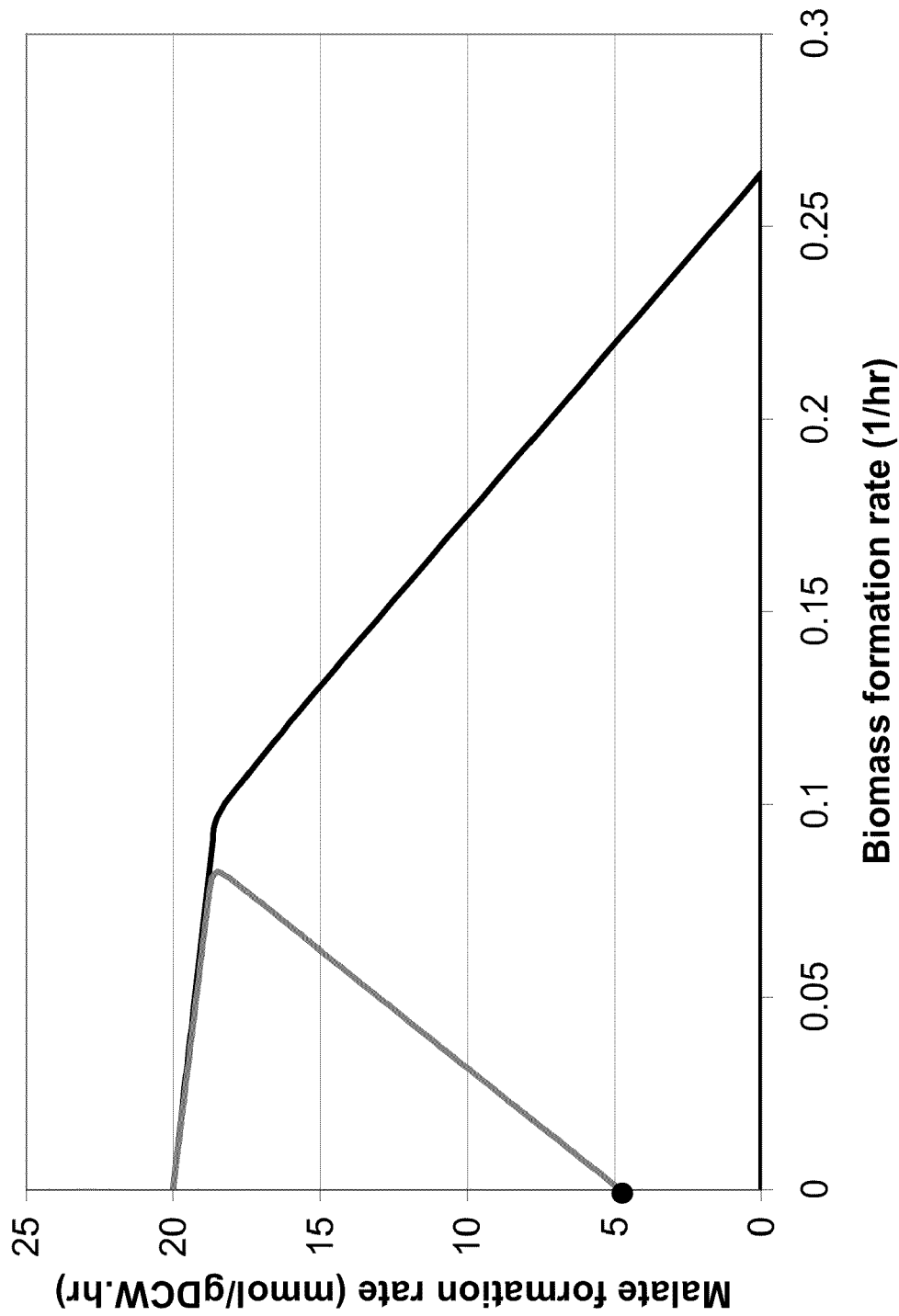
FIG. 8 shows the production curve for a modified malate-producing strain design based on the strain of FIG. 7, replacing deletion of FRD with deletion of ASPT, (grey) compared with that of the wild-type *E. coli* network (black).

One strain, shown in FIG. 7, allows for increased formation of malate by building upon the disruptions in the strain of FIG. 2. As described above, deletions in ADHEr, LDH_D, FRD, ME2 and THD2 allow for the enhanced formation of either fumarate or malate. An additional deletion in fumarase (FUM) prevents or reduces the conversion of malate into fumarate, leading to increase malate production of 1.86 moles per mole of glucose consumed as shown in FIG. 7. Small modifications in this strain lead to another high-yielding strain shown in FIG. 8. Thus, instead of the FRD deletion, this strain has a disruption in aspartase (ASPT). The deletion of ASPT reinforces the effect of the fumarase deletion by preventing the network from converting oxaloacetate into aspartate which can subsequently be transformed into fumarate via aspartase. Without the deletion in ASPT, the strain can produce approximately 1.55 moles of succinate per mole of glucose consumed. This modified strain design with deletions in ADHEr, THD2, LDH_D, ME2, FUM, and ASPT leads to a growth-coupled theoretical yield of 1.85 moles of malate per mole of glucose consumed, shown in FIG. 8, with an expected growth rate of 0.08 per hour. Each of these strains is expected to have a non-zero minimum rate of malate production. Note the grey and black points in FIGS. 7 and 8 respectively. Several other strains with increased malate yields in *E. Coli* have been identified and are listed in Table 2.

Based on these strains, the invention also provides a non-naturally occurring microorganism having a set of metabolic modifications coupling fumarate or malate production to growth of the microorganism, the set of metabolic modifications includes disruption of one or more genes selected from the set of genes encoding proteins that include: (a) a fumarate reductase (FRD), an alcohol dehydrogenase (ADHEr), and a lactate dehydrogenase (LDH_D).

Analysis of the strains for fumarate production allows identification of a minimum set of deletions that increase fumarate production in the network. Note that PPCK was assumed to be reversible in the network. Briefly, deletions in fumarate reductase (FRD), alcohol dehydrogenase (ADHEr), and lactate dehydrogenase (LDH_D) prevent the formation of competing byproducts, namely, succinate, ethanol and lactate. The minimum enzyme disruption set based on the aforementioned strains includes disruption of fumarate reductase, alcohol dehydrogenase and lactate dehydrogenase. This corresponds to the following minimal exemplary gene disruption set:

frd (b4151 or b4152 or b4153 or b4154), adhE (b1421), and ldhA (b1380)

Additional disruptions have been identified by the Opt-Knock framework for the increased formation of fumarate. Note that these disruptions may have been predicted because no regulatory information is accounted for in the metabolic network. Nevertheless, it is predicted that supplementary disruptions or deletions in one or more of the functionalities, namely glutamate dehydrogenase (GLUDy), malic enzyme (ME2), and transhydrogenase (THD2) are useful for increased formation of the diacids of interest. These deletions can be introduced sequentially into *E. coli* K12. If these deletions/disruptions have to be introduced, the minimal set of activities that need to be deleted can be expanded to include the following:

Fumarate reductase, alcohol dehydrogenase, lactate dehydrogenase, and glutamate dehydrogenase, or Fumarate reductase, alcohol dehydrogenase, lactate dehydrogenase, and malic enzyme, or Fumarate reductase, alcohol dehydrogenase, lactate dehydrogenase, malic enzyme, and transhydrogenase Correspondingly, the minimal gene set can be expanded to yield:

frd (b4151 or b4152 or b4153 or b4154), adhE (b1421), ldhA (b1380), and gdhA (b1761), or frd (b4151 or b4152 or b4153 or b4154), adhE (b1421), ldhA (b1380), and maeB (b2463), or frd (b4151 or b4152 or b4153 or b4154), adhE (b1421), ldhA (b1380), pntAB (b1602, b1603), and maeB (b2463)

Further improvement in yields can be attained by disrupting one or more of the following functionalities: phosphotransacetylase (PTAr), the PTS mechanism of glucose transport (GLCpts), hexokinase (HEX 1) or pyruvate formate lyase (PFL). Note that all the isozymes capable of carrying out a given activity should be disrupted or deleted given a possibility of the isozymes becoming active due to adaptive evolution. The enzyme disruption set after introducing these auxiliary deletions are listed below:

Fumarate reductase, alcohol dehydrogenase, lactate dehydrogenase, transhydrogenase, malic enzyme, and hexokinase, or Fumarate reductase, alcohol dehydrogenase, lactate dehydrogenase, malic enzyme, and the PTS transport mechanism of glucose, or Fumarate reductase, alcohol dehydrogenase, lactate dehydrogenase, transhydrogenase, malic enzyme, and pyruvate formate lyase The corresponding gene deletion sets are:

frd (b4151 or b4152 or b4153 or b4154), adhE (b1421), ldhA (b1380), pntAB (b1602, b1603), maeB (b2463) and glk (b2388)

frd (b4151 or b4152 or b4153 or b4154), adhE (b1421), ldhA (b1380), maeB (b2463), and pts (b1101 or b2415 or b2416 or b2417)

frd (b4151 or b4152 or b4153 or b4154), adhE (b1421), ldMA (b1380), pntAB (b1602, b1603), maeB (b2463), and pflAB (b0902, b0903)

For homomalate production, a disruption in fumarase (FUM) is utilized in addition to disruptions in alcohol dehydrogenase (ADHEr), lactate dehydrogenase (LDH_D) and fumarate reductase (FRD). Thus, the minimal enzyme deletion set is:

Fumarate reductase, alcohol dehydrogenase, lactate dehydrogenase, and fumarase

The disruption of these activities corresponds to the deletion of the following genes:

frd (b4151 or b4152 or b4153 or b4154), adhE (b1421), ldha (b1380), and fumABC (b1611, b1612, b4122)

An alternative set of enzyme deletions can also enable homomalate production is as follows:

Alcohol dehydrogenase, lactate dehydrogenase, fumarase and L-aspartase

This corresponds to a minimum gene deletion set of:
adhE (b1421), ldhA (b1380), and fumABC (b1611, b1612, b4122) and aspA (b4139)

Thus, in some embodiments, the present invention provides a non-naturally occurring microbial organism that includes one or more gene disruptions occurring in genes encoding enzymes that increase homomalate production when the gene disruption reduces an activity of the enzyme, whereby the one or more gene disruptions confers increased production of homomalate onto said non-naturally occurring microorganism.

However, as explained earlier for fumarate production, disruptions in one or more out of the following reactions, glutamate dehydrogenase (GLUDy), transhydrogenase (THD2) and malic enzyme (ME2), can be useful, yielding the following minimal enzyme sets for deletion:

Fumarate reductase, alcohol dehydrogenase, lactate dehydrogenase, fumarase, and glutamate dehydrogenase, or Fumarate reductase, alcohol dehydrogenase, lactate dehydrogenase, fumarase, and malic enzyme, or Fumarate reductase, alcohol dehydrogenase, lactate dehydrogenase, fumarase, transhydrogenase and malic enzyme Accordingly, the gene deletion sets expand and are listed below:

frd (b4151 or b4152 or b4153 or b4154), adhE (b1421), ldha (b1380), fumABC (b1611, b1612, b4122), and gdhA (b1761), or frd (b4151 or b4152 or b4153 or b4154), adhE (b1421), ldha (b1380), fumABC (b1611, b1612, b4122), and maeB (b2463), or frd (b4151 or b4152 or b4153 or b4154), adhE (b1421), ldhA (b1380), fumABC (b1611, b1612, b4122), pntAB (b1602, b1603), and maeB (b2463).

Each of these strains may be supplemented with additional deletions if it is determined that the strain does not sufficiently increase the formation of the product. Alternatively, some other enzymes not known to possess significant activity may become active due to adaptive evolution or random mutagenesis and they will also have to be disrupted as well. For example, succinate dehydrogenase which oxidizes succinate to fumarate and is known to be active only under aerobic conditions may assume significant activity even under anaerobic conditions and may have to be disrupted. However, the list of gene disruption sets provided here serves as a starting point for construction of high-yielding malate and fumarate producing strains.

For fumarate and malate production metabolic modifications in eukaryotic organisms sets of metabolic modifications are listed in Table 5. For acrylate production metabolic modifications in eukaryotic organisms can be selected from the set of metabolic modifications listed in Table 6.

The non-naturally occurring eukaryotic organism can have one or more gene disruptions included in a metabolic modification listed in Tables 5 or 6. The one or more gene disruptions can be a deletion. The non-naturally occurring eukaryotic organism of the invention can be selected from a group of eukaryotic organism having a metabolic modification listed in Tables 5 or 6. Non-naturally occurring eukaryotic organisms of the invention include yeast, fungus, or any of a variety of other microorganisms applicable to fermentation processes. Exemplary eukaryotic species include those selected from *Saccharomyces cerevisiae*, *Schizosaccharomyces pombe*, *Kluyveromyces lactis*, *Kluyveromyces marxianus*, *Aspergillus terreus*, *Aspergillus niger*, *Rhizopus arrhizus*, *Rhizopus oryzae*, and *Pichia pastoris*.

The eukaryotic organisms having increased fumarate, malate, or acrylate production are exemplified herein with reference to an *S. cerevisiae* genetic background. However, with the complete genome sequence available for now more than 550 species (with more than half of these available on public databases such as the NCBI), including 395 microorganism genomes and a variety of yeast, fungi, plant, and mammalian genomes, the identification of an alternate species homolog for one or more genes, including for example, orthologs, paralogs and nonorthologous gene displacements, and the interchange of genetic alterations between organisms is routine and well known in the art. Accordingly, the metabolic alterations enabling increased production of the products described herein with reference to a particular organism such as *S. cerevisiae* can be readily applied to other microorganisms, especially other eukaryotic organisms. Given the teachings and guidance provided herein, those skilled in the art will know that a metabolic alteration exemplified in one organism can be applied equally to other organisms.

As described previously, homologues can include orthologs and/or nonorthologous gene displacements. In some instances, such as when a substitute metabolic pathway exists in the species of interest, functional disruption can be accomplished by, for example, deletion of a paralog that catalyzes a similar, yet non-identical metabolic reaction which replaces the referenced reaction. Because there are differences among metabolic networks between different organisms, those skilled in the art will understand that the actual genes disrupted between different organisms may differ. However, given the teachings and guidance provided herein, those skilled in the art also will understand that the methods of the invention can be applied to all microorganisms to identify the cognate metabolic alterations between organisms and to construct an organism in a species of interest that will enhance the coupling of fumarate, malate, or acrylate biosynthesis to growth.

As described previously and further below, exemplary reactions, reaction nomenclature, reactants, products, cofactors and genes encoding enzymes catalyzing a reaction involved in the increased production of fumarate, malate, and acrylate in *S. Cerevisiae* are set forth in Tables 5, 6, 7, and 8.

The invention provides non naturally occurring eukaryotic organisms having growth-coupled production of fumarate, malate, or acrylate. Product production can be optionally obligatorily linked to the exponential growth phase of the microorganism by genetically altering the metabolic pathways of the cell. The genetic alterations can make the formation of the desired product obligatory to growth. Sets of metabolic alterations or transformations that result in elevated levels of fumarate, malate, or acrylate biosynthesis are exemplified in Tables 5 and 6, respectively. Each alteration within a set corresponds to the requisite metabolic reaction that should be functionally disrupted. Functional disruption of all reactions within each set results in the obligatory production of fumarate, malate, or acrylate by the engineered strain during the growth phase. The corresponding reactions to the referenced alterations in Tables 5 and 6, and the gene or genes that potentially encode them in *S. cerevisiae*, are set forth in Table 7.

For example, for each strain exemplified in Table 5, the metabolic alterations that can be generated for increase fumarate or malate production are shown in each row. These alterations include the functional disruption of from one to six or more reactions. In particular, 278 strains are exemplified in Table 5 that have non-naturally occurring metabolic genotypes. Each of these non-naturally occurring alterations result in an enhanced level of fumarate or malate production in the eukaryotic organism compared to a wild-type strain, under appropriate culture conditions. Appropriate conditions include, for example, those exemplified further below in the Example II such as particular carbon sources or reactant availabilities and/or adaptive evolution. Similarly, 495 strains are exemplified in Table 6 that have non-naturally occurring metabolic genotypes. Each of these non-naturally occurring alterations result in an enhanced level of acrylate production during the exponential growth phase of the eukaryotic organism compared to a wild-type strain, under appropriate culture conditions.

Given the teachings and guidance provided herein, those skilled in the art will understand that to disrupt an enzymatic reaction it is necessary to disrupt the catalytic activity of the one or more enzymes involved in the reaction. Disruption can occur by a variety of means including, for example, deletion of an encoding gene or incorporation of a genetic alteration in one or more of the encoding gene sequences as described previously in reference to the disruptions for E. Coli. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is destroyed.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding an enzyme of a targeted metabolic reaction can be practiced in the methods of the invention and incorporated into the non-naturally occurring eukaryotic organisms of the invention in order to achieve the growth-coupled product production.

Herein below are described the designs identified for increasing fumarate, malate, and acrylate production in S. cerevisiae. For prediction of the strains, it was assumed that (i) the glucose uptake rate in the network was 10 mmol/gDCW.hr, (ii) a minimum non-growth associated maintenance requirement of 1 mmol/gDCW.hr was imposed upon the network, and (iii) phosphoenolpyruvate carboxykinase (PPCK) could operate in the carbon-fixing direction towards oxaloacetate. The reversibility of PPCK allows for the fixing of carbon dioxide such that a yield of 2 moles per mole of glucose for each of these products can be attained under microaerobic/anaerobic conditions. More importantly, it allows for production of ATP in the process. The ATP generation accompanying the reverse operability of PPCK supports the energy requirements for biomass formation as well as for product formation and export under anaerobic conditions. Note that the production of fumaric, malic and acrylic acids is otherwise energetically neutral in the S. cerevisiae metabolic network. The native PPCK in S. cerevisiae, encoded by Pck1, plays a key role in gluconeogenesis and operates to consume ATP to form PEP (Haarasilta and Oura, Eur. J. Biochem., 52:1-7 (1975)). Therefore, a heterologous enzyme, for example from Mannheimia succiniciproducens (Lee et al., Appl Environ Microbiol, 72:1939-1948 (2006)), Anaerobiospirillum succiniciproducens (Laivenieks et al., Appl Environ Microbiol, 63:2273-2280 (1997)), or Actinobacillus succinogenes (Kim, P. et al., Appl Environ Microbiol, 70:1238-1241 (2004)) with more favorable kinetics in the desired direction will be introduced into S. cerevisiae. The functioning of the enzyme in the requisite direction may require high concentrations of dissolved carbon dioxide in the fermentation medium. The protein sequences of the PEP carboxykinase enzymes mentioned in the text can be found via the following GenBank accession numbers and are summarized below:

| Gene name | Organism | Accession Number |
|---|---|---|
| pckA | Mannheimia succiniciproducens | YP_089485 (GI: 52426348) |
| pckA | Anaerobiospirillum succiniciproducens | O09460 (GI: 3122621) |
| pck | Actinobacillus succinogenes | ABX39017 (GI: 160415396) |

The designs for fumaric and malic acid production, but not for acrylic acid production, use a small supply of oxygen in the network. This is because diacid production in S. cerevisiae is energetically neutral under anaerobic conditions, even upon assuming the reversibility of PPCK. Assuming that the symport of the fumarate or malate dianion is feasible with a proton at moderately low pH values, one additional proton needs to be pumped out to maintain homeostasis. The ATPase in S. cerevisiae uses one ATP for exporting out each proton which makes fumarate and malate production energetically neutral under anaerobic conditions. A limited supply of oxygen therefore provides for favorable energetics that can enable growth and product export. Note that a more favorable proton translocation stoichiometry of the ATPase can render these designs energetically feasible even in the absence of oxygen. It has been recently shown that introducing point mutations into the ATPase encoded by PMA1 in S. cerevisiae can increase or decrease its proton coupling efficiency and in some cases, bring the number of protons excreted per ATP hydrolyzed closer to two (Guerra, G. et al., Biochim Biophys Acta, 1768:2383-2392 (2007)). Alternatively, a non-native ATPase with an increased coupling efficiency can be introduced, as was demonstrated (Morsomme, P. et al., Embo J, 15:5513-5526 (1996)) where a mutated plant ATPase permitted growth of an ATPase-deficient *S. cerevisiae* strain at a pH of 4.

In some embodiments, microaerobic (substantially anaerobic) designs can be used based on increased formation of the desired product. To examine this, production cones were constructed for each strain by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs were given a low priority.

The fumarate-production strategies identified by the OptKnock framework were ranked on the basis of their (i) theoretical yields, and (ii) growth-coupled fumarate formation characteristics. All the strains with high product yields involve four or more knockouts because fewer knockouts were found to provide markedly lower yields. Strains with high yields include, for example, those with about 70% or more yield. The engineered strains can include further metabolic modifications aimed at limiting the production of the fumarate precursor, malate that is at the same redox state as fumarate. For example, the fumarase enzyme(s) can be manipulated by using techniques such as directed evolution so that the overall kinetics favors the conversion of malate into fumarate. Another option is to use a fumarase enzyme from any of the *Rhizopus* species that are known to produce high concentrations of fumarate without malate formation (e.g. fumR from *R. oryzae*, GenBank accession number: X78576). In another embodiment, one can use the fumarase from *Euglena gracilis* with a $K_m$ value of 0.031 mM for fumaric acid (Shibata et al., *J Bacteriol*, 164:762-768 1985)). Further, if an additional enzyme activity is introduced into *S. cerevisiae* to channel fumarate into a different growth-coupled end product, it will drive the metabolism towards fumarate formation and prevent malate formation. A case in point is the production of acrylic acid. The introduction of an appropriate decarboxylase enzyme can shift the equilibrium between malate and fumarate towards fumarate, thus leading to all carbon being funneled to the desired acrylic acid product. Using all the above options will ensure that the conversion of malate into fumarate is at a higher rate than the export of malate via any of the malate transporters.

For the strains that follow, the enzyme names, their abbreviations, and the corresponding reaction stoichiometries are listed in Table 7. The genes that can be mutated in order to prevent the activities of the enzymes identified for disruption are also shown in Table 7. Finally, metabolites names corresponding to the abbreviations in the reaction equations are listed in Table 8.

Figure 9:
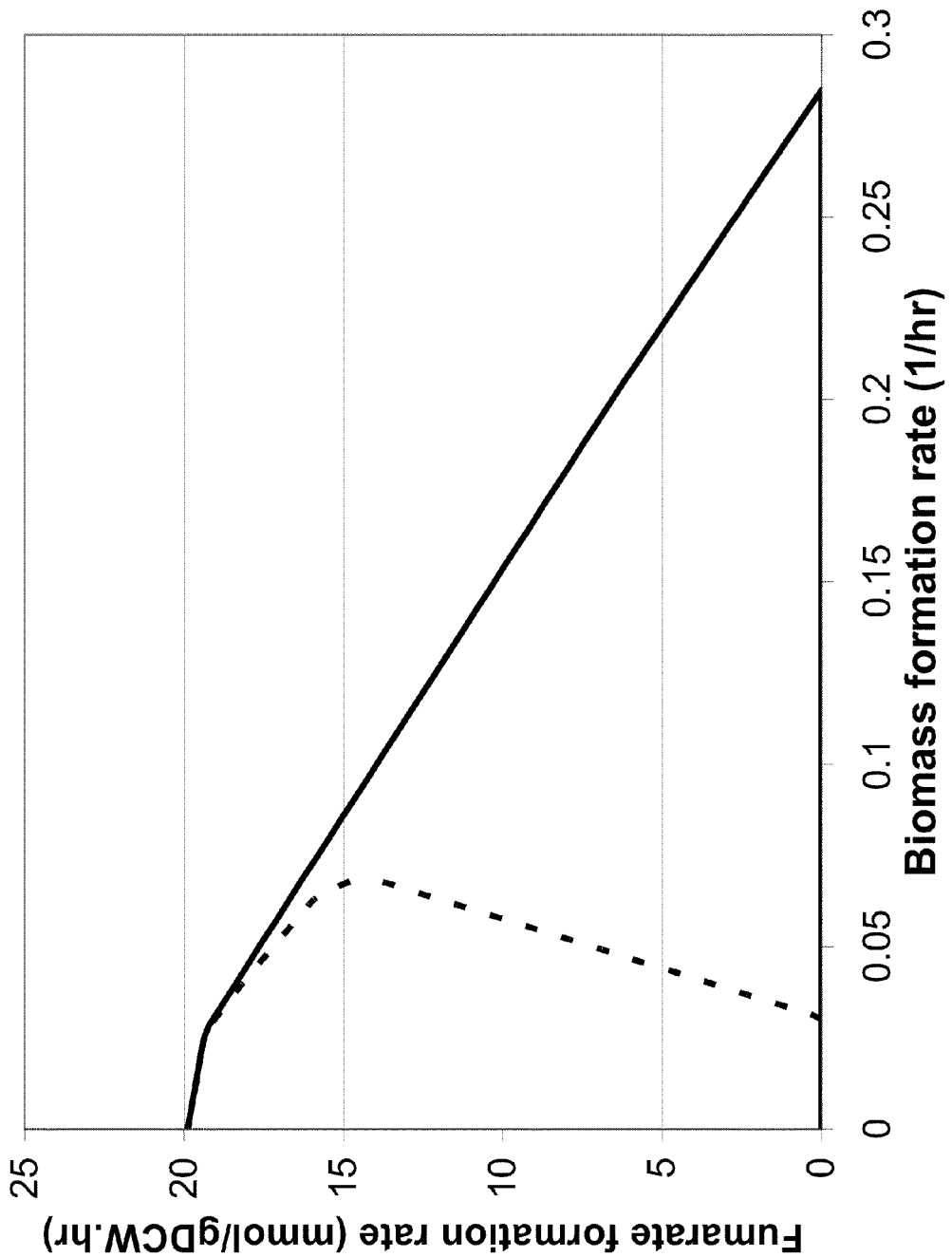
FIG. 9 shows increased fumarate production characteristics of one strain (black, dotted) compared with those of the wild-type *S. cerevisiae* network (black). At the maximum rate of growth, the wild-type network is not expected to form any fumarate.

One strain for fumarate production, shown in FIG. 9, involves disruptions in glycerol-3-phosphate dehydrogenase (G3PD), pyruvate decarboxylase (PYRDC), mitochondrial fumarase (FUMm), and soluble fumarate reductase (FRDcm). The disruptions in G3PD and PYRDC prevent glycerol secretion and reduce ethanol formation respectively. The disruption in FUMm prevents the carbon flux from being routed into the reductive mitochondrial TCA cycle. The network instead employs the cytosolic TCA cycle reactions to form fumarate. Finally, the disruption in FRDcm prevents the conversion of cytosolic fumarate into succinate. This strain is predicted to have a growth-coupled yield of 1.47 moles of fumarate per mole of glucose consumed and the maximum growth rate is anticipated to be 0.07/hr as shown in FIG. 9. If required, the sorbitol reductase activity (encoded by YHR104W) can be removed from the network. All the proposed disruptions can be implemented sequentially based on the necessity to do so.

Figure 10:
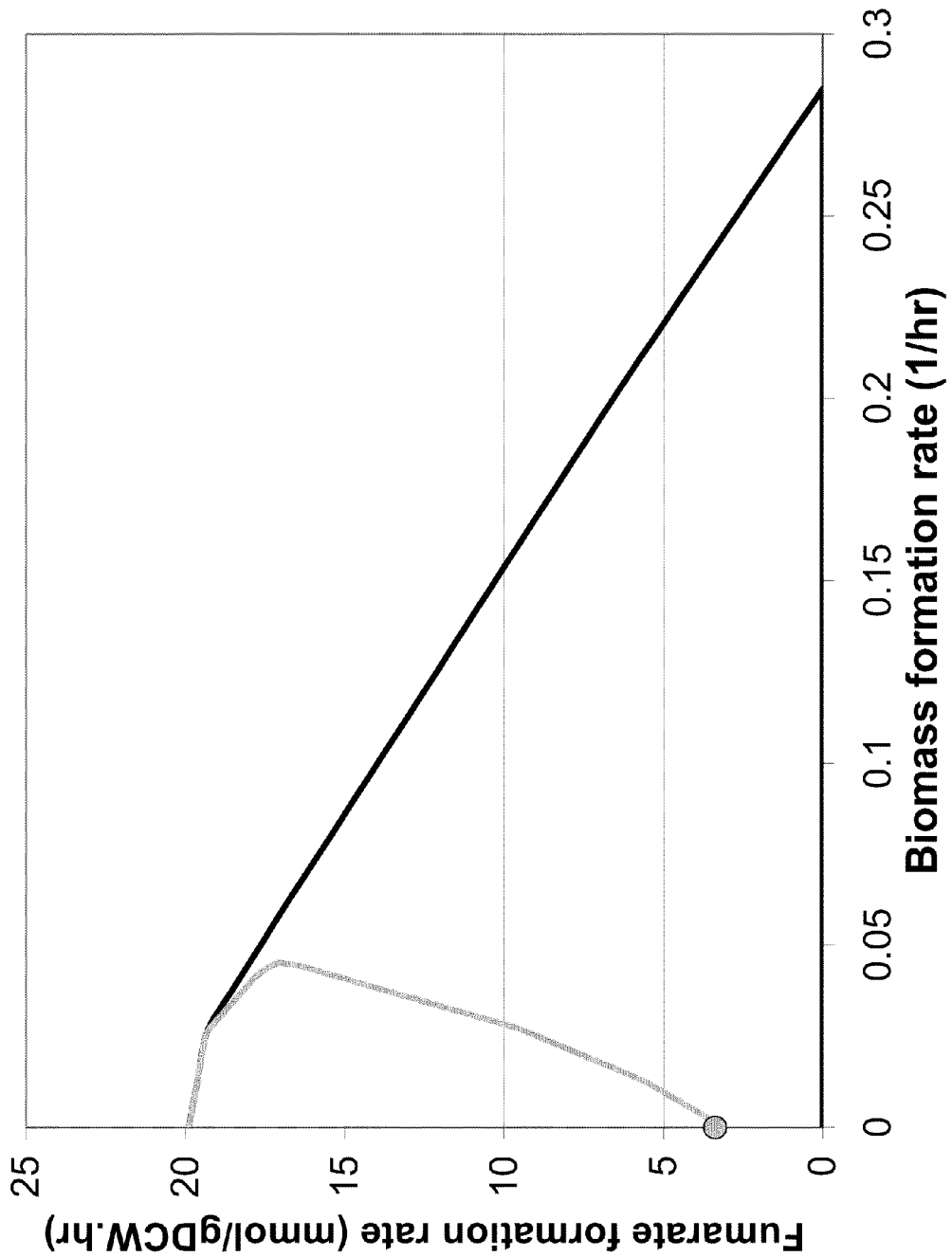
FIG. 10 shows increased fumarate production characteristics of another strain (light gray) compared with those of the wild-type *S. cerevisiae* network (black). The gray point shows the minimum amount of product formation expected from this strain.

The strain shown in FIG. 10 has four disruptions including malic enzyme (ME1m), pyruvate kinase (PYK), fumarase (FUMm), and soluble fumarate reductase (FRDcm), two of which are the same as those in FIG. 9. Under microaerobic conditions, this set of disruptions is expected to yield fumarate up to 1.71 moles/mole of glucose consumed. The disruptions in pyruvate kinase and the malic enzyme are targeted at preventing pyruvate formation in the network such that the maximum amount of PEP can be routed into the reductive TCA cycle using the energy-generating PPCK. As explained earlier, the disruptions in mitochondrial fumarase and in the soluble fumarate reductase prevent the carbon flux from being routed into the reductive mitochondrial TCA cycle and prevent further reduction of fumarate into succinate, respectively. With the imposed disruptions, the strain is expected to produce a minimum of 18% of its maximum theoretical yield see gray point in FIG. 10. The strain is predicted to have a maximum growth rate of 0.045/hr.

Figure 11:
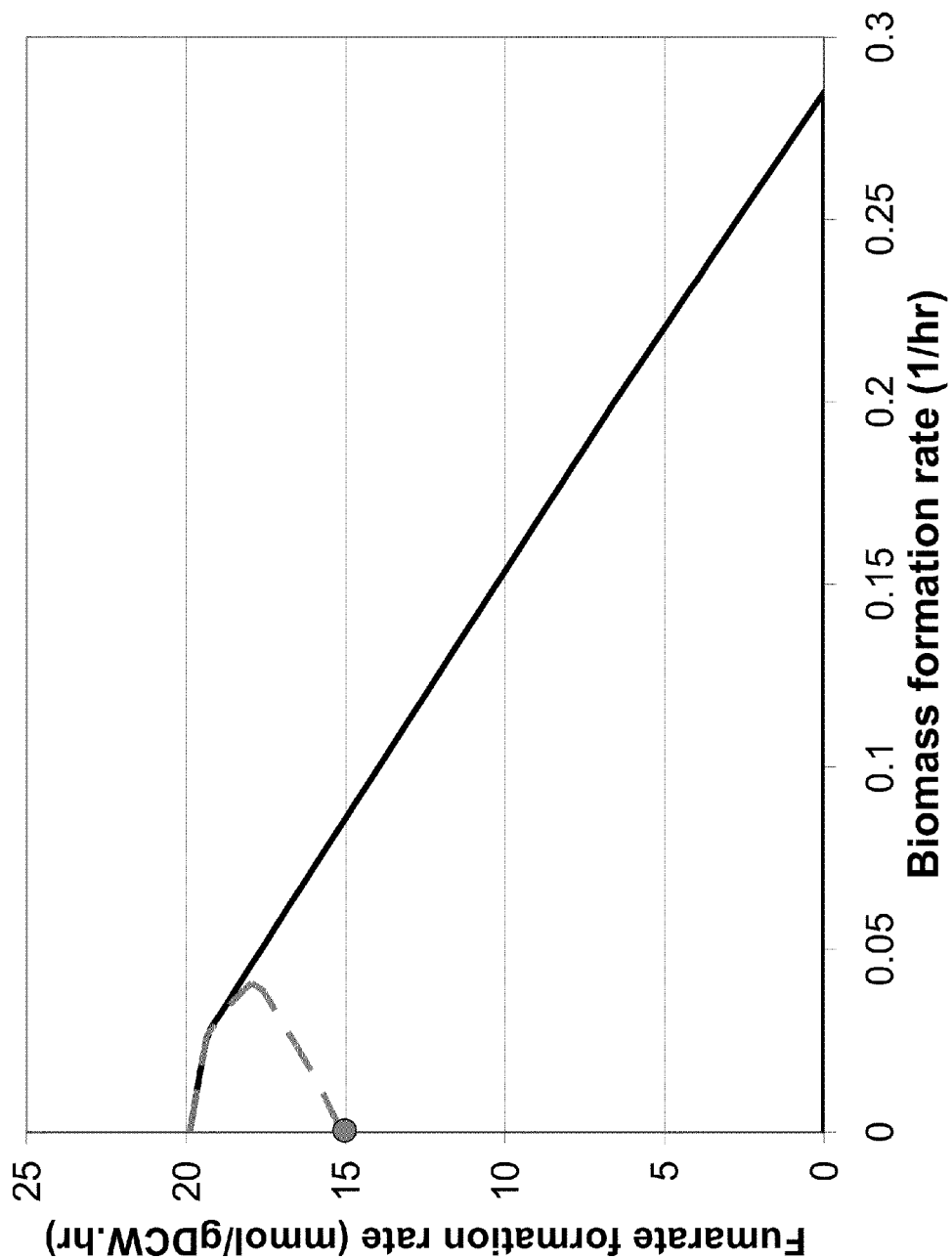
FIG. 11 shows the production curve for yet another strain (dark gray, dashed) compared with the production curve for the wild-type *S. cerevisiae* network (black). The dark gray point shows the minimum amount of fumarate production expected from this design.

The strain in FIG. 11 has an additional disruption in glucose-6-phosphate dehydrogenase as compared to the strain in FIG. 9. The disruption of G6PDH alters the cofactor balance in the network favorably for fumarate production at the cost of biomass production by preventing the NADPH formation required for biomass synthesis. These disruptions lead to an expected maximum growth rate of approximately 0.041 per hour for the strain as shown in FIG. 11. The maximum theoretical fumarate yield is 1.79 moles per mole of glucose consumed. The imposed disruptions reduce the feasible phenotypes significantly such that the strain is anticipated to produce a minimum of 84% of its maximum theoretical yield just to grow as shown by the dark gray point in FIG. 11.

Figure 12:
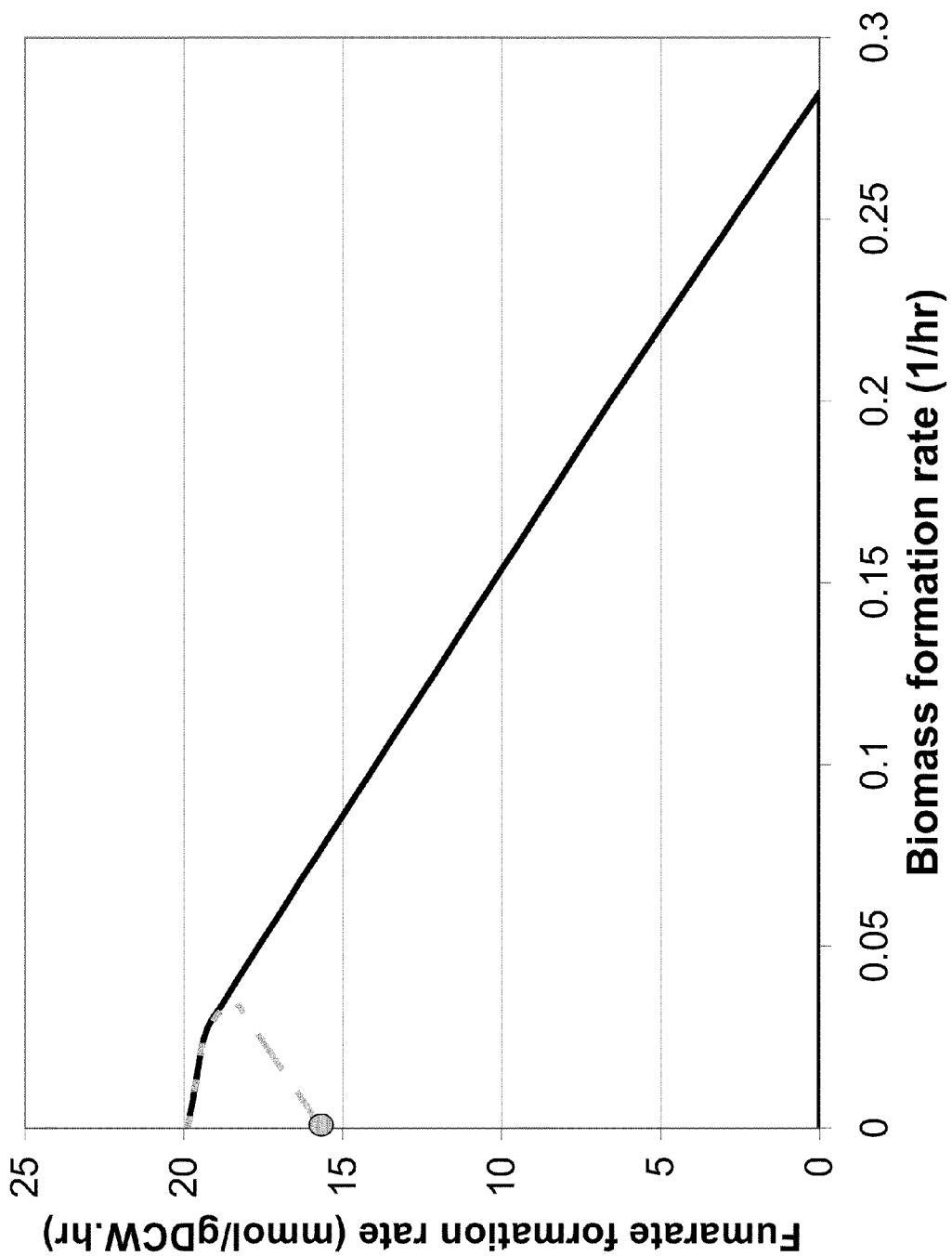
FIG. 12 shows the production curve for still another strain (light gray, dashed) compared with the production curve of the wild type *S. cerevisiae* network (black). The light gray point indicates the minimum amount of product formation expected from this strain.
Figure 13:
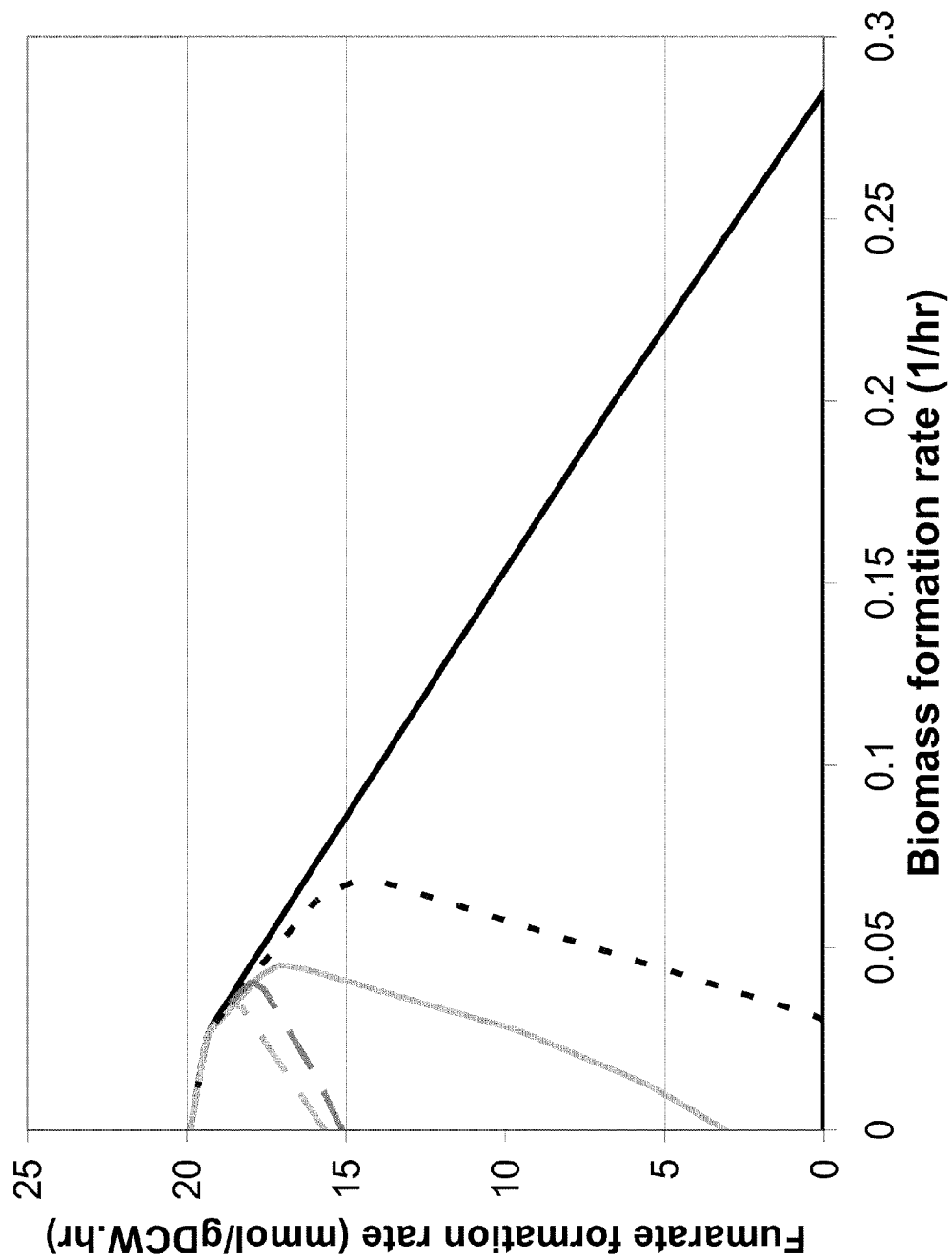
FIG. 13 shows the production curves for various strains in FIG. 9, black, dotted.

Another strain, shown in FIG. 12, has an additional disruption in isocitrate dehydrogenase as compared to the strain in FIG. 11, leading to a marginal increase in the expected maximum theoretical fumarate yield to 1.83 moles per mole of glucose consumed. The rationale is analogous to that explained for the disruption of G6PDH in design. The maximum biomass formation rate is anticipated to decrease from 0.04 per hour to 0.03 per hour.

To provide a comparison of the fumarate production characteristics of the four strains in FIGS. 9-12, FIG. 13 shows their production curves on the same plot and compares them with those of the wild-type *S. cerevisiae* network. All the other designs for fumarate production are listed in Table 5. All the designs proposed for fumarate production described above and in Table 5 can be used for malate production under microaerobic conditions by introducing an additional disruption in the cytosolic fumarase gene that will prevent the conversion of malate into fumarate.

The appropriate reactions for acrylate production from fumarate were added to a genome-scale model of *S. cerevisiae* very similar to the one described in Duarte et al., *Genome Res*, 14:1298-1309 (2004). Acrylic acid is a monocarboxylic acid and it has been assumed that it is exported by proton symport. This mechanism of acrylate export makes its production energetically feasible even under anaerobic conditions when a reversible PPCK in introduced. Several design strategies for producing acrylic acid were identified, a few of which are described in detail here with the remaining designs listed in Table 6.

Figure 14:
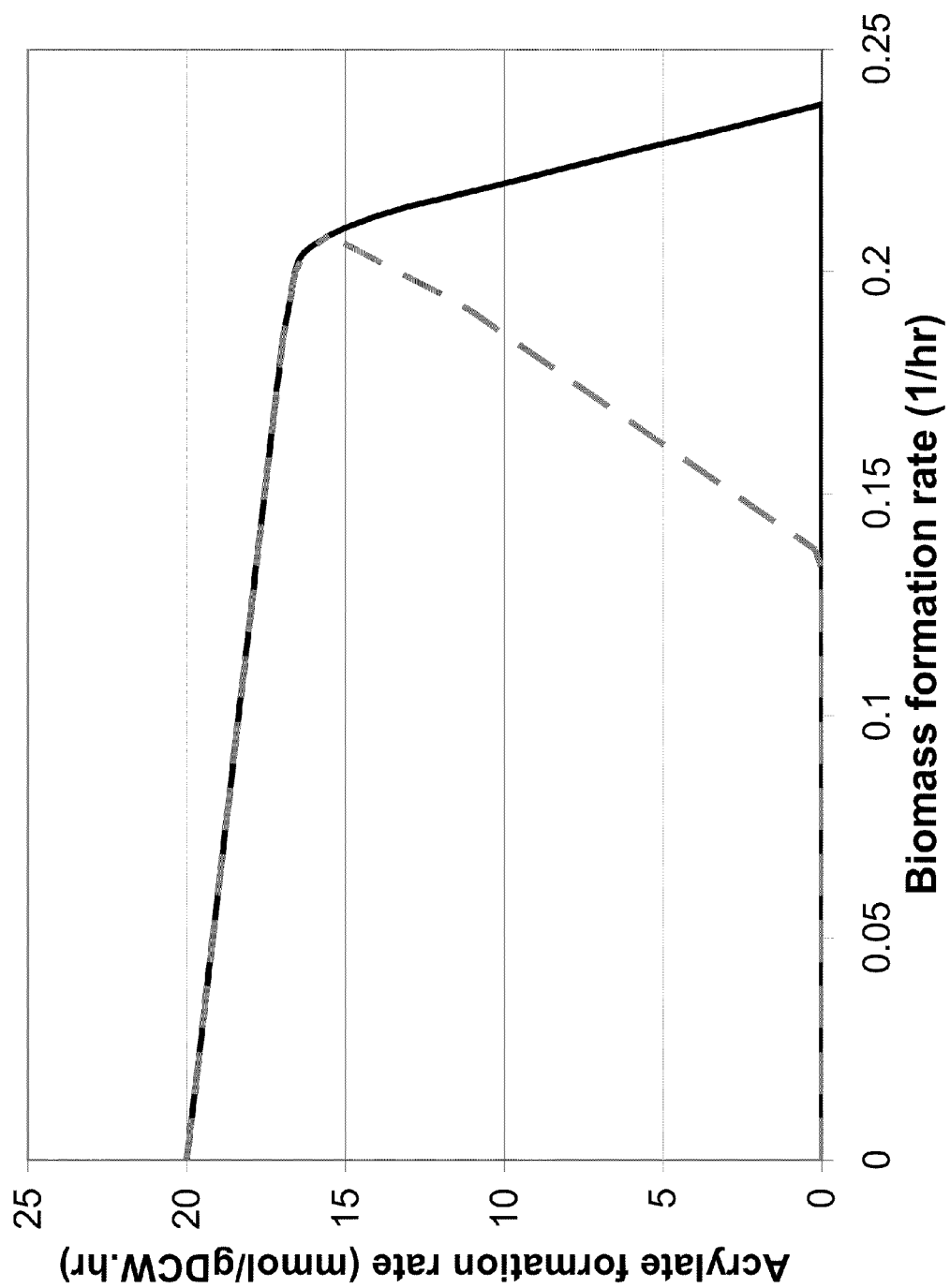
FIG. 14 shows the acrylate production curve for one strain (dark gray, dashed) compared with the production curve for the wild type *S. cerevisiae* network (black).

One strain for acrylate production, shown in FIG. 14, has a disruption in pyruvate decarboxylase (PYRDC). Under anaerobic conditions, a disruption in pyruvate decarboxylase reduces ethanol formation significantly. All the carbon flux is instead redirected towards acrylate production which also allows for the regeneration of the NADH generated in the network, leading to a tight coupling with biomass formation in the network. The maximum product yield is predicted to be 1.55 moles per mole of glucose consumed at the highest growth rate of 0.21 per hour.

Figure 15:
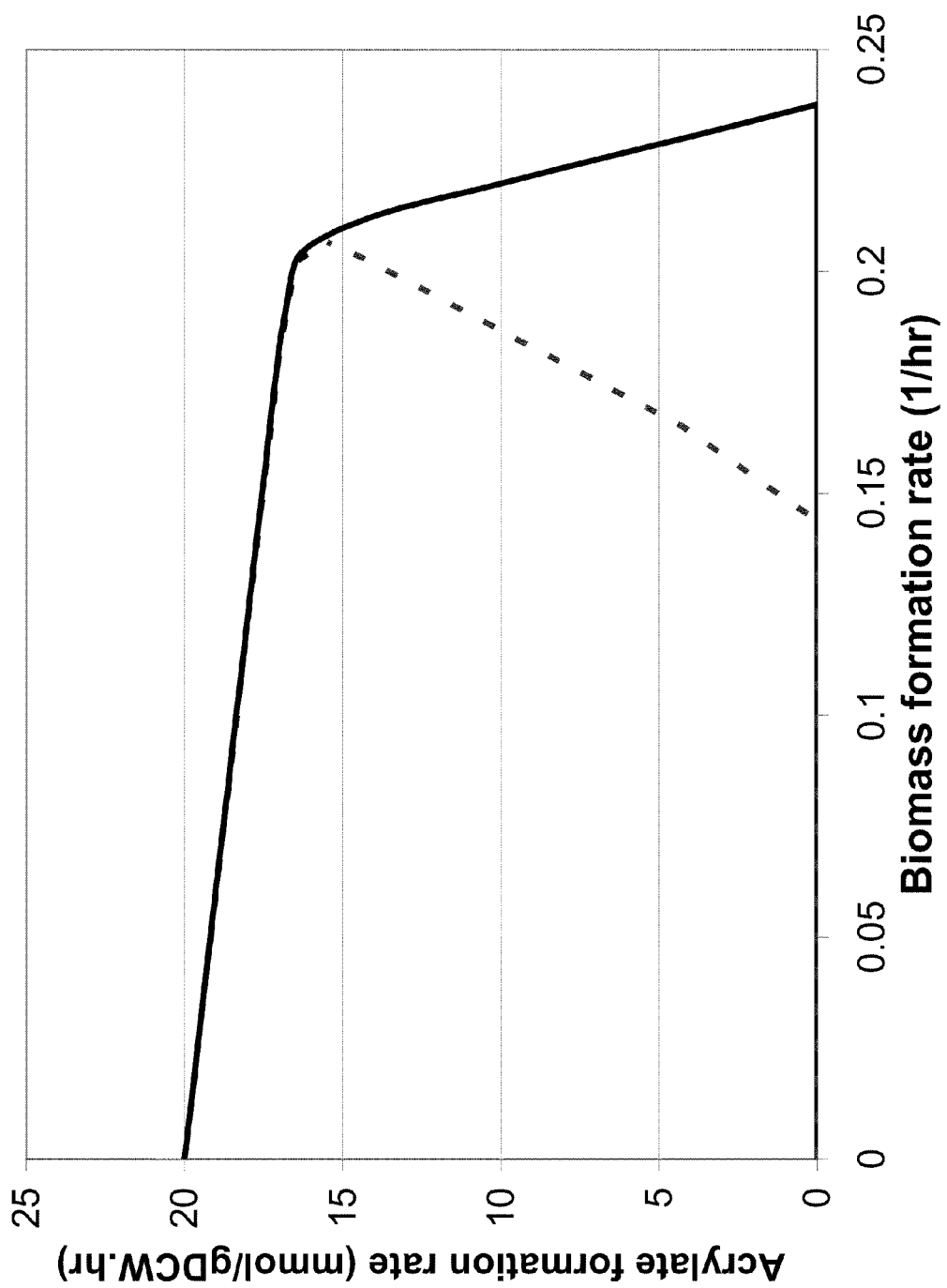
FIG. 15 shows the acrylate production curve for another strain (black, dotted) compared with the production curve for the wild type *S. cerevisiae* network (black).

Another strain, shown in FIG. 15, has disruptions in pyruvate kinase (PYK) and mitochondrial ATP synthase (ATPSm). The disruption in PYK prevents PEP conversion into pyruvate. The disruption of ATP synthase prevents ATP formation in the mitochondrion, removing the incentive for the network to route carbon flux into the mitochondrion. The product of YRJ121W is directly involved in the formation of F1-ATP synthase (beta subunit), while YMR064W is a translational regulator required for expression of the mitochondrial ATPase subunit 9 in yeast (Saltzgaber-Muller et al., *J Biol. Chem.* 258:11465-11470 (1983)). Disruption of either of these two genes does not affect viability of the organism, making them good deletion candidates for lowering or eliminating the ATPSm activity. Other genes can also be targeted for elimination of the ATP synthase activity in *S. cerevisiae* (Tzagoloff and Dieckmann, *Microbiol Rev.* 54:211-225 (1990)). Under anaerobic conditions, the maximum theoretical acrylate yield of the strain is expected to be 1.55 moles per mole of glucose consumed at the maximum predicted growth rate of 0.21 per hour. In microaerobic conditions, this strain provides a slightly higher acrylate yield at 1.69 moles per mole of glucose and the maximum growth rate of the strain is predicted to be 0.23 per hour.

Figure 16:
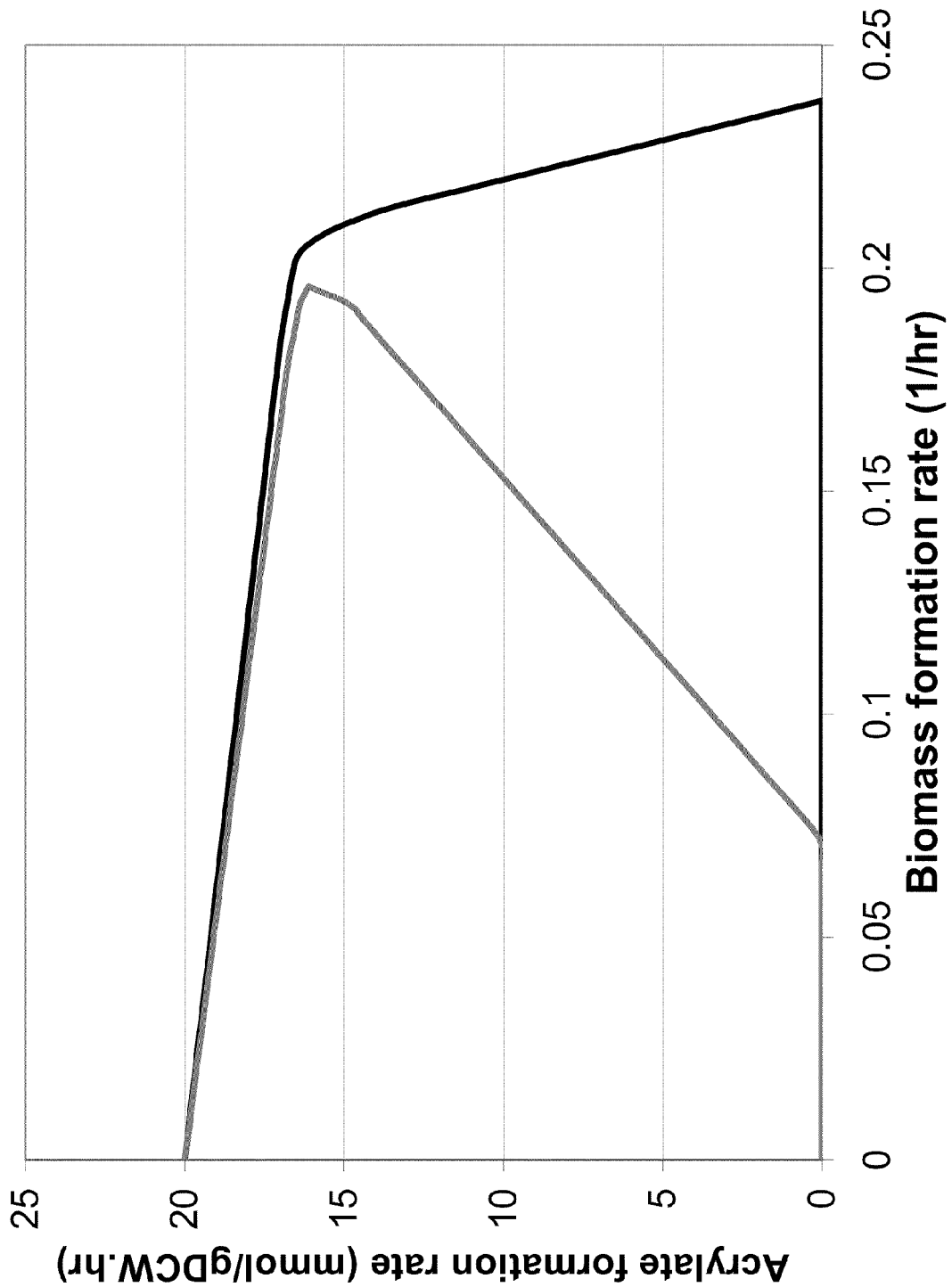
FIG. 16 shows the acrylate production curve for yet another strain (dark gray) compared with the production curve for the wild type *S. cerevisiae* network (black).

Another strain, shown in FIG. 16, has disruptions in malic enzyme (NAD-dependent) (ME1m) and in pyruvate kinase (PYK). These disruptions are geared towards preventing pyruvate formation in the network. Thus, they have a similar effect to the disruption of PYRDC which limits pyruvate formation by preventing its utilization for acetaldehyde and subsequently, ethanol formation. Overall, these two disruptions cause a high flux through PPCK, ultimately leading to a growth-coupled acrylate yield of 1.61 moles per mole of glucose in the network. The strain is calculated to have a maximum growth rate of 0.19 per hour.

Figure 17:
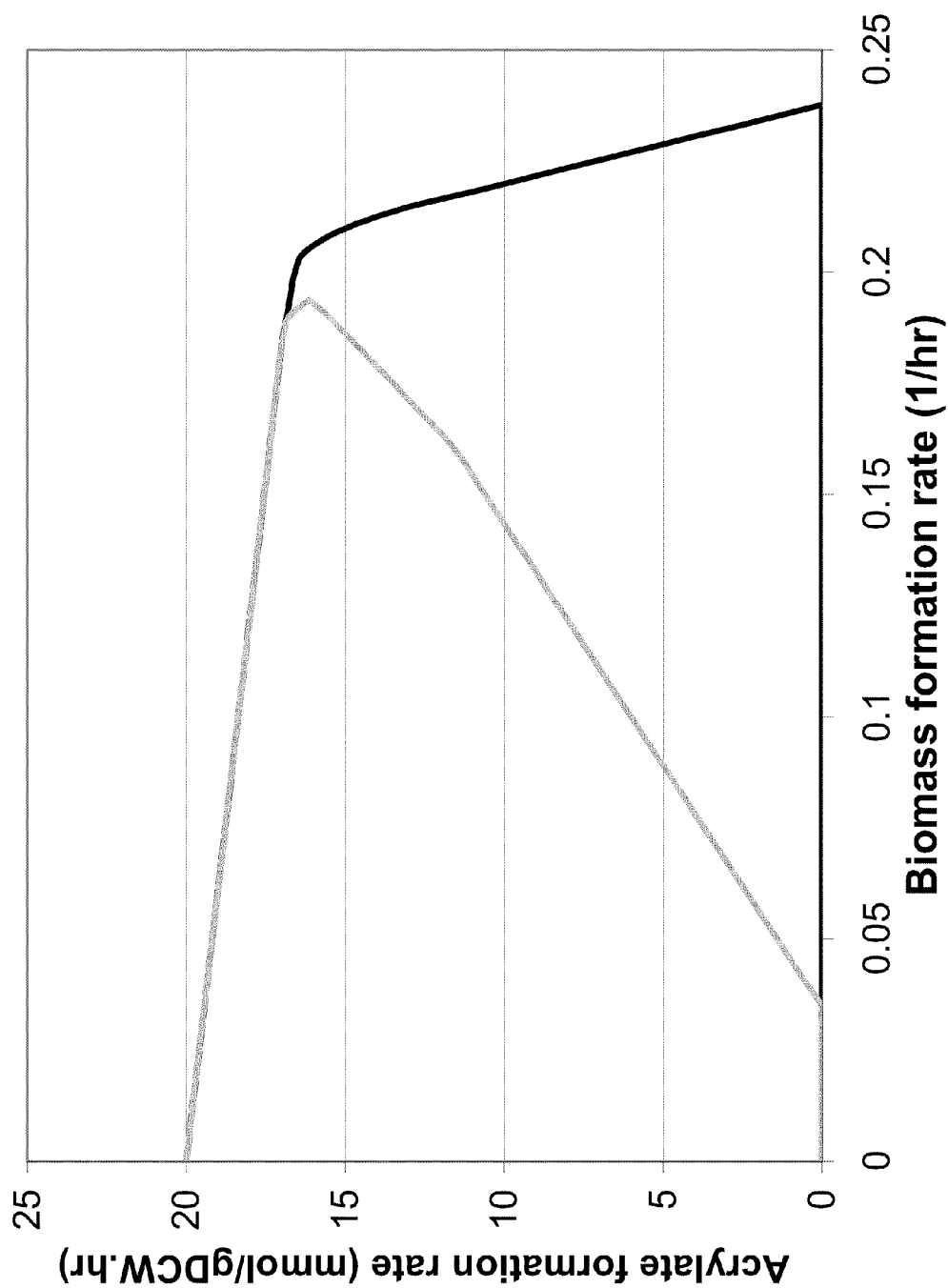
FIG. 17 shows the acrylate production curve for still another strain (light gray) compared with the production curve for the wild type *S. cerevisiae* network (black).

Yet another strain, shown in FIG. 17, has additional disruptions in fumarase (FUMm) and soluble fumarate reductase (FRDcm). These additional disruptions prevent the formation of succinate in the network. The net acrylate yield calculated for this design is 1.62 moles per mole of glucose consumed and the maximum growth rate is predicted to be 0.19 per hour.

Figure 18:
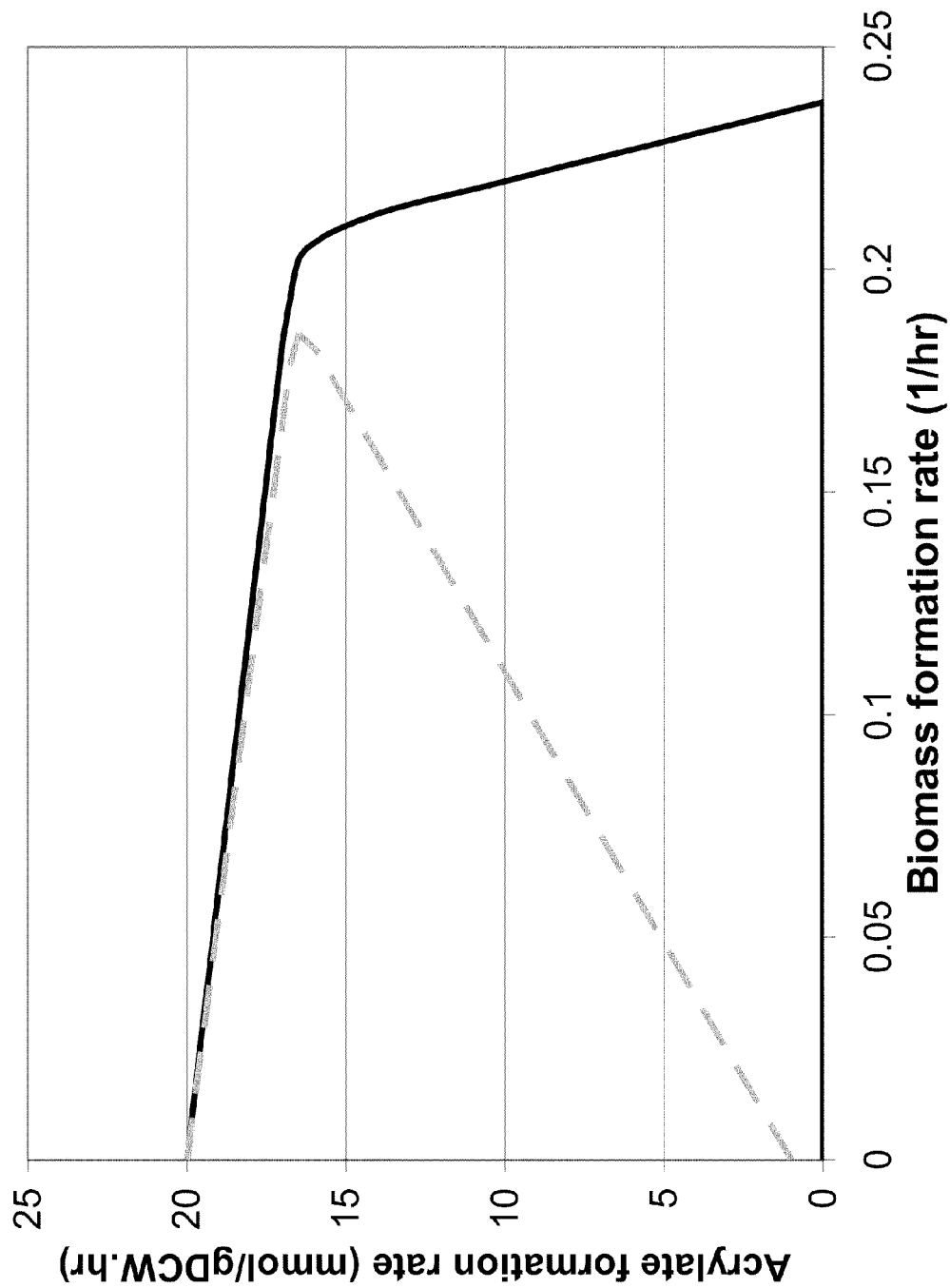
FIG. 18 shows the acrylate production curve for yet still another strain (light gray, dashed) compared with the production curve for the wild type *S. cerevisiae* network (black).

Still another strain, shown in FIG. 18, has additional disruptions in fumarase (FUMm) and soluble fumarate reductase (FRDcm). This strain can be grown in anaerobic conditions leading to acrylate production. The maximum theoretical acrylate yield of the strain is expected to be 1.65 moles per mole of glucose consumed at the maximum predicted growth rate of 0.18 per hour.

Accordingly, the invention also provides a non-naturally occurring eukaryotic organism having a set of metabolic modifications coupling fumarate, malate, or acrylate production to growth of the organism, the set of metabolic modifications includes disruption of one or more genes selected from the set of genes encoding proteins that include: (a) glycerol-3-phosphate dehydrogenase (G3PD), (b) pyruvate decarboxylase (PYRDC), (c) soluble fumarate reductase (FRDcm) and (d) mitochondrial fumarase (FUMm). In other embodiments, the set of metabolic modifications includes disruption of one or more genes selected from the set of genes encoding proteins that include: (a) malic enzyme (ME1m), (b) pyruvate kinase (PYK), (c) soluble fumarate reductase (FRDcm), and (d) mitochondrial fumarase (FUMm).

Based on an analysis of the strains for fumarate production, two alternative minimum set of disruptions can enable growth-coupled fumarate/malate production in the network. Note that PPCK was assumed to be reversible. Briefly, disruptions in glycerol-3-phosphate dehydrogenase (G3PD), pyruvate decarboxylase (PYRDC), soluble fumarate reductase (FRDcm) and mitochondrial fumarase (FUMm) are required for preventing or reducing the formation of competing byproducts, glycerol, ethanol and succinate. An alternative enzyme disruption set entails the removal of malic enzyme (ME1m), pyruvate kinase (PYK), soluble fumarate reductase (FRDcm) and mitochondrial fumarase (FUMm) for coupling fumarate production to growth. These correspond to the following minimal enzyme disruption sets:

Glycerol-3-phosphate dehydrogenase (G3PD), pyruvate decarboxylase (PYRDC), soluble fumarate reductase (FRDcm) and mitochondrial fumarase (FUMm), or Malic enzyme (ME1m), pyruvate kinase (PYK), soluble fumarate reductase (FRDcm) and mitochondrial fumarase (FUMm).

These enzyme disruption sets correspond to the following gene disruption sets: YDL022W (G3PD), YLR044C, YGR087C, YLR134W (isozymes for PYRDC), YPL262W (FUMm), and YEL047C (FRDcm), or YKL029C (ME1m), YOR347c, YAL038W (isozymes for PYK), YPL262W (FUMm), and YEL047C (FRDcm).

Note that all the isozymes capable of carrying out a given activity can be deleted given a possibility of the isozymes becoming active due to adaptive evolution. Further improvement in yields can be attained by deleting one or more of the following functionalities: glucose-6-phosphate dehydrogenase (G6PDH) and cytosolic NADP-dependent isocitrate dehydrogenase (ICDHy). The enzyme disruption sets after introducing these auxiliary disruptions are: Glycerol-3-phosphate dehydrogenase (G3PD), pyruvate decarboxylase (PYRDC), soluble fumarate reductase (FRDcm) and mitochondrial fumarase (FUMm), and glucose-6-phosphate dehydrogenase (G6PDH), or Malic enzyme (ME1m), pyruvate kinase (PYK), soluble fumarate reductase (FRDcm) and mitochondrial fumarase (FUMm), glucose-6-phosphate dehydrogenase (G6PDH) and cytosolic NADP-dependent isocitrate dehydrogenase (ICDHy).

These enzyme sets corresponds to the following gene disruption sets: YDL022W (G3PD), YLR044C, YGR087C, YLR134W (isozymes for PYRDC), YPL262W (FUMm), and YEL047C (FRDcm), YNL241C (G6PDH), or YKL029C (ME1m), YOR347c, YAL038W (isozymes for PYK), YPL262W (FUMm), and YEL047C (FRDcm), YNL241C (G6PDH), and YLR174W (ICDHy).

For malate production, the enzyme disruption sets can be augmented with the disruption of the cytosolic fumarase which is also encoded by YPL262W. Note that YPL262W encodes for both the cytosolic and the mitochondrial fumarases. However, its localization is determined by the N-terminal mitochondrial targeting sequence and its conformation (Sass et al., *J Biol. Chem.* 278:45109-45116 (2003)).

Acrylate production in *S. cerevisiae* is feasible under anaerobic conditions assuming the reversibility of PPCK. Three alternative minimum enzyme disruption sets were identified. These entail (i) disruption in pyruvate decarboxylase, or (ii) disruption in malic enzyme in conjunction with a disruption in pyruvate kinase, or (iii) disruptions in pyruvate kinase and mitochondrial ATP synthase. The corresponding gene disruption sets are: YLR044C, YGR087C, YLR134W (PYRDC), or YKL029C (ME1m), YOR347c, YAL038W (PYK), or YOR347c, YAL038W (encode for PYK isozymes), YJR121W and YMR064W or any other combination of genes that eliminates mitochondrial synthase activity.

Each of these minimal sets can be augmented with supplementary disruptions to further enhance the acrylate yields. The auxiliary disruptions include but are not limited to mitochondrial fumarase, soluble fumarate reductase and glycerol-3-phosphate dehydrogenase. The corresponding gene disruptions are: YPL262W (FUMm), and YEL047C (FRDcm) and YDL022W (G3PD).

The disruption of pyruvate decarboxylase is very similar to the disruption of alcohol dehydrogenase in that both are targeted to prevent ethanol formation in the network. The disruption of alcohol dehydrogenase activity can completely eliminate ethanol formation. However, due to the presence of multiple alcohol dehydrogenases and the substrate promiscuity of these dehydrogenases, it can be difficult to completely remove the alcohol dehydrogenase activity. Therefore, PYRDC is included in the minimum enzyme disruption set.

Each of the strains described above can be supplemented with additional disruptions if it is determined that the predicted strain designs do not sufficiently couple the formation of the product with biomass formation. Alternatively, some other enzymes not known to possess significant activity under the growth conditions can become active due to adaptive evolution or random mutagenesis and can also be knocked out. For example, succinate dehydrogenase that oxidizes succinate to fumarate and is known to be active only under aerobic conditions may assume significant activity even under anaerobic conditions and may have to be knocked out. However, the list of gene disruption sets provided here serves as a starting point for construction of high-yielding growth-coupled malate, fumarate and acrylate production strains.

Therefore, the invention provides a method for producing fumaric acid malic acid, or acrylic acid that includes culturing a non-naturally occurring prokaryotic or eukaryotic microbial organism that includes one or more gene disruptions. The disruptions can occur in genes encoding an enzyme obligatory to coupling fumarate or malate production to growth of the microorganism when the gene disruption reduces an activity of the enzyme, such that the disruptions confer stable growth-coupled production of fumarate or malate onto the non-naturally occurring microorganism.

The non-naturally occurring prokaryotic or eukaryotic organisms of the invention can be employed in the growth-coupled production of fumarate, malate, or acrylate. Essentially any quantity, including commercial quantities, can be synthesized using the growth-coupled fumarate, malate, or acrylate producers of the invention. Because the organisms of the invention obligatorily couple fumarate, malate, or acrylate to continuous growth or near-continuous growth processes are particularly useful for biosynthetic production of fumarate, malate, or acrylate. Such continuous and/or near continuous growth processes are described above and exemplified below in the Example I. Continuous and/or near-continuous microorganism growth processes also are well known in the art. Briefly, continuous and/or near-continuous growth processes involve maintaining the microorganism in an exponential growth or logarithmic phase. Procedures include using apparatuses such as the Evolugator™ evolution machine (Evolugate LLC, Gainesville, Fla.), fermentors and the like. Additionally, shake flask fermentation and grown under microaerobic conditions also can be employed. Given the teachings and guidance provided herein those skilled in the art will understand that the growth-coupled fumarate producing microorganisms can be employed in a variety of different settings under a variety of different conditions using a variety of different processes and/or apparatuses well known in the art.

Generally, the continuous and/or near-continuous production of fumarate, malate, or acrylate will include culturing a non-naturally occurring growth-coupled fumarate, malate, or acrylate producing organism of the invention in sufficient nutrients and medium to sustain and/or nearly sustain growth in an exponential phase. Continuous culture under such conditions can be grown, for example, for a day, 2, 3, 4, 5, 6 or 7 days or more. Additionally, continuous cultures can include time durations of 1 week, 2, 3, 4 or 5 or more weeks and up to several months. It is to be understood that the continuous and/or near-continuous culture conditions also can include all time intervals in between these exemplary periods. In particular embodiments, culturing is conducted in a substantially anaerobic culture medium.

Fumarate, malate, or acrylate can be harvested or isolated at any time point during the continuous and/or near-continuous culture period exemplified above. As exemplified below, the longer the microorganisms are maintained in a continuous and/or near-continuous growth phase, the proportionally greater amount of fumarate and malate can be produced.

One consideration for bioprocessing is whether to use a batch or continuous fermentation scheme. One difference between the two schemes that will influence the amount of product produced is the presence of a preparation, lag, and stationary phase for the batch scheme in addition to the exponential growth phase. In contrast, continuous processes are kept in a state of constant exponential growth and, if properly operated, can run for many months at a time. For growth-associated and mixed-growth-associated product formation, continuous processes provide much higher productivities (i.e., dilution rate times cell mass) due to the elimination of the preparation, lag, and stationary phases. For example, given the following reasonable assumptions:

Monod kinetics (i.e., $\mu=\mu_m \cdot S/(K_s+S)$)
$\mu_m = 1.0$ hr$^{-1}$
final cell concentration/initial cell concentration=20
$t_{prep}+t_{lag}+t_{stat}=5$ hr
feed concentration of limiting nutrient $\gg K_s$ increased productivity from a continuous process has been estimated at 8-fold, Shuler et al, Prentice Hall, Inc.: Upper Saddle River, N.J., 245-247.

Despite advantages in productivity, many more batch processes are in operation than continuous processes for a number of reasons. First, for non-growth associated product formation (e.g., penicillin), the productivity of a batch system may significantly exceed that of a continuous process because the latter would have to operate at very low dilution rates. Next, production strains generally have undergone modifications to their genetic material to improve their biochemical or protein production capabilities. These specialized strains are likely to grow less rapidly than their parental complements whereas continuous processes such as those employing chemostats (fermenters operated in continuous mode) impose large selection pressures for the fastest growing cells. Cells containing recombinant DNA or carrying point mutations leading to the desired overproduction phenotype are susceptible to back-mutation into the original less productive parental strain. It also is possible for strains having single gene disruptions to develop compensatory mutations that will tend to restore the wild-type growth phenotype. The faster growing cells usually out-compete their more productive counterparts for limiting nutrients, drastically reducing productivity. Batch processes, on the other hand, limit the number of generations available by not reusing cells at the end of each cycle, thus decreasing the probability of the production strain reverting back to its wild-type phenotype. Finally, continuous processes are more difficult to operate long-term due to potential engineering obstacles such as equipment failure and foreign organism contamination. The consequences of such failures also are much more considerable for a continuous process than with a batch culture.

For small-volume production of specialty chemicals and/or proteins, the productivity increases of continuous processes rarely outweigh the risks associated with strain stability and reliability. However, for the production of large-volume, growth-associated products such as fumarate, the increases in productivity for a continuous process can result in significant economic gains when compared to a batch process. Although the engineering obstacles associated with continuous bioprocess operation would always be present, the strain stability concerns can be overcome through metabolic engineering strategies that reroute metabolic pathways to reduce or avoid negative selective pressures and favor production of the target product during the exponential growth phase.

The invention provides a method for producing fumaric acid, malic acid, or acrylic acid that includes culturing a non-naturally occurring prokaryotic or eukaryotic organism that includes one or more gene disruptions as described above. The disruptions can occur in genes encoding an enzyme obligatory to coupling fumarate, malate, or acrylate production to growth of the microorganism when the gene disruption reduces an activity of the enzyme, such that the disruptions confer increased production of fumarate, malate, or acrylate onto the non-naturally prokaryotic or eukaryotic organism. The gene disruptions can also be non-growth coupled in other embodiments.

In some embodiments, the gene disruption can include a complete gene deletion. In some embodiments other means to disrupt a gene include, for example, frameshifting by omission or addition of oligonucleotides or by mutations that render the gene inoperable. One skilled in the art will recognize the advantages of gene deletions, however, because of the stability it may confer to the non-naturally occurring organism from reverting to its wild-type. In particular, the gene disruptions are selected from the gene set that includes genes detailed herein above.

In order to confirm the computational predictions, the strains can be constructed, evolved, and tested. Gene deletions are introduced into wild-type, haploid S. cerevisiae, for example, by homologous recombination of the gene interrupted by the KanMX cassette, flanked by loxP sites enabling removal and recycling of the resistance marker (Wach et al., *PCR-based gene targeting in Saccharomyces cerevisiae*, in *Yeast Gene Analysis*, M. F. Tuite, Editor. 1998, Academic Press: San Diego.). Starting with a loxP-kanMX-loxP sequence on a plasmid, an artificial construct with this sequence flanked by fragments of the gene of interest can be created by PCR using primers containing both 45-50 bp target sequence followed by a region homologous to the above cassette. This linear DNA is transformed into wild-type S. cerevisiae, and recombinants are selected by geneticin resistance. Colonies can be purified and tested for correct double crossover by PCR. To remove the KanMX marker, a plasmid containing the Cre recombinase and bleomycin resistance will be introduced, promoting recombination between the loxP sites (Gueldener, U., et al., *A second set of loxP marker cassettes for Cre-mediated multiple gene knockouts in budding yeast*, in *Nucleic Acids Res*. 2002. p. e23.). Finally, the resulting strain can be cured of the Cre plasmid by successive culturing on media without any antibiotic present. The final strain will have a markerless gene deletion, and thus the same method can be used to introduce multiple deletions in the same strain.

The engineered strains can be characterized by measuring the growth rate, the substrate uptake rate, and the product/byproduct secretion rate. Cultures are grown overnight and used as inoculum for a fresh batch culture for which measurements are taken during exponential growth. The growth rate can be determined by measuring optical density using a spectrophotometer (A600). Concentrations of glucose and other organic acid byproducts in the culture supernatant are determined by HPLC using an HPX-87H column (BioRad), and used to calculate uptake and secretion rates. All experiments are performed with triplicate cultures.

The disruption strains are initially expected to exhibit suboptimal growth rates until their metabolic networks have adjusted to their missing functionalities. To assist in this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat Genet*, 36:1056-1058 (2004)). Should the OptKnock predictions prove successful; the growth improvements brought about by adaptive evolution will be accompanied by enhanced rates of fumarate, malate or acrylate production. The OptKnock-generated strains are adaptively evolved in triplicate (running in parallel) due to differences in the evolutionary patterns witnessed previously in *E. coli* ((Fong and Palsson, *Nat Genet*, 36:1056-1058 (2004); Fong et al., *J Bacteriol*, 185:6400-6408 (2003); Ibarra et al., *Nature* 420: 186-189 (2002)) that could potentially result in one strain having superior production qualities over the others. Evolutions will be run for a period of 2-6 weeks, depending upon the rate of growth improvement attained. In general, evolutions will be stopped once a stable phenotype is obtained.

Following the adaptive evolution process, the new strains are characterized again by measuring the growth rate, the substrate uptake rate, and the product/byproduct secretion rate. These results will be compared to the OptKnock predictions by plotting actual growth and production yields along side the production envelopes in the above figures. The most successful OptKnock design/evolution combinations are chosen to pursue further, and are characterized in lab-scale batch and continuous fermentations. The growth-coupled biochemical production concept behind the OptKnock approach should also result in the generation of genetically stable overproducers. Thus, the cultures are maintained in continuous mode for one month to evaluate long-term stability. Periodic samples are taken to ensure that yield and productivity are maintained throughout the experiment.

As will become evident, the teachings contained herein will enable, in a broader sense, the development of methods for decarboxylating alpha, beta-unsaturated carboxylic acids or their salts through the use of naturally occurring or altered decarboxylases. Such alterations can be introduced through a variety of directed and/or adaptive evolution methods.

In some embodiments, the present invention provides a non-naturally occurring microbial organism, that includes a microbial organism having an olefin pathway having at least one exogenous nucleic acid encoding an olefin pathway enzyme expressed in a sufficient amount to produce an olefin.

The olefin pathway includes a decarboxylase. In some embodiments, this exogenous nucleic acid is a heterologous nucleic acid. The microbial organism having this decarboxylase can be optionally cultured under substantially anaerobic conditions.

In other embodiments, the present disclosure provides non-naturally occurring microbial organisms having an acrylate pathway that includes at least one exogenous nucleic acid encoding an acrylate pathway enzyme expressed in a sufficient amount to produce acrylate. This acrylate pathway includes a decarboxylase as described herein below. In particular embodiments, the decarboxylase catalyzes fumarate decarboxylation to provide acrylate.

Decarboxylases (also known as carboxy lyases) catalyze the loss of carbon dioxide from an organic compound or a cellular metabolite possessing a carboxylic acid function. Decarboxylases are prevalent in nature and can require either pyridoxal phosphate or pyruvate as a co-factor, although many require no bound co-factors. Over 50 decarboxylase enzymes have been reported and characterized by biochemical and/or analytical methods.

Figure 19:
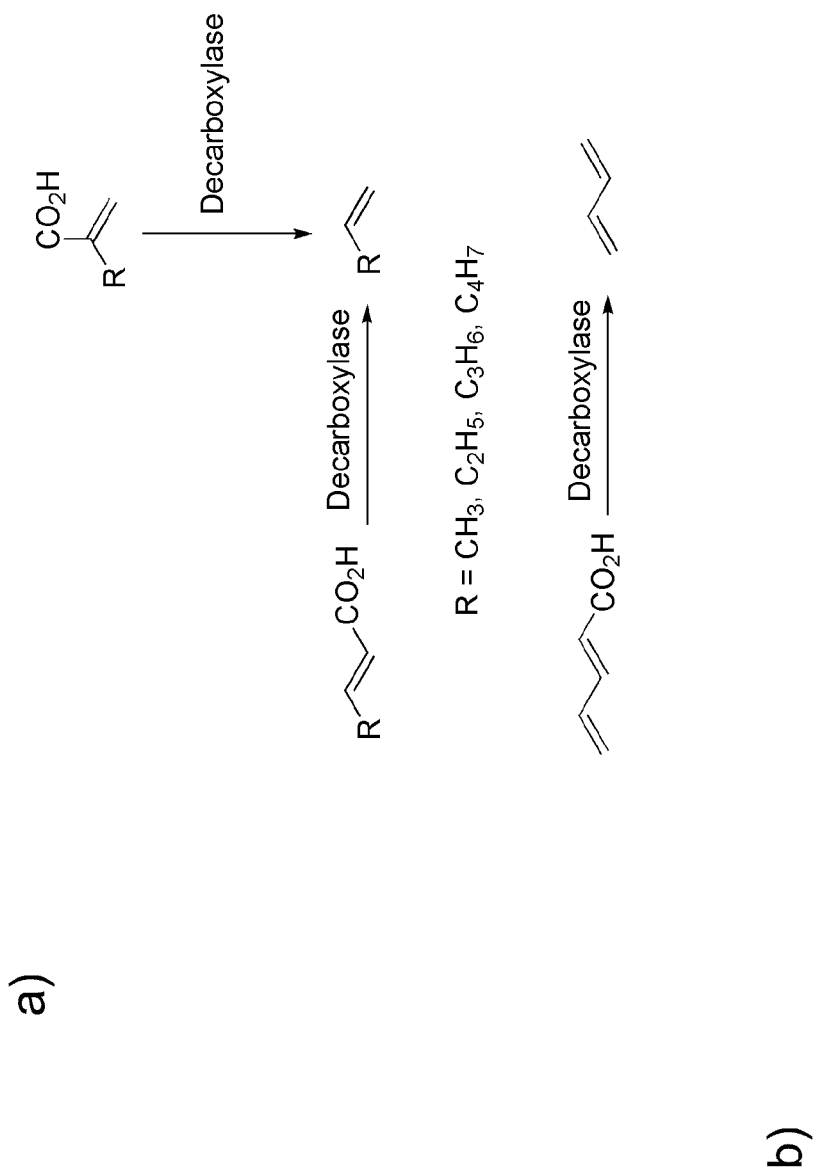
FIGS. 19 *a-b* show the prophetic transformations of a) 1,1- and 1,2-substituted carboxylic acids to terminal olefins catalyzed by a decarboxylase and b) the transformation of a pentadienoic acid to 1,3-butadiene.
Figure 21:
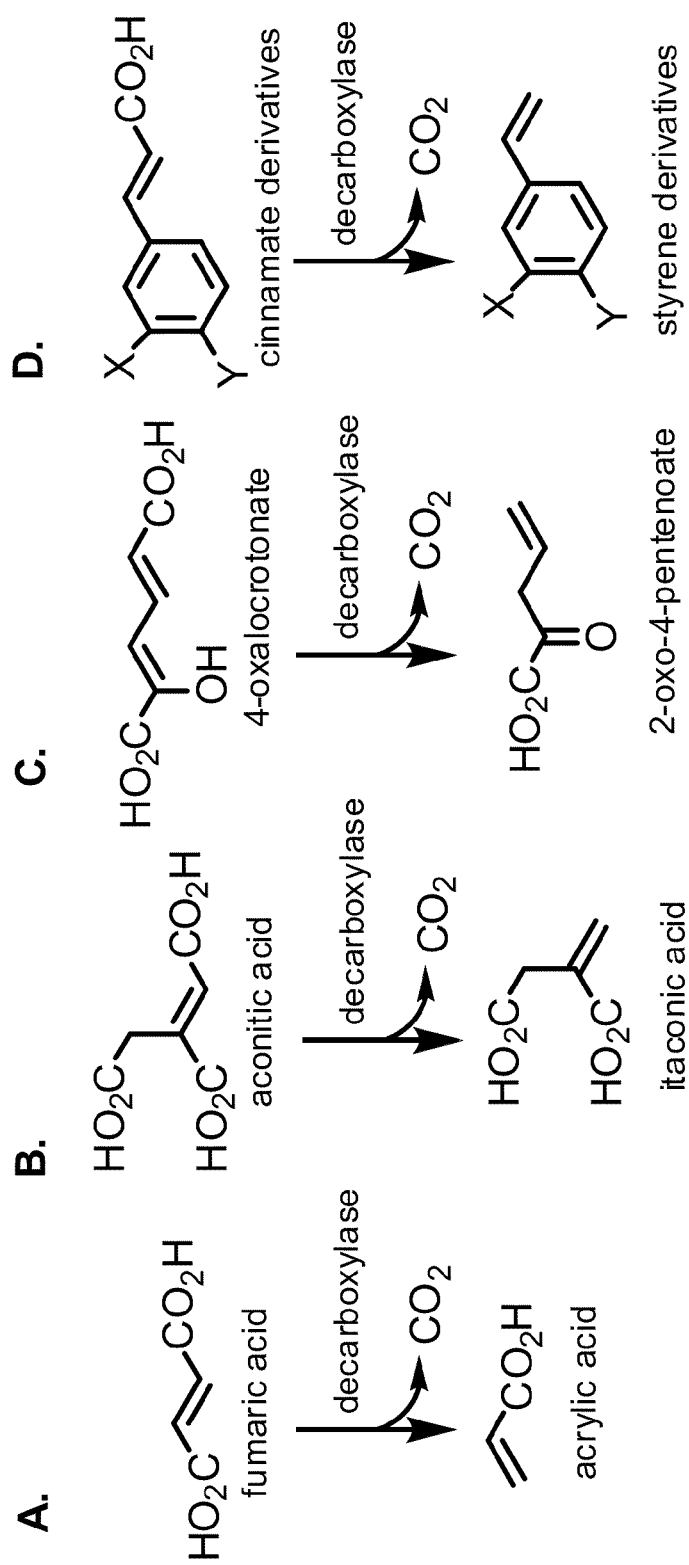
FIG. 21*a* shows the prophetic transformation of fumarate to acrylate catalyzed by a decarboxylase.
FIG. 21*b* shows the decarboxylation of aconitate to itaconate catalyzed by aconitate decarboxylase.
FIG. 21*c* shows the decarboxylation of 4-oxalocrotonate to 2-oxopentenoate catalyzed by 4-oxalocrotonate decarboxylase.
FIG. 21*d* shows the decarboxylation of cinnamate derivatives to styrene derivatives catalyzed by a decarboxylase.

The process in FIGS. 20 and 21A show the decarboxylation of fumaric acid to acrylic acid. Numerous decarboxylase enzymes have been characterized and shown to decarboxylate structurally similar substrates to fumarate (FIGS. 21B-D). These enzymes are applicable for use in the present invention to decarboxylate fumarate and other unsaturated carboxylic acids, as shown in FIG. 19. One enzyme with closely related function is aconitate decarboxylase (FIG. 21B). This enzyme catalyzes the final step in itaconate biosynthesis in a strain of *Candida* and also in the filamentous fungus *Aspergillus terreus*. (Bonnarme et al. *J. Bacteriol.* 177:3573-3578 (1995); Willke et al. *Appl. Microbiol. Biotechnol* 56:289-295 (2001)). Aconitate decarboxylase has been purified and characterized from *Aspergillus terreus* (Dwiarti et al. *J. Biosci. Bioeng.,* 94(1): 29-33 (2002). The gene and protein sequence for the cis-aconitic acid decarboxylase (CAD) enzyme are described in EP2017344 and WO 2009/014437. The protein sequence is listed below along with several close homologs described in EP2017344 and WO2009/014437.

Another enzyme type with similar function is 4-oxalocrotonate decarboxylase (FIG. 21C). This enzyme has been isolated from numerous organisms and characterized. Genes encoding this enzyme include dmpH and dmpE in *Pseudomonas* sp. (strain 600) (Shingler et al. *J. Bacteriol.* 174:711-724 (1992)), xylII and xylIII from *Pseudomonas putida* (Kato et al. *Arch. Microbiol.* 168:457-463 (1997); Stanley et al. *Biochemistry* 39:718-726 (2000); Lian et al. *J. Am. Chem. Soc.* 116, 10403-10411 (1994)) and Reut_B5691 and Reut_B5692 from *Ralstonia eutropha* JMP134 (Hughes et al. *J. Bacteriol.* 158:79-83 (1984). The genes encoding the enzyme from *Pseudomonas* sp. (strain 600) have been cloned and expressed in *E. coli* (Shingler et al. *J. Bacteriol.* 174:711-724 (1992)).

Finally, a class of decarboxylases has been characterized that catalyze the conversion of cinnamate (phenylacrylate) and substituted cinnamate derivatives to the corresponding styrene derivatives (FIG. 21D). These enzymes are common in a variety of organisms and specific genes encoding these enzymes that have been cloned and expressed in *E. coli* are: pad 1 from *Saccharomyces cerevisae* (Clausen et al. *Gene* 142:107-112 (1994), pdc from *Lactobacillus plantarum* (Barthelmebs et al. *Appl. Environ. Microbiol.* 67, 1063-1069 (2001); Qi et al. *Metabolic Engineering* 9: 268-276 (2007); Rodriguez et al. *J. Agric. Food Chem.* 56, 3068-3072 (2008)), pofK (pad) from *Klebsiella oxytoca* (Hashidoko et al. *Biosci. Biotech. Biochem.* 58, 217-218 (1994); Uchiyama et al. *Biosci. Biotech. Biochem.* 72: 116-123 (2008)), and *Pedicoccus pentosaceus* (Barthelmebs et al. *J. Bacteriol.* 182: 6724-6731 (2000); Barthelmebs et al. *Appl. Environ. Microbiol.* 67: 1063-1069 (2001)), and padC from *Bacillus subtilis* and *Bacillus pumilus* (Barthelmebs et al. 2001 supra; Qi, et al supra). A ferulic acid decarboxylase from *Pseudomonas fluorescens* also has been purified and characterized (Huang et al. *J. Bacteriol.* 176: 5912-5918 (1994)). Importantly, this class of enzymes have been shown to be stable and do not require either exogenous or internally bound co-factors, thus making these enzymes ideally suitable for biotransformations (Sariaslani *Annu. Rev. Microbiol.* 61: 51-69 (2007)). A summary of genes encoding these various decarboxylases for carrying out the transformations shown in FIGS. 21B-21D are shown below.

| Gene name | GenBankID | Organism |
| --- | --- | --- |
| CAD | XP_001209273 (GI: 115385453) | *Aspergillus terreus* |
|  | XP_001217495 (GI: 115402837) | *Aspergillus terreus* |
|  | XP_001209946 (GI: 115386810) | *Aspergillus terreus* |
|  | BAE66063 (GI: 83775944) | *Aspergillus oryzae* |
|  | XP_001393934 (GI: 83775944) | *Aspergillus niger* |
|  | XP_391316 (GI: 46139251) | *Gibberella zeae* |
|  | XP_001389415 (GI: 145230213) | *Aspergillus niger* |
|  | XP_001383451 (GI: 126133853) | *Pichia stipitis* |
|  | YP_891060 (GI: 118473159) | *Mycobacterium smegmatis* |
|  | NP_961187 (GI: 41408351) | *Mycobacterium avium* subsp. *pratuberculosis* |
|  | YP_880968 (GI: 118466464) | *Mycobacterium avium* |
|  | ZP_01648681 (GI: 119882410) | *Salinispora arenicola* |
|  | ZP_01648681 (GI: 119882410) | *Salonispora tropica* |
| dmpH | CAA43228.1 (GI: 45685) | *Pseudomonas* sp. CF600 |
| dmpE | CAA43225.1 (GI: 45682) | *Pseudomonas* sp. CF600 |
| xylII | YP_709328.1 (GI: 111116444) | *Pseudomonas putida* |
| xylIII | YP_709353.1 (GI: 111116469) | *Pseudomonas putida* |
| Reut_B5691 | YP_299880.1 (GI: 73539513) | *Ralstonia eutropha* JMP134 |
| Reut_B5692 | YP_299881.1 (GI: 73539514) | *Ralstonia eutropha* JMP134 |
| pad1 | AB368798 (GI: 188496948) | *Saccharomyces cerevisae* |
| pdc | U63827 (GI: 1762615) | *Lactobacillus plantarum* |
| pofK (pad) | AB330293 (GI: 149941607) | *Klebsiella oxytoca* |
| padC | AF017117 (GI: 2394281) | *Bacillus subtilis* |
| pad | AJ276891 (GI: 11322456) | *Pedicoccus pentosaceus* |
| pad | AJ278683 (GI: 11691809) | *Bacillus pumilus* |

Each of the decarboxylases listed above represents a suitable enzyme for the transformation shown in FIGS. 20 and 21A. If the desired activity or productivity of the enzyme is not observed in the conversion of fumarate to acrylate, or if acrylic acid production inhibits the decarboxylase enzymes, the decarboxylase enzymes can be evolved using known protein engineering methods to achieve the required performance. Importantly, it was shown through the use of chimeric enzymes that the C-terminal region of decarboxylases appears to be responsible for substrate specificity (Barthelmebs et al. (2001) supra). Accordingly, directed evolution experiments to broaden the specificity of decarboxylases in order to gain activity with fumarate can be focused on the C-terminal region of these enzymes.

Some of the decarboxylases can exhibit higher activity on the cis-isomer of fumarate known as maleate. Fumarate can be converted to maleate by maleate cis-trans isomerase encoded by the maiA gene from *Alcaligenes faecalis* (Hatakeyama, et al., *Biochem. Biophys. Research Comm.* 239, 74-79 (1997)) or similar genes that can be identified by sequence homology including those from *Geobacillus stearothermophilus* and *Ralstonia pickettii* 12D. Additional maleate cis-trans isomerase enzymes are encoded by the enzymes whose amino acid sequences are described (SEQ ID NO: 1-4) in U.S. Pat. No. 6,133,014, which is incorporated by reference in its entirety. Useful GenBank information for some of these isomerases is shown below.

| Gene name | GenBankID | Organism |
| --- | --- | --- |
| maiA | BAA23002.1 (GI: 2575787) | *Alcaligenes faecalis* |
| maiA | BAA77296 (GI: 4760466) | *Geobacillus stearothermophilus* |
| Rpic12DDRAFT_0600 | ZP_02009633 (GI: 153888491) | *Ralstonia pickettii* 12D |

The exogenous nucleic acid encoding the decarboxylase can come from another organism such as those described above, thus providing a heterologous nucleic acid. Alternatively, in the case of a microbial organism that already has a native decarboxylase capable of decarboxylating fumarate, additional copies of the decarboxylase can be introduced to increase its expression. In addition to incorporating a decarboxylase, a non-naturally occurring microbial organism will have certain energy requirements for growth and maintenance as outlined below.

Engineering the capability for fumarate decarboxylation into *Escherichia coli*, for example, results in a redox-balanced pathway for the production of acrylate from carbohydrates. Provided that symport of the acrylate monoanion is the predominant means of product export, the pathway as depicted in FIG. 20 can be energetically negative because the high energy phosphate bond contained in each PEP molecule gained from glycolysis will be lost upon conversion to oxaloacetate by PEP carboxylase, a native *E. coli* enzyme that is functional during growth on carbohydrates.

This energetic limitation can be remedied by either supplying a limited amount of an external electron acceptor such as oxygen or nitrate to enable energy generation via respiration, or by at least two strain engineering strategies provided herein below. Either strain engineering method ensures that the pathway for production of acrylate via fumarate decarboxylase generates sufficient energy to support cell growth and maintenance under anaerobic or aerobic conditions. Although the non-naturally occurring microbial organism can be grown under aerobic or anaerobic conditions, a substantially anaerobic culture medium is preferred. The two exemplary designs described below can be implemented in order to generate the requisite energy for growth and maintenance under anaerobic conditions.

In one embodiment, a non-naturally occurring microbial organism can include an exogenous nucleic acid encoding at least one malic enzyme to supply the requisite energy for growth and maintenance. Malic enzymes for this purpose can include, without limitation, malic enzyme (NAD-dependent) and malic enzyme (NADP-dependent). For example, one of the native *E. coli* malic enzymes (Takeo, K., *J. Biochem.* 66:379-387 (1969)) or a similar non-native enzyme with higher activity can be expressed to enable the conversion of pyruvate and $CO_2$ to malate. By fixing carbon to pyruvate as opposed to PEP, malic enzyme enables the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl Environ Microbiol* 63:2695-2701 (1997)). Thus, in some embodiments the non-naturally occurring microbial organism can include an exogenous nucleic acid providing a gene such as maeA. A similar observation was made upon overexpressing the malic enzyme from *Ascaris suum* in *E. coli* (Stols et al., *Appl Biochem. Biotechnol* 63-65:153-158 (1997)). The second *E. coli* malic enzyme, encoded by maeB, is NADP-dependent and also decarboxylates oxaloacetate and other alpha-keto acids (Iwakura et al., *J. Biochem.* 85:1355-1365 (1979)) Therefore, in other embodiments the non-naturally occurring microbial organism can include an exogenous nucleic acid providing a gene such as maeB. The relevant malic enzyme gene information is shown below.

| Gene name | Organism | Accession Number |
| --- | --- | --- |
| maeA | *E. coli* | NP_415996 (GI: 90111281) |
| maeB | *E. coli* | NP_416958 (GI: 16130388) |
| NAD-ME | *Ascaris suum* | P27443 (GI: 126732) |

Another option for providing an energetically favorable pathway involves introducing a reversible phosphoenolpyruvate kinase (PPCK) enzyme, which unlike PEP carboxylase, can generate one ATP per phosphoenolpyruvate molecule converted to oxaloacetate. In some embodiments, the non-naturally occurring microbial organism can also include an exogenous nucleic acid encoding a phosphoenolpyruvate carboxykinase. PEP carboxykinase is known to produce oxaloacetate from PEP in rumen bacteria such as *Mannheimia succiniciproducens* (Hong et al., *Nat Biotechnol* 22:1275-1281 (2004)) However, the role of PEP carboxykinase, encoded by pck, in producing oxaloacetate in *E. coli* is believed to be minor as compared to PEP carboxylase, possibly due to the higher $K_m$ for bicarbonate of PEP carboxykinase (Kim et al., *Appl Environ Microbiol* 70:1238-1241 (2004)) Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high NaHCO$_3$ concentrations. In addition, examples of non-native PEP carboxykinase genes that have been cloned and shown to function in *E. coli* include those from *M. succiniciproducens* (Lee et al., *Gene. Biotechnol. Bioprocess Eng.* 7:95-99 (2002)), *Anaerobiospirillum succiniciproducens* (Laivenieks et al. *Appl Environ Microbiol* 63:2273-2280 (1997)), and *Actinobacillus succinogenes* (Kim et al., *Appl Environ Microbiol* 70:1238-1241 (2004)). The relevant PEP carboxykinase gene information is shown below.

| Gene name | Organism | Accession Number |
|---|---|---|
| pck | *E. coli* | NP_417862 (GI: 16131280) |
| pckA | *Mannheimia succiniciproducens* | YP_089485 (GI: 52426348) |
| pckA | *Anaerobiospirillum succiniciproducens* | O09460 (GI: 3122621) |
| pck | *Actinobacillus succinogenes* | ABX39017 (GI: 160415396) |

In addition to the supplying the requisite energy as described above, the formation of acrylate can also be optimized by modifying the non-naturally occurring microbial organism's metabolic production of fumarate. Toward this end, the non-naturally occurring microbial organism can include one or more gene disruptions in addition to the inserted nucleic acid sequences outline above. Gene disruptions can result from, for example, single nucleotide insertion or deletions, stable mutations, and complete gene deletions. Exemplary pathway designs are described below.

The non-naturally occurring microbial organisms that synthesize acrylate can be produced by introducing expressible nucleic acids encoding one or more of the enzymes or proteins participating in one or more acrylate biosynthetic pathways. Depending on the host microbial organism chosen for biosynthesis, nucleic acids for some or all of a particular acrylate biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve acrylate biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as acrylate.

Depending on the acrylate biosynthetic pathway constituents of a selected host microbial organism, the non-naturally occurring microbial organisms of the invention will include at least one exogenously expressed acrylate pathway-encoding nucleic acid and up to all encoding nucleic acids for one or more acrylate biosynthetic pathways. For example, acrylate biosynthesis can be established in a host deficient in a pathway enzyme or protein through exogenous expression of the corresponding encoding nucleic acid. In a host deficient in all enzymes or proteins of an acrylate pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of acrylate can be included, such as a decarboxylase.

Given the teachings and guidance provided herein, those skilled in the art will understand that the number of encoding nucleic acids to introduce in an expressible form will, at least, parallel the acrylate pathway deficiencies of the selected host microbial organism. Therefore, a non-naturally occurring microbial organism of the invention can have one, two, three, four, up to all nucleic acids encoding the enzymes or proteins constituting an acrylate biosynthetic pathway disclosed herein. In some embodiments, the non-naturally occurring microbial organisms also can include other genetic modifications that facilitate or optimize acrylate biosynthesis or that confer other useful functions onto the host microbial organism. One such other functionality can include, for example, augmentation of the synthesis of one or more of the acrylate pathway precursors such as fumarate.

Generally, a host microbial organism is selected such that it produces the precursor of an acrylate pathway, either as a naturally produced molecule or as an engineered product that either provides de novo production of a desired precursor or increased production of a precursor naturally produced by the host microbial organism. For example, fumarate is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of an acrylate pathway.

In some embodiments, a non-naturally occurring microbial organism of the invention is generated from a host that contains the enzymatic capability to synthesize acrylate. In this specific embodiment it can be useful to increase the synthesis or accumulation of an acrylate pathway product to, for example, drive acrylate pathway reactions toward acrylate production. Increased synthesis or accumulation can be accomplished by, for example, overexpression of nucleic acids encoding one or more of the above-described acrylate pathway enzymes or proteins. Over expression the enzyme or enzymes and/or protein or proteins of the acrylate pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing acrylate, through overexpression of one, two, three, four, five, that is, up to all nucleic acids encoding acrylate biosynthetic pathway enzymes or proteins. In addition, a non-naturally occurring organism can be generated by mutagenesis of an endogenous gene that results in an increase in activity of an enzyme in the acrylate biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, an acrylate biosynthetic pathway onto the microbial organism. Alternatively, encoding nucleic acids can be introduced to produce an intermediate microbial organism having the biosynthetic capability to catalyze some of the required reactions to confer acrylate biosynthetic capability. For example, a non-naturally occurring microbial organism having an acrylate biosynthetic pathway can comprise at least one exogenous nucleic acids encoding desired enzymes or proteins, such as a decarboxylase, and the like.

In addition to the biosynthesis of acrylate as described herein, the non-naturally occurring microbial organisms and methods of the invention also can be utilized in various combinations with each other and with other microbial organisms and methods well known in the art to achieve product biosynthesis by other routes. For example, one alternative to produce acrylate other than use of the acrylate producers is through addition of another microbial organism capable of converting an acrylate pathway intermediate to acrylate. One such procedure includes, for example, the fermentation of a microbial organism that produces an acrylate pathway intermediate. The acrylate pathway intermediate can then be used as a substrate for a second microbial organism that converts the acrylate pathway intermediate to acrylate. The acrylate pathway intermediate can be added directly to another culture of the second organism or the original culture of the acrylate pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, acrylate. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of acrylate can be accomplished by constructing a microbial organism that contains biosynthetic pathways for conversion of one pathway intermediate to another pathway intermediate or the product. Alternatively, acrylate also can be biosynthetically produced from microbial organisms through co-culture or co-fermentation using two organisms in the same vessel, where the first microbial organism produces a fumarate intermediate and the second microbial organism converts the intermediate to acrylate.

Microorganisms capable of directly producing acrylate are constructed by introducing genes encoding decarboxylase enzymes into the strains engineered as described above for maximal fumarate production. The following example describes the creation of a microbial organism that can produce acrylic acid from renewable feedstocks such as glucose or sucrose.

To generate an E. coli strain engineered to produce acrylate or acrylic acid, nucleic acids encoding the decarboxylase enzymes are cloned and expressed in E. coli capable of overproducing fumarate using well known molecular biology techniques and recombinant and detection methods well known in the art. Such methods are described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

An acrylate producing strain is constructed, by cloning the individual phenylacrylic acid decarboxylase genes pad1 (AB368798), pdc (U63827), pofK (AB330293), padC (AF017117), pad (AJ276891), and pad (AJ278683) into pZA33 or pZE13 vectors (Expressys, Ruelzheim, Germany) under the IPTG-titratable PA1/lacO promoter. The plasmids are transformed into the fumarate overproducing E. coli strain using standard methods such as electroporation. The resulting genetically engineered organism is cultured in glucose-containing medium following procedures well known in the art (see, for example, Sambrook et al., supra, 2001). Expression of the decarboxylase genes are corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce acrylic acid is confirmed using HPLC, gas chromatography-mass spectrometry (GCMS) and/or liquid chromatography-mass spectrometry (LCMS).

Microbial strains engineered to have a functional acrylic acid synthesis pathway are further augmented by optimization for efficient utilization of the pathway. Briefly, the engineered strain is assessed to determine whether exogenous genes are expressed at a rate limiting level. Flux analysis using $^{13}$C-labeled glucose is performed to assess bottlenecks in the system. Expression is increased for enzymes produced at low levels and that limit the flux through the pathway by, for example, introduction of additional gene copy numbers or changes to the promoter and ribosome binding sites.

To generate better acrylate producers, metabolic modeling is utilized to optimize growth conditions. Modeling is also used to design gene knockouts that additionally optimize utilization of the pathway, as described above. Modeling analysis allows reliable predictions of the effects on cell growth of shifting the metabolism towards more efficient production of acrylic acid. Adaptive evolution is performed to improve both growth and production characteristics (Fong and Palsson, Nat. Genet. 36:1056-1058 (2004)). Based on the results, subsequent rounds of modeling, genetic engineering and adaptive evolution can be applied to the acrylic acid producer to further increase production.

For large-scale production of acrylic acid, the above organism is cultured in a fermenter using a medium known in the art to support growth of the organism under anaerobic conditions. Fermentations are performed in either a batch, fedbatch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained in the optimum range by addition of acids such as $H_2SO_4$ or bases such as NaOH or $Na_2CO_3$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

E. coli and other microorganisms are known to possess fatty acid and organic acid degradation pathways that could lead to acrylate degradation. While fermentative production of acrylic acid under anaerobic conditions should not be accompanied by degradation, should product degradation be observed, the pathways responsible for product degradation will be deleted.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce acrylate.

Sources of encoding nucleic acids for an acrylate pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Candida albicans, Candida boidinii, Aspergillus terreus, Pseudomonas* sp. CF600, *Pseudomonas putida, Ralstonia eutropha* JMP134, *Saccharomyces cerevisae, Lactobacillus plantarum, Klebsiella oxytoca, Bacillus subtilis, Bacillus pumilus, Pedicoccus pentosaceus*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite acrylate biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of acrylate described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative acrylate biosynthetic pathway exists in an unrelated species, acrylate biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms can differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize acrylate.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris. E. coli* is a particularly useful host organism since it is a well characterized microbial organism suitable for genetic engineering. Other particularly useful host organisms include yeast such as *Saccharomyces cerevisiae*.

Methods for constructing and testing the expression levels of a non-naturally occurring acrylate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for production of acrylate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280: 4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more acrylate biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In some embodiments, a method for producing acrylate, includes culturing a non-naturally occurring microbial organism having an acrylate pathway. The pathway includes at least one exogenous nucleic acid encoding an acrylate pathway enzyme expressed in a sufficient amount to produce acrylate under conditions and for a sufficient period of time to produce acrylate. Ideally, the non-naturally occurring microbial organism is in a substantially anaerobic culture medium as described above.

The acrylate pathway includes a decarboxylase gene introduced into an organism that is engineered to produce high levels of fumaric acid under anaerobic conditions from carbon substrates such as glucose or sucrose. Expression of active decarboxylases for the production of chemicals previously has been demonstrated in *E. coli* (Sariaslani, F. S., *Annu. Rev. Microbiol.* 61:51-69 (2007)). In this scenario, decarboxylation of fumaric acid occurs intracellularly and acrylate is produced directly and is secreted from the cell and recovered through standard methods employed for acid separation and purification.

One challenge with direct acrylate production could be the known cellular toxicity of acrylic acid and acrylate salts (Straathof et al., *Appl. Microbiol. Biotechnol.* 67:727-734 (2005)). Selection of an appropriate production organism involves detailed acrylate toxicity assessment in order to determine inherent levels of tolerance. In addition, adaptive evolution methods are applied to the production host to increase tolerance to acrylate up to the required levels of acrylate (e.g., 5-10% final titers). Previous studies have found evolution to be useful for increasing tolerance of microorganisms to organic acids (Steiner 2003; Patnaik 2002). It has been estimated that production of at least 50 g/L acrylate should be possible through fermentation processes (Straathof et al., *Appl. Microbiol. Biotechnol.* 67, 727-734 (2005)).

Should the toxicity of acrylate prove too high for effective production (the world wide web at toxnet.nlm.nih.gov/cgi-bin/sis/search/r?dbs+hsdb:@term+@rn+@rel+79-10-7 indicates that toxicity to bacteria is low), a second approach involves primary production and secretion of fumarate into a fermentation broth, followed by secondary addition of separately produced decarboxylase enzyme. This approach allows effective conversion of fumarate to acrylate without concern for cell viability. Subsequent processing will be the same as above, involving separation and purification of acrylic acid directly from the broth with no need to separate or isolate fumaric acid prior to treatment with decarboxylase.

An alternative to this production mode is to engineer a decarboxylase enzyme so that it is secreted from the fumarate-producing cell, in which case acrylate production occurs in the same vessel as fumarate production. This approach is particularly effective if decarboxylase enzyme production and secretion are subject to inducible programming (e.g., using a temperature sensitive promoter) such that the enzyme is produced and secreted into the broth following completion of fumarate production.

Thus, in some embodiments, the present invention provides a method for producing acrylate, that includes culturing a first non-naturally occurring microbial organism having one or more gene disruptions. Again, the one or more gene disruptions can occur in one or more genes encoding one or more enzymes obligatory to coupling fumarate production to growth of the microorganism when the disruptions reduce an activity of the enzymes such that the disruptions confer stable growth-coupled production of fumarate. Finally, one adds a decarboxylase to the cultured first non-naturally occurring microbial organism, said decarboxylase catalyzing the decarboxylation of fumarate.

In some embodiments, the decarboxylase is expressed in a second non-naturally occurring microbial organism. In such an instance, the first and second non-naturally occurring microbial organisms can be co-cultured. Additionally, the decarboxylase can also be secreted by a second non-naturally occurring microbial organism which still allows for the first and second microbial organisms to be co-cultured.

Suitable purification and/or assays to test for the production of acrylate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art.

The acrylate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the acrylate producers can be cultured for the biosynthetic production of acrylate.

For the production of acrylate, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can be, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of acrylate.

In addition to renewable feedstocks such as those exemplified above, the acrylate microbial organisms of the invention also can be modified for growth on syngas as its source of carbon. In this specific embodiment, one or more proteins or enzymes are expressed in the acrylate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

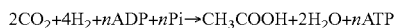

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: cobalamide corrinoid/iron-sulfur protein, methyltransferase, carbon monoxide dehydrogenase, acetyl-CoA synthase, acetyl-CoA synthase disulfide reductase and hydrogenase. Following the teachings and guidance provided herein for introducing a sufficient number of encoding nucleic acids to generate an acrylate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, acrylate and any of the intermediate metabolites in the acrylate pathway. All that is required is to engineer in one or more of the required enzyme or protein activities to achieve biosynthesis of the desired compound or intermediate including, for example, inclusion of some or all of the acrylate biosynthetic pathways. Accordingly, the invention provides a non-naturally occurring microbial organism that produces and/or secretes acrylate when grown on a carbohydrate or other carbon source and produces and/or secretes any of the intermediate metabolites shown in the acrylate pathway when grown on a carbohydrate or other carbon source. The acrylate producing microbial organisms of the invention can initiate synthesis from an intermediate, for example, fumarate.

The non-naturally occurring microbial organisms of the invention are constructed using methods well known in the art as exemplified herein to exogenously express at least one nucleic acid encoding an acrylate pathway enzyme or protein in sufficient amounts to produce acrylate. It is understood that the microbial organisms of the invention are cultured under conditions sufficient to produce acrylate. Following the teachings and guidance provided herein, the non-naturally occurring microbial organisms of the invention can achieve biosynthesis of acrylate resulting in intracellular concentrations between about 0.1-200 mM or more. Generally, the intracellular concentration of acrylate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

The fumarate, malate, or acrylate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the fumarate, malate, or acrylate producers can be cultured for the biosynthetic production of fumarate, malate, or acrylate.

For the production of fumarate, malate, or acrylate, the recombinant strains are cultured in a medium with carbon source and other essential nutrients. It is highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in U.S. patent application Ser. No. 11/891,602, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of fumarate, malate, or acrylate.

In addition to renewable feedstocks such as those exemplified above, the fumarate, malate, or acrylate microbial organisms of the invention also can be modified for growth on syngas as its source of carbon. In this specific embodiment, one or more proteins or enzymes are expressed in the fumarate, malate, or acrylate producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

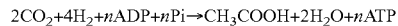

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a fumarate, malate, or acrylate pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, fumarate, malate, or acrylate and any of the intermediate metabolites in the fumarate, malate, or acrylate pathway. All that is required is to engineer in one or more of the required enzyme or protein activities to achieve biosynthesis of the desired compound or intermediate including, for example, inclusion of some or all of the fumarate, malate, or acrylate biosynthetic pathways. Accordingly, the invention provides a non-naturally occurring microbial organism that produces and/or secretes fumarate, malate, or acrylate when grown on a carbohydrate or other carbon source and produces and/or secretes any of the intermediate metabolites shown in the fumarate, malate, or acrylate pathway when grown on a carbohydrate or other carbon source. The fumarate, malate, or acrylate producing microbial organisms of the invention can initiate synthesis from any of the aforementioned intermediates.

The non-naturally occurring microbial organisms of the invention are constructed using methods well known in the art as exemplified herein to exogenously express at least one nucleic acid encoding a fumarate, malate, or acrylate pathway enzyme or protein in sufficient amounts to produce fumarate, malate, or acrylate. It is understood that the microbial organisms of the invention are cultured under conditions sufficient to produce fumarate, malate, or acrylate. Following the teachings and guidance provided herein, the non-naturally occurring microbial organisms of the invention can achieve biosynthesis of fumarate, malate, or acrylate resulting in intracellular concentrations between about 0.1-200 mM or more. Generally, the intracellular concentration of fumarate, malate, or acrylate is between about 3-200 mM, particularly between about 10-175 mM and more particularly between about 50-150 mM, including about 50 mM, 75 mM, 100 mM, 125 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application Ser. No. 11/891,602, filed Aug. 10, 2007. Any of these conditions can be employed with the non-naturally occurring microbial organisms as well as other anaerobic conditions well known in the art. Under such anaerobic conditions, the fumarate, malate, or acrylate producers can synthesize fumarate, malate, or acrylate at intracellular concentrations of 5-10 mM or more as well as all other concentrations exemplified herein. It is understood that, even though the above description refers to intracellular concentrations, fumarate, malate, or acrylate producing microbial organisms can produce fumarate, malate, or acrylate intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of fumarate, malate, or acrylate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of fumarate, malate, or acrylate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of fumarate, malate, or acrylate. Generally, and as with non-continuous culture procedures, the continuous and/or near-continuous production of fumarate, malate, or acrylate can include culturing a non-naturally occurring fumarate, malate, or acrylate producing organism of the invention in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of fumarate, malate, or acrylate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the fumarate, malate, or acrylate producers of the invention for continuous production of substantial quantities of fumarate, malate, or acrylate, the fumarate, malate, or acrylate producers also can be, for example, simultaneously subjected to chemical synthesis procedures to convert the product to other compounds or the product can be separated from the fermentation culture and sequentially subjected to chemical conversion to convert the product to other compounds, if desired.

Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng* 22:11-19 (2005); Huisman et al., Biocatalysis in the pharmaceutical and biotechnology industries, pp. 717-742 (2007) CRC Press, R. N. Patel, Ed.); Otten et al., *Biomol. Eng* 22:1-9 (2005); and Sen et al., *Appl Biochem. Biotechnol* 143:212-223 (2007).) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J. Theor. Biol.* 234:497-509 (2005).) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucl. Acids Res* 32:e145 (2004); and Fujii et al., *Nat. Protoc.* 1:2493-2497 (2006).) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, W. P., *Proc Natl Acad Sci U.S.A.* 91:10747-10751 (1994); and Stemmer, W. P., *Nature* 370:389-391 (1994).) typically involves digestion of 2 or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious random neutral mutations that might confer antigenicity.

Staggered Extension (StEP) (Zhao et al., *Nat. Biotechnol* 16:258-261 (1998).) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998).) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al., *Nucleic Acids Res* 27:e18 (1999); and Volkov et al., *Methods Enzymol.* 328:456-463 (2000).) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol* 19:354-359 (2001).) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003).) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist et al., *Methods Mol. Biol.* 352:191-204 (2007); Bergquist et al., *Biomol. Eng* 22:63-72 (2005); Gibbs et al., *Gene* 271:13-20 (2001).) This can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci U.S.A* 96:3562-3567 (1999); Ostermeier et al., *Nat. Biotechnol* 17:1205-1209 (1999).) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is almost the same as ITCHY except that phosphothioate dNTPs are used to generate truncations. (Lutz et al., *Nucleic Acids Res* 29:E16 (2001).) Relative to ITCHY, THIO-ITCHY can be easier to optimize, provide more reproducibility, and adjustability.

SCRATCHY-ITCHY combined with DNA shuffling is a combination of DNA shuffling and ITCHY; therefore, allowing multiple crossovers. (Lutz et al. 2001, *Proc Natl Acad Sci U.S.A.* 98:11248-11253 (2001).) SCRATCHY combines the best features of ITCHY and DNA shuffling. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005).) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J* 3:74-82 (2008); Wong et al., *Nucleic Acids Res* 32:e26 (2004); and Wong et al., *Anal. Biochem.* 341:187-189 (2005).) Using this technique it can be possible to generate a large library of mutants within 2-3 days using simple methods. This is very non-directed compared to mutational bias of DNA polymerases. Differences in this approach makes this technique complementary (or alternative) to epPCR.

In Synthetic Shuffling, overlapping oligonucleotides are designed to encode "all genetic diversity in targets" and allow a very high diversity for the shuffled progeny. (Ness et al., *Nat. Biotechnol* 20:1251-1255 (2002).) In this technique, one can design the fragments to be shuffled. This aids in increasing the resulting diversity of the progeny. One can design sequence/codon biases to make more distantly related sequences recombine at rates approaching more closely related sequences and it doesn't require possessing the template genes physically.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005).) The gene is reassembled using internal PCR primer extension with proofreading polymerase. The sizes for shuffling are directly controllable using varying dUPT::dTTP ratios. This is an end point reaction using simple methods for uracil incorporation and cleavage. One can use other nucleotide analogs such as 8-oxo-guanine with this method. Additionally, the technique works well with very short fragments (86 bp) and has a low error rate. Chemical cleavage of DNA means very few unshuffled clones.

In Sequence Homology-Independent Protein Recombination (SHIPREC) a linker is used to facilitate fusion between 2 distantly/unrelated genes; nuclease treatment is used to generate a range of chimeras between the two. Result is a single crossover library of these fusions. (Sieber et al., *Nat. Biotechnol* 19:456-460 (2001).) This produces a limited type of shuffling; mutagenesis is a separate process. This technique can create a library of chimeras with varying fractions of each of 2 unrelated parent genes. No homology is needed. SHIPREC was tested with a heme-binding domain of a bacterial CP450 fused to N-terminal regions of a mammalian CP450; this produced mammalian activity in a more soluble enzyme.

In Gene Site Saturation Mutagenesis (GSSM) the starting materials are a supercoiled dsDNA plasmid with insert and 2 primers degenerate at the desired site for mutations. (Kretz et al., *Methods Enzymol.* 388:3-11 (2004).) Primers carry the mutation of interest and anneal to the same sequence on opposite strands of DNA; mutation in the middle of the primer and ~20 nucleotides of correct sequence flanking on each side. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at one site with no nonsense codons and equal or near-equal representation of most possible alleles. It does not require prior knowledge of structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al., *Methods Enzymol.* 208:564-586 (1991); and Reidhaar-Olson et al., *Science* 241:53-57 (1988).) Simultaneous substitutions at 2 or 3 sites are possible using this technique. Additionally, the method tests a large multiplicity of possible sequence changes at a limited range of sites. It has been used to explore the information content of lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz et al., *Angew. Chem. Int. Ed Engl.* 40:3589-3591 (2001).) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional ts mutator plasmids allow increases of 20- to 4000-X in random and natural mutation frequency during selection and to block accumulation of deleterious mutations when selection is not required. (Selifonova et al., *Appl Environ Microbiol* 67:3645-3649 (2001).) This technology is based on a plasmid-derived mutD5 gene, which encodes a mutant subunit of DNA polymerase III. This subunit binds to endogenous DNA polymerase III and compromises the proofreading ability of polymerase III in any of the strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows plasmid curing at 41° C. It should be noted that mutator strains have been explored for quite some time (e.g., see Winter and coworkers, *J. Mol. Biol.* 260:359-3680 (1996). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., *Proc Natl Acad Sci U.S.A* 102:8466-8471 (2005).) Rather than saturating each site with all possible amino acid changes, a set of 9 is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and should increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (on the world-wide web at verenium.com/Pages/Technology/EnzymeTech/TechEnzyTGR.html) Typically this technology is used in combination with ultra-high-throughput screening to query the represented sequence space for desired improvements. This technique allows multiple gene recombination independent of homology. The exact number and position of cross-over events can be pre-determined using fragments designed via bioinformatic analysis. This technology leads to a very high level of diversity with virtually no parental gene reformation and a low level of inactive genes. Combined with GSSM, a large range of mutations can be tested for improved activity. The method allows "blending" and "fine tuning" of DNA shuffling, e.g. codon usage can be optimized.

In Silico Protein Design Automation PDA is an optimization algorithm that anchors the structurally defined protein backbone possessing a particular fold, and searches sequence space for amino acid substitutions that can stabilize the fold and overall protein energetics. (Hayes et al., *Proc Natl Acad Sci U.S.A.* 99:15926-15931 (2002).) This technology allows in silico structure-based entropy predictions in order to search for structural tolerance toward protein amino acid variations. Statistical mechanics is applied to calculate coupling interactions at each position—structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). Choice of sequence variants to test is related to predictions based on most favorable thermodynamics and ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves 1) Use knowledge of structure/function to choose a likely site for enzyme improvement. 2) Saturation mutagenesis at chosen site using Stratagene QuikChange (or other suitable means). 3) Screen/select for desired properties. 4) With improved clone(s), start over at another site and continue repeating. (Reetz et al., *Nat. Protoc.* 2:891-903 (2007); and Reetz et al., *Angew. Chem. Int. Ed Engl.* 45:7745-7751 (2006).) This is a proven methodology assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

To generate better producers, metabolic modeling can be utilized to optimize growth conditions. Modeling can also be used to design gene disruptions that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of fumarate, malate, or acrylate.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

It is understood that modifications which do not substantially affect the activity of the various embodiments of this invention are also included within the definition of the invention provided herein. Accordingly, the following examples are intended to illustrate but not limit the present invention.

Example I

Microorganisms Having Growth-Coupled Production of Fumarate

This Example describes the construction in silico designed strains for the increased production of fumarate in E. Coli.

Escherichia coli K-12 MG1655 serves as the wild-type strain into which the deletions are introduced. The strains are constructed by incorporating in-frame deletions using homologous recombination via the λ Red recombinase system of Datsenko and Wanner. (Datsenko and Wanner, *Proc Natl Acad Sci U.S.A.*, 97(12):6640-5 (2000).) The approach involves replacing a chromosomal sequence (i.e., the gene targeted for removal) with a selectable antibiotic resistance gene, which itself is later removed. Knockouts are integrated one by one into the recipient strain. No antibiotic resistance markers will remain after each deletion allowing accumulation of multiple mutations in each target strain. The deletion technology completely removes the gene targeted for removal so as to substantially reduce the possibility of the constructed mutants reverting back to the wild-type.

As described further below, one exemplary growth condition for achieving biosynthesis of fumarate/malate includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, fumarate, malate, and other organic acid byproducts in the culture supernatant are determined by HPLC using an HPX-87H column (Bio-Rad), and are used to calculate uptake and secretion rates. All experiments are performed with triplicate cultures.

The knockout strains can exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several E. coli mutants that had been adaptively evolved on various substrates to reach the growth rates predicted a priori by an in silico model. (Fong and Palsson, *Nat Genet,* 36(10):1056-8 (2004).)

Should the OptKnock predictions prove successful; the growth improvements brought about by adaptive evolution will be accompanied by enhanced rates of fumarate and/or malate production. The OptKnock-generated strains are adaptively evolved in triplicate (running in parallel) due to differences in the evolutionary patterns witnessed previously in *E. coli* (Fong and Palsson, *Nat Genet,* 36(10):1056-8 (2004); Fong et al., *J Bacteriol,* 185(21):6400-6408 (2003); Ibarra et al., *Nature* 420:186-189 (2002)) that could potentially result in one strain having superior production qualities over the others. Evolutions are run for a period of 2-6 weeks, depending upon the rate of growth improvement attained. In general, evolutions are stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The conditions required for each evolution are summarized on table 7. The evolutions are performed in triplicate (i.e., 18 evolutions total) due to differences in the evolutionary patterns witnessed previously Donnelly et al., *Appl Biochem Biotechnol* 70-72: 187-98 (1998); Vemuri et al., *Appl Environ Microbiol* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness[25]. In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology.

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Example II

Microorganisms having Growth-Coupled Production of Fumarate

This Example describes the construction in silico designed strains for the increased production of fumarate in *S. cerevisiae*.

Gene deletions are introduced into wild-type, haploid *S. cerevisiae* by homologous recombination of the gene interrupted by the KanMX cassette, flanked by loxP sites enabling removal and recycling of the resistance marker (Wach, A., et al., *PCR-based gene targeting in Saccharomyces cerevisiae*, in *Yeast Gene Analysis*, M. F. Tuite, Editor. 1998, Academic Press: San Diego.). Starting with a loxP-kanMX-loxP sequence on a plasmid, an artificial construct with this sequence flanked by fragments of the gene of interest will be created by PCR using primers containing both 45-50 bp target sequence followed by a region homologous to the above cassette. This linear DNA will be transformed into wild-type *S. cerevisiae*, and recombinants will be selected by geneticin resistance. Colonies will be purified and tested for correct double crossover by PCR. To remove the KanMX marker, a plasmid containing the Cre recombinase and bleomycin resistance will be introduced, promoting recombination between the loxP sites (Gueldener et al., *Nucleic Acids Res.* 30:e23 (2002)). Finally, the resulting strain can be cured of the Cre plasmid by successive culturing on media without any antibiotic present. The final strain will have a markerless gene deletion, and thus the same method can be used to introduce multiple deletions in the same strain.

As described further below, one exemplary growth condition for achieving biosynthesis of fumarate includes anaerobic culture or fermentation conditions. In certain embodiments, the non-naturally occurring eukaryotic organism of the invention can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. One skilled in the art will recognize substantially anaerobic conditions include microaerobic conditions. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The engineered strains are characterized by measuring the growth rate, the substrate uptake rate, and the product/byproduct secretion rate. Cultures are grown overnight and used as inoculum for a fresh batch culture for which measurements are taken during exponential growth. The growth rate is determined by measuring optical density using a spectrophotometer (A600). Concentrations of glucose, fumarate, malate, and other organic acid byproducts in the culture supernatant are determined by HPLC using an HPX-87H column (Bio-Rad), and are used to calculate uptake and secretion rates. All experiments are performed with triplicate cultures.

The knockout strains can exhibit suboptimal growth rates until their metabolic networks have adjusted to their missing functionalities. To enable this adjustment, the strains are adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model. (Fong and Palsson, *Nat Genet*, 36:1056-1058 (2004).) These teachings can be applied to *S. cerevisiae*.

Should the OptKnock predictions prove successful; the growth improvements brought about by adaptive evolution will be accompanied by enhanced rates of fumarate production, and further strains can be engineered in a similar matter to optimize malate or acrylate production. The OptKnock-generated strains are adaptively evolved in triplicate (running in parallel) due to differences in the evolutionary patterns witnessed previously in *E. coli* (Fong and Palsson, *Nat Genet*, 36:1056-1058 (2004); Fong et al., *J Bacteriol*, 185:6400-6408 (2003); Ibarra et al., *Nature* 420:186-189 (2002)) that could potentially result in one strain having superior production qualities over the others. Evolutions are run for a period of 2-6 weeks, depending upon the rate of growth improvement attained. In general, evolutions are stopped once a stable phenotype is obtained.

The adaptive evolution procedure involves maintaining the cells in prolonged exponential growth by the serial passage of batch cultures into fresh medium before the stationary phase is attained. Briefly, one procedure allows cells to reach mid-exponential growth ($A_{600}$=0.5) before being diluted and passed to fresh medium (i.e., M9 minimal media with 2 g/L carbon source). This process is repeated, allowing for about 500 generations for each culture. Culture samples are taken, frozen with liquid nitrogen, and the optical culture density recorded for each day throughout the course of the evolutions. The evolutions are performed in triplicate due to differences in the evolutionary patterns witnessed previously Donnelly et al., *Appl Biochem Biotechnol* 70-72: 187-98 (1998); Vemuri et al., *Appl Environ Microbiol* 68:1715-27 (2002), that could potentially result in one strain having superior production qualities over the others. The adaptive evolution step can take up to about two months or more. The adaptive evolution step also can be less than two months depending on the strain design, for example.

Another process can evolve cells using automation technology and is commercially available by Evolugate, LLC (Gainesville, Fla.) under a service contract. The procedure employs the Evolugator™ evolution machine which results in significant time and effort savings over non-automated evolution techniques. Cells are maintained in prolonged exponential growth by the serial passage of batch cultures into fresh medium before the stationary phase is attained. By automating optical density measurement and liquid handling, the Evolugator can perform serial transfer at high rates using large culture volumes, thus approaching the efficiency of a chemostat for evolution of cell fitness. In contrast to a chemostat, which maintains cells in a single vessel, the machine operates by moving from one "reactor" to the next in subdivided regions of a spool of tubing, thus eliminating any selection for wall-growth. Culture samples are taken, frozen with liquid nitrogen, and the optical culture density recorded each day throughout the course of the evolutions. The Evolugator is used for each strain until a stable growth rate is achieved. Growth rate improvements of nearly 50% have been observed in two weeks using this device. The above-described strains are adaptively evolved in triplicate (running in parallel). At ten day intervals, culture samples are taken from the Evolugator, purified on agar plates, and cultured in triplicate as discussed above to assess strain physiology.

Following the adaptive evolution process, the new strains are again characterized by measuring the growth rate, the substrate uptake rate, and the product/byproduct secretion rate. These results are compared to the OptKnock predictions by plotting actual growth and production yields along side the production envelopes. The most successful OptKnock design/evolution combinations are chosen to pursue further, and is characterized in lab-scale batch and continuous fermentations. The growth-coupled biochemical production concept behind the OptKnock approach should also result in the generation of genetically stable overproducers. Thus, the cultures can be maintained in continuous mode for one month to evaluate long-term stability. Periodic samples will be taken to ensure that yield and productivity are maintained throughout the experiment.

Example III

Acrylate Biosynthesis

This Example describes the generation of a microbial organism capable of producing acrylate using a decarboxylase metabolic pathway.

Escherichia coli is used as a target organism to engineer a decarboxylase pathway (FIG. 1), and testing growth and acrylate production from glucose. E. coli provides a good model for developing a non-naturally occurring microorganism capable of producing acrylate, from glucose since it is amenable to genetic manipulation and is known to be capable of producing various products, like ethanol, effectively under anaerobic conditions from glucose.

To generate an E. coli strain engineered to produce primary alcohol, nucleic acids encoding proteins and enzymes required for the acrylate production pathway via fumarate decarboxylation as described above, are expressed in E. coli using well known molecular biology techniques (see, for example, Sambrook, supra, 2001; Ausubel supra, 1999; Roberts et al., supra, 1989). The pad1 gene (AB368798), encoding a decarboxylase under anaerobic conditions, are cloned into the pZE13 vector under the PA1/lacO promoter. The of plasmid is transformed into E. coli strain MG1655 to express the enzyme aconitate decarboxylase required for decarboxylation of fumarate to acrylate.

The engineered production organism containing a decarboxylase enzyme is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until acrylate reaches a concentration of between 10-200 g/L, with the cell density being between 5 and 50 g/L. Upon completion of the cultivation period, the fermenter contents are passed through a cell separation unit (e.g., centrifuge) to remove cells and cell debris, and the fermentation broth and acrylate is separated from the broth and purified by standard methods for organic acid recovery.

Example IV

Acrylate from Biologically Produced Fumarate

Escherichia coli K-12 MG1655 is used as one reference wild-type strain into which the deletions are introduced. The knockouts are integrated, for example, one-by-one into the recipient strain allowing the accumulation of several deletions. The deletion methodology completely removes the gene targeted for removal so as to avoid the possibility of the constructed mutants reverting back to their wild-type.

The strains are constructed by incorporating in-frame deletions using homologous recombination by well known methods such as the λ Red recombinase system (Datsenko and Wanner, Proc Natl Acad Sci U.S.A., 97:6640-6645 (2000)). The approach involves replacing a chromosomal sequence (i.e., the gene targeted for removal) with a selectable antibiotic resistance gene, which itself is later removed. The knockouts are integrated sequentially into the recipient strain. Antibiotic resistance markers are removed after each deletion, thus allowing accumulation of multiple mutations in each target strain.

An organism engineered for high level fumarate production is grown in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial glucose concentration of 20 g/L. As the cells grow and utilize the glucose, additional 70% glucose is fed into the bioreactor at a rate approximately balancing glucose consumption. The temperature of the bioreactor is maintained at 30 degrees C. Growth continues for approximately 24 hours, until fumarate reaches a concentration of between 10-200 g/L, with the cell density being between 5 and 50 g/L. Upon completion of the cultivation period, a decarboxylase enzyme is added either directly to the fermenter or after initial removal of cells and cell debris. After agitating for the required length of time required for complete conversion of fumarate to acrylate, the acrylate is recovered as described above.

TABLE 1

The list of all strains identified by OptKnock that are most likely to provide increased fumarate yields in E. Coli.

| | | | | | | |
|---|---|---|---|---|---|---|
| 1. | ACKr | ADHEr | AKGD | ASNS2 | ATPS4r | LDH_D |
| 2. | ACKr | ADHEr | AKGD | ATPS4r | CBMK2 | LDH_D |
| 3. | ACKr | ADHEr | AKGD | ATPS4r | GLUDy | LDH_D |
| 4. | ACKr | ADHEr | AKGD | ATPS4r | LDH_D | |
| 5. | ACKr | ADHEr | AKGD | ATPS4r | LDH_D | RPE |
| 6. | ACKr | ADHEr | AKGD | ATPS4r | LDH_D | TAL |
| 7. | ACKr | ADHEr | AKGD | ATPS4r | LDH_D | TKT1 |
| 8. | ACKr | ADHEr | AKGD | ATPS4r | LDH_D | TKT2 |
| 9. | ACKr | ADHEr | ASNS2 | ATPS4r | LDH_D | SUCOAS |
| 10. | ACKr | ADHEr | ASNS2 | LDH_D | ME2 | SUCD4 |
| 11. | ACKr | ADHEr | ATPS4r | CBMK2 | LDH_D | SUCOAS |
| 12. | ACKr | ADHEr | ATPS4r | GLUDy | LDH_D | SUCOAS |
| 13. | ACKr | ADHEr | ATPS4r | LDH_D | PDH | PFLi |
| 14. | ACKr | ADHEr | ATPS4r | LDH_D | RPE | SUCOAS |

TABLE 1-continued

The list of all strains identified by OptKnock that are most likely to provide increased fumarate yields in *E. Coli*.

| | | | | | | |
|---|---|---|---|---|---|---|
| 15. ACKr | ADHEr | ATPS4r | LDH_D | SUCOAS | | |
| 16. ACKr | ADHEr | ATPS4r | LDH_D | SUCOAS | TAL | |
| 17. ACKr | ADHEr | ATPS4r | LDH_D | SUCOAS | TKT1 | |
| 18. ACKr | ADHEr | ATPS4r | LDH_D | SUCOAS | TKT2 | |
| 19. ACKr | ADHEr | CBMK2 | FRD2 | LDH_D | ME2 | THD2 |
| 20. ACKr | ADHEr | CBMK2 | LDH_D | ME2 | SUCD4 | |
| 21. ACKr | ADHEr | FRD2 | G5SD | LDH_D | ME2 | THD2 |
| 22. ACKr | ADHEr | FRD2 | GLCpts | GLUDy | LDH_D | ME2 |
| 23. ACKr | ADHEr | FRD2 | GLU5K | LDH_D | ME2 | THD2 |
| 24. ACKr | ADHEr | FRD2 | LDH_D | ME2 | PFLi | THD2 |
| 25. ACKr | ADHEr | FRD2 | LDH_D | ME2 | THD2 | |
| 26. ACKr | ADHEr | GLCpts | GLUDy | LDH_D | ME2 | SUCD4 |
| 27. ACKr | ADHEr | GLCpts | LDH_D | ME2 | SUCD4 | |
| 28. ACKr | ADHEr | GLUDy | LDH_D | ME2 | SUCD4 | |
| 29. ACKr | ADHEr | LDH_D | ME2 | SUCD4 | | |
| 30. ACKr | AKGD | ASNS2 | ATPS4r | | | |
| 31. ACKr | AKGD | ASNS2 | ATPS4r | CBMK2 | | |
| 32. ACKr | AKGD | ASNS2 | ATPS4r | GLUDy | | |
| 33. ACKr | AKGD | ASNS2 | ATPS4r | RPE | | |
| 34. ACKr | AKGD | ASNS2 | ATPS4r | TAL | | |
| 35. ACKr | AKGD | ASNS2 | ATPS4r | TKT1 | | |
| 36. ACKr | AKGD | ASNS2 | ATPS4r | TKT2 | | |
| 37. ACKr | AKGD | ATPS4r | | | | |
| 38. ACKr | AKGD | ATPS4r | CBMK2 | | | |
| 39. ACKr | AKGD | ATPS4r | CBMK2 | GLUDy | | |
| 40. ACKr | AKGD | ATPS4r | CBMK2 | RPE | | |
| 41. ACKr | AKGD | ATPS4r | CBMK2 | TAL | | |
| 42. ACKr | AKGD | ATPS4r | CBMK2 | TKT1 | | |
| 43. ACKr | AKGD | ATPS4r | CBMK2 | TKT2 | | |
| 44. ACKr | AKGD | ATPS4r | GLUDy | | | |
| 45. ACKr | AKGD | ATPS4r | GLUDy | RPE | | |
| 46. ACKr | AKGD | ATPS4r | GLUDy | TAL | | |
| 47. ACKr | AKGD | ATPS4r | GLUDy | TKT1 | | |
| 48. ACKr | AKGD | ATPS4r | GLUDy | TKT2 | | |
| 49. ACKr | AKGD | ATPS4r | PPCK | PYK | | |
| 50. ACKr | AKGD | ATPS4r | RPE | | | |
| 51. ACKr | AKGD | ATPS4r | TAL | | | |
| 52. ACKr | AKGD | ATPS4r | TKT1 | | | |
| 53. ACKr | AKGD | ATPS4r | TKT2 | | | |
| 54. ACKr | ASNS2 | ATPS4r | CBMK2 | SUCOAS | | |
| 55. ACKr | ASNS2 | ATPS4r | GLUDy | SUCOAS | | |
| 56. ACKr | ASNS2 | ATPS4r | RPE | SUCOAS | | |
| 57. ACKr | ASNS2 | ATPS4r | SUCOAS | | | |
| 58. ACKr | ASNS2 | ATPS4r | SUCOAS | TAL | | |
| 59. ACKr | ASNS2 | ATPS4r | SUCOAS | TKT1 | | |
| 60. ACKr | ASNS2 | ATPS4r | SUCOAS | TKT2 | | |
| 61. ACKr | ATPS4r | CBMK2 | GLUDy | SUCOAS | | |
| 62. ACKr | ATPS4r | CBMK2 | RPE | SUCOAS | | |
| 63. ACKr | ATPS4r | CBMK2 | SUCOAS | | | |
| 64. ACKr | ATPS4r | CBMK2 | SUCOAS | TAL | | |
| 65. ACKr | ATPS4r | CBMK2 | SUCOAS | TKT1 | | |
| 66. ACKr | ATPS4r | CBMK2 | SUCOAS | TKT2 | | |
| 67. ACKr | ATPS4r | FUM | PPCK | | | |
| 68. ACKr | ATPS4r | GLUDy | RPE | SUCOAS | | |
| 69. ACKr | ATPS4r | GLUDy | SUCOAS | | | |
| 70. ACKr | ATPS4r | GLUDy | SUCOAS | TAL | | |
| 71. ACKr | ATPS4r | GLUDy | SUCOAS | TKT1 | | |
| 72. ACKr | ATPS4r | GLUDy | SUCOAS | TKT2 | | |
| 73. ACKr | ATPS4r | MDH | PPCK | | | |
| 74. ACKr | ATPS4r | PDH | PFLi | | | |
| 75. ACKr | ATPS4r | PPCK | PYK | SUCOAS | | |
| 76. ACKr | ATPS4r | RPE | SUCOAS | | | |
| 77. ACKr | ATPS4r | SUCOAS | | | | |
| 78. ACKr | ATPS4r | SUCOAS | TAL | | | |
| 79. ACKr | ATPS4r | SUCOAS | TKT1 | | | |
| 80. ACKr | ATPS4r | SUCOAS | TKT2 | | | |
| 81. ACKr | FRD2 | ME1x | ME2 | PYK | | |
| 82. ACKr | ME1x | ME2 | PYK | SUCD4 | | |
| 83. ADHEr | AKGD | ASNS2 | ATPS4r | LDH_D | PTAr | |
| 84. ADHEr | AKGD | ATPS4r | CBMK2 | LDH_D | PTAr | |
| 85. ADHEr | AKGD | ATPS4r | GLUDy | LDH_D | PTAr | |
| 86. ADHEr | AKGD | ATPS4r | LDH_D | PTAr | | |
| 87. ADHEr | AKGD | ATPS4r | LDH_D | PTAr | RPE | |
| 88. ADHEr | AKGD | ATPS4r | LDH_D | PTAr | TAL | |
| 89. ADHEr | AKGD | ATPS4r | LDH_D | PTAr | TKT1 | |
| 90. ADHEr | AKGD | ATPS4r | LDH_D | PTAr | TKT2 | |
| 91. ADHEr | ALAR | ASNS2 | LDH_D | ME2 | PRO1z | SUCD4 |

TABLE 1-continued

The list of all strains identified by OptKnock that are most likely to provide increased fumarate yields in *E. Coli*.

| # | | | | | | | |
|---|---|---|---|---|---|---|---|
| 92. | ADHEr | ALAR | CBMK2 | GLUDy | LDH_D | PRO1z | SUCD4 |
| 93. | ADHEr | ALAR | CBMK2 | LDH_D | ME2 | PRO1z | SUCD4 |
| 94. | ADHEr | ALAR | FUM | LDH_D | PRO1z | SUCD4 | |
| 95. | ADHEr | ALAR | G5SD | LDH_D | ME2 | PRO1z | SUCD4 |
| 96. | ADHEr | ALAR | GLCpts | LDH_D | ME2 | PRO1z | SUCD4 |
| 97. | ADHEr | ALAR | GLU5K | LDH_D | ME2 | PRO1z | SUCD4 |
| 98. | ADHEr | ALAR | GLUDy | LDH_D | ME2 | PRO1z | SUCD4 |
| 99. | ADHEr | ALAR | GLUDy | LDH_D | PRO1z | SUCD4 | |
| 100. | ADHEr | ALAR | GLUDy | LDH_D | PRO1z | SUCD4 | THD2 |
| 101. | ADHEr | ALAR | LDH_D | ME2 | PRO1z | SUCD4 | |
| 102. | ADHEr | ALAR | LDH_D | ME2 | PRO1z | SUCD4 | THD2 |
| 103. | ADHEr | ASNS2 | ATPS4r | LDH_D | PDH | PFLi | |
| 104. | ADHEr | ASNS2 | ATPS4r | LDH_D | PTAr | SUCOAS | |
| 105. | ADHEr | ASNS2 | CBMK2 | FRD2 | G5SD | GLUDy | LDH_D |
| 106. | ADHEr | ASNS2 | CBMK2 | FRD2 | G5SD | LDH_D | ME2 |
| 107. | ADHEr | ASNS2 | CBMK2 | FRD2 | GLU5K | GLUDy | LDH_D |
| 108. | ADHEr | ASNS2 | CBMK2 | FRD2 | GLU5K | LDH_D | ME2 |
| 109. | ADHEr | ASNS2 | CBMK2 | FRD2 | LDH_D | ME2 | |
| 110. | ADHEr | ASNS2 | DAAD | LDH_D | ME2 | PRO1z | SUCD4 |
| 111. | ADHEr | ASNS2 | FRD2 | G5SD | GLUDy | LDH_D | |
| 112. | ADHEr | ASNS2 | FRD2 | G5SD | GLUDy | LDH_D | ME2 |
| 113. | ADHEr | ASNS2 | FRD2 | G5SD | GLUDy | LDH_D | THD2 |
| 114. | ADHEr | ASNS2 | FRD2 | G5SD | LDH_D | ME2 | |
| 115. | ADHEr | ASNS2 | FRD2 | G5SD | LDH_D | ME2 | THD2 |
| 116. | ADHEr | ASNS2 | FRD2 | GLU5K | GLUDy | LDH_D | |
| 117. | ADHEr | ASNS2 | FRD2 | GLU5K | GLUDy | LDH_D | ME2 |
| 118. | ADHEr | ASNS2 | FRD2 | GLU5K | GLUDy | LDH_D | THD2 |
| 119. | ADHEr | ASNS2 | FRD2 | GLU5K | LDH_D | ME2 | |
| 120. | ADHEr | ASNS2 | FRD2 | GLU5K | LDH_D | ME2 | THD2 |
| 121. | ADHEr | ASNS2 | FRD2 | LDH_D | ME2 | | |
| 122. | ADHEr | ASNS2 | FRD2 | LDH_D | ME2 | | |
| 123. | ADHEr | ASNS2 | G5SD | GLUDy | LDH_D | PRO1z | SUCD4 |
| 124. | ADHEr | ASNS2 | G5SD | LDH_D | ME2 | SUCD4 | THD2 |
| 125. | ADHEr | ASNS2 | GLU5K | GLUDy | LDH_D | PRO1z | SUCD4 |
| 126. | ADHEr | ASNS2 | GLU5K | LDH_D | ME2 | SUCD4 | THD2 |
| 127. | ADHEr | ASNS2 | LDH_D | ME2 | PTAr | SUCD4 | |
| 128. | ADHEr | ATPS4r | CBMK2 | LDH_D | PDH | PFLi | |
| 129. | ADHEr | ATPS4r | CBMK2 | LDH_D | PTAr | SUCOAS | |
| 130. | ADHEr | ATPS4r | G5SD | LDH_D | PDH | PFLi | |
| 131. | ADHEr | ATPS4r | GLU5K | LDH_D | PDH | PFLi | |
| 132. | ADHEr | ATPS4r | GLUDy | LDH_D | PDH | PFLi | |
| 133. | ADHEr | ATPS4r | GLUDy | LDH_D | PTAr | SUCOAS | |
| 134. | ADHEr | ATPS4r | LDH_D | NADH12 | PFLi | THD2 | |
| 135. | ADHEr | ATPS4r | LDH_D | PDH | PFLi | | |
| 136. | ADHEr | ATPS4r | LDH_D | PDH | PFLi | PTAr | |
| 137. | ADHEr | ATPS4r | LDH_D | PDH | PFLi | RPE | |
| 138. | ADHEr | ATPS4r | LDH_D | PDH | PFLi | TAL | |
| 139. | ADHEr | ATPS4r | LDH_D | PDH | PFLi | TKT1 | |
| 140. | ADHEr | ATPS4r | LDH_D | PDH | PFLi | TKT2 | |
| 141. | ADHEr | ATPS4r | LDH_D | PTAr | RPE | SUCOAS | |
| 142. | ADHEr | ATPS4r | LDH_D | PTAr | SUCOAS | | |
| 143. | ADHEr | ATPS4r | LDH_D | PTAr | SUCOAS | TAL | |
| 144. | ADHEr | ATPS4r | LDH_D | PTAr | SUCOAS | TKT1 | |
| 145. | ADHEr | ATPS4r | LDH_D | PTAr | SUCOAS | TKT2 | |
| 146. | ADHEr | CBMK2 | DAAD | GLUDy | LDH_D | PRO1z | SUCD4 |
| 147. | ADHEr | CBMK2 | DAAD | LDH_D | ME2 | PRO1z | SUCD4 |
| 148. | ADHEr | CBMK2 | FRD2 | G5SD | LDH_D | ME2 | |
| 149. | ADHEr | CBMK2 | FRD2 | GLCpts | GLUDy | LDH_D | ME2 |
| 150. | ADHEr | CBMK2 | FRD2 | GLCpts | LDH_D | ME2 | |
| 151. | ADHEr | CBMK2 | FRD2 | GLU5K | LDH_D | ME2 | |
| 152. | ADHEr | CBMK2 | FRD2 | GLUDy | LDH_D | | |
| 153. | ADHEr | CBMK2 | FRD2 | GLUDy | LDH_D | ME2 | |
| 154. | ADHEr | CBMK2 | FRD2 | GLUDy | LDH_D | ME2 | THD2 |
| 155. | ADHEr | CBMK2 | FRD2 | GLUDy | LDH_D | THD2 | |
| 156. | ADHEr | CBMK2 | FRD2 | LDH_D | ME2 | | |
| 157. | ADHEr | CBMK2 | FRD2 | LDH_D | ME2 | PFLi | THD2 |
| 158. | ADHEr | CBMK2 | FRD2 | LDH_D | ME2 | PTAr | THD2 |
| 159. | ADHEr | CBMK2 | FRD2 | LDH_D | ME2 | THD2 | |
| 160. | ADHEr | CBMK2 | GLUDy | LDH_D | ME2 | PRO1z | SUCD4 |
| 161. | ADHEr | CBMK2 | GLUDy | LDH_D | ME2 | SUCD4 | THD2 |
| 162. | ADHEr | CBMK2 | GLUDy | LDH_D | PRO1z | SUCD4 | |
| 163. | ADHEr | CBMK2 | GLUDy | LDH_D | PRO1z | SUCD4 | THD2 |
| 164. | ADHEr | CBMK2 | LDH_D | ME2 | PTAr | SUCD4 | |
| 165. | ADHEr | CBMK2 | LDH_D | ME2 | SUCD4 | THD2 | |
| 166. | ADHEr | DAAD | FUM | LDH_D | PRO1z | SUCD4 | |
| 167. | ADHEr | DAAD | G5SD | LDH_D | ME2 | PRO1z | SUCD4 |
| 168. | ADHEr | DAAD | GLCpts | LDH_D | ME2 | PRO1z | SUCD4 |

TABLE 1-continued

The list of all strains identified by OptKnock that are most likely to provide increased fumarate yields in *E. Coli*.

| # | | | | | | |
|---|---|---|---|---|---|---|
| 169. | ADHEr | DAAD | GLU5K | LDH_D | ME2 | PRO1z | SUCD4 |
| 170. | ADHEr | DAAD | GLUDy | LDH_D | ME2 | PRO1z | SUCD4 |
| 171. | ADHEr | DAAD | GLUDy | LDH_D | PRO1z | SUCD4 | |
| 172. | ADHEr | DAAD | GLUDy | LDH_D | PRO1z | SUCD4 | THD2 |
| 173. | ADHEr | DAAD | LDH_D | ME2 | PRO1z | SUCD4 | |
| 174. | ADHEr | DAAD | LDH_D | ME2 | PRO1z | SUCD4 | THD2 |
| 175. | ADHEr | FDH2 | GLUDy | LDH_D | NADH12 | NADH6 | PRO1z |
| 176. | ADHEr | FDH2 | LDH_D | ME2 | NADH12 | NADH6 | THD2 |
| 177. | ADHEr | FRD2 | FUM | LDH_D | | | |
| 178. | ADHEr | FRD2 | FUM | LDH_D | MDH | PYK | |
| 179. | ADHEr | FRD2 | G5SD | GLCpts | LDH_D | ME2 | |
| 180. | ADHEr | FRD2 | G5SD | LDH_D | ME2 | | |
| 181. | ADHEr | FRD2 | G5SD | LDH_D | ME2 | PTAr | THD2 |
| 182. | ADHEr | FRD2 | GLCpts | GLU5K | LDH_D | ME2 | |
| 183. | ADHEr | FRD2 | GLCpts | GLUDy | LDH_D | ME2 | |
| 184. | ADHEr | FRD2 | GLCpts | GLUDy | LDH_D | ME2 | PTAr |
| 185. | ADHEr | FRD2 | GLCpts | LDH_D | ME1x | ME2 | PYK |
| 186. | ADHEr | FRD2 | GLCpts | LDH_D | ME2 | | |
| 187. | ADHEr | FRD2 | GLU5K | LDH_D | ME2 | | |
| 188. | ADHEr | FRD2 | GLU5K | LDH_D | ME2 | PTAr | THD2 |
| 189. | ADHEr | FRD2 | GLUDy | HEX1 | LDH_D | ME2 | THD2 |
| 190. | ADHEr | FRD2 | GLUDy | HEX1 | LDH_D | THD2 | |
| 191. | ADHEr | FRD2 | GLUDy | LDH_D | | | |
| 192. | ADHEr | FRD2 | GLUDy | LDH_D | ME2 | | |
| 193. | ADHEr | FRD2 | GLUDy | LDH_D | ME2 | PFLi | THD2 |
| 194. | ADHEr | FRD2 | GLUDy | LDH_D | ME2 | THD2 | |
| 195. | ADHEr | FRD2 | GLUDy | LDH_D | THD2 | | |
| 196. | ADHEr | FRD2 | HEX1 | LDH_D | ME2 | THD2 | |
| 197. | ADHEr | FRD2 | LDH_D | ME2 | | | |
| 198. | ADHEr | FRD2 | LDH_D | ME2 | PFLi | PTAr | THD2 |
| 199. | ADHEr | FRD2 | LDH_D | ME2 | PFLi | THD2 | |
| 200. | ADHEr | FRD2 | LDH_D | ME2 | PTAr | THD2 | |
| 201. | ADHEr | FRD2 | LDH_D | ME2 | THD2 | | |
| 202. | ADHEr | FRD2 | ME1x | ME2 | PYK | | |
| 203. | ADHEr | GLCpts | GLUDy | LDH_D | ME2 | PRO1z | SUCD4 |
| 204. | ADHEr | GLCpts | GLUDy | LDH_D | ME2 | PTAr | SUCD4 |
| 205. | ADHEr | GLCpts | LDH_D | ME1x | ME2 | PYK | SUCD4 |
| 206. | ADHEr | GLCpts | LDH_D | ME2 | PTAr | SUCD4 | |
| 207. | ADHEr | GLU5K | LDH_D | | | | |
| 208. | ADHEr | GLUDy | HEX1 | LDH_D | ME2 | SUCD4 | THD2 |
| 209. | ADHEr | GLUDy | HEX1 | LDH_D | PRO1z | SUCD4 | THD2 |
| 210. | ADHEr | GLUDy | LDH_D | ME2 | PRO1z | SUCD4 | |
| 211. | ADHEr | GLUDy | LDH_D | ME2 | PRO1z | SUCD4 | THD2 |
| 212. | ADHEr | GLUDy | LDH_D | ME2 | PTAr | SUCD4 | |
| 213. | ADHEr | GLUDy | LDH_D | ME2 | SUCD4 | THD2 | |
| 214. | ADHEr | GLUDy | LDH_D | PRO1z | SUCD4 | | |
| 215. | ADHEr | GLUDy | LDH_D | PRO1z | SUCD4 | THD2 | |
| 216. | ADHEr | GLUDy | LDH_D | SUCOAS | TKT2 | | |
| 217. | ADHEr | HEX1 | LDH_D | ME2 | SUCD4 | THD2 | |
| 218. | ADHEr | LDH_D | ME2 | PTAr | SUCD4 | | |
| 219. | ADHEr | LDH_D | ME2 | SUCD4 | THD2 | | |
| 220. | ADHEr | THD2 | | | | | |
| 221. | AKGD | ASNS2 | ATPS4r | CBMK2 | PTAr | | |
| 222. | AKGD | ASNS2 | ATPS4r | GLUDy | PTAr | | |
| 223. | AKGD | ASNS2 | ATPS4r | PTAr | | | |
| 224. | AKGD | ASNS2 | ATPS4r | PTAr | RPE | | |
| 225. | AKGD | ASNS2 | ATPS4r | PTAr | TAL | | |
| 226. | AKGD | ASNS2 | ATPS4r | PTAr | TKT1 | | |
| 227. | AKGD | ASNS2 | ATPS4r | PTAr | TKT2 | | |
| 228. | AKGD | ATPS4r | CBMK2 | GLUDy | PTAr | | |
| 229. | AKGD | ATPS4r | CBMK2 | PTAr | | | |
| 230. | AKGD | ATPS4r | CBMK2 | PTAr | RPE | | |
| 231. | AKGD | ATPS4r | CBMK2 | PTAr | TAL | | |
| 232. | AKGD | ATPS4r | CBMK2 | PTAr | TKT1 | | |
| 233. | AKGD | ATPS4r | CBMK2 | PTAr | TKT2 | | |
| 234. | AKGD | ATPS4r | GLUDy | PTAr | | | |
| 235. | AKGD | ATPS4r | GLUDy | PTAr | RPE | | |
| 236. | AKGD | ATPS4r | GLUDy | PTAr | TAL | | |
| 237. | AKGD | ATPS4r | GLUDy | PTAr | TKT1 | | |
| 238. | AKGD | ATPS4r | GLUDy | PTAr | TKT2 | | |
| 239. | AKGD | ATPS4r | PPCK | PTAr | PYK | | |
| 240. | AKGD | ATPS4r | PTAr | | | | |
| 241. | AKGD | ATPS4r | PTAr | RPE | | | |
| 242. | AKGD | ATPS4r | PTAr | TAL | | | |
| 243. | AKGD | ATPS4r | PTAr | TKT1 | | | |
| 244. | AKGD | ATPS4r | PTAr | TKT2 | | | |
| 245. | ALAR | FUM | PRO1z | SUCD4 | | | |

TABLE 1-continued

The list of all strains identified by OptKnock that are most likely to provide increased fumarate yields in *E. Coli*.

| # | | | | |
|---|---|---|---|---|
| 246. | ASNS2 | ATPS4r | CBMK2 | PTAr | SUCOAS |
| 247. | ASNS2 | ATPS4r | FRD2 | PFLi | |
| 248. | ASNS2 | ATPS4r | GLUDy | PTAr | SUCOAS |
| 249. | ASNS2 | ATPS4r | PDH | PFLi | |
| 250. | ASNS2 | ATPS4r | PTAr | RPE | SUCOAS |
| 251. | ASNS2 | ATPS4r | PTAr | SUCOAS | |
| 252. | ASNS2 | ATPS4r | PTAr | SUCOAS | TAL |
| 253. | ASNS2 | ATPS4r | PTAr | SUCOAS | TKT1 |
| 254. | ASNS2 | ATPS4r | PTAr | SUCOAS | TKT2 |
| 255. | ATPS4r | CBMK2 | FRD2 | PFLi | |
| 256. | ATPS4r | CBMK2 | GLUDy | PTAr | SUCOAS |
| 257. | ATPS4r | CBMK2 | PDH | PFLi | |
| 258. | ATPS4r | CBMK2 | PTAr | RPE | SUCOAS |
| 259. | ATPS4r | CBMK2 | PTAr | SUCOAS | |
| 260. | ATPS4r | CBMK2 | PTAr | SUCOAS | TAL |
| 261. | ATPS4r | CBMK2 | PTAr | SUCOAS | TKT1 |
| 262. | ATPS4r | CBMK2 | PTAr | SUCOAS | TKT2 |
| 263. | ATPS4r | FBA | FRD2 | GLUDy | PFLi |
| 264. | ATPS4r | FBA | FRD2 | PFLi | |
| 265. | ATPS4r | FDH2 | PTAr | THD5 | |
| 266. | ATPS4r | FRD2 | G5SD | PFLi | |
| 267. | ATPS4r | FRD2 | GLU5K | PFLi | |
| 268. | ATPS4r | FRD2 | GLUDy | PFK | PFLi |
| 269. | ATPS4r | FRD2 | GLUDy | PFLi | |
| 270. | ATPS4r | FRD2 | GLUDy | PFLi | PGI |
| 271. | ATPS4r | FRD2 | GLUDy | PFLi | TPI |
| 272. | ATPS4r | FRD2 | ME1x | ME2 | PYK |
| 273. | ATPS4r | FRD2 | ME2 | PFLi | THD2 |
| 274. | ATPS4r | FRD2 | PFK | PFLi | |
| 275. | ATPS4r | FRD2 | PFLi | | |
| 276. | ATPS4r | FRD2 | PFLi | PGI | |
| 277. | ATPS4r | FRD2 | PFLi | PPCK | PYK |
| 278. | ATPS4r | FRD2 | PFLi | TPI | |
| 279. | ATPS4r | FUM | PPCK | PTAr | |
| 280. | ATPS4r | G5SD | PDH | PFLi | |
| 281. | ATPS4r | GLCpts | ME1x | ME2 | PYK |
| 282. | ATPS4r | GLU5K | PDH | PFLi | |
| 283. | ATPS4r | GLUDy | PDH | PFLi | |
| 284. | ATPS4r | GLUDy | PTAr | RPE | SUCOAS |
| 285. | ATPS4r | GLUDy | PTAr | SUCOAS | |
| 286. | ATPS4r | GLUDy | PTAr | SUCOAS | TAL |
| 287. | ATPS4r | GLUDy | PTAr | SUCOAS | TKT1 |
| 288. | ATPS4r | GLUDy | PTAr | SUCOAS | TKT2 |
| 289. | ATPS4r | MDH | PPCK | PTAr | |
| 290. | ATPS4r | ME1x | ME2 | PYK | SUCD4 |
| 291. | ATPS4r | ME2 | NADH12 | PFLi | THD2 |
| 292. | ATPS4r | PDH | PFLi | | |
| 293. | ATPS4r | PDH | PFLi | PPCK | PYK |
| 294. | ATPS4r | PDH | PFLi | PTAr | |
| 295. | ATPS4r | PDH | PFLi | RPE | |
| 296. | ATPS4r | PDH | PFLi | TAL | |
| 297. | ATPS4r | PDH | PFLi | TKT1 | |
| 298. | ATPS4r | PDH | PFLi | TKT2 | |
| 299. | ATPS4r | PPCK | PTAr | PYK | SUCOAS |
| 300. | ATPS4r | PTAr | RPE | SUCOAS | |
| 301. | ATPS4r | PTAr | SUCOAS | | |
| 302. | ATPS4r | PTAr | SUCOAS | TAL | |
| 303. | ATPS4r | PTAr | SUCOAS | TKT1 | |
| 304. | ATPS4r | PTAr | SUCOAS | TKT2 | |
| 305. | CBMK2 | PGDH | TKT1 | | |
| 306. | DAAD | FUM | PRO1z | SUCD4 | |
| 307. | EDA | FRD2 | FUM | MDH | PYK |
| 308. | EDA | FRD2 | ME1x | ME2 | PYK |
| 309. | EDA | FUM | MDH | PYK | SUCD4 |
| 310. | EDA | ME1x | ME2 | PYK | SUCD4 |
| 311. | ENO | FUM | SUCD4 | | |
| 312. | FRD2 | FUM | | | |
| 313. | FRD2 | FUM | G6PDHy | MDH | PYK |
| 314. | FRD2 | FUM | GLCpts | MDH | PYK |
| 315. | FRD2 | FUM | MDH | PGDHY | PYK |
| 316. | FRD2 | FUM | MDH | PGL | PYK |
| 317. | FRD2 | FUM | MDH | PYK | |
| 318. | FRD2 | G6PDHy | ME1x | ME2 | PYK |
| 319. | FRD2 | GLCpts | ME1x | ME2 | PYK |
| 320. | FRD2 | GLUDy | ME1x | ME2 | PYK |
| 321. | FRD2 | MDH | ME1x | ME2 | |
| 322. | FRD2 | ME1x | ME2 | PFLi | PYK |

TABLE 1-continued

The list of all strains identified by OptKnock that are most likely to provide increased fumarate yields in E. Coli.

| # | | | | | |
|---|---|---|---|---|---|
| 323. | FRD2 | ME1x | ME2 | PGDHY | PYK |
| 324. | FRD2 | ME1x | ME2 | PGL | PYK |
| 325. | FRD2 | ME1x | ME2 | PTAr | PYK |
| 326. | FRD2 | ME1x | ME2 | PYK | |
| 327. | FRD2 | ME1x | ME2 | PYK | RPE |
| 328. | FRD2 | ME1x | ME2 | PYK | TKT2 |
| 329. | FUM | G6PDHy | MDH | PYK | SUCD4 |
| 330. | FUM | GLCpts | MDH | PYK | SUCD4 |
| 331. | FUM | GLUDy | PRO1z | SUCD4 | |
| 332. | FUM | MDH | PGDHY | PYK | SUCD4 |
| 333. | FUM | MDH | PGL | PYK | SUCD4 |
| 334. | FUM | MDH | SUCD4 | | |
| 335. | FUM | ME2 | SUCD4 | | |
| 336. | FUM | PGM | SUCD4 | | |
| 337. | FUM | PPCK | SUCD4 | | |
| 338. | G6PDHy | ME1x | ME2 | PYK | SUCD4 |
| 339. | GLCpts | ME1x | ME2 | PYK | SUCD4 |
| 340. | GLUDy | ME1x | ME2 | PYK | SUCD4 |
| 341. | MDH | ME1x | ME2 | SUCD4 | |
| 342. | ME1x | ME2 | PFLi | PYK | SUCD4 |
| 343. | ME1x | ME2 | PGDHY | PYK | SUCD4 |
| 344. | ME1x | ME2 | PGL | PYK | SUCD4 |
| 345. | ME1x | ME2 | PTAr | PYK | SUCD4 |
| 346. | ME1x | ME2 | PYK | RPE | SUCD4 |
| 347. | ME1x | ME2 | PYK | SUCD4 | |
| 348. | ME1x | ME2 | PYK | SUCD4 | TKT2 |

TABLE 2

The list of all strains identified by OptKnock that are most likely to provide increased malate yields in E. Coli. Note that some of the malate production strategies overlap with the fumarate production strains.

| # | | | | | |
|---|---|---|---|---|---|
| 1. | AKGD | ATPS4r | PTAr | | |
| 2. | ACKr | AKGD | ATPS4r | | |
| 3. | ACKr | ATPS4r | SUCOAS | | |
| 4. | ATPS4r | PTAr | SUCOAS | | |
| 5. | ATPS4r | PDH | PFLi | | |
| 6. | ATPS4r | FRD2 | PFLi | | |
| 7. | LDH_D | PFK | SUCOAS | | |
| 8. | ADHEr | FRD2 | GLUDy | LDH_D | |
| 9. | ADHEr | FRD2 | LDH_D | ME2 | |
| 10. | ACKr | AKGD | ATPS4r | GLUDy | |
| 11. | AKGD | ATPS4r | GLUDy | PTAr | |
| 12. | ATPS4r | GLUDy | PTAr | SUCOAS | |
| 13. | ACKr | ATPS4r | GLUDy | SUCOAS | |
| 14. | AKGD | ATPS4r | PTAr | TKT2 | |
| 15. | ACKr | AKGD | ATPS4r | TKT2 | |
| 16. | ATPS4r | PTAr | SUCOAS | TKT2 | |
| 17. | ACKr | ATPS4r | SUCOAS | TKT2 | |
| 18. | ATPS4r | FUM | GLUDy | PFLi | |
| 19. | ACKr | AKGD | ATPS4r | RPE | |
| 20. | AKGD | ATPS4r | PTAr | RPE | |
| 21. | ACKr | ATPS4r | RPE | SUCOAS | |
| 22. | ATPS4r | PTAr | RPE | SUCOAS | |
| 23. | ACKr | AKGD | ATPS4r | TKT1 | |
| 24. | AKGD | ATPS4r | PTAr | TAL | |
| 25. | AKGD | ATPS4r | PTAr | TKT1 | |
| 26. | ACKr | AKGD | ATPS4r | TAL | |
| 27. | AKGD | ATPS4r | CBMK2 | PTAr | |
| 28. | ACKr | AKGD | ATPS4r | CBMK2 | |
| 29. | ACKr | ATPS4r | SUCOAS | TAL | |
| 30. | ATPS4r | PTAr | SUCOAS | TAL | |
| 31. | ACKr | ATPS4r | SUCOAS | TKT1 | |
| 32. | ATPS4r | PTAr | SUCOAS | TKT1 | |
| 33. | ACKr | AKGD | ASNS2 | ATPS4r | |
| 34. | AKGD | ASNS2 | ATPS4r | PTAr | |
| 35. | ATPS4r | CBMK2 | PTAr | SUCOAS | |
| 36. | ACKr | ATPS4r | CBMK2 | SUCOAS | |
| 37. | ACKr | ASNS2 | ATPS4r | SUCOAS | |
| 38. | ASNS2 | ATPS4r | PTAr | SUCOAS | |
| 39. | ATPS4r | FRD2 | PFLi | PGI | |
| 40. | ATPS4r | FRD2 | PFK | PFLi | |
| 41. | ATPS4r | FRD2 | PFLi | TPI | |
| 42. | ATPS4r | FBA | FRD2 | PFLi | |
| 43. | FRD2 | ME1x | ME2 | PYK | |
| 44. | ME1x | ME2 | PYK | SUCD4 | |
| 45. | ATPS4r | FRD2 | GLUDy | PFLi | |
| 46. | ATPS4r | GLUDy | PDH | PFLi | |
| 47. | ACKr | ATPS4r | PDH | PFLi | |
| 48. | ATPS4r | PDH | PFLi | PTAr | |
| 49. | ATPS4r | PDH | PFLi | TKT2 | |
| 50. | ATPS4r | PDH | PFLi | RPE | |
| 51. | ATPS4r | PDH | PFLi | TAL | |
| 52. | ATPS4r | PDH | PFLi | TKT1 | |
| 53. | ATPS4r | CBMK2 | PDH | PFLi | |
| 54. | ATPS4r | GLU5K | PDH | PFLi | |
| 55. | ATPS4r | G5SD | PDH | PFLi | |
| 56. | ASNS2 | ATPS4r | PDH | PFLi | |
| 57. | ASPT | ATPS4r | FUM | PFLi | |
| 58. | ATPS4r | CBMK2 | FRD2 | PFLi | |
| 59. | ATPS4r | FRD2 | GLU5K | PFLi | |
| 60. | ATPS4r | FRD2 | G5SD | PFLi | |
| 61. | ASNS2 | ATPS4r | FRD2 | PFLi | |
| 62. | ADHEr | ATPS4r | FUM | GLUDy | |
| 63. | MDH | ME1x | ME2 | SUCD4 | |
| 64. | FRD2 | MDH | ME1x | ME2 | |
| 65. | ATPS4r | MDH | PPCK | PTAr | |
| 66. | ACKr | ATPS4r | MDH | PPCK | |
| 67. | ADHEr | FRD2 | LDH_D | ME2 | THD2 |
| 68. | ADHEr | FRD2 | GLUDy | LDH_D | THD2 |
| 69. | ADHEr | FRD2 | GLUDy | LDH_D | ME2 |
| 70. | ADHEr | CBMK2 | FRD2 | GLUDy | LDH_D |
| 71. | ADHEr | LDH_D | ME2 | SUCD4 | THD2 |
| 72. | ADHEr | FUM | GLUDy | LDH_D | SUCD4 |
| 73. | ADHEr | ASPT | FUM | GLUDy | LDH_D |
| 74. | ADHEr | FRD2 | GLCpts | LDH_D | ME2 |
| 75. | ADHEr | GLUDy | LDH_D | PRO1z | SUCD4 |
| 76. | ADHEr | CBMK2 | FRD2 | LDH_D | ME2 |
| 77. | ADHEr | FRD2 | GLU5K | LDH_D | ME2 |
| 78. | ADHEr | FRD2 | G5SD | LDH_D | ME2 |
| 79. | ADHEr | ASNS2 | FRD2 | LDH_D | ME2 |
| 80. | ADHEr | FUM | GLUDy | LDH_D | NADH6 |

TABLE 2-continued

The list of all strains identified by OptKnock that are most likely to provide increased malate yields in *E. Coli*. Note that some of the malate production strategies overlap with the fumarate production strains.

| | | | | | |
|---|---|---|---|---|---|
| 81. | ADHEr | ASPT | FUM | LDH_D | ME2 |
| 82. | FRD2 | GLCpts | ME1x | ME2 | PYK |
| 83. | GLCpts | ME1x | ME2 | PYK | SUCD4 |
| 84. | ACKr | ADHEr | LDH_D | ME2 | SUCD4 |
| 85. | ADHEr | LDH_D | ME2 | PTAr | SUCD4 |
| 86. | ADHEr | FRD2 | ME1x | ME2 | PYK |
| 87. | FRD2 | ME1x | ME2 | PGL | PYK |
| 88. | FRD2 | G6PDHy | ME1x | ME2 | PYK |
| 89. | FRD2 | ME1x | ME2 | PGDHY | PYK |
| 90. | EDA | ME1x | ME2 | PYK | SUCD4 |
| 91. | EDA | FRD2 | ME1x | ME2 | PYK |
| 92. | ME1x | ME2 | PGDHY | PYK | SUCD4 |
| 93. | ME1x | ME2 | PGL | PYK | SUCD4 |
| 94. | G6PDHy | ME1x | ME2 | PYK | SUCD4 |
| 95. | ACKr | AKGD | ATPS4r | PPCK | PYK |
| 96. | AKGD | ATPS4r | PPCK | PTAr | PYK |
| 97. | FRD2 | ME1x | ME2 | PFLi | PYK |
| 98. | ACKr | ATPS4r | PPCK | PYK | SUCOAS |
| 99. | ATPS4r | PPCK | PTAr | PYK | SUCOAS |
| 100. | FRD2 | ME1x | ME2 | PTAr | PYK |
| 101. | ACKr | ME1x | ME2 | PYK | SUCD4 |
| 102. | ME1x | ME2 | PTAr | PYK | SUCD4 |
| 103. | ACKr | FRD2 | ME1x | ME2 | PYK |
| 104. | ACKr | AKGD | ATPS4r | GLUDy | TKT2 |
| 105. | AKGD | ATPS4r | GLUDy | PTAr | TKT2 |
| 106. | ATPS4r | GLUDy | PTAr | SUCOAS | TKT2 |
| 107. | ACKr | ATPS4r | GLUDy | SUCOAS | TKT2 |
| 108. | AKGD | ATPS4r | GLUDy | PTAr | RPE |
| 109. | ACKr | AKGD | ATPS4r | GLUDy | RPE |
| 110. | ATPS4r | GLUDy | PTAr | RPE | SUCOAS |
| 111. | ATPS4r | GLUDy | RPE | SUCOAS | |
| 112. | AKGD | ATPS4r | GLUDy | PTAr | TAL |
| 113. | ACKr | AKGD | ATPS4r | GLUDy | TAL |
| 114. | AKGD | ATPS4r | GLUDy | PTAr | TKT1 |
| 115. | ACKr | AKGD | ATPS4r | GLUDy | TKT1 |
| 116. | ATPS4r | FRD2 | PFLi | PPCK | PYK |
| 117. | ATPS4r | GLUDy | PTAr | SUCOAS | TKT1 |
| 118. | ACKr | ATPS4r | GLUDy | SUCOAS | TKT1 |
| 119. | ACKr | ATPS4r | GLUDy | SUCOAS | TAL |
| 120. | ATPS4r | GLUDy | PTAr | SUCOAS | TAL |
| 121. | ACKr | ATPS4r | CBMK2 | GLUDy | |
| 122. | AKGD | ATPS4r | CBMK2 | GLUDy | PTAr |
| 123. | ACKr | AKGD | ASNS2 | ATPS4r | GLUDy |
| 124. | AKGD | ASNS2 | ATPS4r | GLUDy | PTAr |
| 125. | ATPS4r | CBMK2 | GLUDy | PTAr | SUCOAS |
| 126. | ACKr | ATPS4r | CBMK2 | GLUDy | SUCOAS |
| 127. | ASNS2 | ATPS4r | GLUDy | PTAr | SUCOAS |
| 128. | ACKr | ASNS2 | ATPS4r | GLUDy | SUCOAS |
| 129. | ATPS4r | FUM | GLUDy | PFLi | TKT2 |
| 130. | ATPS4r | FUM | ME2 | PFLi | THD2 |
| 131. | ACKr | AKGD | ATPS4r | CBMK2 | TKT2 |
| 132. | AKGD | ATPS4r | CBMK2 | PTAr | TKT2 |
| 133. | ATPS4r | ME2 | NADH12 | PFLi | THD2 |
| 134. | ATPS4r | FUM | GLUDy | PFLi | RPE |
| 135. | AKGD | ASNS2 | ATPS4r | PTAr | TKT2 |
| 136. | ACKr | AKGD | ASNS2 | ATPS4r | TKT2 |
| 137. | ACKr | ATPS4r | CBMK2 | SUCOAS | TKT2 |
| 138. | ATPS4r | CBMK2 | PTAr | SUCOAS | TKT2 |
| 139. | ATPS4r | FUM | GLUDy | PFLi | TKT1 |
| 140. | ATPS4r | FUM | GLUDy | PFLi | TAL |
| 141. | ACKr | ASNS2 | ATPS4r | SUCOAS | TKT2 |
| 142. | ASNS2 | ATPS4r | PTAr | SUCOAS | TKT2 |
| 143. | ATPS4r | CBMK2 | FUM | GLUDy | PFLi |
| 144. | ACKr | ATPS4r | FUM | GLUDy | PFLi |
| 145. | ATPS4r | FUM | GLUDy | PFLi | PTAr |
| 146. | ACKr | AKGD | ATPS4r | CBMK2 | RPE |
| 147. | AKGD | ATPS4r | CBMK2 | PTAr | RPE |
| 148. | ATPS4r | FUM | GLU5K | GLUDy | PFLi |
| 149. | ATPS4r | FUM | G5SD | GLUDy | PFLi |
| 150. | ASNS2 | ATPS4r | FUM | GLUDy | PFLi |
| 151. | AKGD | ASNS2 | ATPS4r | PTAr | RPE |
| 152. | ACKr | AKGD | ASNS2 | ATPS4r | RPE |
| 153. | ATPS4r | CBMK2 | PTAr | RPE | SUCOAS |
| 154. | ATPS4r | CBMK2 | PTAr | RPE | SUCOAS |
| 155. | ASNS2 | ATPS4r | PTAr | RPE | SUCOAS |
| 156. | ACKr | ASNS2 | ATPS4r | RPE | SUCOAS |
| 157. | AKGD | ATPS4r | CBMK2 | PTAr | TAL |
| 158. | AKGD | ATPS4r | CBMK2 | PTAr | TKT1 |
| 159. | ACKr | AKGD | ATPS4r | CBMK2 | TAL |
| 160. | ACKr | AKGD | ATPS4r | CBMK2 | TKT1 |
| 161. | ACKr | AKGD | ASNS2 | ATPS4r | TAL |
| 162. | AKGD | ASNS2 | ATPS4r | PTAr | TKT1 |
| 163. | AKGD | ASNS2 | ATPS4r | PTAr | TAL |
| 164. | ACKr | AKGD | ASNS2 | ATPS4r | TKT1 |
| 165. | ACKr | ATPS4r | CBMK2 | SUCOAS | TKT1 |
| 166. | ACKr | ATPS4r | CBMK2 | SUCOAS | TAL |
| 167. | ATPS4r | CBMK2 | PTAr | SUCOAS | TKT1 |
| 168. | ATPS4r | CBMK2 | PTAr | SUCOAS | TAL |
| 169. | AKGD | ASNS2 | ATPS4r | CBMK2 | PTAr |
| 170. | ACKr | AKGD | ASNS2 | ATPS4r | CBMK2 |
| 171. | ACKr | ASNS2 | ATPS4r | SUCOAS | TAL |
| 172. | ASNS2 | ATPS4r | PTAr | SUCOAS | TKT1 |
| 173. | ASNS2 | ATPS4r | PTAr | SUCOAS | TAL |
| 174. | ACKr | ASNS2 | ATPS4r | SUCOAS | TKT1 |
| 175. | ACKr | ASNS2 | ATPS4r | CBMK2 | SUCOAS |
| 176. | ASNS2 | ATPS4r | CBMK2 | PTAr | SUCOAS |
| 177. | ATPS4r | GLCpts | ME1x | ME2 | PYK |
| 178. | ATPS4r | FRD2 | ME2 | PFLi | THD2 |
| 179. | ME1x | ME2 | PFLi | PYK | SUCD4 |
| 180. | FRD2 | GLUDy | ME1x | ME2 | PYK |
| 181. | GLUDy | ME1x | ME2 | PYK | SUCD4 |
| 182. | FRD2 | ME1x | ME2 | PYK | TKT2 |
| 183. | ME1x | ME2 | PYK | SUCD4 | TKT2 |
| 184. | ATPS4r | FRD2 | GLUDy | PFLi | PGI |
| 185. | ATPS4r | FRD2 | GLUDy | PFLi | TPI |
| 186. | ATPS4r | FBA | FRD2 | GLUDy | PFLi |
| 187. | ATPS4r | FRD2 | GLUDy | PFK | PFLi |
| 188. | ATPS4r | PDH | PFLi | PPCK | PYK |
| 189. | ME1x | ME2 | PYK | RPE | SUCD4 |
| 190. | FRD2 | ME1x | ME2 | PYK | RPE |
| 191. | ATPS4r | FRD2 | ME1x | ME2 | PYK |
| 192. | ATPS4r | ME1x | ME2 | PYK | SUCD4 |
| 193. | FUM | GLUDy | ME1x | ME2 | PYK |
| 194. | ASPT | ATPS4r | FUM | PFLi | PGI |
| 195. | FRD2 | ME1x | ME2 | PYK | TKT1 |
| 196. | ME1x | ME2 | PYK | SUCD4 | TAL |
| 197. | ME1x | ME2 | PYK | SUCD4 | TKT1 |
| 198. | FRD2 | ME1x | ME2 | PYK | TAL |
| 199. | ASPT | ATPS4r | FUM | PFLi | TPI |
| 200. | ASPT | ATPS4r | FUM | PFK | PFLi |

TABLE 3

A list of all the reaction stoichiometries and the associated genes known to be associated with the reactions identified for deletion in the strains listed in Tables 1 and 2.

| Reaction Abbreviation | Reaction Name | Reaction Stoichiometry | Associated genes |
|---|---|---|---|
| ACKr | Acetate kinase | [c]: ac + atp <==> actp + adp | (b3115 or b2296 or b1849) |
| ADHEr | Alcohol dehydrogenase | [c]: accoa + (2) h + (2) nadh <==> coa + etoh + (2) nad | (b0356 or b1478 or b1241) |

TABLE 3-continued

A list of all the reaction stoichiometries and the associated genes known to be associated with the reactions identified for deletion in the strains listed in Tables 1 and 2.

| Reaction Abbreviation | Reaction Name | Reaction Stoichiometry | Associated genes |
|---|---|---|---|
| AKGD | Alpha-ketoglutarate dehydrogenase | [c]: akg + coa + nad --> co2 + nadh + succoa | (b0116 and b0726 and b0727) |
| ALAR | Alanine racemase | [c]: ala-L <==> ala-D | b4053 |
| ASNS2 | Asparagine synthetase | [c]: asp-L + atp + nh4 --> amp + asn-L + h + ppi | b3744 |
| ASPT | L-aspartase | [c]: asp-L --> fum + nh4 | b4139 |
| ATPS4r | ATP synthase | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | Carbamate kinase | [c]: atp + co2 + nh4 --> adp + cbp + (2) h | (b0521 or b0323 or b2874) |
| DAAD | D-amino acid dehydrogenase | [c]: ala-D + fad + h2o --> fadh2 + nh4 + pyr | b1189 |
| EDA | 2-dehydro-3-deoxy-phosphogluconate aldolase | [c]: 2ddg6p --> g3p + pyr | b1850 |
| ENO | Enolase | [c]: 2pg <==> h2o + pep | b2779 |
| FBA | Fructose-bis-phosphate aldolase | [c]: fdp <==> dhap + g3p | (b2097 or b2925 or b1773) |
| FRD | Fumarate reductase | [c]: fum + mq18 --> mqn8 + succ | (b4151 and b4152 and b4153 and b4154) |
| FUM | Fumarase | [c]: fum + h2o <==> mal-L | (b1612 or b4122 or b1611) |
| G5SD | Glutamate-5-semialdehyde dehyrogenase | [c]: glu5p + h + nadph --> glu5sa + nadp + pi | b0243 |
| G6PDHy | Glucose-6-phosphate dehydrogenase | [c]: g6p + nadp <==> 6pgl + h + nadph | b1852 |
| GLCpts | D-glucose transport via PTS mechanism | glc-D[e] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | Gluatmate-5-kinase | [c]: atp + glu-L --> adp + glu5p | b0242 |
| GLUDy | Glutamate dehydrogenase | [c]: glu-L + h2o + nadp <==> akg + h + nadph + nh4 | b1761 |
| HEX1 | Hexokinase | [c]: atp + glc-D --> adp + g6p + h | b2388 |
| LDH_D | Lactate dehydrogenase | [c]: lac-D + nad <==> h + nadh + pyr | b1380 or b2133 |
| MDH | Malate dehydrogenase | [c]: mal-L + nad <==> h + nadh + oaa | b3236 |
| ME1x | Malic enzyme (NAD) | [c]: mal-L + nad --> co2 + nadh + pyr | b1479 |
| ME2 | Malic enzyme (NADP) | [c]: mal-L + nadp --> co2 + nadph + pyr | b2463 |
| NADH12 | NADH dehydrogenase (ubiquinone-8) | [c]: h + nadh + ubq8 --> nad + ubq8h2 | b1109 |
| NADH6 | NADH dehydrogenase (ubiquinone-8 and 3.5 protons) | (4.5) h[c] + nadh[c] + ubq8[c] --> (3.5) h[e] + nad[c] + ubq8h2[c] | (b2276 and b2277 and b2278 and b2279 and b2280 and b2281 and b2282 and b2283 and b2284 and b2285 and b2286 and b2287 and b2288) |
| PDH | Pyruvate dehydrogenase | [c]: coa + nad + pyr --> accoa + co2 + nadh | ((b0114 and b0115 and b0116) or (b0116 and b0726 and b0727) or (b0116 and b2903 and b2904 and b2905)) |
| PFK | Phosphofructokinase | [c]: atp + f6p --> adp + fdp + h | (b3916 or b1723) |
| PFLi | Pyruvate formate lyase | [c]: coa + pyr --> accoa + for | (((b0902 and b0903) and b2579) or (b0902 and b0903) or (b0902 and b3114) or (b3951 and b3952)) |
| PGDH | Phosphogluconate dehyrogenase | [c]: 6pgc + nadp --> co2 + nadph + ru5p-D | b2029 |
| PGDHY | Phosphogluconate dehydratase | [c]: 6pgc --> 2ddg6p + h2o | b1851 |
| PGI | Glucose-6-phosphate isomerase | [c]: g6p <==> f6p | b4025 |
| PGL | 6-Phosphogluconolactonase | [c]: 6pgl + h2o --> 6pgc + h | b0767 |
| PGM | Phosphoglycerate mutase | [c]: 3pg <==> 2pg | b3612 |
| PPC | Phosphoenolpyruvate carboxylase | [c]: co2 + h2o + pep --> h + oaa + pi | b3956 |
| PPCK | Phosphoenolpyruvate carboxykinase | [c]: atp + oaa --> adp + co2 + pep | b3403 |
| PRO1z | Proline oxidase | [c]: fad + pro-L --> 1pyr5c + fadh2 + h | b1014 |
| PTAr | Phosphotransacetylase | [c]: accoa + pi <==> actp + coa | b2297 |
| PYK | Pyruvate kinase | [c]: adp + h + pep --> atp + pyr | (b1854 or b1676) |
| RPE | Ribulose-5-phosphate-5-epimerase | [c]: ru5p-D <==> xu5p-D | (b4301 or b3386) |

TABLE 3-continued

A list of all the reaction stoichiometries and the associated genes known to be associated with the reactions identified for deletion in the strains listed in Tables 1 and 2.

| Reaction Abbreviation | Reaction Name | Reaction Stoichiometry | Associated genes |
|---|---|---|---|
| SUCD4 | Succinate dehydrogenase | [c]: fadh2 + ubq8 <==> fad + ubq8h2 | (b0721 and b0722 and b0723 and b0724) |
| SUCOAS | Succinyl-CoA synthetase | [c]: atp + coa + succ <==> adp + pi + succoa | (b0728 and b0729) |
| TAL | Transaldoalse | [c]: g3p + s7p <==> e4p + f6p | (b2464 or b0008) |
| THD2 | NADP transhydrogenase | (2) h[e] + nadh[c] + nadp[c] --> (2) h[c] + nad[c] + nadph[c] | (b1602 and b1603) |
| THD5 | NAD transhydrogenase | [c]: nad + nadph --> nadh + nadp | (b3962 or (b1602 and b1603)) |
| TKT1 | Transketolase | [c]: r5p + xu5p-D <==> g3p + s7p | (b2935 or b2465) |
| TKT2 | Transketolase | [c]: e4p + xu5p-D <==> f6p + g3p | (b2935 or b2465) |
| TPI | Triosephosphate isomerase | [c]: dhap <==> g3p | b3919 |
| VALTA | Valine transaminase | [c]: akg + val-L <==> 3mob + glu-L | b3770 |

TABLE 4

List of the metabolite abbreviations, the corresponding names and locations of all the metabolites that participate in the reactions listed in Table 3.

| Metabolite Abbreviation | Compartment | Metabolite Name |
|---|---|---|
| 13dpg | Cytosol | 3-Phospho-D-glyceroyl phosphate |
| 1pyr5c | Cytosol | 1-Pyrroline-5-carboxylate |
| 2ddg6p | Cytosol | 2-Dehydro-3-deoxy-D-gluconate 6-phosphate |
| 2pg | Cytosol | D-Glycerate 2-phosphate |
| 3mob | Cytosol | 3-Methyl-2-oxobutanoate |
| 3pg | Cytosol | 3-Phospho-D-glycerate |
| 6pgc | Cytosol | 6-Phospho-D-gluconate |
| 6pgl | Cytosol | 6 phospho-D-glucono-1,5-lactone |
| ac | Cytosol | Acetate |
| accoa | Cytosol | Acetyl-CoA |
| actp | Cytosol | Acetyl phosphate |
| adp | Cytosol | Adenosine diphosphate |
| akg | Cytosol | 2-Oxoglutarate |
| ala-D | Cytosol | D-alanine |
| ala-L | Cytosol | L-alanine |
| amp | Cytosol | Adenosine monophosphate |
| asn-L | Cytosol | L-asparagine |
| asp-L | Cytosol | L-aspartate |
| atp | Cytosol | Adenosine triphosphate |
| cbp | Cytosol | Carbamoyl phosphate |
| co2 | Cytosol | Carbon dioxide |
| coa | Cytosol | Coenzyme A |
| dha | Cytosol | Dihydroxyacetone |
| dhap | Cytosol | Dihydroxyacetone phosphate |
| e4p | Cytosol | D-Erythrose 4-phosphate |
| etoh | Cytosol | Ethanol |
| f6p | Cytosol | D-Fructose 6-phosphate |
| fad | Cytosol | Flavin adenine dinucleotide |
| fadh2 | Cytosol | Flavin adenine dinucleotide-reduced |
| fdp | Cytosol | D-Fructose 1,6-bisphosphate |
| for | Cytosol | Formate |
| fum | Cytosol | Fumarate |
| g3p | Cytosol | Glyceraldehyde 3-phosphate |
| g6p | Cytosol | D-Glucose 6-phosphate |
| glc-D[e] | Extra-organism | D-Glucose |
| glu5p | Cytosol | L-glutamate 5-phosphate |
| glu5sa | Cytosol | L-glutamate 5-semialdehyde |
| glu-L | Cytosol | L-Glutamate |
| h | Cytosol | H$^+$ |
| h[e] | Extra-organism | H$^+$ |
| h2o | Cytosol | Water |
| lac-D | Cytosol | D-Lactate |
| mal-L | Cytosol | L-Malate |
| mql-8 | Cytosol | Menaquinol-8 |
| mqn-8 | Cytosol | Menaquinone-8 |
| nad | Cytosol | Nicotinamide adenine dinucleotide |
| nadh | Cytosol | Nicotinamide adenine dinucleotide-reduced |
| nadp | Cytosol | Nicotinamide adenine dinucleotide phosphate |
| nadph | Cytosol | Nicotinamide adenine dinucleotide phosphate-reduced |
| nh4 | Cytosol | Ammonium |
| o2 | Cytosol | Oxygen |
| oaa | Cytosol | Oxaloacetate |
| pep | Cytosol | Phosphoenolpyruvate |
| pi | Cytosol | Phosphate |
| ppi | Cytosol | Diphosphate |
| pyr | Cytosol | Pyruvate |
| r5p | Cytosol | alpha-D-Ribose 5-phosphate |
| ru5p-D | Cytosol | D-Ribulose 5-phosphate |
| s7p | Cytosol | Sedoheptulose 7-phosphate |
| succ | Cytosol | Succinate |
| succoa | Cytosol | Succinyl-CoA |
| ubq8 | Cytosol | Ubiquinone-8 |
| ubq8h2 | Cytosol | Ubiquinol-8 |
| val-L | Cytosol | L-valine |
| xu5p-D | Cytosol | D-Xylulose 5-phosphate |

TABLE 5

The list of all strains identified by OptKnock that are most likely to provide increased fumarate yields in S. Cerevisiae under microaerobic culture conditions. These same designs can be used for malate production if the cytosolic fumarase (FUM) is deleted additionally.

| | | | | | | |
|---|---|---|---|---|---|---|
| 1 | FRDm | FUM | | | | |
| 2 | ME1m | PYK | FRDm | FUMm | | |
| 3 | ME1m | G3PDm | | PYK | SUCD3-u6m | |
| 4 | G3PDm | | GLY3PP | | SUCD3-u6m | ALCD2x |
| 5 | GLY3PP | | FRDm | FUMm | | ALCD2x |
| 6 | G3PD | FRDm | FUMm | | ALCD2x | |

TABLE 5-continued

The list of all strains identified by OptKnock that are most likely to provide increased
fumarate yields in *S. Cerevisiae* under microaerobic culture conditions. These same designs can
be used for malate production if the cytosolic fumarase (FUM) is deleted additionally.

|  |  |  |  |  |  |  |
|---|---|---|---|---|---|---|
| 7 | G3PD | G3PD1irm |  | SUCD3-u6m | ALCD2x |  |
| 8 | G3PD | G3PDm |  | SUCD3-u6m | ALCD2x |  |
| 9 | G3PDm |  | PYK | MDHm | SUCD3-u6m |  |
| 10 | PYK | FRDm | FUMm |  | MDHm |  |
| 11 | G3PD | G3PDm |  | SUCD3-u6m | PYRDC |  |
| 12 | G3PDm |  | GLY3PP |  | SUCD3-u6m | PYRDC |
| 13 | GLY3PP | FRDm | FUMm |  | PYRDC |  |
| 14 | G3PD | FRDm | FUMm | PYRDC |  |  |
| 15 | G3PD | G3PD1irm |  | SUCD3-u6m | PYRDC |  |
| 16 | G3PDm |  | SUCD3-u6m |  | PYRDC | ATPtm-3H |
| 17 | FRDm | FUMm |  | PYRDC |  | ATPtm-3H |
| 18 | ATPSm |  | FRDm | FUMm |  | PYRDC |
| 19 | G3PDm |  | ATPSm |  | SUCD3-u6m | PYRDC |
| 20 | FRDm | FUMm |  | ALCD2x |  | ATPtm-3H |
| 21 | G3PDm |  | SUCD3-u6m |  | ALCD2x | ATPtm-3H |
| 22 | ATPSm |  | FRDm | FUMm |  | ALCD2x |
| 23 | G3PDm |  | ATPSm |  | SUCD3-u6m | ALCD2x |
| 24 | ME1m | FRDm | FUMm |  | PYRDC |  |
| 25 | ME1m | G3PDm |  | SUCD3-u6m | PYRDC |  |
| 26 | G3PDm |  | MDHm |  | SUCD3-u6m | PYRDC |
| 27 | FRDm | FUMm |  | MDHm | PYRDC |  |
| 28 | ME1m | G3PDm |  | SUCD3-u6m | ALCD2x |  |
| 29 | ME1m | FRDm | FUMm |  | ALCD2x |  |
| 30 | G3PDm |  | MDHm |  | SUCD3-u6m | ALCD2x |
| 31 | FRDm | FUMm |  | MDHm | ALCD2x |  |
| 32 | ASPTA1 |  | G3PDm |  | GLY3PP | SUCD3-u6m |
| 33 | ASPTA1 |  | G3PD | FRDm | FUMm |  |
| 34 | ASPTA1 |  | GLY3PP |  | FRDm | FUMm |
| 35 | ASPTA1 |  | G3PD | G3PDm | SUCD3-u6m |  |
| 36 | ASPTA1 |  | G3PD | G3PD1irm | SUCD3-u6m |  |
| 37 | G3PDm |  | GLY3PP |  | HSK | SUCD3-u6m |
| 38 | G3PDm |  | GLY3PP |  | SUCD3-u6m | THRS |
| 39 | G3PD | FRDm | FUMm |  | THRS |  |
| 40 | GLY3PP |  | HSK | FRDm | FUMm |  |
| 41 | G3PD | G3PDm |  | HSK | SUCD3-u6m |  |
| 42 | G3PD | G3PD1irm |  | HSK | SUCD3-u6m |  |
| 43 | G3PD | G3PD1irm |  | SUCD3-u6m | THRS |  |
| 44 | GLY3PP |  | FRDm | FUMm |  | THRS |
| 45 | G3PD | HSK | FRDm | FUMm |  |  |
| 46 | G3PD | G3PDm |  | SUCD3-u6m | THRS |  |
| 47 | G3PD | FRDm | FUMm |  | PGL |  |
| 48 | G3PD | FRDm | FUMm |  | PGDH |  |
| 49 | G3PD | G3PD1irm |  | SUCD3-u6m | PGDH |  |
| 50 | G3PD | G3PDm |  | SUCD3-u6m | PGDH |  |
| 51 | G3PDm |  | GLY3PP |  | SUCD3-u6m | G6PDH |
| 52 | G3PD | G3PDm |  | SUCD3-u6m | G6PDH |  |
| 53 | G3PDm |  | GLY3PP |  | SUCD3-u6m | PGL |
| 54 | G3PDm |  | GLY3PP |  | SUCD3-u6m | PGDH |
| 55 | GLY3PP |  | FRDm | FUMm |  | G6PDH |
| 56 | G3PD | G3PDm |  | SUCD3-u6m | PGL |  |
| 57 | G3PD | G3PD1irm |  | SUCD3-u6m | PGL |  |
| 58 | GLY3PP |  | FRDm | FUMm |  | PGL |
| 59 | GLY3PP |  | FRDm | FUMm |  | PGDH |
| 60 | G3PD | G3PD1irm |  | SUCD3-u6m | G6PDH |  |
| 61 | G3PD | FRDm | FUMm |  | G6PDH |  |
| 62 | G3PD | G3PDm |  | SUCD3-u6m | TKT1 |  |
| 63 | G3PDm |  | GLY3PP |  | SUCD3-u6m | TKT1 |
| 64 | G3PD | FRDm | FUMm |  | TKT1 |  |
| 65 | G3PD | G3PD1irm |  | SUCD3-u6m | TKT1 |  |
| 66 | GLY3PP |  | FRDm | FUMm |  | TKT1 |
| 67 | G3PDm |  | GLY3PP |  | SUCD3-u6m | RPE |
| 68 | G3PD | G3PDm |  | SUCD3-u6m | RPE |  |
| 69 | GLY3PP |  | FRDm | FUMm |  | RPE |
| 70 | G3PD | G3PD1irm |  | SUCD3-u6m | RPE |  |
| 71 | G3PD | FRDm | FUMm |  | RPE |  |
| 72 | G3PDm |  | SERD_L |  | PGI | SUCD3-u6m |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| | | | | | | | |
|---|---|---|---|---|---|---|---|
| 73 | SERD_L | | PGI | FRDm | FUMm | | |
| 74 | GLY3PP | | FRDm | FUMm | THRA | | |
| 75 | G3PD | FRDm | FUMm | | THRA | | |
| 76 | G3PDm | | GLY3PP | | SUCD3-u6m | | THRA |
| 77 | G3PD | G3PDm | | SUCD3-u6m | | THRA | |
| 78 | G3PD | G3PD1irm | | SUCD3-u6m | | THRA | |
| 79 | ALATA_L | | ASPTA1 | | SUCOASAm | | PSP_L |
| 80 | ALATA_L | | ASPTA1 | | PSERT | | PDHcm |
| 81 | ALATA_L | | ASPTA1 | | AKGDbm | | PGCD |
| 82 | ALATA_L | | ASPTA1 | | SUCOASAm | | PSERT |
| 83 | ALATA_L | | ASPTA1 | | SUCOASAm | | PGCD |
| 84 | ALATA_L | | ASPTA1 | | AKGDam | | PSERT |
| 85 | ALATA_L | | ASPTA1 | | AKGDbm | | PSERT |
| 86 | ALATA_L | | ASPTA1 | | PSP_L | | PDHcm |
| 87 | ALATA_L | | ASPTA1 | | AKGDbm | | PSP_L |
| 88 | ALATA_L | | ASPTA1 | | PGCD | PDHcm | |
| 89 | ALATA_L | | ASPTA1 | | AKGDam | | PSP_L |
| 90 | ALATA_L | | ASPTA1 | | AKGDam | | PGCD |
| 91 | ASPTA1 | | ICL | SUCOASAm | | PSP_L | |
| 92 | ASPTA1 | | SUCOASAm | | AGT | PSP_L | |
| 93 | ASPTA1 | | SUCOASAm | | AGT | PSERT | |
| 94 | ASPTA1 | | SUCOASAm | | AGT | PGCD | |
| 95 | ASPTA1 | | ICL | | SUCOASAm | | PSERT |
| 96 | ASPTA1 | | ICL | | SUCOASAm | | PGCD |
| 97 | ASPTA1 | | AGT | PSP_L | | PDHcm | |
| 98 | ASPTA1 | | ICL | AKGDbm | | PSP_L | |
| 99 | ASPTA1 | | AKGDam | | AGT | PSP_L | |
| 100 | ASPTA1 | | AGT | PGCD | PDHcm | | |
| 101 | ASPTA1 | | AKGDbm | | AGT | PGCD | |
| 102 | ASPTA1 | | AKGDbm | | AGT | PSERT | |
| 103 | ASPTA1 | | ICL | PGCD | PDHcm | | |
| 104 | ASPTA1 | | ICL | AKGDbm | | PGCD | |
| 105 | ASPTA1 | | AGT | PSERT | | PDHcm | |
| 106 | ASPTA1 | | ICL | PSP_L | | PDHcm | |
| 107 | ASPTA1 | | ICL | AKGDam | | PSERT | |
| 108 | ASPTA1 | | ICL | AKGDam | | PSP_L | |
| 109 | ASPTA1 | | ICL | PSERT | | PDHcm | |
| 110 | ASPTA1 | | AKGDbm | | AGT | PSP_L | |
| 111 | ASPTA1 | | ICL | AKGDam | | PGCD | |
| 112 | ASPTA1 | | AKGDam | | AGT | PSERT | |
| 113 | ASPTA1 | | AKGDam | | AGT | PGCD | |
| 114 | ASPTA1 | | ICL | AKGDbm | | PSERT | |
| 115 | GLY3PP | | HSDxi | | FRDm | FUMm | |
| 116 | G3PD | HSDxi | | FRDm | FUMm | | |
| 117 | G3PD | G3PDm | | HSDxi | | SUCD3-u6m | |
| 118 | G3PD | G3PD1irm | | HSDxi | | SUCD3-u6m | |
| 119 | G3PDm | | GLY3PP | | HSDxi | | SUCD3-u6m |
| 120 | G3PDm | | FUm | SUCD1rm | | SUCD3-u6m | |
| 121 | G3PDm | | FUm | FUMm | | SUCD3-u6m | |
| 122 | G3PDm | | MDH | NADH2-u6cm | | NADH2-u6m | |
| 123 | ASPTA1 | | ME1m | | PSERT | PDHm | PYK |
| 124 | ASPTA1 | | ME1m | | PSP_L | PDHm | PYK |
| 125 | ASPTA1 | | ME1m | | PGCD | PDHm | PYK |
| 126 | ASPTA1 | | ME1m | | ME2m | PSP_L | PYK |
| 127 | ASPTA1 | | ME1m | | ME2m | PGCD | PYK |
| 128 | ASPTA1 | | ME1m | | ME2m | PSERT | PYK |
| 129 | ASPTA1 | | ORNTA | | ME1m | PSP_L | PYK |
| 130 | ASPTA1 | | ORNTA | | ME1m | PGCD | PYK |
| 131 | ASPTA1 | | ORNTA | | ME1m | PSERT | PYK |
| 132 | ASPTA1 | | ME1m | | PRO1xm | PSP_L | PYK |
| 133 | ASPTA1 | | ME1m | | PRO1xm | PSERT | PYK |
| 134 | ASPTA1 | | ME1m | | P5CDm | PSP_L | PYK |
| 135 | ASPTA1 | | ME1m | | PRO1xm | PGCD | PYK |
| 136 | ASPTA1 | | ME1m | | P5CDm | PGCD | PYK |
| 137 | ASPTA1 | | ME1m | | PRO1xm | PSERT | PYK |
| 138 | ASPTA1m | | ME1m | | PSP_L | PDHm | PYK |
| 139 | ASPTA1m | | ME1m | | PSERT | PDHm | PYK |
| 140 | ASPTA1m | | ME1m | | PGCD | PDHm | PYK |
| 141 | ASPTA1m | | ME1m | | PRO1xm | PSP_L | PYK |
| 142 | ASPTA1m | | ME1m | | P5CDm | PGCD | PYK |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| # | 1 | 2 | 3 | 4 | 5 | 6 | 7 |
|---|---|---|---|---|---|---|---|
| 143 | ASPTA1m | | ME1m | | PRO1xm | | PGCD | PYK |
| 144 | ASPTA1m | | ME1m | | PRO1xm | | PSERT | PYK |
| 145 | ASPTA1m | | ME1m | | P5CDm | | PSERT | PYK |
| 146 | ASPTA1m | | ME1m | | P5CDm | | PSP_L | PYK |
| 147 | ASPTA1m | | ME1m | | PSERT | | PDHcm | PYK |
| 148 | ASPTA1m | | ME1m | | SUCOASAm | | PSERT | PYK |
| 149 | ASPTA1m | | ME1m | | AKGDam | | PSP_L | PYK |
| 150 | ASPTA1m | | ME1m | | AKGDbm | | PSERT | PYK |
| 151 | ASPTA1m | | ME1m | | SUCOASAm | | PGCD | PYK |
| 152 | ASPTA1m | | ME1m | | AKGDam | | PGCD | PYK |
| 153 | ASPTA1m | | ME1m | | SUCOASAm | | PSP_L | PYK |
| 154 | ASPTA1m | | ME1m | | AKGDam | | PSERT | PYK |
| 155 | ASPTA1m | | ME1m | | PSP_L | | PDHcm | PYK |
| 156 | ASPTA1m | | ME1m | | PGCD | PDHcm | | PYK |
| 157 | ASPTA1m | | ME1m | | AKGDbm | | PGCD | PYK |
| 158 | ASPTA1m | | ME1m | | AKGDbm | | PSP_L | PYK |
| 159 | ASPTA1m | | ORNTA | | ME1m | | PSP_L | PYK |
| 160 | ASPTA1m | | ORNTA | | ME1m | | PGCD | PYK |
| 161 | ASPTA1m | | ORNTA | | ME1m | | PSERT | PYK |
| 162 | ME1m | ME2m | | ACONTm | | PSP_L | | PYK |
| 163 | ME1m | ME2m | | ACONTm | | | PGCD | PYK |
| 164 | ME1m | ME2m | | ACONTm | | PSERT | | PYK |
| 165 | ASPTA1m | | ME1m | | ME2m | | PSP_L | PYK |
| 166 | ASPTA1m | | ME1m | | ME2m | | PGCD | PYK |
| 167 | ASPTA1m | | ME1m | | ME2m | | PSERT | PYK |
| 168 | ME1m | ME2m | | ICDHy | | PSERT | | PYK |
| 169 | ME1m | ME2m | | ACONT | | PSERT | | PYK |
| 170 | ME1m | ME2m | | ACONT | | PSP_L | | PYK |
| 171 | ME1m | ME2m | | ICDHy | | PSP_L | | PYK |
| 172 | ME1m | ME2m | | ICDHy | | PGCD | | PYK |
| 173 | ME1m | ME2m | | ACONT | | PGCD | | PYK |
| 174 | ME1m | ME2m | | ICDHxm | | PSP_L | | PYK |
| 175 | ME1m | ME2m | | ICDHxm | | PGCD | | PYK |
| 176 | ME1m | ME2m | | ICDHxm | | PSERT | | PYK |
| 177 | ME1m | ME2m | | G3PDm | | PYK | SUCD3-u6m | |
| 178 | ME1m | ME2m | | PYK | FRDm | FUMm | | |
| 179 | ME1m | PYK | FRDm | FUMm | | PGDH | | |
| 180 | ME1m | G3PDm | | PYK | SUCD3-u6m | PGDH | | |
| 181 | ME1m | PYK | FRDm | FUMm | | PGL | | |
| 182 | ME1m | PYK | FRDm | FUMm | | G6PDH | | |
| 183 | ME1m | G3PDm | | PYK | SUCD3-u6m | PGL | | |
| 184 | ME1m | G3PDm | | PYK | SUCD3-u6m | G6PDH | | |
| 185 | ME1m | G3PDm | | PYK | SUCD3-u6m | TKT1 | | |
| 186 | ME1m | PYK | FRDm | FUMm | | TKT1 | | |
| 187 | ME1m | G3PDm | | PYK | SUCD3-u6m | RPE | | |
| 188 | ME1m | PYK | FRDm | FUMm | | RPE | | |
| 189 | ME1m | PYK | FRDm | FUMm | | TKT2 | | |
| 190 | ME1m | G3PDm | | PYK | SUCD3-u6m | TKT2 | | |
| 191 | ME1m | ME2m | | PSP_L | | PYK | PGDH | |
| 192 | ME1m | ME2m | | PSERT | | PYK | PGDH | |
| 193 | ME1m | ME2m | | PGCD | PYK | PGDH | | |
| 194 | ME1m | ME2m | | PSERT | | PYK | PGL | |
| 195 | ME1m | ME2m | | PSERT | | PYK | G6PDH | |
| 196 | ME1m | ME2m | | PGCD | PYK | PGL | | |
| 197 | ME1m | ME2m | | PSP_L | | PYK | PGL | |
| 198 | ME1m | ME2m | | PSP_L | | PYK | G6PDH | |
| 199 | ME1m | ME2m | | PGCD | PYK | G6PDH | | |
| 200 | ME1m | ME2m | | PSERT | | PYK | TKT1 | |
| 201 | ME1m | ME2m | | PGCD | PYK | TKT1 | | |
| 202 | ME1m | ME2m | | PSP_L | | PYK | TKT1 | |
| 203 | ME1m | ME2m | | PSERT | | PYK | RPE | |
| 204 | ME1m | ME2m | | PSP_L | | PYK | RPE | |
| 205 | ME1m | ME2m | | PGCD | PYK | RPE | | |
| 206 | ME1m | ME2m | | PSP_L | | PYK | TKT2 | |
| 207 | ME1m | ME2m | | PSERT | | PYK | TKT2 | |
| 208 | ME1m | ME2m | | PGCD | PYK | TKT2 | | |
| 209 | ATPSm | | FRDm | FUMm | | PGDH | PYRDC | |
| 210 | G3PDm | | ATPSm | | SUCD3-u6m | PGDH | PYRDC | |
| 211 | ATPSm | | FRDm | FUMm | | G6PDH | PYRDC | |
| 212 | G3PDm | | ATPSm | | SUCD3-u6m | PGL | PYRDC | |
| 213 | ATPSm | | FRDm | FUMm | | PGL | PYRDC | |
| 214 | G3PDm | | ATPSm | | SUCD3-u6m | G6PDH | | PYRDC |
| 215 | G3PDm | | ATPSm | | SUCD3-u6m | TKT1 | PYRDC | |
| 216 | ATPSm | | FRDm | FUMm | | TKT1 | PYRDC | |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| # | | | | | | | | |
|---|---|---|---|---|---|---|---|---|
| 217 | G3PDm | | SUCD3-u6m | | PGL | PYRDC | | ATPtm-3H |
| 218 | FRDm | FUMm | | PGDH | PYRDC | | ATPtm-3H | |
| 219 | G3PDm | | SUCD3-u6m | | PGDH | PYRDC | | ATPtm-3H |
| 220 | G3PDm | | SUCD3-u6m | | G6PDH | | PYRDC | ATPtm-3H |
| 221 | FRDm | FUMm | | PGL | PYRDC | | ATPtm-3H | |
| 222 | FRDm | FUMm | | G6PDH | | PYRDC | ATPtm-3H | |
| 223 | G3PDm | | SUCD3-u6m | | TKT1 | PYRDC | | ATPtm-3H |
| 224 | FRDm | FUMm | | TKT1 | PYRDC | | ATPtm-3H | |
| 225 | G3PDm | ATPSm | | | SUCD3-u6m | RPE | PYRDC | |
| 226 | ATPSm | | FRDm | FUMm | | RPE | PYRDC | |
| 227 | G3PDm | | SUCD3-u6m | | RPE | PYRDC | | ATPtm-3H |
| 228 | FRDm | FUMm | | RPE | PYRDC | | ATPtm-3H | |
| 229 | G3PDm | ATPSm | | | SUCD3-u6m | TKT2 | PYRDC | |
| 230 | ATPSm | | FRDm | FUMm | | TKT2 | PYRDC | |
| 231 | FRDm | FUMm | | TKT2 | PYRDC | | ATPtm-3H | |
| 232 | G3PDm | | SUCD3-u6m | | TKT2 | PYRDC | | ATPtm-3H |
| 233 | ME2m | FRDm | FUMm | | ALCD2x | | ATPtm-3H | |
| 234 | ME2m | G3PDm | | SUCD3-u6m | | ALCD2x | | ATPtm-3H |
| 235 | ME1m | ME2m | | MTHFD | | SERD_L | PYK | G6PDH |
| 236 | ME1m | ME2m | | MTHFD | | SERD_L | PYK | PGL |
| 237 | ME1m | ME2m | | MTHFD | | SERD_L | PYK | PGDH |
| 238 | ASPTA1 | | GHMT2 | | ME1m | | SERD_L | PDHm | PYK |
| 239 | ORNTA | | ME1m | | MTHFD | | SERD_L | PYK | G6PDH |
| 240 | G3PD | FRDm | FUm | PYRDC | | | | |
| 241 | G3PD | FRDm | FUMmPGDH | PYRDC | | | | |
| 242 | G3PD | FRDm | FUMmPGL | PYRDC | | | | |
| 243 | G3PD | G3PD1irm | | SUCD3-u6m | | G6PDH | PYRDC | |
| 244 | G3PD | G3PDm | | SUCD3-u6m | | PGL | PYRDC | |
| 245 | G3PD | G3PD1irm | | SUCD3-u6m | | PGDH | PYRDC | |
| 246 | G3PD | FRDm | FUMm | G6PDH | PYRDC | | | |
| 247 | G3PD | G3PDm | | SUCD3-u6m | | G6PDH | PYRDC | |
| 248 | G3PD | G3PD1irm | | SUCD3-u6m | | PGL | PYRDC | |
| 249 | G3PD | G3PDm | | SUCD3-u6m | | PGDH | PYRDC | |
| 250 | G3PD | G3PDm | | SUCD3-u6m | | TKT1 | PYRDC | |
| 251 | G3PD | G3PD1irm | | SUCD3-u6m | | TKT1 | PYRDC | |
| 252 | G3PD | FRDm | FUMm | TKT1 | PYRDC | | | |
| 253 | G3PD | G3PD1irm | | SUCD3-u6m | | RPE | PYRDC | |
| 254 | G3PD | G3PDm | | SUCD3-u6m | | RPE | PYRDC | |
| 255 | G3PD | FRDm | FUMm | RPE | PYRDC | | | |
| 256 | G3PD | G3PD1irm | | SUCD3-u6m | | TKT2 | PYRDC | |
| 257 | G3PD | G3PDm | | SUCD3-u6m | | TKT2 | PYRDC | |
| 258 | G3PD | FRDm | FUMm | TKT2 | PYRDC | | | |
| 259 | ASPTA1 | | G3PD | G3PD1irm | | SUCD3-u6m | PYRDC | |
| 260 | ASPTA1 | | G3PD | G3PDm | | SUCD3-u6m | PYRDC | |
| 261 | ASPTA1 | | G3PD | FRDm | FUMm | PYRDC | | |
| 262 | G3PD | G3PD1irm | | HSDxi | SUCD3-u6m | | PYRDC | |
| 263 | G3PD | G3PDm | | HSDxi | SUCD3-u6m | | PYRDC | |
| 264 | G3PD | HSDxi | FRDm | FUMm | PYRDC | | | |
| 265 | G3PD | G3PD1irm | | SUCD3-u6m | | ALCD2x | PYRDC | |
| 266 | G3PD | G3PDm | | SUCD3-u6m | | ALCD2x | PYRDC | |
| 267 | G3PD | FRDm | FUMmALCD2x | | PYRDC | | | |
| 268 | ACONT | | GLUDC | | G3PD | PYRDC | | ALDD2y |
| 269 | ICDHyG3PD | | G3PD1irm | | SUCD3-u6m | | PGL | PYRDC |
| 270 | ICDHyG3PD | | FRDm | FUMm | G6PDH | | PYRDC | |
| 271 | ACONT | | G3PD | G3PD1irm | | SUCD3-u6m | PGL | PYRDC |
| 272 | ACONT | | G3PD | FRDm | FUMm | PGDH | PYRDC | |
| 273 | ACONT | | G3PD | G3PD1irm | | SUCD3-u6m | | G6PDH | PYRDC |
| 274 | ICDHyG3PD | | G3PDm | | SUCD3-u6m | | G6PDH | | PYRDC |

TABLE 5-continued

The list of all strains identified by OptKnock that are most likely to provide increased fumarate yields in *S. Cerevisiae* under microaerobic culture conditions. These same designs can be used for malate production if the cytosolic fumarase (FUM) is deleted additionally.

| 275 | ACONT | G3PD | FRDm | FUMm | G6PDH | | PYRDC | |
| --- | --- | --- | --- | --- | --- | --- | --- | --- |
| 276 | ACONT | G3PD | G3PDm | | SUCD3-u6m | | G6PDH | PYRDC |
| 277 | ACONT | G3PD | G3PDm | | SUCD3-u6m | | PGDH | PYRDC |
| 278 | ICDHyG3PD | G3PDm | | SUCD3-u6m | | PGL | PYRDC | |

TABLE 6

The list of all strains identified by OptKnock that are most likely to provide increased acrylate yields in *S. cerevisiae* under anaerobic conditions.

| 1 | PYRDC | | | | |
| --- | --- | --- | --- | --- | --- |
| 2 | ALCD2x | | | | |
| 3 | ATPtm-3H | | | | |
| 4 | ATPSm | | | | |
| 5 | ME1m | | | | |
| 6 | PDHm | PYRDC | | | |
| 7 | ME1m | PYK | | | |
| 8 | ATPSm | | ATPS | | |
| 9 | ME1m | ATPS | | | |
| 10 | ATPS | ATPtm-3H | | | |
| 11 | PDHm | ATPtm-3H | | | |
| 12 | PDHm | ALCD2x | | | |
| 13 | PDHm | ATPSm | | | |
| 14 | PSERT | | ALCD2x | | |
| 15 | PSP_L | ALCD2x | | | |
| 16 | PGCD | ALCD2x | | | |
| 17 | ALCD2x | | ATPS | | |
| 18 | PYRDC | | IPPSm | | |
| 19 | PGCD | PYRDC | | | |
| 20 | PSP_L | PYRDC | | | |
| 21 | PSERT | | PYRDC | | |
| 22 | PYRDC | | ATPS | | |
| 23 | PGCD | ATPSm | | | |
| 24 | PSP_L | ATPSm | | | |
| 25 | PSERT | | ATPSm | | |
| 26 | PSERT | | ATPtm-3H | | |
| 27 | PGCD | ATPtm-3H | | | |
| 28 | PSP_L | ATPtm-3H | | | |
| 29 | ME1m | PDHm | | | |
| 30 | ME1m | PGCD | | | |
| 31 | ME1m | PSP_L | | | |
| 32 | ME1m | PSERT | | | |
| 33 | GLU5K | | PYRDC | | |
| 34 | GHMT2m | | ATPSm | | |
| 35 | ATPtm-3H | | IPPSm | | |
| 36 | ALCD2x | | IPPSm | | |
| 37 | ATPSm | | IPPSm | | |
| 38 | PYK | ATPSm | | | |
| 39 | ORNTA | | ATPtm-3H | | |
| 40 | MDHm | | | DHORD4u | |
| 41 | G3PDm | | SUCD3-u6m | | ALCD2x |
| 42 | G3PDm | | ATPSm | | | SUCD3-u6m |
| 43 | GLU5K | | PDHm | PYRDC | |
| 44 | PDHm | PYRDC | | IPPS | |
| 45 | G3PDm | | SUCD3-u6m | | ATPtm-3H |
| 46 | ME1m | G3PDm | | SUCD3-u6m | |
| 47 | PGCD | PDHm | ATPSm | | |
| 48 | PSP_L | PDHm | ATPSm | | |
| 49 | PSERT | | PDHm | ATPSm | |
| 50 | PSERT | | PDHm | ALCD2x | |
| 51 | PGCD | PDHm | ALCD2x | | |
| 52 | PSP_L | PDHm | ALCD2x | | |
| 53 | PDHm | PYK | ATPSm | | |
| 54 | ME1m | PSP_L | PYK | | |
| 55 | ME1m | PSERT | | PYK | |
| 56 | ME1m | PGCD | PYK | | |
| 57 | G3PDm | | SUCD3-u6m | | PYRDC |
| 58 | PSERT | | PDHm | ATPtm-3H | |
| 59 | PSP_L | PDHm | ATPtm-3H | | |
| 60 | PGCD | PDHm | ATPtm-3H | | |
| 61 | PGCD | ATPSm | | | ALCD2x |

TABLE 6-continued

The list of all strains identified by OptKnock that are most likely to provide increased acrylate yields in *S. cerevisiae* under anaerobic conditions.

| # | C1 | C2 | C3 | C4 | C5 | C6 |
|---|---|---|---|---|---|---|
| 62 | PSP_L | ATPSm | | | ALCD2x | |
| 63 | PSERT | | ATPSm | | | ALCD2x |
| 64 | ME2m | ATPSm | | ATPS | | |
| 65 | ME1m | PGCD | PDHm | | | |
| 66 | ME1m | PSERT | | PDHm | | |
| 67 | ME1m | PSP_L | PDHm | | | |
| 68 | ME2m | ATPS | ATPtm-3H | | | |
| 69 | ME2m | PYRDC | | ATPS | | |
| 70 | ORNTA | | ATPS | ATPtm-3H | | |
| 71 | GHMT2m | | PDHm | ATPSm | | |
| 72 | ACONT | | ATPS | ATPtm-3H | | |
| 73 | ICDHyATPS | | | ATPtm-3H | | |
| 74 | GHMT2 | | ATPS | ATPtm-3H | | |
| 75 | ME1m | PSP_L | ALCD2x | | | |
| 76 | ME1m | PGCD | ALCD2x | | | |
| 77 | ME1m | PSERT | | ALCD2x | | |
| 78 | ASPTA1m | | ATPS | ATPtm-3H | | |
| 79 | FTHFLm | | PYK | ATPSm | | |
| 80 | MTHFDm | | PYK | ATPSm | | |
| 81 | MTHFCm | | PYK | ATPSm | | |
| 82 | MTHFC | | ATPS | ATPtm-3H | | |
| 83 | GHMT2 | | ALCD2x | | ATPS | |
| 84 | PSP_L | PYRDC | | IPPSm | | |
| 85 | PSERT | | PYRDC | | IPPSm | |
| 86 | PGCD | PYRDC | | IPPSm | | |
| 87 | ICDHy | PYRDC | | ATPS | | |
| 88 | ACONT | | PYRDC | | ATPS | |
| 89 | PGCD | ATPSm | | | IPPSm | |
| 90 | PSP_L | ATPSm | | | IPPSm | |
| 91 | PSERT | | ATPSm | | | IPPSm |
| 92 | ORNTA | | PYRDC | | ATPS | |
| 93 | PGCD | ATPtm-3H | | IPPSm | | |
| 94 | PSERT | | ATPtm-3H | | IPPSm | |
| 95 | PSP_L | ATPtm-3H | | IPPSm | | |
| 96 | GLU5K | | ALCD2x | | ATPS | |
| 97 | ALCD2x | | ATPS | IPPS | | |
| 98 | GLU5K | | PYRDC | | IPPSm | |
| 99 | GLU5K | | PGCD | PYRDC | | |
| 100 | GLU5K | | PSP_L | PYRDC | | |
| 101 | GLU5K | | PSERT | | | PYRDC |
| 102 | GLU5K | | PYRDC | | ATPS | |
| 103 | ORNTA | | PGCD | ATPtm-3H | | |
| 104 | ORNTA | | PSERT | | ATPtm-3H | |
| 105 | ORNTA | | PSP_L | ATPtm-3H | | |
| 106 | PYK | ATPSm | | | ATPtm-3H | |
| 107 | ASPTA1m | | PSERT | | ATPtm-3H | |
| 108 | ASPTA1m | | PSP_L | ATPtm-3H | | |
| 109 | ASPTA1m | | PGCD | ATPtm-3H | | |
| 110 | PYK | ATPSm | | | IPPSm | |
| 111 | GHMT2 | | GHMT2m | | ALCD2x | |
| 112 | MTHFC | | PSP_L | ATPtm-3H | | |
| 113 | MTHFC | | PGCD | ATPtm-3H | | |
| 114 | MTHFC | | PSERT | | ATPtm-3H | |
| 115 | GHMT2m | | ATPSm | | | IPPSm |
| 116 | GHMT2 | | GHMT2m | | ATPtm-3H | |
| 117 | GHMT2 | | GHMT2m | | PYRDC | |
| 118 | GHMT2m | | PYK | ATPSm | | |
| 119 | GLU5K | | GHMT2m | | ATPSm | |
| 120 | G5SD | G5SD2 | | PYRDC | | |
| 121 | GHMT2m | | ATPSm | | | ALCD2x |
| 122 | ORNTA | | ATPtm-3H | | IPPSm | |
| 123 | MTHFC | | GHMT2m | | ALCD2x | |
| 124 | MTHFC | | GHMT2m | | ATPtm-3H | |
| 125 | ME2m | ICDHym | | ATPtm-3H | | |
| 126 | ME2m | ACONTm | | ATPtm-3H | | |
| 127 | GLU5K | | ALCD2x | | THRA | |
| 128 | ASPTA1m | | THRA | ATPtm-3H | | |
| 129 | GHMT2 | | ME1m | GHMT2m | | |
| 130 | PSERT | | MDHm | | DHORD4u | |
| 131 | PSP_L | MDHm | | DHORD4u | | |
| 132 | PGCD | MDHm | | DHORD4u | | |
| 133 | ME1m | MTHFC | | GHMT2m | | |
| 134 | MDHm | | DHORD4u | | ATPS | |
| 135 | PDHm | MDHm | | DHORD4u | | |
| 136 | MDHm | | DHORD4u | | IPPSm | |
| 137 | ORNTA | | MDHm | | DHORD4u | |
| 138 | MDHm | | DHORD4u | | ALDD2y | |

TABLE 6-continued

The list of all strains identified by OptKnock that are most likely to provide increased acrylate yields in *S. cerevisiae* under anaerobic conditions.

| # | | | | | | |
|---|---|---|---|---|---|---|
| 139 | ASPTA1m | | MDHm | | DHORD4u | |
| 140 | MDHm | | NADH2-u6m | | SUCD3-u6m | |
| 141 | TPI | MDH | DHORD4u | | | |
| 142 | MDH | DHORD4u | | ATPS | | |
| 143 | FUM | SUCD1rm | | ATPS | | |
| 144 | FUM | FUMmATPS | | | | |
| 145 | TPI | FUM | SUCD1rm | | | |
| 146 | TPI | FUM | FUMm | | | |
| 147 | G3PDm | | PDHm | SUCD3-u6m | | PYRDC |
| 148 | GLU5K | | G3PDm | | SUCD3-u6m | ALCD2x |
| 149 | G3PDm | | SUCD3-u6m | ALCD2x | | IPPS |
| 150 | GLU5K | | PDHm | PYRDC | | IPPS |
| 151 | G5SD | G5SD2 | | PDHm | PYRDC | |
| 152 | ASPTA1m | | ACONTm | | PDHm | PYRDC |
| 153 | ME1m | G3PDm | | PYK | SUCD3-u6m | |
| 154 | ORNTA | | G3PDm | | SUCD3-u6m | ATPtm-3H |
| 155 | ME2m | G3PDm | | SUCD3-u6m | | ATPtm-3H |
| 156 | ICDHy | G3PDm | | SUCD3-u6m | | ATPtm-3H |
| 157 | ACONT | | G3PDm | | SUCD3-u6m | ATPtm-3H |
| 158 | GHMT2 | | G3PDm | | SUCD3-u6m | ATPtm-3H |
| 159 | ASPTA1m | | G3PDm | | SUCD3-u6m | ATPtm-3H |
| 160 | MTHFC | | G3PDm | | SUCD3-u6m | ATPtm-3H |
| 161 | ME2m | G3PDm | | SUCD3-u6m | | PYRDC |
| 162 | ME1m | ME2m | PGCD | PYK | | |
| 163 | ME1m | ME2m | PSP_L | PYK | | |
| 164 | ME1m | ME2m | PSERT | | PYK | |
| 165 | PDHm | PYK | ATPSm | | | IPPSm |
| 166 | ORNTA | PYK | ME1m | PSP_L | PYK | |
| 167 | ORNTA | | ME1m | PSERT | PYK | |
| 168 | ORNTA | | ME1m | PGCD | PYK | |
| 169 | ICDHy | G3PDm | | SUCD3-u6m | | PYRDC |
| 170 | ACONT | | G3PDm | | SUCD3-u6m | PYRDC |
| 171 | ORNTA | | G3PDm | | SUCD3-u6m | PYRDC |
| 172 | ORNTA | | PGCD | PDHm | ATPtm-3H | |
| 173 | ORNTA | | PSERT | | PDHm | ATPtm-3H |
| 174 | ORNTA | | PSP_L | PDHm | ATPtm-3H | |
| 175 | ME1m | | PGCD | PYK | ATPSm | |
| 176 | ME1m | | PSERT | | PYK | ATPSm |
| 177 | ME1m | PSP_L | PYK | ATPSm | | |
| 178 | G3PD | G3PD1irm | | ATPSm | | SUCD3-u6m |
| 179 | MTHFD | | PSP_L | PDHm | ALCD2x | |
| 180 | MTHFD | | PGCD | PDHm | ALCD2x | |
| 181 | MTHFD | | PSERT | | PDHm | ALCD2x |
| 182 | ME1m | G3PD | G3PD1irm | | SUCD3-u6m | |
| 183 | MTHFC | | PSP_L | PDHm | ALCD2x | |
| 184 | MTHFC | | PSERT | | PDHm | ALCD2x |
| 185 | MTHFC | | PGCD | PDHm | ALCD2x | |
| 186 | ASPTA1m | | PSP_L | PDHm | ALCD2x | |
| 187 | ASPTA1m | | PGCD | PDHm | ALCD2x | |
| 188 | ASPTA1m | | PSERT | | PDHm | ALCD2x |
| 189 | ME2m | PGCD | PDHm | | ATPtm-3H | |
| 190 | ME2m | PSERT | | PDHm | ATPtm-3H | |
| 191 | ME2m | PSP_L | PDHm | ATPtm-3H | | |
| 192 | ME1m | MTHFC | | PSP_L | PYK | |
| 193 | ME1m | MTHFC | | PSERT | | PYK |
| 194 | ME1m | MTHFC | | PGCD | PYK | |
| 195 | ASPTA1m | | PGCD | ATPSm | | ALCD2x |
| 196 | ASPTA1m | | PSERT | | ATPSm | ALCD2x |
| 197 | ASPTA1m | | PSP_L | ATPSm | | ALCD2x |
| 198 | GHMT2 | | PSP_L | PDHm | ATPtm-3H | |
| 199 | GHMT2 | | PGCD | PDHm | ATPtm-3H | |
| 200 | GHMT2 | | PSERT | | PDHm | ATPtm-3H |
| 201 | ASPTA1m | | PGCD | PDHm | ATPtm-3H | |
| 202 | ASPTA1m | | PSERT | | PDHm | ATPtm-3H |
| 203 | ASPTA1m | | PSP_L | PDHm | ATPtm-3H | |
| 204 | ACONT | | PSP_L | PDHm | ATPtm-3H | |
| 205 | ACONT | | PSERT | | PDHm | ATPtm-3H |
| 206 | ACONT | | PGCD | PDHm | ATPtm-3H | |
| 207 | ICDHyPSP_L | | PDHm | ATPtm-3H | | |
| 208 | ICDHyPGCD | | PDHm | ATPtm-3H | | |
| 209 | ICDHyPSERT | | PDHm | ATPtm-3H | | |
| 210 | MTHFC | | PSP_L | PDHm | ATPtm-3H | |
| 211 | MTHFC | | PGCD | PDHm | ATPtm-3H | |
| 212 | MTHFC | | PSERT | | PDHm | ATPtm-3H |
| 213 | GLU5K | | G3PDm | | SUCD3-u6m | PYRDC |
| 214 | G3PD | G3PD1irm | | SUCD3-u6m | | ATPtm-3H |
| 215 | GHMT2 | | GHMT2m | | PDHm | ATPtm-3H |

TABLE 6-continued

The list of all strains identified by OptKnock that are most likely to provide increased acrylate yields in *S. cerevisiae* under anaerobic conditions.

| # | 1 | 2 | 3 | 4 | 5 | 6 |
|---|---|---|---|---|---|---|
| 216 | MTHFDm | | PYK | ATPSm | | IPPSm |
| 217 | MTHFCm | | PYK | ATPSm | | IPPSm |
| 218 | FTHFLm | | PYK | ATPSm | | IPPSm |
| 219 | ME2m | PSP_L | ALCD2x | | ATPtm-3H | |
| 220 | ME2m | PSERT | ALCD2x | | ATPtm-3H | |
| 221 | ME2m | PGCD | ALCD2x | | ATPtm-3H | |
| 222 | GHMT2 | | GHMT2m | | PDHm | ALCD2x |
| 223 | ME2m | MTHFC | | ATPS | ATPtm-3H | |
| 224 | ME2m | MTHFC | | PYRDC | | ATPS |
| 225 | GLU5K | | GHMT2m | | PDHm | ATPSm |
| 226 | ORNTA | | ACONT | | ATPS | ATPtm-3H |
| 227 | ORNTA | | ICDHyATPS | | ATPtm-3H | |
| 228 | ORNTA | | ICDHy | PYRDC | | ATPS |
| 229 | ORNTA | | ACONT | | PYRDC | ATPS |
| 230 | ASPTA1m | | FTHFLm | | PYK | ATPSm |
| 231 | ASPTA1m | | MTHFDm | | PYK | ATPSm |
| 232 | ASPTA1m | | MTHFCm | | PYK | ATPSm |
| 233 | ORNTA | | MTHFC | | ATPS | ATPtm-3H |
| 234 | GHMT2 | | GHMT2m | | PDHm | ATPSm |
| 235 | MTHFC | | PSERT | | PYK | ATPSm |
| 236 | MTHFC | | PGCD | PYK | ATPSm | |
| 237 | MTHFC | | PSP_L | PYK | ATPSm | |
| 238 | GHMT2 | | ICDHyATPS | | ATPtm-3H | |
| 239 | GHMT2 | | ACONT | | ATPS | ATPtm-3H |
| 240 | G3PD | G3PD1irm | | SUCD3-u6m | | PYRDC |
| 241 | FTHFLr | | PSERT | | PYK | ATPSm |
| 242 | FTHFLr | | PSP_L | PYK | ATPSm | |
| 243 | FTHFLr | | PGCD | PYK | ATPSm | |
| 244 | ACONT | | PSERT | | ALCD2x | ATPtm-3H |
| 245 | ICDHyPSP_L | | ALCD2x | | ATPtm-3H | |
| 246 | ACONT | | PGCD | ALCD2x | | ATPtm-3H |
| 247 | ICDHyPGCD | | ALCD2x | | ATPtm-3H | |
| 248 | ICDHyPSERT | | ALCD2x | | ATPtm-3H | |
| 249 | ACONT | | PSP_L | ALCD2x | | ATPtm-3H |
| 250 | ICDHyPYK | | ATPSm | | ATPtm-3H | |
| 251 | ACONT | | PYK | ATPSm | | ATPtm-3H |
| 252 | ICDHyMTHFC | | | ATPS | ATPtm-3H | |
| 253 | ACONT | | MTHFC | | ATPS | ATPtm-3H |
| 254 | ORNTA | | PGCD | ALCD2x | | ATPtm-3H |
| 255 | ORNTA | | PSERT | | ALCD2x | ATPtm-3H |
| 256 | ORNTA | | PSP_L | ALCD2x | | ATPtm-3H |
| 257 | MTHFDm | | PSP_L | PYK | ATPSm | |
| 258 | FTHFLm | | PGCD | PYK | ATPSm | |
| 259 | MTHFCm | | PSP_L | PYK | ATPSm | |
| 260 | MTHFDm | | PSERT | | PYK | ATPSm |
| 261 | MTHFDm | | PGCD | PYK | ATPSm | |
| 262 | MTHFCm | | PGCD | PYK | ATPSm | |
| 263 | MTHFCm | | PSERT | | PYK | ATPSm |
| 264 | FTHFLm | | PSERT | | PYK | ATPSm |
| 265 | FTHFLm | | PSP_L | PYK | ATPSm | |
| 266 | MTHFD | | MTHFD2 | | ATPS | ATPtm-3H |
| 267 | ORNTA | | PYK | ATPSm | | ATPtm-3H |
| 268 | ASPTA1m | | MTHFC | | ATPS | ATPtm-3H |
| 269 | MTHFC | | PYK | ATPSm | | ATPtm-3H |
| 270 | ICDHyGLY3PP | | | PYRDC | | ATPS |
| 271 | ACONT | | GLY3PP | | PYRDC | ATPS |
| 272 | ICDHyG3PD | PYRDC | | ATPS | | |
| 273 | ACONT | | G3PD | PYRDC | | ATPS |
| 274 | MTHFC | | GHMT2m | | PDHm | ATPtm-3H |
| 275 | MTHFC | | GHMT2m | | PDHm | ALCD2x |
| 276 | GHMT2 | | PSERT | | ALCD2x | ATPS |
| 277 | GHMT2 | | PGCD | ALCD2x | | ATPS |
| 278 | GHMT2 | | PSP_L | ALCD2x | | ATPS |
| 279 | FTHFLr | | PYK | ATPSm | | ATPtm-3H |
| 280 | PYK | ATPSm | | | ATPtm-3H | IPPSm |
| 281 | ACONT | | MTHFC | | PYRDC | ATPS |
| 282 | ICDHyMTHFC | | | PYRDC | | ATPS |
| 283 | ORNTA | | MTHFC | | PYRDC | ATPS |
| 284 | GHMT2 | | FTHFCLm | | ALCD2x | ATPS |
| 285 | GHMT2 | | THFATm | | ALCD2x | ATPS |
| 286 | GHMT2 | | ALCD2x | ATPS | IPPS | |
| 287 | ORNTA | | PDHm | THRA | ATPtm-3H | |
| 288 | GLU5K | | PSERT | | PYRDC | IPPSm |
| 289 | GLU5K | | PGCD | PYRDC | IPPSm | |
| 290 | GLU5K | | PSP_L | PYRDC | IPPSm | |
| 291 | ASPTA1m | | ORNTA | | PYRDC | ATPS |
| 292 | ORNTA | | PGCD | ATPtm-3H | | IPPSm |

TABLE 6-continued

The list of all strains identified by OptKnock that are most likely to provide increased acrylate yields in *S. cerevisiae* under anaerobic conditions.

| # | | | | | | |
|---|---|---|---|---|---|---|
| 293 | ORNTA | | PSERT | | ATPtm-3H | IPPSm |
| 294 | ORNTA | | PSP_L | ATPtm-3H | | IPPSm |
| 295 | PGCD | PYK | ATPSm | | ATPtm-3H | |
| 296 | PSP_L | PYK | ATPSm | | ATPtm-3H | |
| 297 | PSERT | | PYK | ATPSm | | ATPtm-3H |
| 298 | ASPTA1m | | PSERT | | ATPtm-3H | IPPSm |
| 299 | ASPTA1m | | PGCD | ATPtm-3H | | IPPSm |
| 300 | ASPTA1m | | PSP_L | ATPtm-3H | | IPPSm |
| 301 | ME1m | G3PD | MDHm | | SUCD3-u6m | |
| 302 | MTHFC | | PGCD | ATPtm-3H | | IPPSm |
| 303 | MTHFC | | PSP_L | ATPtm-3H | | IPPSm |
| 304 | MTHFC | | PSERT | | ATPtm-3H | IPPSm |
| 305 | GHMT2 | | PSERT | ALCD2x | | ATPtm-3H |
| 306 | GHMT2 | | PSP_L | ALCD2x | | ATPtm-3H |
| 307 | GHMT2 | | PGCD | ALCD2x | | ATPtm-3H |
| 308 | G3PD | MDHm | | SUCD3-u6m | | PYRDC |
| 309 | GHMT2 | | GHMT2m | | ALCD2x | ATPtm-3H |
| 310 | GLU5K | | PSP_L | ALCD2x | | ATPS |
| 311 | GLU5K | | PSERT | ALCD2x | | ATPS |
| 312 | GLU5K | | PGCD | ALCD2x | | ATPS |
| 313 | PSERT | | PDHm | MDHm | | DHORD4u |
| 314 | PSP_L | PDHm | MDHm | | DHORD4u | |
| 315 | PGCD | PDHm | MDHm | | DHORD4u | |
| 316 | GLU5K | | PSP_L | ALCD2x | | PYRDC |
| 317 | GLU5K | | PGCD | ALCD2x | | PYRDC |
| 318 | GLU5K | | PSERT | ALCD2x | | PYRDC |
| 319 | GLU5K | | ALCD2x | ATPS | IPPS | |
| 320 | PSP_L | ALCD2x | | ATPS | IPPS | |
| 321 | PGCD | ALCD2x | | ATPS | IPPS | |
| 322 | PSERT | | ALCD2x | ATPS | IPPS | |
| 323 | ASPTA1m | | PYK | ATPSm | | ATPtm-3H |
| 324 | GHMT2 | | ME1m | GHMT2m | | PDHm |
| 325 | MTHFD | | G3PD | PYRDC | | ATPS |
| 326 | MTHFD | | GLY3PP | | PYRDC | ATPS |
| 327 | G5SD | G5SD2 | | ALCD2x | | ATPS |
| 328 | ACONT | | ICDHxm | | PYK | ATPSm |
| 329 | ICDHxm | | ICDHyPYK | | ATPSm | |
| 330 | ASPTA1m | | ACONTm | | ALCD2x | ATPS |
| 331 | ASPTA1m | | G5SD2 | | ALCD2x | ATPS |
| 332 | G5SD | G5SD2 | | PYRDC | | IPPSm |
| 333 | G5SD | G5SD2 | | PSP_L | PYRDC | |
| 334 | G5SD | G5SD2 | | PSERT | PYRDC | |
| 335 | G5SD | G5SD2 | | PGCD | PYRDC | |
| 336 | MTHFC | | G3PD | PYRDC | | ATPS |
| 337 | MTHFC | | GLY3PP | | PYRDC | ATPS |
| 338 | G5SD | G5SD2 | | PYRDC | ATPS | |
| 339 | GLU5K | | GHMT2m | | ATPSm | | ALCD2x |
| 340 | GHMT2 | | GHMT2m | | ATPtm-3H | IPPSm |
| 341 | GHMT2m | | PYK | ATPSm | | ATPtm-3H |
| 342 | G3PD | MDHm | | SUCD3-u6m | | ALCD2x |
| 343 | ASPTA1m | | MTHFC | | PGCD | ATPtm-3H |
| 344 | ASPTA1m | | MTHFC | | PSERT | ATPtm-3H |
| 345 | ASPTA1m | | MTHFC | | PSP_L | ATPtm-3H |
| 346 | ASPTA1m | | ME2m | PSP_L | ATPtm-3H | |
| 347 | ASPTA1m | | ME2m | PSERT | | ATPtm-3H |
| 348 | ASPTA1m | | ME2m | PGCD | ATPtm-3H | |
| 349 | GHMT2m | | PYK | ATPSm | | IPPSm |
| 350 | GLU5K | | GHMT2m | | PGCD | ATPSm | IPPSm |
| 351 | ME2m | ICDHym | | PGCD | ATPtm-3H | |
| 352 | ME2m | ACONTm | | PSP_L | ATPtm-3H | |
| 353 | ME2m | ICDHym | | PSP_L | ATPtm-3H | |
| 354 | ME2m | ACONTm | | PSERT | | ATPtm-3H |
| 355 | ME2m | ACONTm | | PGCD | | ATPtm-3H |
| 356 | ME2m | ICDHym | | PSERT | | ATPtm-3H |
| 357 | MTHFD | | MTHFD2 | | GHMT2m | ALCD2x |
| 358 | MTHFD | | MTHFD2 | | PSP_L | ATPtm-3H |
| 359 | MTHFD | | MTHFD2 | | PSERT | ATPtm-3H |
| 360 | MTHFD | | MTHFD2 | | PGCD | ATPtm-3H |
| 361 | GHMT2 | | GHMT2m | | ATPSm | | IPPSm |
| 362 | GHMT2m | | PYK | ATPSm | | ALCD2x |
| 363 | ME1m | MTHFC | | GHMT2m | | PDHm |
| 364 | THFATm | | PYK | ATPtm-3H | | IPPSm |
| 365 | FTHFCLm | | PYK | ATPtm-3H | IPPSm | |
| 366 | ACONT | | GHMT2m | | PYK | ATPSm |
| 367 | ICDHyGHMT2m | | | PYK | ATPSm | |
| 368 | GHMT2 | | ORNTA | | GHMT2m | ATPtm-3H |
| 369 | GHMT2 | | THFATm | | GHMT2m | PYRDC |

TABLE 6-continued

The list of all strains identified by OptKnock that are most likely to provide increased acrylate yields in *S. cerevisiae* under anaerobic conditions.

| # | Col1 | Col2 | Col3 | Col4 | Col5 | Col6 |
|---|------|------|------|------|------|------|
| 370 | GHMT2 | | FTHFCLm | | GHMT2m | PYRDC |
| 371 | ME2m | GLU5K | | ACONTm | | PYRDC |
| 372 | ME2m | GLU5K | | ICDHym | | PYRDC |
| 373 | MTHFD | | MTHFD2 | | GHMT2m | ATPtm-3H |
| 374 | MTHFD | | MTHFD2 | | GHMT2m | PYRDC |
| 375 | G5SD2 | | GHMT2m | | PYK | ATPSm |
| 376 | GLU5K | | GHMT2m | | PYK | ATPSm |
| 377 | ASPTA1m | | GHMT2m | | PYK | ATPSm |
| 378 | MTHFD | | MTHFD2 | | GHMT2m | ATPSm |
| 379 | G5SD | G5SD2 | | GHMT2m | | ATPSm |
| 380 | MTHFC | | GHMT2m | | ATPtm-3H | IPPSm |
| 381 | ASPTA1m | | ACONTm | | GHMT2m | ATPSm |
| 382 | MTHFC | | GHMT2m | | ALCD2x | IPPSm |
| 383 | ME2m | MTHFC | | PYK | ATPSm | |
| 384 | ASPTA1m | | G5SD2 | | GHMT2m | ATPSm |
| 385 | G5SD2 | | MTHFD | | GHMT2m | ATPSm |
| 386 | ME2m | FTHFLr | | PYK | ATPSm | |
| 387 | THFATm | | PYK | | TKT2 | ATPtm-3H |
| 388 | FTHFCLm | | PYK | | TKT2 | ATPtm-3H |
| 389 | ORNTA | | THFATm | | PYK | ATPtm-3H |
| 390 | ORNTA | | FTHFCLm | | PYK | ATPtm-3H |
| 391 | ASPTA1m | | FTHFCLm | | PYK | ATPtm-3H |
| 392 | ASPTA1m | | THFATm | | PYK | ATPtm-3H |
| 393 | ORNTA | | MTHFC | | GHMT2m | ATPtm-3H |
| 394 | PDHm | ATPSm | | | MDHm | PPND |
| 395 | MTHFC | | THFATm | | PYK | ATPtm-3H |
| 396 | FTHFCLm | | MTHFC | | PYK | ATPtm-3H |
| 397 | GHMT2 | | THFATm | | PYK | ATPtm-3H |
| 398 | GHMT2 | | FTHFCLm | | PYK | ATPtm-3H |
| 399 | GHMT2 | | ORNTA | | FTHFCLm | ALCD2x |
| 400 | GHMT2 | | ORNTA | | THFATm | ALCD2x |
| 401 | G5SD | G5SD2 | | ALCD2x | | THRA |
| 402 | PSP_L | MDHm | | DHORD4u | | IPPSm |
| 403 | PSERT | | MDHm | DHORD4u | | IPPSm |
| 404 | PGCD | MDHm | | DHORD4u | | IPPSm |
| 405 | ORNTA | | PSERT | | MDHm | DHORD4u |
| 406 | ORNTA | | PSP_L | MDHm | | DHORD4u |
| 407 | ORNTA | | PGCD | MDHm | | DHORD4u |
| 408 | GHMT2 | | ORNTA | | ME1m | GHMT2m |
| 409 | ME1m | MTHFD | | MTHFD2 | | GHMT2m |
| 410 | PSERT | | MDHm | | DHORD4u | ALDD2y |
| 411 | PGCD | MDHm | | DHORD4u | | ALDD2y |
| 412 | PSP_L | MDHm | | DHORD4u | | ALDD2y |
| 413 | ASPTA1m | | PGCD | MDHm | | DHORD4u |
| 414 | ASPTA1m | | PSP_L | MDHm | | DHORD4u |
| 415 | ASPTA1m | | PSERT | | MDHm | DHORD4u |
| 416 | PGCD | MDHm | | NADH2-u6m | | SUCD3-u6m |
| 417 | PSERT | | MDHm | | NADH2-u6m | SUCD3-u6m |
| 418 | PSP_L | MDHm | | NADH2-u6m | | SUCD3-u6m |
| 419 | PYK | MDHm | | DHORD4u | | ATPS |
| 420 | MDHm | | NADH2-u6m | | SUCD3-u6m | ATPS |
| 421 | PDHm | MDHm | | DHORD4u | | ALDD2y |
| 422 | GHMT2 | | GHMT2m | | MDHm | DHORD4u |
| 423 | ORNTA | | PDHm | MDHm | | DHORD4u |
| 424 | ASPTA1m | | PDHm | MDHm | | DHORD4u |
| 425 | PDHm | MDHm | | NADH2-u6m | | SUCD3-u6m |
| 426 | ORNTA | | MDHm | | DHORD4u | IPPSm |
| 427 | MDHm | | DHORD4u | | ALDD2y | IPPSm |
| 428 | ASPTA1m | | MDHm | | DHORD4u | IPPSm |
| 429 | MDHm | | NADH2-u6m | | SUCD3-u6m | IPPSm |
| 430 | MTHFC | | GHMT2m | | MDHm | DHORD4u |
| 431 | ORNTA | | MDHm | | DHORD4u | ALDD2y |
| 432 | ME2m | ICDHym | | MDHm | | DHORD4u |
| 433 | ME2m | ACONTm | | MDHm | | DHORD4u |
| 434 | ORNTA | | MDHm | | NADH2-u6m | SUCD3-u6m |
| 435 | ASPTA1m | | MDHm | | DHORD4u | ALDD2y |
| 436 | MDHm | | NADH2-u6m | | SUCD3-u6m | ALDD2y |
| 437 | ASPTA1m | | MDHm | | NADH2-u6m | SUCD3-u6m |
| 438 | PSERT | | TPI | MDH | | DHORD4u |
| 439 | PSP_L | TPI | | MDH | | DHORD4u |
| 440 | PGCD | TPI | | MDH | | DHORD4u |
| 441 | TPI | | MDH | | DHORD4u | THRA |
| 442 | PDHm | TPI | | MDH | | DHORD4u |
| 443 | TPI | FDH | | MDH | | DHORD4u |

TABLE 6-continued

The list of all strains identified by OptKnock that are most likely to provide increased acrylate yields in *S. cerevisiae* under anaerobic conditions.

| | | | | | | | |
|---|---|---|---|---|---|---|---|
| 444 | TPI | MDH | NADH2-u6m | SUCD3-u6m | | | |
| 445 | G3PDm | | TPI | MDH | NADH2-u6m | | |
| 446 | G3PD1irm | | TPI | MDH | NADH2-u6m | | |
| 447 | GLYCLm | | PGI | MDH | DHORD4u | | |
| 448 | GHMT2 | | PGI | MDH | DHORD4u | | |
| 449 | GHMT2m | | PGI | MDH | DHORD4u | | |
| 450 | G3PD1irm | | PGI | MDH | NADH2-u6m | | |
| 451 | G3PDm | | PGI | MDH | NADH2-u6m | | |
| 452 | MDH | DHORD4u | | ATPS | ALDD2y | | |
| 453 | ME2m | MDH | DHORD4u | | ATPS | | |
| 454 | ICDHy | MDH | DHORD4u | | ATPS | | |
| 455 | ACONT | | MDH | DHORD4u | | ATPS | |
| 456 | GHMT2 | | MDH | DHORD4u | | ATPS | |
| 457 | ORNTA | | MDH | DHORD4u | | ATPS | |
| 458 | MTHFC | | MDH | DHORD4u | | ATPS | |
| 459 | MDH | NADH2-u6m | | SUCD3-u6m | | ATPS | |
| 460 | G3PD1irm | | MDH | NADH2-u6m | | ATPS | |
| 461 | G3PDm | | MDH | NADH2-u6m | | ATPS | |
| 462 | ASPTA1 | | FUM | FUMmATPS | | | |
| 463 | PSERT | | TPI | FUM | FUMm | | |
| 464 | PSP_L | TPI | FUM | FUMm | | | |
| 465 | PGCD | TPI | FUM | FUMm | | | |
| 466 | G3PDm | | FUM | FUMm | SUCD3-u6m | | |
| 467 | G3PDm | | FUM | SUCD1rm | | SUCD3-u6m | |
| 468 | G3PDm | | MDH | SUCD3-u6m | | DHORD4u | |
| 469 | G3PDm | | MDH | NADH2-u6m | | SUCD3-u6m | |
| 470 | ASPTA1 | | TPI | FUM | FUMm | | |
| 471 | FTHFLr | | TPI | FUM | FUMm | | |
| 472 | MTHFC | | TPI | FUM | FUMm | | |
| 473 | GHMT2 | | TPI | FUM | FUMm | | |
| 474 | GLU5K | | G3PDm | | PDHm | SUCD3-u6m | PYRDC |
| 475 | G3PDm | | PDHm | SUCD3-u6m | | PYRDC | IPPS |
| 476 | GLU5K | | G3PDm | | SUCD3-u6m | ALCD2x | IPPS |
| 477 | G5SD | G5SD2 | | G3PDm | | SUCD3-u6m | ALCD2x |
| 478 | ASPTA1m | | ACONTm | | G3PDm | SUCD3-u6m | ALCD2x |
| 479 | G3PDm | | NADH2-u6cm | | NADH2-u6m | DHORD4u | ALCD2x |
| 480 | G3PD | PDHm | MDHm | | SUCD3-u6m | | PYRDC |
| 481 | G5SD | G5SD2 | | PDHm | PYRDC | IPPS | |
| 482 | G3PDm | | ATPSm | | NADH2-u6cm | NADH2-u6m | DHORD4u |
| 483 | ASPTA1m | | ACONTm | | PDHm | PYRDC | IPPS |
| 484 | ASPTA1m | | ICDHxm | | ICDHym | PDHm | PYRDC | ATPtm-3H |
| 485 | ORNTA | | MTHFC | | G3PDm | SUCD3-u6m | ATPtm-3H |
| 486 | G3PD | PDHm | MDHm | | SUCD3-u6m | ALCD2x | |
| 487 | ME2m | MTHFD | | G3PDm | | SUCD3-u6m | ATPtm-3H |
| 488 | GHMT2 | | ME2m | G3PDm | | SUCD3-u6m | ATPtm-3H |
| 489 | ACONT | | MTHFC | G3PDm | | SUCD3-u6m | ATPtm-3H |
| 490 | ICDHyMTHFC | | | G3PDm | | SUCD3-u6m | ATPtm-3H |
| 491 | MTHFD | | MTHFD2 | | G3PDm | SUCD3-u6m | ATPtm-3H |
| 492 | ASPTA1m | | GHMT2 | | G3PDm | SUCD3-u6m | ATPtm-3H |
| 493 | ASPTA1m | | MTHFC | | G3PDm | SUCD3-u6m | ATPtm-3H |
| 494 | MTHFD | | G3PDm | | GHMT2m | SUCD3-u6m | ATPtm-3H |
| 495 | G3PDm | | NADH2-u6cm | | NADH2-u6m | DHORD4u | ATPtm-3H |

TABLE 7

A list of all the reaction stoichiometries and the associated genes known to be associated with the reactions identified for disruption in the strains listed in Tables 5 and 6. [c] refers to cytosol and [m] refers to mitochondrion, indicating the organelle where the reaction takes place

| Reaction Abbreviation | Reaction Name | Reaction Stoichiometry | Associated genes |
|---|---|---|---|
| ACONT | aconitase | [c]: cit <==> icit | YLR304C |
| ACONTm | aconitate hydratase | [m]: cit <==> icit | YJL200C, YLR304C |
| AGT | alanine-glyoxylate transaminase | [c]: ala-L + glx <==> gly + pyr | YFL030W |

TABLE 7-continued

A list of all the reaction stoichiometries and the associated genes known to be associated with the reactions identified for disruption in the strains listed in Tables 5 and 6. [c] refers to cytosol and [m] refers to mitochondrion, indicating the organelle where the reaction takes place

| Reaction Abbreviation | Reaction Name | Reaction Stoichiometry | Associated genes |
|---|---|---|---|
| AKGDam | oxoglutarate dehydrogenase (lipoamide) | [m]: akg + h + lpam <==> co2 + sdhlam | YIL125W, YDR148C, YFL018C |
| AKGDbm | oxoglutarate dehydrogenase (dihydrolipoamide S-succinyltransferase) | [m]: coa + sdhlam --> dhlam + succoa | YIL125W, YDR148C, YFL018C |
| ALATA_L | L-alanine transaminase | [c]: akg + ala-L <==> glu-L + pyr | YDR111C |
| ALCD2x | alcohol dehydrogenase (ethanol: NAD) | [c]: etoh + nad <==> acald + h + nadh | YGL256W, YMR303C, YDL168W, YOL086C, YBR145W |
| ASPTA1 | aspartate transaminase | [c]: akg + asp-L <==> glu-L + oaa | YLR027C |
| ASPTA1m | aspartate transaminase, mitochondrial | [m]: akg + asp-L <==> glu-L + oaa | YKL106W |
| ATPSm | ATP synthase, mitochondrial | adp[m] + (3) h[c] + pi[m] --> atp[m] + (2) h[m] + h2o[m] | YBL099W + YPL078C + YDL004W + YDR377W + YOL077W-A + YJR121W + YDR322C-A + Q0080 + YBR039W + YDL181W + Q0130 + YKL016C + YDR298C + YML081C-A + YPL271W + Q0085 + YPR020W + YLR295C, YBL099W + YDL004W + YPL078C + YDR377W + YJR121W + Q0080 + YBR039W + YDL181W + YKL016C + Q0130 + YDR298C + YML081C-A + YPL271W + Q0085 + YLR295C |
| ATPtm-3H | ADP/ATP transporter, mitochondrial | adp[c] + atp[m] + (3) h[c] --> adp[m] + atp[c] + (3) h[m] | YBL030C, YBR085W, YMR056C |
| FRDcm | fumarate reductase, cytosolic/mitochondrial | fadh2[m] + fum[c] --> fad[m] + succ[c] | YEL047C |
| FRDm | fumarate reductase | [m]: fadh2 + fum --> fad + succ | YJR051W |
| FUMm | fumarase, mitochondrial | [m]: fum + h2o <==> mal-L | YPL262W |
| G3PD | Glycerol-3-phosphate dehydrogenase (NAD) | [c]: dhap + h + nadh --> glyc3p + nad | YDL022W |
| G3PD1irm | glycerol-3-phosphate dehydrogenase (NAD), mitochondrial | [m]: dhap + h + nadh --> glyc3p + nad | YOL059W |
| G3PDm | glycerol-3-phosphate dehydrogenase | [m]: fad + glyc3p --> dhap + fadh2 | YIL155C |
| G6PDH | glucose 6-phosphate dehydrogenase | [c]: g6p + nadp --> 6pgl + h + nadph | YNL241C |
| GHMT2 | glycine hydroxymethyltransferase | [c]: ser-L + thf --> gly + h2o + mlthf | YLR058C |
| GLY3PP | glycerol-3-phosphatase | [c]: glyc3p + h2o --> glyc + pi | YER062C, YIL053W |
| HSDxi | homoserine dehydrogenase (NADH), irreversible | [c]: aspsa + h + nadh --> hom-L + nad | YJR139C |
| HSK | homoserine kinase | [c]: atp + hom-L --> adp + h + phom | YHR025W |
| ICDHxm | Isocitrate dehydrogenase (NAD+) | [m]: icit + nad --> akg + co2 + nadh | YOR136W + YNL037C |
| ICDHy | isocitrate dehydrogenase (NADP) | [c]: icit + nadp <==> akg + co2 + nadph | YLR174W |
| ICL | Isocitrate lyase | [c]: icit --> glx + succ | YER065C |
| MDH | malate dehydrogenase | [c]: mal-L + nad <==> h + nadh + oaa | YOL126C |
| MDHm | malate dehydrogenase, mitochondrial | [m]: mal-L + nad <==> h + nadh + oaa | YKL085W |
| ME1m | malic enzyme (NAD), mitochondrial | [m]: mal-L + nad --> co2 + nadh + pyr | YKL029C |
| ME2m | malic enzyme (NADP), mitochondrial | [m]: mal-L + nadp --> co2 + nadph + pyr | YKL029C |
| MTHFD | methylenetetrahydrofolate dehydrogenase (NADP) | [c]: mlthf + nadp <==> methf + nadph | YGR204W |
| NADH2-u6cm | NADH dehydrogenase, cytosolic/mitochondrial | h[c] + nadh[c] + q6[m] --> nad[c] + q6h2[m] | YMR145C, YDL085W |
| ORNTA | ornithine transaminase | [c]: akg + orn-L --> glu-L + glu5sa | YLR438W |
| P5CDm | 1-pyrroline-5-carboxylate dehydrogenase, mitochondrial | [m]: 1pyr5c + (2) h2o + nad --> glu-L + h + nadh | |

TABLE 7-continued

A list of all the reaction stoichiometries and the associated genes known to be associated with the reactions identified for disruption in the strains listed in Tables 5 and 6. [c] refers to cytosol and [m] refers to mitochondrion, indicating the organelle where the reaction takes place

| Reaction Abbreviation | Reaction Name | Reaction Stoichiometry | Associated genes |
|---|---|---|---|
| PDHcm | part of pyruvate dehydrogenase (dihydrolipoamide dehydrogenase) | [m]: dhlam + nad --> h + lpam + nadh | YIL125W, YDR148C, YFL018C |
| PDHm | pyruvate dehydrogenase, mitochondrial | [m]: coa + nad + pyr --> accoa + co2 + nadh | YER178W + YBR221C, YNL071W, YFL018C |
| PGCD | phosphoglycerate dehydrogenase | [c]: 3pg + nad --> 3php + h + nadh | YIL074C, YER081W |
| PGDH | phosphogluconate dehydrogenase | [c]: 6pgc + nadp --> co2 + nadph + ru5p-D | YHR183W, YGR256W |
| PGL | 6-phosphogluconolactonase | [c]: 6pgl + h2o --> 6pgc + h | YNR034W, YGR248W, YHR163W |
| PRO1xm | proline oxidase (NAD), mitochondrial | [m]: nad + pro-L --> 1pyr5c + (2) h + nadh | YLR142W |
| PSERT | phosphoserine transaminase | [c]: 3php + glu-L --> akg + pser-L | YOR184W |
| PSP_L | phosphoserine phosphatase (L-serine) | [c]: h2o + pser-L --> pi + ser-L | YGR208W |
| PYK | pyruvate kinase | [c]: adp + h + pep --> atp + pyr | YAL038W, YOR347C |
| PYRDC | pyruvate decarboxylase | [c]: h + pyr --> acald + co2 | YGR087C, YLR044C, YLR134W |
| RPE | ribulose 5-phosphate 3-epimerase | [c]: ru5p-D <==> xu5p-D | YJL121C |
| SERD_L | L-serine deaminase | [c]: ser-L --> nh4 + pyr | YIL168W, YCL064C |
| SUCD2_u6m | succinate dehydrogenase (ubiquinone-6), mitochondrial | [m]: q6 + succ <==> fum + q6h2 | YKL148C + YMR118C + YLL041C + YDR178W, YKL141W + YLL041C + YJL045W + YDR178W, YKL148C + YKL141W + YLL041C + YLR164W, YKL148C + YKL141W + YLL041C + YDR178W |
| SUCD3-u6m | succinate dehydrogenase (ubiquinone-6), mitochondrial | [m]: fadh2 + q6 <==> fad + q6h2 | YKL148C + YMR118C + YLL041C + YDR178W, YKL141W + YLL041C + YJL045W + YDR178W, YKL148C + YKL141W + YLL041C + YLR164W, YKL148C + YKL141W + YLL041C + YDR178W |
| SUCOASAm | Succinate--CoA ligase (ADP-forming) | [m]: atp + coa + succ <==> adp + pi + succoa | YOR142W + YGR244C |
| THRA | threonine aldolase | [c]: thr-L <==> acald + gly | YEL046C |
| THRS | threonine synthase | [c]: h2o + phom --> pi + thr-L | YCR053W |
| TKT2 | transketolase | [c]: e4p + xu5p-D <==> f6p + g3p | YBR117C, YPR074C |

TABLE 8

List of the metabolite abbreviations, the corresponding names of all the metabolites that participate in the reactions listed in Table 7.

| Metabolite Abbreviation | Metabolite Name |
|---|---|
| 1pyr5c | 1-Pyrroline-5-carboxylate |
| 3pg | 3-Phospho-D-glycerate |
| 3php | 3-Phosphohydroxypyruvate |
| 6pgc | 6-Phospho-D-gluconate |
| 6pgl | 6-phospho-D-glucono-1,5-lactone |
| acald | Acetaldehyde |
| accoa | Acetyl-CoA |
| adp | ADP |
| akg | 2-Oxoglutarate |
| ala-L | L-Alanine |
| asp-L | L-Aspartate |
| aspsa | L-Aspartate 4-semialdehyde |
| atp | ATP |
| cit | Citrate |
| co2 | CO2 |
| coa | Coenzyme A |
| dhap | Dihydroxyacetone phosphate |
| dhlam | Dihydrolipoamide |
| e4p | D-Erythrose 4-phosphate |
| etoh | Ethanol |
| f6p | D-Fructose 6-phosphate |
| fad | FAD |
| fadh2 | FADH2 |
| fum | Fumarate |
| g3p | Glyceraldehyde 3-phosphate |
| g6p | D-Glucose 6-phosphate |
| glu-L | L-Glutamate |
| glu5sa | L-Glutamate 5-semialdehyde |
| glx | Glyoxylate |
| gly | Glycine |
| glyc | Glycerol |
| glyc3p | sn-Glycerol 3-phosphate |
| h | H+ |
| h2o | H2O |
| hom-L | L-Homoserine |
| icit | Isocitrate |
| lpam | Lipoamide |
| mal-L | L-Malate |
| methf | 5,10-Methenyltetrahydrofolate |
| mlthf | 5,10-Methylenetetrahydrofolate |
| nad | Nicotinamide adenine dinucleotide |
| nadh | Nicotinamide adenine dinucleotide-reduced |
| nh4 | Ammonium |
| oaa | Oxaloacetate |
| orn-L | L-Ornithine |
| pep | Phosphoenolpyruvate |
| phom | O-Phospho-L-homoserine |
| pi | Phosphate |

TABLE 8-continued

List of the metabolite abbreviations, the corresponding names of all the metabolites that participate in the reactions listed in Table 7.

| Metabolite Abbreviation | Metabolite Name |
|---|---|
| pro-L | L-Proline |
| pser-L | O-Phospho-L-serine |
| pyr | Pyruvate |
| q6 | Ubiquinone-6 |
| q6h2 | Ubiquinol-6 |
| ru5p-D | D-Ribulose 5-phosphate |
| sdhlam | S-Succinyldihydrolipoamide |
| ser-L | L-Serine |
| succ | Succinate |
| succoa | Succinyl-CoA |
| thf | 5,6,7,8-Tetrahydrofolate |
| thr-L | L-Threonine |
| xu5p-D | D-Xylulose 5-phosphate |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A non-naturally occurring microbial organism for acrylate production having an exogenous nucleic acid encoding a decarboxylase that catalyzes fumarate decarboxylation expressed in a sufficient amount to produce acrylate from fumarate.

2. The non-naturally occurring microbial organism of claim 1 further comprising an exogenous nucleic acid encoding at least one malic enzyme selected from the group consisting of malic enzyme (NAD-dependent) and malic enzyme (NADP dependent).

3. The non-naturally occurring microbial organism of claim 1 further comprising an exogenous nucleic acid encoding a phosphoenolpyruvate carboxykinase.

4. The non-naturally occurring microbial organism of claim 1 further comprising one or more gene disruptions of a gene encoding an enzyme selected from the group consisting of a fumarate reductase, an alcohol dehydrogenase, and a lactate dehydrogenase.

5. The non-naturally occurring microbial organism of claim 1 further comprising an exogenous nucleic acid encoding at least one maleate cis-trans isomerase.

* * * * *